United States Patent
Umaña et al.

(10) Patent No.: US 7,722,867 B2
(45) Date of Patent: May 25, 2010

(54) ANTIGEN BINDING MOLECULES THAT BIND EGFR, VECTORS ENCODING SAME, AND USES THEREOF

(75) Inventors: Pablo Umaña, Zurich (CH); Ekkehard Mössner, Kreuzlingen (CH)

(73) Assignee: Glycart Biotechnology AG, Schlieren-Zürich (CH)

(*) Notice: Subject to any disclaimer, the term of this patent is extended or adjusted under 35 U.S.C. 154(b) by 730 days.

(21) Appl. No.: 11/348,526

(22) Filed: Feb. 7, 2006

(65) Prior Publication Data
US 2006/0269545 A1 Nov. 30, 2006
US 2008/0279858 A9 Nov. 13, 2008

Related U.S. Application Data

(60) Provisional application No. 60/650,115, filed on Feb. 7, 2005.

(51) Int. Cl.
A61K 39/395 (2006.01)
C12P 21/08 (2006.01)
C12P 19/34 (2006.01)
C07K 16/28 (2006.01)
C12N 5/10 (2006.01)
C12N 15/54 (2006.01)
C12N 15/13 (2006.01)
C12N 15/03 (2006.01)
C12N 15/09 (2006.01)
C12N 15/00 (2006.01)

(52) U.S. Cl. .............. 424/130.1; 424/133.1; 424/135.1; 424/143.1; 435/69.1; 435/193; 435/326; 435/334; 435/252.3; 435/252.33; 435/320.1; 530/387.1; 530/387.3; 530/388.22; 536/23.53; 536/23.2

(58) Field of Classification Search .................. None
See application file for complete search history.

(56) References Cited

U.S. PATENT DOCUMENTS

| | | | |
|---|---|---|---|
| 4,816,567 A | 3/1989 | Cabilly et al. | |
| 5,225,539 A | 7/1993 | Winter | |
| 5,558,864 A | 9/1996 | Bendig et al. | |
| 5,891,996 A | 4/1999 | Mateo de Acosta del Rio et al. | |
| 6,180,370 B1 | 1/2001 | Queen et al. | |
| 6,342,219 B1* | 1/2002 | Thorpe et al. ............ | 424/145.1 |
| 6,602,684 B1 | 8/2003 | Umaña et al. | |
| 6,632,927 B2 | 10/2003 | Adair et al. | |
| 6,737,056 B1 | 5/2004 | Presta | |
| 6,815,184 B2 | 11/2004 | Stomp et al. | |
| 2001/0049105 A1 | 12/2001 | Singh et al. | |
| 2002/0128448 A1 | 9/2002 | Reff | |
| 2003/0039649 A1 | 2/2003 | Foote | |
| 2003/0040606 A1 | 2/2003 | Leung | |
| 2003/0115614 A1 | 6/2003 | Kanda et al. | |
| 2003/0157108 A1 | 8/2003 | Presta | |
| 2003/0175269 A1 | 9/2003 | Black et al. | |
| 2003/0175884 A1 | 9/2003 | Umaña et al. | |
| 2003/0190689 A1 | 10/2003 | Crosby et al. | |
| 2004/0072290 A1 | 4/2004 | Umaña et al. | |
| 2004/0093621 A1 | 5/2004 | Shitara et al. | |
| 2004/0110282 A1 | 6/2004 | Kanda et al. | |
| 2004/0110704 A1 | 6/2004 | Yamane et al. | |
| 2004/0132066 A1 | 7/2004 | Balint et al. | |
| 2004/0132097 A1 | 7/2004 | Bacus et al. | |
| 2004/0132101 A1 | 7/2004 | Lazar et al. | |
| 2004/0132140 A1 | 7/2004 | Satoh et al. | |
| 2004/0241817 A1 | 12/2004 | Umaña et al. | |
| 2005/0074843 A1 | 4/2005 | Umaña et al. | |
| 2005/0079605 A1 | 4/2005 | Umaña et al. | |
| 2005/0123546 A1 | 6/2005 | Umaña et al. | |
| 2005/0272128 A1 | 12/2005 | Umaña et al. | |

FOREIGN PATENT DOCUMENTS

| | | |
|---|---|---|
| EP | 1 176 195 A1 | 1/2002 |
| WO | WO 95/20045 A1 | 7/1995 |
| WO | WO 99/54342 A1 | 10/1999 |
| WO | WO 03/056914 A1 | 7/2003 |
| WO | WO 03/078614 A2 | 9/2003 |
| WO | WO 03/084570 A1 | 10/2003 |
| WO | WO 03/085119 A1 | 10/2003 |
| WO | WO 2004/024927 A1 | 3/2004 |
| WO | WO 2004/057002 A2 | 7/2004 |

(Continued)

OTHER PUBLICATIONS

Rudikoff et al, Proc Natl Acad Sci USA vol. 79 pp. 1979-1983, 1982.*
Kobrin et al, J Immunology 146: 2017-2020, 1991.*
Barrios et al, J Molecular Recognition 17: 332-338, 2004.*
Kabat, E.A., et al., *Sequences of Proteins of Immunological Interest*, U.S. Department of Health and Human Services, Public Health Services, National Institutes of Health, pp. i-xx, (1983).
Co-pending U.S. Appl. No. 11/889,215, inventors Umaña, P., et al., filed Aug. 9, 2007.

(Continued)

*Primary Examiner*—Phuong Huynh
(74) *Attorney, Agent, or Firm*—Sterne, Kessler, Goldstein & Fox P.L.L.C.

(57) ABSTRACT

The present invention relates to antigen binding molecules (ABMs). In particular embodiments, the present invention relates to recombinant monoclonal antibodies, including chimeric, primatized or humanized antibodies specific for human EGFR. In addition, the present invention relates to nucleic acid molecules encoding such ABMs, and vectors and host cells comprising such nucleic acid molecules. The invention further relates to methods for producing the ABMs of the invention, and to methods of using these ABMs in treatment of disease. In addition, the present invention relates to ABMs with modified glycosylation having improved therapeutic properties, including antibodies with increased Fc receptor binding and increased effector function.

57 Claims, 29 Drawing Sheets

FOREIGN PATENT DOCUMENTS

| | | |
|---|---|---|
| WO | WO 2004/063351 A2 | 7/2004 |
| WO | WO 2004/065540 A2 | 8/2004 |
| WO | WO 2004/099249 A2 | 11/2004 |
| WO | WO 2005/056606 A2 | 6/2005 |
| WO | WO 2005/056759 A1 | 6/2005 |
| WO | WO 2007/031875 A2 | 3/2007 |

OTHER PUBLICATIONS

Co-pending U.S. Appl. No. 11/892,010, inventors Umaña, P., et al., filed Aug. 17, 2007.

Co-pending U.S. Appl. No. 11/889,981, inventors Umaña, P., et al., filed Aug. 17, 2007.

Arteaga, C.L. and Baselga, J., "Clinical Trial Design and End Points for Epidermal Growth Factor Receptor-targeted Therapies: Implications for Drug Development and Practice," *Clin. Cancer Res. 9*:1579-1589, The American Association for Cancer Research (2003).

Bleeker, W.K., et al., "Dual Mode of Action of a Human Anti-Epidermal Growth Factor Receptor Monoclonal Antibody for Cancer Therapy," *J. Immunol. 173*:4699-4707, The American Association of Immunologists, Inc. (2004).

Modjtahedi, H., et al., "Antitumor Activity of Combinations of Antibodies Directed Against Different Epitopes on the Extracellular Domain of the Human EGF Receptor," *Cell Biophysics 22*:129-146, Humana Press Inc. (1993).

Sumitomo, M., et al., "ZD1839 Modulates Paclitaxel Response in Renal Cancer by Blocking Paclitaxel-Induced Activation of the Epidermal Growth Factor Receptor-Extracellular Signal-Regulated Kinase Pathway," *Clin. Cancer Res. 10*:794-801, The American Association for Cancer Research (2004).

Davies, J., et al., "Expression of GnTIII in a Recombinant Anti-CD20 CHO Production Cell Line: Expression of Antibodies with Altered Glycoforms Leads to an Increase in ADCC Through Higher Affinity for FcγRIII," *Biotechnol. Bioeng. 74*:288-294, John Wiley & Sons, Inc. (2001).

Shields, R.L., et al., "Lack of Fucose on Human IgG1 N-Linked Oligosaccharide Improves Binding to Human FcγRIII and Antibody-dependent Cellular Toxicity," *J. Biol. Chem. 277*: 26733-26740, The American Society for Biochemistry and Molecular Biology, Inc. (2002).

Andersen, D.C. and Krummen, L., "Recombinant protein expression for therapeutic applications," *Curr. Opin. Biotechnol. 13*:117-123, Elsevier Science Ltd. (2002).

Appelbaum, F.R., "Radiolabeled Monoclonal Antibodies in the Treatment of Non-Hodgkin's Lymphoma," *Hematol./Oncol. Clin. N. Am. 5*:1013-1025, W.B. Saunders (1991).

Atalay, G., et al., "Novel therapeutic strategies targeting the epidermal growth factor receptor (EGFR) family and its downstream effectors in breast cancer," *Ann. Oncol. 14*:1346-1363, Oxford University Press (2003).

Becker, J., "Signal transduction inhibitors—a work in progress," *Nat. Biotechnol. 22*:15-18, Nature America Publishing (Jan. 2004).

Bier, H., et al., "Dose-dependent access of murine anti-epidermal growth factor receptor monoclonal antibody to tumor cells in patients with advanced laryngeal and hypopharyngeal carcinoma," *Eur. Arch. Otorhinolaryngol. 252*:433-439, Springer-Verlag (1995).

Borth, N., et al., "Efficient Selection of High-Producing Subclones During Gene Amplification of Recombinant Chinese Hamster Ovary Cells by Flow Cytometry and Cell Sorting," *Biotechnol. Bioeng. 71*:266-273, John Wiley & Sons, Inc. (2001).

Boulianne, G.L., et al., "Production of functional chimaeric mouse/human antibody," *Nature 312*:643-646, Macmillan Journals Ltd. (1984).

Bowie, J.U., et al., "Deciphering the Message in Protein Sequences: Tolerance to Amino Acid Substitutions," *Science 247*:1306-1310, American Association for the Advancement of Science (1990).

Carter, P., et al., "Humanization of an anti-p185$^{HER2}$ antibody for human cancer therapy," *Proc. Natl. Acad. Sci. USA 89*:4285-4289, National Academy of Sciences (1992).

Cartron, G., et al., "Therapeutic activity of humanized anti-CD20 monoclonal antibody and polymorphism in IgG Fc receptor FcγRIIIa gene," *Blood 99*:754-758, American Society of Hematology (2002).

Chadd, H.E. and Chamow, S.M., "Therapeutic antibody expression technology," *Curr. Opin. Biotechnol. 12*:188-194, Elsevier Science Ltd. (2001).

Chothia, C., et al., "Structural Repertoire of the Human $V_H$ Segments," *J. Mol. Biol. 227*:799-817, Academic Press Limited (1992).

Chothia, C. and Lesk, A.M., "Canonical Structures for the Hypervariable Regions of Immunoglobulins, "*J. Mol. Biol. 196*:901-917, Academic Press Limited (1987).

Clynes, R.A., et al., "Inhibitory Fc receptors modulate in vivo cytotoxicity against tumor targets," *Nat. Med. 6*:443-446, Nature Publishing Company (2000).

Colbère-Garapin, F., et al., "A New Dominant Hybrid Selective Marker for Higher Eukaryotic Cells," *J. Mol. Biol. 150*:1-14, Academic Press Inc. (London) Ltd. (1981).

Cumming, D.A., "Glycosylation of recombinant protein therapeutics: control and functional implications," *Glycobiol 1*:115-130, Oxford University Press (1991).

Deo, Y.M., et al., "Clinical significance of IgG Fc receptors and FcγR-directed immunotherapies," *Immunol. Today 18*:127-135, Elsevier Science Ltd. (1997).

Dickson, S., "Scientists Produce Chimeric Monoclonal Abs," *Genetic Engineering News*, 5:1 and 33, Mary Ann Liebert, Inc. (1985).

Dillman, R.O., "Magic Bullets at Last! Finally-Approval of a Monoclonal Antibody for the Treatment of Cancer!!!," *Cancer Biother. Radiopharm. 12*:223-225, Mary Ann Liebert, Inc. (1997).

Eary, J.F., et al., "Imaging and Treatment of B-Cell Lymphoma," *J. Nucl. Med. 31*:1257-1268, Society of Nuclear Medicine (1990).

Ferrara, C., et al., "The Carbohydrate at FcγRIIIa Asn-162. An Element Required for High Affinity Binding to Non-Fucosylated IgG Glycoforms," *J. Biol. Chem. 281*:5032-5036, American Society for Biochemistry and Molecular Biology, Inc. (Feb. 2006).

Frost, J.D., et al., "A Phase I/IB Trial of Murine Monoclonal Anti-GD2 Antibody 14.G2a plus Interleukin-2 in Children with Refractory Neuroblastoma," *Cancer 80*:317-333, John Wiley & Sons, Inc. (1997).

Gadella, T.W.J. and Jovin, T.M., "Oligomerization of Epidermal Growth Factor Receptors on A431 Cells Studied by time-resolved Fluorescence Imaging Microscopy. A Stereochemical Model for Tyrosine Kinase Receptor Activation," *J. Cell. Biol. 129*:1543-1558, The Rockefeller University Press (1995).

Giddings, G., "Transgenic plants as protein factories," *Curr. Opin. Biotechnol. 12*:450-454, Elsevier Science Ltd. (2001).

Goldenberg, M.M., "Trastuzumab, a Recombinant DNA-Derived Humanized Monoclonal Antibody, a Novel Agent for the Treatment of Metastatic Breast Cancer," *Clin. Ther. 21*:309-318, Excerpta Medica, Inc. (1999).

Goldstein, N.I., et al., "Biological Efficacy of a Chimeric Antibody to the Epidermal Growth Factor Receptor in a Human Tumor Xenograft Model," *Clin. Cancer Res. 1*:1311-1318, American Association for Cancer Research (1995).

Hartman, S.C. and Mulligan, R.C., "Two dominant-acting selectable markers for gene transfer studies in mammalian cells," *Proc. Natl. Acad. Sci. USA 85*:8047-8051, National Academy of Sciences (1988).

Herbst, R.S. and Shin, D.M., "Monoclonal Antibodies to Target Epidermal Growth Factor Receptor-Positive Tumors. A New Paradigm for Cancer Therapy," *Cancer 94*:1593-611, Wiley (2002).

Hudson, P.J. and Souriau, C., "Engineered antibodies," *Nat. Med. 9*:129-134, Nature Publishing Company (2003).

Jefferis, R., et al., "IgG-Fc-mediated effector functions: molecular definition of interaction sites for effector ligands and the role of glycosylation," *Immunol. Rev. 163*:59-76, Munksgaard (1998).

Jenkins, N., et al., "Getting the glycosylation right: Implications for the biotechnology industry," *Nat. Biotechnol. 14*:975-981, Nature America Publishing (1996).

Jones, P.T., et al., "Replacing the complementarity-determining regions in a human antibody with those from a mouse," *Nature 321*:522-525, Macmillan Journals Ltd. (1986).

Kalergis, A.M. and Ravetch, J.V., "Inducing Tumor Immunity through the Selective Engagement of Activating Fcγ Receptors on Dendritic Cells," *J. Exp. Med. 195*:1653-1659, The Rockefeller University Press (2002).

Lifely, M.R., et al., "Glycosylation and biological activity of CAMPATH-1H expressed in different cell lines and grown under different culture conditions," *Glycobiol.* 5:813-822, Oxford University Press (1995).

Lund, J., et al., "Multiple Interactions of IgG with Its Core Oligosaccharide Can Modulate Recognition by Complement and Human Fcγ Receptor I and Influence the Synthesis of Its Oligosaccharide Chains," *J. Immunol.* 157:4963-4969., American Association of Immunologists (1996).

Marx, J.L., "Antibodies Made to Order," *Science* 229:455-456, American Association for the Advancement of Science (1985).

Masui, H., et al., "Growth Inhibition of Human Tumor Cells in Athymic Mice by Anti-Epidermal Growth Factor Receptor Monoclonal Antibodies," *Cancer Res.* 44:1002-1007, American Association for Cancer Research (1984).

Masui, H., et al., "Mechanism of Antitumor Activity in Mice for Anti-Epidermal Growth Factor Receptor Monoclonal Antibodies with Different Isotypes," *Cancer Res.* 46:5592-5598, American Association for Cancer Research (1986).

Medelsohn, J. and Baselga, J., "The EGF receptor family as targets for cancer therapy," *Oncogene* 19:6550-6565, Macmillan Publishers Ltd. (2000).

Mitchell, P., "Erbitux diagnostic latest adjunct to cancer therapy," *Nat. Biotechnol.* 22:363-364, Nature America Publishing (Apr. 2004).

Modjtahedi, H., et al., "Phase I trial and tumour localisation of the anti-EGFR monoclonal antibody ICR62 in head and neck or lung cancer," *Brit. J. Cancer* 73:228-235, Macmillan Press Ltd. (1996).

Modjtahedi, H., et al., "Anti-EGFR Monoclonal Antibodies Which Act As EGF, TGFα, HB-EGF and BTC Antagonists Block the Binding of Epiregulin to EGFR-Expressing Tumours," *Int. J. Cancer* 75:310-316, Wiley-Liss, Inc. (1998).

Morrison, S.L., et al., "Chimeric human antibody molecules: Mouse antigen-binding domains with human constant region domains," *Proc. Natl. Acad. Sci. USA* 81:6851-6855, National Academy of Science (1984).

Morrison, S.L., "Transfectomas Provide Novel Chimeric Antibodies," *Science* 229:1202-1207, American Association for the Advancement of Science (1985).

Morrison, S.L. and Oi, V.T., "Genetically Engineered Antibody Molecules," *Adv. Immunol.* 44:65-92, Academic Press, Inc. (1989).

Mulligan, R.C. and Berg, P., "Selection for animal cells that express the *Escherichia coli* gene coding for xanthine-guanine phosphoribosyltransferase," *Proc. Natl. Acad. Sci. USA* 78:2072-2076, National Academy of Science (1981).

Munro, A., "Uses of chimaeric antibodies," *Nature* 312:597, Nature Publishing Group (1984).

Murthy, U., et al., "Binding of an Antagonistic Monoclonal Antibody to an Intact and Fragmented EGF-Receptor Polypeptide," *Arch. Biochem. Biophys.* 252:549-560, Academic Press, Inc. (1987).

Nagy, P., et al., "EGF-Induced Redistribution of erbB2 on Breast Tumor Cells: Flow and Image Cytometric Energy Transfer Measurements," *Cytometry* 32:120-131, Wiley-Liss, Inc. (1998).

Needle, M.N., "Safety Experience With IMC-C225, an Anti-Epidermal Growth Factor Receptor Antibody," *Sem. Oncol.* 29:55-60, W.B. Saunders Company (2002).

Neuberger, M.S., et al., "A hapten-specific chimaeric IgE antibody with human physiological effector function," *Nature* 314:268-270, Macmillan Journals Ltd. (1985).

O'Hare, K., et al., "Transformation of mouse fibroblasts to methotrexate resistance by a recombinant plasmid expressing a prokaryotic dihydrofolate reductase," *Proc. Natl. Acad. Sci. USA* 78:1527-1531, National Academy of Science (1981).

Padlan, E.A., "A Possible Procedure for Reducing the Immunogenicity of Antibody Variable Domains While Preserving Their Ligand-Binding Properties," *Mol. Immunol.* 28:489-498, Pergamon Press plc (1991).

Padlan, E.A., "Anatomy of the Antibody Molecule," *Mol. Immunol.* 31:169-217, Elsevier Science Ltd. (1994).

Padlan, E.A., et al., "Identification of specificity-determining residues in antibodies," *FASEB J.* 9:133-139, Federation of American Societies for Experimental Biology (1995).

Presta, L.G., et al., "Humanization of an Antibody Directed Against IgE," *J. Immunol.* 151:2623-2632, American Association of Immunologists (1993).

Riechmann, L., et al., "Reshaping human antibodies for therapy," *Nature* 332:323-327, Macmillan Magazines Ltd. (1988).

Sahagan, B.G., et al., "A Genetically Engineered Murine/Human Chimeric Antibody Retains Specificity for Human Tumor-Associated Antigen," *J. Immunol.* 137:1066-1074, American Association of Immunologists (1986).

Schachter, H., "Biosynthetic controls that determine the branching and microheterogeneity of protein-bound oligosaccharides," *Biochem. Cell Biol.* 64:163-181, National Research Council of Canada (1986).

Scher, H.I., et al., "Changing Pattern of Expression of the Epidermal Growth Factor Receptor and Transforming Growth Factor α in the Progression of Prostatic Neoplasms," *Clin. Cancer Res.* 1:545-550, American Association for Cancer Research (1995).

Selvin, P.R., "The renaissance of fluorescence resonance energy transfer," *Nat. Struct. Biol.* 7:730-734, Nature America Inc. (2000).

Sims, M.J., et al., "A Humanized CD18 Antibody Can Block Function without Cell Destruction," *J. Immunol.* 151:2296-2308, American Association of Immunologists (1993).

Sun, L.K., et al., "Chimeric Antibodies with 17-1A-Derived Variable and Human Constant Regions," *Hybridoma* 5:S17-S20, Mary Ann Liebert, Inc., Publishers (1986).

Surfus, J.E., et al., "Anti-Renal-Cell Carcinoma Chimeric Antibody G250 Facilitates Antibody-Dependent Cellular Cytotoxicity with In Vitro and In Vivo Interleukin-2-Activated Effectors," *J. Immunother.* 19:184-191, Lippincott-Raven Publishers (1996).

Tamura, M., et al., "Structural Correlates of an Anticarcinoma Antibody: Identification of Specificity-Determining Residues (SDRs) and Development of a Minimally Immunogenic Antibody Variant by Retention of SDRs Only," *J Immunol.* 164:1432-1441. American Association of Immunologists (2000).

Tan, P., et al., ""Superhumanized" Antibodies: Reduction of Immunogenic Potential by Complementarity-Determining Region Grafting with Human Germline Sequences: Application to an Anti-CD28," *J Immunol.* 164:1119-1125, American Association of Immunologists (2002).

Tsao, A.S. and Herbst, R.S., "Factors that determine response to EGFR inhibitors," *Signal* 4:4-9, Adis International Limited (2003).

Ullrich, A., et al., "Human epidermal growth factor receptor cDNA sequence and aberrant expression of the amplified gene in A431 epidermoid carcinoma cells," *Nature* 309:418-425, Macmillan Journals Ltd. (1984).

Umaña, P., et al., "Engineered glycoforms of an antineuroblastoma IgG1 with optimized antibody-dependent cellular cytotoxic activity," *Nat. Biotechnol.* 17:176-180, Nature America, Inc. (1999).

Vanhoefer, U., et al., "Phase I Study of the Humanized Antiepidermal Growth Factor Receptor Monoclonal Antibody EMD72000 in Patients With Advanced Solid Tumors That Express the Epidermal Growth Factor Receptor," *J. Clin. Oncol.* 22:175-184, American Society of Clinical Oncology (Jan. 2004).

Verhoeyen, M., et al., "Reshaping Human Antibodies: Grafting an Antilysozyme Activity," *Science* 239:1534-1536, American Association for the Advancement of Science (1988).

Vitetta, E.S., et al., "Redesigning Nature's Poisons to Create Anti-Tumor Reagents," *Science* 238:1098-1104, American Association for the Advancement of Science (1987).

Werner, R.G., et al., "Appropriate Mammalian Expression Systems for Biopharmaceuticals," *Arzneim.-Forsch./Drug Res.* 48:870-880, Editio Cantor Verlages (1998).

Wormald, M.R., et al., "Variations in Oligosaccharide-Protein Interactions in Immunoglobulin G Determine the Site-Specific Glycosylation Profiles and Modulate the Dynamic Motion of the Fc Oligosaccharides," *Biochem.* 36:1370-1380, American Chemical Society (1997).

Wright, A. and Morrison, S.L., "Effect of glycosylation on antibody function: implications for genetic engineering," *Trends Biotechnol.* 15:26-32, Elsevier Science Ltd. (1997).

Wu, H., et al., "Humanization of a Murine Monoclonal Antibody by Simultaneous Optimization of Framework and CDR Residues," *J. Mol. Biol.* 294:151-162, Academic Press (1999).

Yang, X.-D., et al., "Development of ABX-EGF, a fully human anti-EGF receptor monoclonal antibody, for cancer therapy," *Crit. Rev. Oncol./Hematol.* 38:17-23, Elsevier Science Ireland Ltd. (2001).

Zuck, P., et al., "Ligand-receptor binding measured by laser-scanning imaging," *Proc. Natl. Acad. Sci. USA* 96:11122-11127, National Academy of Sciences (1999).

Dialog File 351, Accession No. 13715137, Derwent WPI English language abstract for WO 03/084570 A1 (listed on accompanying PTO/SB/08A as document FP5), Aug. 30, 2006.

Dialog File 351, Accession No. 13715167, Derwent WPI English language abstract for WO 03/085119 A1 (listed on accompanying PTO/SB/08B as document FP6), Aug. 30, 2006.

Bianco, R., et al., "Monoclonal Antibodies Targeting the Epidermal Growth Factor Receptor," *Current Drug Targets* 6:275-287, Bentham Science Publishers Ltd (May 2005).

* cited by examiner

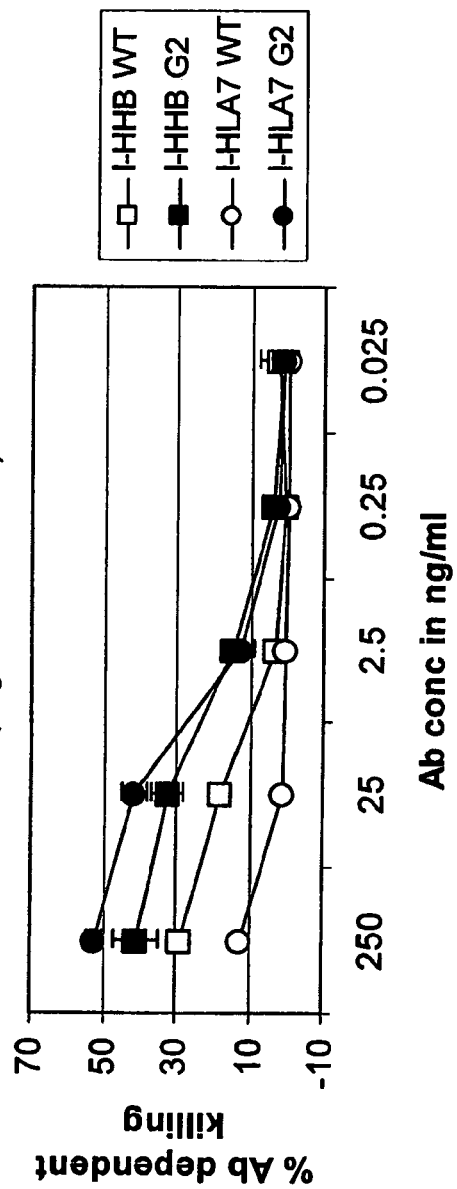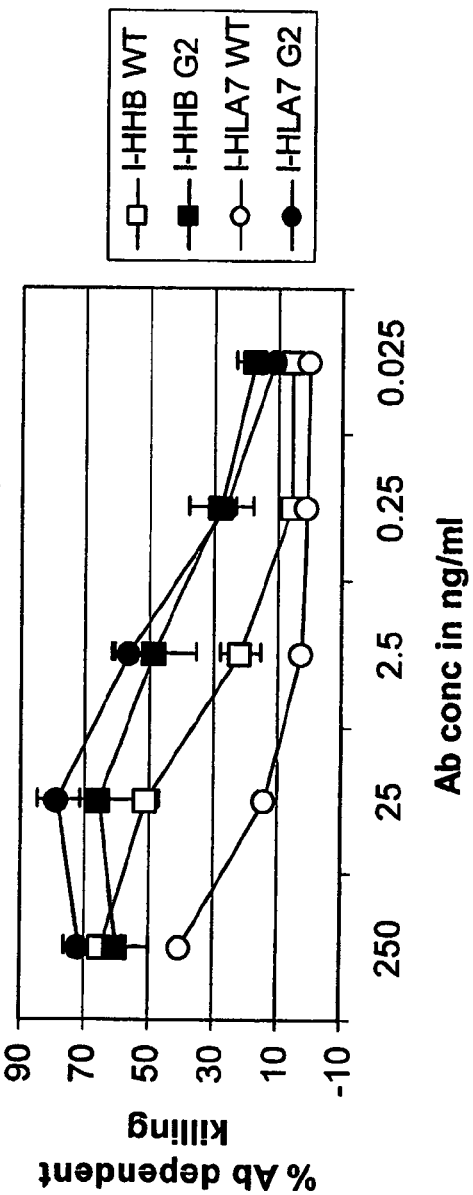

Figure 13

MALDI/TOF-MS oligosaccharide profile for glycoengineered humanized anti-EGFR IgG1 antibody IHHB-KC.

| m/z | Rel. Intens. | Res. | Intens. | SN |
|---|---|---|---|---|
| 1009.834 | 1 | 3726 | 269.03 | 4.1 |
| 1118.344 | 1 | 3309 | 133.89 | 3.9 |
| 1134.297 | 0 | 1927 | 99.75 | 1.6 |
| 1177.408 | 2 | 3018 | 421.05 | 6.7 |
| 1257.426 | 2 | 3405 | 470.43 | 8.3 |
| 1280.369 | 0 | 1846 | 110.16 | 1.9 |
| 1321.449 | 2 | 3309 | 508.14 | 8.5 |
| 1339.474 | 28 | 3882 | 7233.69 | 108.8 |
| 1378.254 | 1 | 1950 | 159.13 | 2.8 |
| 1403.450 | 1 | 4294 | 187.02 | 3.3 |
| 1441.530 | 1 | 3818 | 237.40 | 4.4 |
| 1485.518 | 10 | 4362 | 2610.39 | 36.4 |
| 1501.529 | 20 | 4512 | 5077.41 | 64.1 |
| 1524.505 | 2 | 3193 | 451.80 | 7.3 |
| 1542.558 | 100 | 4881 | 25605.72 | 305.6 |
| 1576.416 | 1 | 3487 | 190.68 | 2.7 |
| 1647.578 | 6 | 4726 | 1462.14 | 23.7 |
| 1663.586 | 26 | 5398 | 6601.39 | 80.2 |
| 1688.619 | 35 | 5329 | 8983.81 | 100.7 |
| 1704.625 | 13 | 5326 | 3204.99 | 48.8 |
| 1809.631 | 4 | 5004 | 911.91 | 17.2 |
| 1825.639 | 2 | 5340 | 517.42 | 9.1 |
| 1850.657 | 12 | 5824 | 3035.19 | 55.1 |
| 1866.677 | 0 | 6100 | 73.94 | 1.5 |
| 1971.671 | 1 | 5910 | 148.65 | 3.5 |
| 2012.658 | 0 | 5832 | 127.04 | 3.1 |

ANTI-EGFR PRECISION PROFILE

REPRESENTATIVE ANTI-EGFR CALIBRATION CURVE

Serum concentrations of anti-EGFR on Day 1 of weekly intravenous administration of anti-EGFR to male cynomolgus monkeys Serum concentrations of anti-EGFR on Day 1 of weekly intravenous administration of anti-EGFR to female cynomolgus monkeys Relationship between areas under the serum anti-EGFR concentration-time curves
($AUC_{168}$) and dose level on Day 1 of weekly intravenous administration of anti-EGFR to
cynomolgus monkeys Serum concentrations of anti-EGFR during weekly intravenous administration of anti-EGFR to male cynomolgus monkeys Serum concentrations of anti-EGFR during weekly intravenous administration of
anti-EGFR to female cynomolgus monkeys

SEQUENCE LISTING

```
<160> NUMBER OF SEQ ID NOS: 127

<210> SEQ ID NO 1
<211> LENGTH: 120
<212> TYPE: PRT
<213> ORGANISM: Rattus sp.
<220> FEATURE:
<223> OTHER INFORMATION: ICR62 VH

<400> SEQUENCE: 1

Gln Val Asn Leu Leu Gln Ser Gly Ala Ala Leu Val Lys Pro Gly Ala
1               5                   10                  15

Ser Val Lys Leu Ser Cys Lys Gly Ser Gly Phe Thr Phe Thr Asp Tyr
            20                  25                  30
```

-continued

Lys Ile His Trp Val Lys Gln Ser His Gly Lys Ser Leu Glu Trp Ile
            35                  40                  45

Gly Tyr Phe Asn Pro Asn Ser Gly Tyr Ser Thr Tyr Asn Glu Lys Phe
        50                  55                  60

Lys Ser Lys Ala Thr Leu Thr Ala Asp Lys Ser Thr Asp Thr Ala Tyr
 65                 70                  75                  80

Met Glu Leu Thr Ser Leu Thr Ser Glu Asp Ser Ala Thr Tyr Tyr Cys
                85                  90                  95

Thr Arg Leu Ser Pro Gly Gly Tyr Tyr Val Met Asp Ala Trp Gly Gln
            100                 105                 110

Gly Ala Ser Val Thr Val Ser Ser
            115                 120

<210> SEQ ID NO 2
<211> LENGTH: 359
<212> TYPE: DNA
<213> ORGANISM: Rattus sp.
<220> FEATURE:
<223> OTHER INFORMATION: ICR62 VH

<400> SEQUENCE: 2
caggtcaacc tactgcagtc tggggctgca ctggtgaagc ctggggcctc tgtgaagttg      60
tcttgcaaag gttctggttt tacattcact gactacaaga tacactgggt gaagcagagt     120
catggaaaga gccttgagtg gattgggtat tttaatccta acagtggtta tagtacctac     180
aatgaaaagt tcaagagcaa ggccacattg actgcagaca atccaccga tacagcctat      240 atggagctta ccagtctgac atctgaggac tctgcaacct attactgtac aagactatcc     300
ccagggggtt actatgttat ggatgcctgg ggtcaaggag cttcagtcac tgtctcctc     359

<210> SEQ ID NO 3
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 3

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Thr Phe Thr Asp Tyr
            20                  25                  30

Ala Ile Ser Trp Val Arg Gln Ala Pro Gly Gln Gly Leu Glu Trp Met
        35                  40                  45

Gly Gly Ile Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
 65                 70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
            115                 120

<210> SEQ ID NO 4
<211> LENGTH: 360
<212> TYPE: DNA

<213> ORGANISM: Artificial Sequence
<220> FEATURE:
<223> OTHER INFORMATION: Rat-human chimeric DNA

<400> SEQUENCE: 4

```
caggtgcagc tggtgcagtc tggggctgag gtgaagaagc ctgggtcctc ggtgaaggtc      60
tcctgcaagg cttctggatt tacattcact gactacgcca tcagctgggt gcgacaggcc     120
cctggacaag ggctcgagtg gatgggaggg atcaatccta acagtggtta tagtacctac     180
gcacagaagt tccagggcag ggtcaccatt accgcggaca atccacgag cacagcctac      240
atggagctga gcagcctgag atctgaggac acggccgtgt attactgtgc gagactatcc     300
ccaggcggtt actatgttat ggatgcctgg ggccaaggga ccaccgtgac cgtctcctca     360
```

<210> SEQ ID NO 5
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 5

```
Gln Val Gln Leu Val Gln Ser Gly Ala Glu Val Lys Lys Pro Gly Ser
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120
```

<210> SEQ ID NO 6
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 6

```
caggtgcagc tggtgcagtc tggggctgag gtgaagaagc ctgggtcctc ggtgaaggtc      60
tcctgcaagg gttctggttt tacattcact gactacaaga tacactgggt gcgacaggcc     120
cctggacaag ggctcgagtg gatgggatat ttcaacccta acagcggtta tagtacctac     180
gcacagaagt tccagggcag ggtcaccatt accgcggaca atccacgag cacagcctac      240
atggagctga gcagcctgag atctgaggac acggccgtgt attactgtgc gagactatcc     300
ccaggcggtt actatgttat ggatgcctgg ggccaaggga ccaccgtgac cgtctcctca     360
```

<210> SEQ ID NO 7
<211> LENGTH: 120
<212> TYPE: PRT
<213> ORGANISM: Artificial Sequence -continued

```
<220> FEATURE:
<223> OTHER INFORMATION: Rat-human chimeric polypeptide

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Asn Glu Lys Phe
    50                  55                  60

Lys Ser Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 8
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 8
caggtgcagc tggtgcagtc tggggctgag gtgaagaagc ctgggtcctc ggtgaaggtc      60
tcctgcaagg gttctggttt tacattcact gactacaaga tacactgggt gcgacaggcc    120
cctggacaag ggctcgagtg gatgggatat ttcaacccta acagcggtta tagtacctac    180
aatgaaaagt tcaagagcag ggtcaccatt accgcggaca aatccacgag cacagcctac    240
atggagctga gcagcctgag atctgaggac acggccgtgt attactgtgc gagactatcc    300
ccaggcggtt actatgttat ggatgcctgg ggccaaggga ccaccgtgac cgtctcctca    360

<210> SEQ ID NO 9
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Tyr Ser Thr Tyr Ala Gln Lys Phe
    50                  55                  60

Gln Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 10
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 10
caggtgcagc tggtgcagtc tggggctgag gtgaagaagc ctggggcctc ggtgaaggtc      60
tcctgcaagg cctctggttt tacattcact gactactata tgcactgggt gcgacaggcc     120
cctggacaag ggctcgagtg gatgggctgg atcaatccta acagtggtta tagtacctac     180
gcacagaagt tccagggcag ggtcaccatg accgccgaca cgtccatcag cacagcctac     240
atggagctga gcaggctgag atctgacgac acggccgtgt attactgtgc gagactatcc     300
ccaggcggtt actatgttat ggatgcctgg ggccaaggga ccaccgtgac cgtctcctca     360

<210> SEQ ID NO 11
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 12
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 12
caggtgcagc tggtgcagtc tggggctgag gtgaagaagc tggagcctc ggtgaaggtc       60 tcctgcaagg gttctggttt tacattcact gactacaaga tccactgggt gcgacaggcc    120
cctggacaag ggctcgagtg gatgggatac ttcaacccta acagcggtta tagtacctac    180
gcacagaagt tccagggcag ggtcaccatg accgccgaca cgtccatcag cacagcctac    240
```

```
atggagctga gcaggctgag atctgacgac acggccgtgt attactgtgc gagactatcc    300
ccaggcggtt actatgttat ggatgcctgg ggccaaggga ccaccgtgac cgtctcctca    360
```

<210> SEQ ID NO 13
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Asn Glu Lys Phe
    50                  55                  60

Lys Ser Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120
```

<210> SEQ ID NO 14
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 14

```
caggtgcagc tggtgcagtc tggggctgag gtgaagaagc ctggagcctc agtgaaggtc     60
tcctgcaagg gttctggttt tacattcact gactacaaga tccactgggt gcgacaggcc    120
cctggacaag gctcgagtg gatgggatac ttcaacccta cagcggtta cagtacttac    180 aacgagaagt tcaagagccg ggtcaccatg accgccgaca cgtccatcag cacagcctac    240
atggagctga gcaggctgag atctgacgac acggccgtgt attactgtgc gagactatcc    300 ccaggggggtt actatgttat ggatgcctgg ggccaaggga ccaccgtgac cgtctcctca    360
```

<210> SEQ ID NO 15
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 15

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45
```

Gly Tyr Phe Asn Pro Asn Ser Gly Tyr Ser Thr Tyr Ala Gln Lys Phe
            50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Ser Pro Gly Gly Tyr Tyr Val Met Asp Ala Trp Gly Gln
                100                 105                 110

Gly Thr Thr Val Thr Val Ser Ser
            115                 120

<210> SEQ ID NO 16
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 16
caggtgcagc tggtgcagtc tggggctgag gtgaagaagc ctgggtcctc ggtgaaggtc    60
tcctgcaagg cctctggttt cacattcact gactacaaga tacactgggt gcgacaggcc   120
cctggacaag gctcgagtg gatgggatat ttcaaccc ta acagcggtta tagtacctac   180
gcacagaagt tccagggcag ggtcaccatt accgcggaca atccacgag cacagcctac   240 atggagctga gcagcctgag atctgaggac acggccgtgt attactgtgc gagactatcc   300
ccaggcggtt actatgttat ggatgcctgg ggccaaggga ccaccgtgac cgtctcctca   360

<210> SEQ ID NO 17
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 17

Gln Val Gln Leu Val Gln Ser Gly Ala Glu Val Lys Lys Pro Gly Ser
 1               5                  10                  15

Ser Val Lys Val Ser Cys Lys Gly Ser Gly Phe Thr Phe Thr Asp Tyr
                 20                  25                  30

Lys Ile Ser Trp Val Arg Gln Ala Pro Gly Gln Gly Leu Glu Trp Met
             35                  40                  45

Gly Tyr Phe Asn Pro Asn Ser Gly Tyr Ser Thr Tyr Ala Gln Lys Phe
            50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Ser Pro Gly Gly Tyr Tyr Val Met Asp Ala Trp Gly Gln
                100                 105                 110

Gly Thr Thr Val Thr Val Ser Ser
            115                 120

<210> SEQ ID NO 18
<211> LENGTH: 360
<212> TYPE: DNA
<213> ORGANISM: Artificial Sequence
<220> FEATURE:
<223> OTHER INFORMATION: Rat-human chimeric DNA -continued

<400> SEQUENCE: 18

```
caggtgcagc tggtgcagtc tggggctgag gtgaagaagc ctgggtcctc ggtgaaggtc    60
tcctgcaagg gttctggttt cacattcact gactacaaga tatcctgggt gcgacaggct   120
cctggacaag ggctcgagtg gatgggatat ttcaaccctaacagcggtta tagtacctac   180 gcacagaagt tccagggcag ggtcaccatt accgcggaca atccacgag acagcctac    240 atggagctga gcagcctgag atctgaggac acggccgtgt attactgtgc gagactatcc   300
ccaggcggtt actatgttat ggatgcctgg ggccaaggga ccaccgtgac cgtctcctca   360
```

<210> SEQ ID NO 19
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 19

```
Gln Val Gln Leu Val Gln Ser Gly Ala Glu Val Lys Lys Pro Gly Ser
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120
```

<210> SEQ ID NO 20
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 20

```
caggtgcagc tggtgcagtc tggggctgag gtgaagaagc ctgggtcctc ggtgaaggtc    60
tcctgcaagg gttctggttt tacattcact gactacaaga tacactgggt gcgacaggcc   120
cctggacaag ggctcgagtg gatgggatat ttcaaccctaacagcggtta ttcgaactac   180 gcacagaagt tccagggcag ggtcaccatt accgcggaca atccacgag acagcctac    240 atggagctga gcagcctgag atctgaggac acggccgtgt attactgtgc gagactatcc   300
ccaggcggtt actatgttat ggatgcctgg ggccaaggga ccaccgtgac cgtctcctca   360
```

<210> SEQ ID NO 21
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ala Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
            115                 120

<210> SEQ ID NO 22
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 22
caggtgcagc tggtgcagtc tggggctgag gtgaagaagc ctgggtcctc ggtgaaggtc      60
tcctgcaagg gttctggttt tacattcact gactacaaga tacactgggt gcgacaggcc    120
cctggacaag ggctcgagtg gatgggatat ttcaaccctaacagcggtta tgccacgtac    180
gcacagaagt tccagggcag ggtcaccatt accgcggaca atccacgagcacagcctac     240
atggagctga gcagcctgag atctgaggac acggccgtgtattactgtgcgagactatcc    300
ccaggcggtt actatgttat ggatgcctgg ggccaaggga ccaccgtgac cgtctcctca    360

<210> SEQ ID NO 23
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Tyr Ser Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Pro Gly Gly Tyr Tyr Val Met Asp Ala Trp Gly Gln
            100                 105                 110

```
Gly Thr Thr Val Thr Val Ser Ser
        115                 120

<210> SEQ ID NO 24
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 24
caggtgcagc tggtgcagtc tggggctgag gtgaagaagc ctggagcctc ggtgaaggtc      60
tcctgcaagg cctctggttt tacattcact gactactata tgcactgggt gcgacaggcc     120
cctggacaag ggctcgagtg gatgggctgg atcaatccta acagtggtta tagtacctac     180
agcccaagct tccaaggcca ggtcaccatc tcagccgaca gtccatcag caccgcctac      240 ctgcagtgga gcagcctgaa ggcctcggac accgccatgt attactgtgc gagactatcc     300
ccaggcggtt actatgttat ggatgcctgg ggccaaggga ccaccgtgac cgtctcctca     360

<210> SEQ ID NO 25
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Tyr Ser Thr Tyr Asn Glu Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 26
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 26
caggtgcagc tggtgcagtc tggggctgag gtgaagaagc ctggagcctc ggtgaaggtc      60
tcctgcaagg cctctggttt tacattcact gactactata tgcactgggt gcgacaggcc     120
cctggacaag ggctcgagtg gatgggctgg atcaatccta acagtggtta tagtacctac     180
aacgagaagt tccaaggcca ggtcaccatc tcagccgaca gtccatcag caccgcctac      240 ctgcagtgga gcagcctgaa ggcctcggac accgccatgt attactgtgc gagactatcc     300
```

```
ccaggcggtt actatgttat ggatgcctgg ggccaaggga ccaccgtgac cgtctcctca    360
```

```
<210> SEQ ID NO 27
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 27
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Tyr Ser Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

```
<210> SEQ ID NO 28
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 28
```

```
caggtgcagc tggtgcagtc tggggctgag gtgaagaagc ctggagcctc ggtgaaggtc     60
tcctgcaagg cctctggtta cacattcact gactactata tgcactgggt gcgacaggcc    120
cctggacaag gctcgagtg gatgggctgg atcaatccta acagtggtta tagtacctac    180
agcccaagct tccaaggcca ggtcaccatc tcagccgaca gtccatcag caccgcctac    240
ctgcagtgga gcagcctgaa ggcctcggac accgccatgt attactgtgc gagactatcc    300
ccaggcggtt actatgttat ggatgcctgg ggccaaggga ccaccgtgac cgtctcctca    360
```

```
<210> SEQ ID NO 29
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 29
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Tyr Ser Thr Tyr Asn Glu Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 30
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 30
caggtgcagc tggtgcagtc tggggctgag gtgaagaagc ctggagcctc ggtgaaggtc      60
tcctgcaagg cctctggtta cacattcact gactactata tgcactgggt gcgacaggcc     120
cctggacaag ggctcgagtg gatgggctgg atcaatccta acagtggtta tagtacctac     180
aacgagaagt tccaaggcca ggtcaccatc tcagccgaca gtccatcagc accgcctac      240 ctgcagtgga gcagcctgaa ggcctcggac accgccatgt attactgtgc gagactatcc     300
ccaggcggtt actatgttat ggatgcctgg ggccaaggga ccaccgtgac cgtctcctca     360

<210> SEQ ID NO 31
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 31

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Tyr Ser Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 32
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 32

```
cagatgcagc tggtgcagtc tgggccagag gtgaagaagc ctggaacctc ggtgaaggtc      60
tcctgcaagg cctctggttt tacattcact gactactata tgcactgggt gcgacaggcc     120
cctggacaag ggctcgagtg gatgggctgg atcaatccta acagtggtta tagtacctac     180
agcccaagct tccaaggcca ggtcaccatc tcagccgaca gtccatcag caccgcctac      240 ctgcagtgga gcagcctgaa ggcctcggac accgccatgt attactgtgc gagactatcc     300
ccaggcggtt actatgttat ggatgcctgg ggccaaggga ccaccgtgac cgtctcctca     360
```

<210> SEQ ID NO 33
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 33

```
Gln Met Gln Leu Val Gln Ser Gly Pro Glu Val Lys Lys Pro Gly Thr
  1               5                  10                  15

Ser Val Lys Val Ser Cys Lys Ala Ser Gly Phe Thr Phe Thr Asp Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Tyr Ser Thr Tyr Asn Glu Lys Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120
```

<210> SEQ ID NO 34
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 34

```
cagatgcagc tggtgcagtc tgggccagag gtgaagaagc ctggaacctc ggtgaaggtc      60
tcctgcaagg cctctggttt tacattcact gactactata tgcactgggt gcgacaggcc     120
cctggacaag ggctcgagtg gatgggctgg atcaatccta acagtggtta tagtacctac     180
aacgagaagt tccaaggcca ggtcaccatc tcagccgaca gtccatcag caccgcctac      240 ctgcagtgga gcagcctgaa ggcctcggac accgccatgt attactgtgc gagactatcc     300
ccaggcggtt actatgttat ggatgcctgg ggccaaggga ccaccgtgac cgtctcctca     360
```

<210> SEQ ID NO 35
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 35

```
Gln Met Gln Leu Val Gln Ser Gly Pro Glu Val Lys Lys Pro Gly Thr
  1               5                  10                  15
```

```
1               5                   10                  15
Ser Val Lys Val Ser Cys Lys Ala Ser Gly Phe Thr Phe Thr Asp Tyr
                20                  25                  30

Lys Ile His Trp Val Arg Gln Ala Arg Gly Gln Arg Leu Glu Trp Ile
            35                  40                  45

Gly Trp Ile Asn Pro Asn Ser Gly Tyr Ser Thr Tyr Asn Glu Lys Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Pro Gly Gly Tyr Tyr Val Met Asp Ala Trp Gly Gln
                100                 105                 110

Gly Thr Thr Val Thr Val Ser Ser
                115                 120

<210> SEQ ID NO 36
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 36
cagatgcagc tggtgcagtc tgggccagag gtgaagaagc ctggaacctc ggtgaaggtc       60
tcctgcaagg cctctggttt tacattcact gactacaaga tccactgggt gcgacaggcc      120
cgcggacaac ggctcgagtg gatcggctgg atcaatccta acagtggtta tagtacctac      180
aacgagaagt tccaaggcca ggtcaccatc tcagccgaca agtccatcag caccgcctac      240
ctgcagtgga gcagcctgaa ggcctcggac accgccatgt attactgtgc gagactatcc      300
ccaggcggtt actatgttat ggatgcctgg ggccaaggga ccaccgtgac cgtctcctca      360

<210> SEQ ID NO 37
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 37

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Asp Tyr
                20                  25                  30

Lys Ile His Trp Val Arg Gln Ala Pro Gly Gln Gly Leu Glu Trp Met
            35                  40                  45

Gly Tyr Phe Asn Pro Asn Ser Gly Tyr Ser Thr Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
                100                 105                 110

Gly Thr Thr Val Thr Val Ser Ser
                115                 120
```

```
<210> SEQ ID NO 38
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 38
cagatgcagc tggtgcagtc tgggccagag gtgaagaagc ctggaacctc ggtgaaggtc      60
tcctgcaagg cctctggttt tacattcact gactacaaga tccactgggt gcgacaggcc     120
cctggacaag ggctcgagtg gatgggatat ttcaacccta acagcggtta tagtacctac     180
gcacagaagt tccagggcag ggtcaccatt accgcggaca atccacgag cacagcctac      240 atggagctga gcagcctgag atctgaggac acggccgtgt attactgtgc gagactatcc     300
ccaggcggtt actatgttat ggatgcctgg ggccaaggga ccaccgtgac cgtctcctca     360

<210> SEQ ID NO 39
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 39

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 40
<211> LENGTH: 360
<212> TYPE: DNA
<213> ORGANISM: Artificial Sequence
<220> FEATURE:
<223> OTHER INFORMATION: Rat-human chimeric DNA

<400> SEQUENCE: 40
gaggtgcagc tcgtgcagtc tggcgctgag gtgaagaagc tggcgagtc gttgaagatc       60 tcctgcaagg gttctggtta ttcattcact gactacaaga tccactgggt gcgacaggcc     120
cctggacaag ggctcgagtg gatgggatat ttcaacccta acagcggtta tagtacctac     180
gcacagaagt tccagggcag ggtcaccatt accgcggaca atccacgag cacagcctac      240 atggagctga gcagcctgag atctgaggac acggccgtgt attactgtgc gagactatcc     300
ccaggcggtt actatgttat ggatgcctgg ggccaaggga ccaccgtgac cgtctcctca     360
```

<210> SEQ ID NO 41
<211> LENGTH: 19
<212> TYPE: PRT
<213> ORGANISM: Homo sapiens

<400> SEQUENCE: 41

Met Asp Trp Thr Trp Arg Ile Leu Phe Leu Val Ala Ala Thr Gly
1               5                   10                  15

Ala His Ser

<210> SEQ ID NO 42
<211> LENGTH: 57
<212> TYPE: DNA
<213> ORGANISM: Homo sapiens

<400> SEQUENCE: 42
atggactgga cctggaggat cctcttcttg gtggcagcag ccacaggagc ccactcc      57

<210> SEQ ID NO 43
<211> LENGTH: 108
<212> TYPE: PRT
<213> ORGANISM: Rattus sp.
<220> FEATURE:
<223> OTHER INFORMATION: ICR62 VL

<400> SEQUENCE: 43

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Asn Tyr
            20                  25                  30

Leu Asn Trp Tyr Gln Gln Lys Leu Gly Glu Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Leu Glu Leu Lys Arg Thr
            100                 105

<210> SEQ ID NO 44
<211> LENGTH: 324
<212> TYPE: DNA
<213> ORGANISM: Rattus sp.
<220> FEATURE:
<223> OTHER INFORMATION: ICR62 VL

<400> SEQUENCE: 44
gacatccaga tgacccagtc tccttcattc ctgtctgcat ctgtgggaga cagagtcact      60
atcaactgca aagcaagtca gaatattaac aattacttaa actggtatca gcaaaagctt     120
ggagaagctc ccaaacgcct gatatataat acaaacaatt tgcaaacagg catcccatca     180
aggttcagtg gcagtggatc tggtacagat tacacactca ccatcagcag cctgcagcct     240
gaagattttg ccacatattt ctgcttgcag cataatagtt ttcccacgtt tggagctggg     300
accaagctgg aactgaaacg tacg                                            324

<210> SEQ ID NO 45
<211> LENGTH: 108
<212> TYPE: PRT

<213> ORGANISM: Artificial Sequence
<220> FEATURE:
<223> OTHER INFORMATION: Rat-human chimeric polypeptide

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr
            100                 105

<210> SEQ ID NO 46
<211> LENGTH: 324
<212> TYPE: DNA
<213> ORGANISM: Artificial Sequence
<220> FEATURE:
<223> OTHER INFORMATION: Rat-human chimeric DNA

<400> SEQUENCE: 46
gatatccaga tgacccagtc tccatcctcc ctgtctgcat ctgtcggaga ccgggtcacc    60
atcacctgcc gggcaagtca gggcattaac aattacttaa attggtacca gcagaagcca   120
gggaaagccc ctaagcgcct gatctataat accaacaact tgcagacagg cgtcccatca   180
aggttcagcg gcagtggatc cgggacagaa ttcactctca ccatcagcag cctgcagcct   240
gaagattttg ccacctatta ctgcttgcag cataatagtt ttcccacgtt tggccagggc   300
accaagctcg agatcaagcg tacg                                         324

<210> SEQ ID NO 47
<211> LENGTH: 22
<212> TYPE: PRT
<213> ORGANISM: Homo sapiens

<400> SEQUENCE: 47

Met Asp Met Arg Val Pro Ala Gln Leu Leu Gly Leu Leu Leu Leu Trp
1               5                   10                  15

Phe Pro Gly Ala Arg Cys
            20

<210> SEQ ID NO 48
<211> LENGTH: 66
<212> TYPE: DNA
<213> ORGANISM: Homo sapiens

<400> SEQUENCE: 48
atggacatga gggtccccgc tcagctcctg ggcctcctgc tgctctggtt cccaggtgcc    60
aggtgt                                                              66

<210> SEQ ID NO 49
<211> LENGTH: 109
<212> TYPE: PRT

<213> ORGANISM: Artificial Sequence
<220> FEATURE:
<223> OTHER INFORMATION: Rat-human chimeric polypeptide

<400> SEQUENCE: 49

| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Arg | Ala | Ser | Gln | Gly | Ile | Asn | Asn | Tyr |
| | | | 20 | | | | | 25 | | | | | 30 | | |

| Leu | Asn | Trp | Tyr | Gln | Gln | Lys | Pro | Gly | Lys | Ala | Pro | Lys | Arg | Leu | Ile |
| | | | 35 | | | | | 40 | | | | | 45 | | |

| Tyr | Asn | Thr | Asn | Asn | Leu | Gln | Thr | Gly | Val | Pro | Ser | Arg | Phe | Ser | Gly |
| | 50 | | | | | 55 | | | | | 60 | | | | |

| Ser | Gly | Ser | Gly | Thr | Glu | Tyr | Thr | Leu | Thr | Ile | Ser | Ser | Leu | Gln | Pro |
| 65 | | | | | 70 | | | | | 75 | | | | | 80 |

| Glu | Asp | Phe | Ala | Thr | Tyr | Tyr | Cys | Leu | Gln | His | Asn | Ser | Phe | Pro | Thr |
| | | | | 85 | | | | | 90 | | | | | 95 | |

| Phe | Gly | Gln | Gly | Thr | Lys | Leu | Glu | Ile | Lys | Arg | Thr | Val | | | |
| | | | | 100 | | | | | 105 | | | | | | |

<210> SEQ ID NO 50
<211> LENGTH: 327
<212> TYPE: DNA
<213> ORGANISM: Artificial Sequence
<220> FEATURE:
<223> OTHER INFORMATION: Rat-human chimeric DNA

<400> SEQUENCE: 50

```
gatatccaga tgacccagtc tccatcctcc ctgtctgcat ctgtcggaga ccgggtcacc      60
atcacctgcc gggcaagtca gggcattaac aattacttaa attggtacca gcagaagcca    120
gggaaagccc ctaagcgcct gatctataat accaacaact tgcagacagg cgtcccatca    180
aggttcagcg gcagtggatc cgggacagaa tacactctca ccatcagcag cctgcagcct    240
gaagattttg ccacctatta ctgcttgcag cataatagtt ttcccacgtt tggccagggc    300
accaagctcg agatcaagcg tacggtg                                        327
```

<210> SEQ ID NO 51
<211> LENGTH: 109
<212> TYPE: PRT
<213> ORGANISM: Artificial Sequence
<220> FEATURE:
<223> OTHER INFORMATION: Rat-human chimeric polypeptide

<400> SEQUENCE: 51

| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Lys | Ala | Ser | Gln | Asn | Ile | Asn | Asn | Tyr |
| | | | 20 | | | | | 25 | | | | | 30 | | |

| Leu | Asn | Trp | Tyr | Gln | Gln | Lys | Pro | Gly | Lys | Ala | Pro | Lys | Arg | Leu | Ile |
| | | | 35 | | | | | 40 | | | | | 45 | | |

| Tyr | Asn | Thr | Asn | Asn | Leu | Gln | Thr | Gly | Val | Pro | Ser | Arg | Phe | Ser | Gly |
| | 50 | | | | | 55 | | | | | 60 | | | | |

| Ser | Gly | Ser | Gly | Thr | Glu | Tyr | Thr | Leu | Thr | Ile | Ser | Ser | Leu | Gln | Pro |
| 65 | | | | | 70 | | | | | 75 | | | | | 80 |

| Glu | Asp | Phe | Ala | Thr | Tyr | Tyr | Cys | Leu | Gln | His | Asn | Ser | Phe | Pro | Thr |
| | | | | 85 | | | | | 90 | | | | | 95 | |

| Phe | Gly | Gln | Gly | Thr | Lys | Leu | Glu | Ile | Lys | Arg | Thr | Val | | | |
| | | | | 100 | | | | | 105 | | | | | | |

<210> SEQ ID NO 52
<211> LENGTH: 327
<212> TYPE: DNA
<213> ORGANISM: Artificial Sequence
<220> FEATURE:
<223> OTHER INFORMATION: Rat-human chimeric DNA

<400> SEQUENCE: 52

```
gatatccaga tgacccagtc tccatcctcc ctgtctgcat ctgtcggaga ccgggtcacc      60
atcacctgca agcaagtca gaatattaac aattacttaa actggtacca gcagaagcca     120
gggaaagccc ctaagcgcct gatctataat accaacaact tgcagacagg cgtcccatca     180
aggttcagcg gcagtggatc cgggacagaa tacactctca ccatcagcag cctgcagcct     240
gaagattttg ccacctatta ctgcttgcag cataatagtt ttcccacgtt tggccagggc     300
accaagctcg agatcaagcg tacggtg                                        327
```

<210> SEQ ID NO 53
<211> LENGTH: 5
<212> TYPE: PRT
<213> ORGANISM: Artificial Sequence
<220> FEATURE:
<223> OTHER INFORMATION: Heavy Chain CDR1 Kabat

<400> SEQUENCE: 53

Asp Tyr Lys Ile His
1               5

<210> SEQ ID NO 54
<211> LENGTH: 15
<212> TYPE: DNA
<213> ORGANISM: Artificial Sequence
<220> FEATURE:
<223> OTHER INFORMATION: Heavy Chain CDR1 Kabat

<400> SEQUENCE: 54

```
gactacaaga tacac                                                      15
```

<210> SEQ ID NO 55
<211> LENGTH: 5
<212> TYPE: PRT
<213> ORGANISM: Artificial Sequence
<220> FEATURE:
<223> OTHER INFORMATION: Heavy Chain CDR1 Kabat

<400> SEQUENCE: 55

Asp Tyr Ala Ile Ser
1               5

<210> SEQ ID NO 56
<211> LENGTH: 15
<212> TYPE: DNA
<213> ORGANISM: Artificial Sequence
<220> FEATURE:
<223> OTHER INFORMATION: Heavy Chain CDR1 Kabat

<400> SEQUENCE: 56

```
gactacgcca tcagc                                                      15
```

<210> SEQ ID NO 57
<211> LENGTH: 5
<212> TYPE: PRT
<213> ORGANISM: Artificial Sequence
<220> FEATURE:

```
<223> OTHER INFORMATION: Heavy Chain CDR1 Kabat

<400> SEQUENCE: 57

Asp Tyr Tyr Met His
1               5

<210> SEQ ID NO 58
<211> LENGTH: 15
<212> TYPE: DNA
<213> ORGANISM: Artificial Sequence
<220> FEATURE:
<223> OTHER INFORMATION: Heavy Chain CDR1 Kabat

<400> SEQUENCE: 58
gactactata tgcac                                                      15

<210> SEQ ID NO 59
<211> LENGTH: 7
<212> TYPE: PRT
<213> ORGANISM: Artificial Sequence
<220> FEATURE:
<223> OTHER INFORMATION: Heavy Chain CDR1 Chothia

<400> SEQUENCE: 59

Gly Phe Thr Phe Thr Asp Tyr
1               5

<210> SEQ ID NO 60
<211> LENGTH: 21
<212> TYPE: DNA
<213> ORGANISM: Artificial Sequence
<220> FEATURE:
<223> OTHER INFORMATION: Heavy Chain CDR1 Chothia

<400> SEQUENCE: 60
ggttttacat tcactgacta c                                               21

<210> SEQ ID NO 61
<211> LENGTH: 7
<212> TYPE: PRT
<213> ORGANISM: Artificial Sequence
<220> FEATURE:
<223> OTHER INFORMATION: Heavy Chain CDR1 Chothia

<400> SEQUENCE: 61

Gly Tyr Thr Phe Thr Asp Tyr
1               5

<210> SEQ ID NO 62
<211> LENGTH: 21
<212> TYPE: DNA
<213> ORGANISM: Artificial Sequence
<220> FEATURE:
<223> OTHER INFORMATION: Heavy Chain CDR1 Chothia

<400> SEQUENCE: 62
ggttacacat tcactgacta c                                               21

<210> SEQ ID NO 63
<211> LENGTH: 7
<212> TYPE: PRT
<213> ORGANISM: Artificial Sequence
<220> FEATURE:
<223> OTHER INFORMATION: Heavy Chain CDR1 Chothia

<400> SEQUENCE: 63
```

```
Gly Tyr Ser Phe Thr Asp Tyr
1               5
```

<210> SEQ ID NO 64
<211> LENGTH: 21
<212> TYPE: DNA
<213> ORGANISM: Artificial Sequence
<220> FEATURE:
<223> OTHER INFORMATION: Heavy Chain CDR1 Chothia

<400> SEQUENCE: 64
ggttattcat tcactgacta c                                        21

<210> SEQ ID NO 65
<211> LENGTH: 10
<212> TYPE: PRT
<213> ORGANISM: Artificial Sequence
<220> FEATURE:
<223> OTHER INFORMATION: Heavy Chain CDR1 AbM

<400> SEQUENCE: 65

```
Gly Phe Thr Phe Thr Asp Tyr Lys Ile His
1               5                   10
```

<210> SEQ ID NO 66
<211> LENGTH: 30
<212> TYPE: DNA
<213> ORGANISM: Artificial Sequence
<220> FEATURE:
<223> OTHER INFORMATION: Heavy Chain CDR1 AbM

<400> SEQUENCE: 66
ggttttacat tcactgacta caagatacac                                30

<210> SEQ ID NO 67
<211> LENGTH: 10
<212> TYPE: PRT
<213> ORGANISM: Artificial Sequence
<220> FEATURE:
<223> OTHER INFORMATION: Heavy Chain CDR1 AbM

<400> SEQUENCE: 67

```
Gly Phe Thr Phe Thr Asp Tyr Ala Ile Ser
1               5                   10
```

<210> SEQ ID NO 68
<211> LENGTH: 30
<212> TYPE: DNA
<213> ORGANISM: Artificial Sequence
<220> FEATURE:
<223> OTHER INFORMATION: Heavy Chain CDR1 AbM

<400> SEQUENCE: 68
ggttttacat tcactgacta cgccatcagc                                30

<210> SEQ ID NO 69
<211> LENGTH: 10
<212> TYPE: PRT
<213> ORGANISM: Artificial Sequence
<220> FEATURE:
<223> OTHER INFORMATION: Heavy Chain CDR1 AbM

<400> SEQUENCE: 69

```
Gly Phe Thr Phe Thr Asp Tyr Tyr Met His
1               5                   10
```

<210> SEQ ID NO 70
<211> LENGTH: 30
<212> TYPE: DNA
<213> ORGANISM: Artificial Sequence
<220> FEATURE:
<223> OTHER INFORMATION: Heavy Chain CDR1 AbM

<400> SEQUENCE: 70
ggttttacat tcactgacta ctatatgcac        30

<210> SEQ ID NO 71
<211> LENGTH: 10
<212> TYPE: PRT
<213> ORGANISM: Artificial Sequence
<220> FEATURE:
<223> OTHER INFORMATION: Heavy Chain CDR1 AbM

<400> SEQUENCE: 71

Gly Tyr Thr Phe Thr Asp Tyr Tyr Met His
1               5                   10

<210> SEQ ID NO 72
<211> LENGTH: 30
<212> TYPE: DNA
<213> ORGANISM: Artificial Sequence
<220> FEATURE:
<223> OTHER INFORMATION: Heavy Chain CDR1 AbM

<400> SEQUENCE: 72
ggttacacat tcactgacta ctatatgcac        30

<210> SEQ ID NO 73
<211> LENGTH: 10
<212> TYPE: PRT
<213> ORGANISM: Artificial Sequence
<220> FEATURE:
<223> OTHER INFORMATION: Heavy Chain CDR1 AbM

<400> SEQUENCE: 73

Gly Tyr Ser Phe Thr Asp Tyr Lys Ile His
1               5                   10

<210> SEQ ID NO 74
<211> LENGTH: 30
<212> TYPE: DNA
<213> ORGANISM: Artificial Sequence
<220> FEATURE:
<223> OTHER INFORMATION: Heavy Chain CDR1 AbM

<400> SEQUENCE: 74
ggttattcat tcactgacta caagatacac        30

<210> SEQ ID NO 75
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 75

Tyr Phe Asn Pro Asn Ser Gly Tyr Ser Thr Tyr Asn Glu Lys Phe Lys
1               5                   10                  15

Ser

<210> SEQ ID NO 76
<211> LENGTH: 51

```
<212> TYPE: DNA
<213> ORGANISM: Artificial Sequence
<220> FEATURE:
<223> OTHER INFORMATION: Heavy Chain CDR2 Kabat

<400> SEQUENCE: 76
tattttaatc ctaacagtgg ttatagtacc tacaatgaaa agttcaagag c                    51

<210> SEQ ID NO 77
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 77

Gly Ile Asn Pro Asn Ser Gly Tyr Ser Thr Tyr Ala Gln Lys Phe Gln
1               5                   10                  15

Gly

<210> SEQ ID NO 78
<211> LENGTH: 51
<212> TYPE: DNA
<213> ORGANISM: Artificial Sequence
<220> FEATURE:
<223> OTHER INFORMATION: Heavy Chain CDR2 Kabat

<400> SEQUENCE: 78
gggatcaatc ctaacagtgg ttatagtacc tacgcacaga agttccaggg c                    51

<210> SEQ ID NO 79
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 79

Tyr Phe Asn Pro Asn Ser Gly Tyr Ser Thr Tyr Ala Gln Lys Phe Gln
1               5                   10                  15

Gly

<210> SEQ ID NO 80
<211> LENGTH: 51
<212> TYPE: DNA
<213> ORGANISM: Artificial Sequence
<220> FEATURE:
<223> OTHER INFORMATION: Heavy Chain CDR2 Kabat

<400> SEQUENCE: 80
tatttcaacc ctaacagcgg ttatagtacc tacgcacaga agttccaggg c                    51

<210> SEQ ID NO 81
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 81

Trp Ile Asn Pro Asn Ser Gly Tyr Ser Thr Tyr Ala Gln Lys Phe Gln
1               5                   10                  15

Gly
```

```
<210> SEQ ID NO 82
<211> LENGTH: 51
<212> TYPE: DNA
<213> ORGANISM: Artificial Sequence
<220> FEATURE:
<223> OTHER INFORMATION: Heavy Chain CDR2 Kabat

<400> SEQUENCE: 82
tggatcaatc ctaacagtgg ttatagtacc tacgcacaga agtttcaggg c            51

<210> SEQ ID NO 83
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 83

Trp Ile Asn Pro Asn Ser Gly Tyr Ser Thr Tyr Ser Pro Ser Phe Gln
1               5                   10                  15

Gly

<210> SEQ ID NO 84
<211> LENGTH: 51
<212> TYPE: DNA
<213> ORGANISM: Artificial Sequence
<220> FEATURE:
<223> OTHER INFORMATION: Heavy Chain CDR2 Kabat

<400> SEQUENCE: 84
tggatcaatc ctaacagtgg ttatagtacc tacagcccaa gcttccaagg c            51

<210> SEQ ID NO 85
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 85

Trp Ile Asn Pro Asn Ser Gly Tyr Ser Thr Tyr Asn Glu Lys Phe Gln
1               5                   10                  15

Gly

<210> SEQ ID NO 86
<211> LENGTH: 51
<212> TYPE: DNA
<213> ORGANISM: Artificial Sequence
<220> FEATURE:
<223> OTHER INFORMATION: Heavy Chain CDR2 Kabat

<400> SEQUENCE: 86
tggatcaatc ctaacagtgg ttatagtacc tacaacgaga agttccaagg c            51

<210> SEQ ID NO 87
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 87

Tyr Phe Asn Pro Asn Ser Gly Tyr Ser Asn Tyr Ala Gln Lys Phe Gln
1               5                   10                  15

Gly
```

<210> SEQ ID NO 88
<211> LENGTH: 51
<212> TYPE: DNA
<213> ORGANISM: Artificial Sequence
<220> FEATURE:
<223> OTHER INFORMATION: Heavy Chain CDR2 Kabat

<400> SEQUENCE: 88
tatttcaacc ctaacagcgg ttattcgaac tacgcacaga agttccaggg c            51

<210> SEQ ID NO 89
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 89

Tyr Phe Asn Pro Asn Ser Gly Tyr Ala Thr Tyr Ala Gln Lys Phe Gln
1               5                   10                  15

Gly

<210> SEQ ID NO 90
<211> LENGTH: 51
<212> TYPE: DNA
<213> ORGANISM: Artificial Sequence
<220> FEATURE:
<223> OTHER INFORMATION: Heavy Chain CDR2 Kabat

<400> SEQUENCE: 90
tatttcaacc ctaacagcgg ttatgccacg tacgcacaga agttccaggg c            51

<210> SEQ ID NO 91
<211> LENGTH: 8
<212> TYPE: PRT
<213> ORGANISM: Artificial Sequence
<220> FEATURE:
<223> OTHER INFORMATION: Heavy Chain CDR2 Chothia

<400> SEQUENCE: 91

Asn Pro Asn Ser Gly Tyr Ser Thr
1               5

<210> SEQ ID NO 92
<211> LENGTH: 24
<212> TYPE: DNA
<213> ORGANISM: Artificial Sequence
<220> FEATURE:
<223> OTHER INFORMATION: Heavy Chain CDR2 Chothia

<400> SEQUENCE: 92
aatcctaaca gtggttatag tacc                                          24

<210> SEQ ID NO 93
<211> LENGTH: 8
<212> TYPE: PRT
<213> ORGANISM: Artificial Sequence
<220> FEATURE:
<223> OTHER INFORMATION: Heavy Chain CDR2 Chothia

<400> SEQUENCE: 93

Asn Pro Asn Ser Gly Tyr Ser Asn
1               5

<210> SEQ ID NO 94
<211> LENGTH: 24
<212> TYPE: DNA
<213> ORGANISM: Artificial Sequence
<220> FEATURE:
<223> OTHER INFORMATION: Heavy Chain CDR2 Chothia

<400> SEQUENCE: 94
aaccctaaca gcggttattc gaac                                          24

<210> SEQ ID NO 95
<211> LENGTH: 8
<212> TYPE: PRT
<213> ORGANISM: Artificial Sequence
<220> FEATURE:
<223> OTHER INFORMATION: Heavy Chain CDR2 Chothia

<400> SEQUENCE: 95

Asn Pro Asn Ser Gly Tyr Ala Thr
1               5

<210> SEQ ID NO 96
<211> LENGTH: 24
<212> TYPE: DNA
<213> ORGANISM: Artificial Sequence
<220> FEATURE:
<223> OTHER INFORMATION: Heavy Chain CDR2 Chothia

<400> SEQUENCE: 96
aaccctaaca gcggttatgc cacg                                          24

<210> SEQ ID NO 97
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 97

Tyr Phe Asn Pro Asn Ser Gly Tyr Ser Thr
1               5                   10

<210> SEQ ID NO 98
<211> LENGTH: 30
<212> TYPE: DNA
<213> ORGANISM: Artificial Sequence
<220> FEATURE:
<223> OTHER INFORMATION: Heavy Chain CDR2 AbM

<400> SEQUENCE: 98
tattttaatc ctaacagtgg ttatagtacc                                    30

<210> SEQ ID NO 99
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 99

Gly Ile Asn Pro Asn Ser Gly Tyr Ser Thr
1               5                   10

<210> SEQ ID NO 100
<211> LENGTH: 30
<212> TYPE: DNA
<213> ORGANISM: Artificial Sequence

```
<220> FEATURE:
<223> OTHER INFORMATION: Heavy Chain CDR2 AbM

<400> SEQUENCE: 100
gggatcaatc ctaacagtgg ttatagtacc                                    30

<210> SEQ ID NO 101
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 101

Trp Ile Asn Pro Asn Ser Gly Tyr Ser Thr
1               5                   10

<210> SEQ ID NO 102
<211> LENGTH: 30
<212> TYPE: DNA
<213> ORGANISM: Artificial Sequence
<220> FEATURE:
<223> OTHER INFORMATION: Heavy Chain CDR2 AbM

<400> SEQUENCE: 102
tggatcaatc ctaacagtgg ttatagtacc                                    30

<210> SEQ ID NO 103
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 103

Tyr Phe Asn Pro Asn Ser Gly Tyr Ser Asn
1               5                   10

<210> SEQ ID NO 104
<211> LENGTH: 30
<212> TYPE: DNA
<213> ORGANISM: Artificial Sequence
<220> FEATURE:
<223> OTHER INFORMATION: Heavy Chain CDR2 AbM

<400> SEQUENCE: 104
tatttcaacc ctaacagcgg ttattcgaac                                    30

<210> SEQ ID NO 105
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 105

Tyr Phe Asn Pro Asn Ser Gly Tyr Ala Thr
1               5                   10

<210> SEQ ID NO 106
<211> LENGTH: 30
<212> TYPE: DNA
<213> ORGANISM: Artificial Sequence
<220> FEATURE:
<223> OTHER INFORMATION: Heavy Chain CDR2 AbM

<400> SEQUENCE: 106
```

```
tatttcaacc ctaacagcgg ttatgccacg                                              30
```

<210> SEQ ID NO 107
<211> LENGTH: 11
<212> TYPE: PRT
<213> ORGANISM: Artificial Sequence
<220> FEATURE:
<223> OTHER INFORMATION: Heavy Chain CDR3 Kabat Chothia AbM

<400> SEQUENCE: 107

Leu Ser Pro Gly Gly Tyr Tyr Val Met Asp Ala
1               5                   10

<210> SEQ ID NO 108
<211> LENGTH: 33
<212> TYPE: DNA
<213> ORGANISM: Artificial Sequence
<220> FEATURE:
<223> OTHER INFORMATION: Heavy Chain CDR3 Kabat Chothia AbM

<400> SEQUENCE: 108

```
ctatccccag gcggttacta tgttatggat gcc                                          33
```

<210> SEQ ID NO 109
<211> LENGTH: 328
<212> TYPE: PRT
<213> ORGANISM: Homo sapiens
<220> FEATURE:
<223> OTHER INFORMATION: IgG1 constant region

<400> SEQUENCE: 109

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Ser
        50                  55                  60

Ser Val Val Thr Val Pro Ser Ser Ser Leu Gly Thr Gln Thr Tyr Ile
65                  70                  75                  80

Cys Asn Val Asn His Lys Pro Ser Asn Thr Lys Val Asp Lys Lys Ala
                85                  90                  95

Glu Pro Lys Ser Cys Asp Lys Thr His Thr Cys Pro Pro Cys Pro Ala
                100                 105                 110

Pro Glu Leu Leu Gly Gly Pro Ser Val Phe Leu Phe Pro Pro Lys Pro
            115                 120                 125

Lys Asp Thr Leu Met Ile Ser Arg Thr Pro Glu Val Thr Cys Val Val
        130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
            245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
            275                 280                 285

Ser Lys Leu Thr Val Asp Lys Ser Arg Trp Gln Gln Gly Asn Val Phe
        290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 110
<211> LENGTH: 987
<212> TYPE: DNA
<213> ORGANISM: Homo sapiens
<220> FEATURE:
<223> OTHER INFORMATION: IgG1 constant region

<400> SEQUENCE: 110
accaagggcc catcggtctt ccccctggca ccctcctcca gagcacctc tggggggcaca      60 gcggccctgg gctgcctggt caaggactac ttccccgaac cggtgacggt gtcgtggaac     120
tcaggcgccc tgaccagcgg cgtgcacacc ttcccggctg tcctacagtc ctcaggactc     180
tactccctca gcagcgtggt gaccgtgccc tccagcagct gggcaccca gacctacatc      240 tgcaacgtga atcacaagcc cagcaacacc aaggtggaca agaaagcaga gcccaaatct     300
tgtgacaaaa ctcacacatg cccaccgtgc ccagcacctg aactcctggg gggaccgtca     360
gtcttcctct tccccccaaa acccaaggac accctcatga tctcccggac ccctgaggtc     420
acatgcgtgg tggtggacgt gagccacgaa gaccctgagg tcaagttcaa ctggtacgtg     480
gacggcgtgg aggtgcataa tgccaagaca agccgcggg aggagcagta caacagcacg      540
taccgtgtgg tcagcgtcct caccgtcctg caccaggact ggctgaatgg caaggagtac     600
aagtgcaagg tctccaacaa agccctccca gcccccatcg agaaaaccat ctccaaagcc     660
aaagggcagc cccgagaacc acaggtgtac accctgcccc catcccggga tgagctgacc     720
aagaaccagg tcagcctgac ctgcctggtc aaaggcttct atcccagcga catcgccgtg     780
gagtgggaga gcaatgggca gccggagaac aactacaaga ccacgcctcc cgtgctggac     840
tccgacggct ccttcttcct ctacagcaag ctcaccgtgg acaagagcag gtggcagcag     900
gggaacgtct tctcatgctc cgtgatgcat gaggctctgc acaaccacta cacgcagaag     960
agcctctccc tgtctccggg taaatga                                         987

<210> SEQ ID NO 111
<211> LENGTH: 11
<212> TYPE: PRT
<213> ORGANISM: Artificial Sequence
<220> FEATURE:
<223> OTHER INFORMATION: Kabat Light Chain CDR1

<400> SEQUENCE: 111

Lys Ala Ser Gln Asn Ile Asn Asn Tyr Leu Asn
1               5                   10

<210> SEQ ID NO 112
<211> LENGTH: 33
<212> TYPE: DNA
<213> ORGANISM: Artificial Sequence
<220> FEATURE:
<223> OTHER INFORMATION: Kabat Light Chain CDR1

<400> SEQUENCE: 112
aaagcaagtc agaatattaa caattactta aac                33

<210> SEQ ID NO 113
<211> LENGTH: 11
<212> TYPE: PRT
<213> ORGANISM: Artificial Sequence
<220> FEATURE:
<223> OTHER INFORMATION: Kabat Light Chain CDR1

<400> SEQUENCE: 113

Arg Ala Ser Gln Gly Ile Asn Asn Tyr Leu Asn
1               5                   10

<210> SEQ ID NO 114
<211> LENGTH: 33
<212> TYPE: DNA
<213> ORGANISM: Artificial Sequence
<220> FEATURE:
<223> OTHER INFORMATION: Kabat Light Chain CDR1

<400> SEQUENCE: 114
cgggcaagtc agggcattaa caattactta aat                33

<210> SEQ ID NO 115
<211> LENGTH: 7
<212> TYPE: PRT
<213> ORGANISM: Artificial Sequence
<220> FEATURE:
<223> OTHER INFORMATION: Kabat Light Chain CDR2

<400> SEQUENCE: 115

Asn Thr Asn Asn Leu Gln Thr
1               5

<210> SEQ ID NO 116
<211> LENGTH: 21
<212> TYPE: DNA
<213> ORGANISM: Artificial Sequence
<220> FEATURE:
<223> OTHER INFORMATION: Kabat Light Chain CDR2

<400> SEQUENCE: 116
aatacaaaca atttgcaaac a                21

<210> SEQ ID NO 117
<211> LENGTH: 8
<212> TYPE: PRT
<213> ORGANISM: Artificial Sequence
<220> FEATURE:
<223> OTHER INFORMATION: Kabat Light Chain CDR3

<400> SEQUENCE: 117

Leu Gln His Asn Ser Phe Pro Thr
1               5

<210> SEQ ID NO 118
<211> LENGTH: 21
<212> TYPE: DNA

<213> ORGANISM: Artificial Sequence
<220> FEATURE:
<223> OTHER INFORMATION: Kabat Light Chain CDR2

<400> SEQUENCE: 118
aataccaaca acttgcagac a                                              21

<210> SEQ ID NO 119
<211> LENGTH: 24
<212> TYPE: DNA
<213> ORGANISM: Artificial Sequence
<220> FEATURE:
<223> OTHER INFORMATION: Kabat Light Chain CDR3

<400> SEQUENCE: 119
ttgcagcata atagttttcc cacg                                           24

<210> SEQ ID NO 120
<211> LENGTH: 361
<212> TYPE: DNA
<213> ORGANISM: Artificial Sequence
<220> FEATURE:
<223> OTHER INFORMATION: Rat-human chimeric DNA

<400> SEQUENCE: 120
gaggtgcagc tcgtgcagtc tggcgctgag gtgaagaagc ctggcgagtc gttgaagatc    60
tcctgcaagg gttctggtta ttcattcact gactacaaga tccactgggt gcgacagatg   120
cctggaaagg gcctcgagtg gatgggctac ttcaatccta acagtggtta tagtacctac   180
agcccaagct tccaaggcca ggtcaccatc tcagccgaca gtccatcag caccgcctac    240 ctgcagtgga gcagcctgaa ggcctcggac accgccatgt attactgtgc gagactatcc   300
ccaggcggtt actatgttat ggatgcctgg ggccaaggga ccaccgtgac cgtctcctca   360
g                                                                   361

<210> SEQ ID NO 121
<211> LENGTH: 120
<212> TYPE: PRT
<213> ORGANISM: Artificial Sequence
<220> FEATURE:
<223> OTHER INFORMATION: Rat-human chimeric polypeptide

<400> SEQUENCE: 121

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Lys Ile His Trp Val Arg Gln Met Pro Gly Lys Gly Leu Glu Trp Met
            35                  40                  45

Gly Tyr Phe Asn Pro Asn Ser Gly Tyr Ser Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

```
<210> SEQ ID NO 122
<211> LENGTH: 15
<212> TYPE: DNA
<213> ORGANISM: Artificial
<220> FEATURE:
<223> OTHER INFORMATION: Kabat Heavy Chain CDR1

<400> SEQUENCE: 122
gactacaaga tatcc                                                      15

<210> SEQ ID NO 123
<211> LENGTH: 5
<212> TYPE: PRT
<213> ORGANISM: Artificial
<220> FEATURE:
<223> OTHER INFORMATION: Kabat Heavy Chain CDR1

<400> SEQUENCE: 123

Asp Tyr Lys Ile Ser
1               5

<210> SEQ ID NO 124
<211> LENGTH: 30
<212> TYPE: DNA
<213> ORGANISM: Artificial
<220> FEATURE:
<223> OTHER INFORMATION: AbM Heavy Chain CDR1

<400> SEQUENCE: 124
ggtttcacat tcactgacta caagatatcc                                      30

<210> SEQ ID NO 125
<211> LENGTH: 10
<212> TYPE: PRT
<213> ORGANISM: Artificial
<220> FEATURE:
<223> OTHER INFORMATION: AbM Heavy Chain CDR1

<400> SEQUENCE: 125

Gly Phe Thr Phe Thr Asp Tyr Lys Ile Ser
1               5                   10

<210> SEQ ID NO 126
<211> LENGTH: 51
<212> TYPE: DNA
<213> ORGANISM: Artificial
<220> FEATURE:
<223> OTHER INFORMATION: Kabat Heavy Chain CDR2

<400> SEQUENCE: 126
tacttcaatc ctaacagtgg ttatagtacc tacagcccaa gcttccaagg c              51

<210> SEQ ID NO 127
<211> LENGTH: 17
<212> TYPE: PRT
<213> ORGANISM: Artificial
<220> FEATURE:
<223> OTHER INFORMATION: Kabat Heavy Chain CDR2

<400> SEQUENCE: 127

Tyr Phe Asn Pro Asn Ser Gly Tyr Ser Thr Tyr Ser Pro Ser Phe Gln
1               5                   10                  15

Gly
```

ANTIGEN BINDING MOLECULES THAT BIND EGFR, VECTORS ENCODING SAME, AND USES THEREOF

CROSS-REFERENCE TO RELATED APPLICATIONS

This application claims the benefit of U.S. Provisional Application No. 60/650,115, filed Feb. 7, 2005, the entire contents of which are herein incorporated by reference.

BACKGROUND OF THE INVENTION

1. Field of the Invention

The present invention relates to antigen binding molecules (ABMs). In particular embodiments, the present invention relates to recombinant monoclonal antibodies, including chimeric, primatized or humanized antibodies specific for human epidermal growth factor receptor (EGFR). In addition, the present invention relates to nucleic acid molecules encoding such ABMs, and vectors and host cells comprising such nucleic acid molecules. The invention further relates to methods for producing the ABMs of the invention, and to methods of using these ABMs in treatment of disease. In addition, the present invention relates to ABMs with modified glycosylation having improved therapeutic properties, including antibodies with increased Fc receptor binding and increased effector function.

2. Background Art

EGFR and Anti-EGFR Antibodies

Human epidermal growth factor receptor (also known as HER-1 or Erb-B1, and referred to herein as "EGFR") is a 170 kDa transmembrane receptor encoded by the c-erbB protooncogene, and exhibits intrinsic tyrosine kinase activity (Modjtahedi et al., *Br. J. Cancer* 73:228-235 (1996); Herbst and Shin, *Cancer* 94:1593-1611 (2002)). SwissProt database entry P00533 provides the sequence of EGFR. There are also isoforms and variants of EGFR (e.g., alternative RNA transcripts, truncated versions, polymorphisms, etc.) including but not limited to those identified by Swissprot database entry numbers P00533-1, P00533-2, P00533-3, and P00533-4. EGFR is known to bind ligands including epidermal growth factor (EGF), transforming growth factor-α (TGf-α), amphiregulin, heparin-binding EGF (hb-EGF), betacellulin, and epiregulin (Herbst and Shin, *Cancer* 94:1593-1611 (2002); Mendelsohn and Baselga, *Oncogene* 19:6550-6565 (2000)). EGFR regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay et al., *Ann. Oncology* 14:1346-1363 (2003); Tsao and Herbst, *Signal* 4:4-9 (2003); Herbst and Shin, *Cancer* 94:1593-1611 (2002); Modjtahedi et al., *Br. J Cancer* 73:228-235 (1996)).

Overexpression of EGFR has been reported in numerous human malignant conditions, including cancers of the bladder, brain, head and neck, pancreas, lung, breast, ovary, colon, prostate, and kidney. (Atalay et al., *Ann. Oncology* 14:1346-1363 (2003); Herbst and Shin, *Cancer* 94:1593-1611 (2002) Modjtahedi et al., *Br. J Cancer* 73:228-235 (1996)). In many of these conditions, the overexpression of EGFR correlates or is associated with poor prognosis of the patients. (Herbst and Shin, *Cancer* 94:1593-1611 (2002) Modjtahedi et al., *Br. J Cancer* 73:228-235 (1996)). EGFR is also expressed in the cells of normal tissues, particularly the epithelial tissues of the skin, liver, and gastrointestinal tract, although at generally lower levels than in malignant cells (Herbst and Shin, *Cancer* 94:1593-1611 (2002)).

Unconjugated monoclonal antibodies (mAbs) can be useful medicines for the treatment of cancer, as demonstrated by the U.S. Food and Drug Administration's approval of Trastuzumab (Herceptin™; Genentech Inc,) for the treatment of advanced breast cancer (Grillo-Lopez, A.-J., et al., *Semin. Oncol.* 26:66-73 (1999); Goldenberg, M. M., *Clin. Ther.* 21:309-18 (1999)), Rituximab (Rituxan™; IDEC Pharmaceuticals, San Diego, Calif., and Genentech Inc., San Francisco, Calif.), for the treatment of CD20 positive B-cell, low-grade or follicular Non-Hodgkin's lymphoma, Gemtuzumab (Mylotarg™, Celltech/Wyeth-Ayerst) for the treatment of relapsed acute myeloid leukemia, and Alemtuzumab (CAMPATH™, Millenium Pharmaceuticals/Schering AG) for the treatment of B cell chronic lymphocytic leukemia. The success of these products relies not only on their efficacy but also on their outstanding safety profiles (Grillo-Lopez, A. J., et al., *Semin. Oncol.* 26:66-73 (1999); Goldenberg, M. M., *Clin. Ther.* 21:309-18 (1999)). In spite of the achievements of these drugs, there is currently a large interest in obtaining higher specific antibody activity than what is typically afforded by unconjugated mAb therapy.

The results of a number of studies suggest that Fc-receptor-dependent mechanisms contribute substantially to the action of cytotoxic antibodies against tumors and indicate that an optimal antibody against tumors would bind preferentially to activation Fc receptors and minimally to the inhibitory partner FcγRIIB. (Clynes, R. A., et al., *Nature Medicine* 6(4):443-446 (2000); Kalergis, A. M., and Ravetch, J. V., *J. Exp. Med.* 195(12):1653-1659 (June 2002). For example, the results of at least one study suggest that polymorphism in the FcγRIIIa receptor, in particular, is strongly associated with the efficacy of antibody therapy. (Cartron, G., et al., *Blood* 99(3):754-757 (February 2002)). That study showed that patients homozygous for FcγRIIIa have a better response to Rituximab than heterozygous patients. The authors concluded that the superior response was due to better in vivo binding of the antibody to FcγRIIIa, which resulted in better ADCC activity against lymphoma cells. (Cartron, G., et al., *Blood* 99(3):754-757 (February 2002)).

Various strategies to target EGFR and block EGFR signaling pathways have been reported. Small-molecule tyrosine kinase inhibitors like gefitinib, erlotinib, and CI-1033 block autophosphorylation of EGFR in the intracellular tyrosine kinase region, thereby inhibiting downstream signaling events (Tsao and Herbst, *Signal* 4: 4-9 (2003)). Monoclonal antibodies, on the other hand, target the extracellular portion of EGFR, which results in blocking ligand binding and thereby inhibits downstream events such as cell proliferation (Tsao and Herbst, *Signal* 4: 4-9 (2003)).

Several murine monoclonal antibodies have been generated which achieve such a block in vitro and which have been evaluated for their ability to affect tumor growth in mouse xenograft models (Masui, et al., *Cancer Res.* 46:5592-5598 (1986); Masui, et al., *Cancer Res.* 44:1002-1007 (1984); Goldstein, et al., *Clin. Cancer Res.* 1: 1311-1318 (1995)). For example, EMD 55900 (EMD Pharmaceuticals) is a murine anti-EGFR monoclonal antibody that was raised against human epidermoid carcinoma cell line A431 and was tested in clinical studies of patients with advanced squamous cell carcinoma of the larynx or hypopharynx (Bier et al., *Eur. Arch. Otohinolaryngol.* 252:433-9 (1995)). In addition, the rat monoclonal antibodies ICR16, ICR62, and ICR80, which bind the extracellular domain of EGFR, have been shown to be effective at inhibiting the binding of EGF and TGF-α the receptor. (Modjtahedi et al., *Int. J. Cancer* 75:310-316 (1998)). The murine monoclonal antibody 425 is another MAb that was raised against the human A431 carcinoma cell line and was found to bind to a polypeptide epitope on the external domain of the human epidermal growth factor receptor. (Murthy et al., *Arch. Biochem. Biophys.* 252(2):549-560 (1987). A potential problem with the use of murine antibodies in therapeutic treatments is that non-human monoclonal antibodies can be recognized by the human host as a foreign protein; therefore, repeated injections of such foreign antibodies can lead to the induction of immune responses leading to harmful hypersensitivity reactions. For murine-based monoclonal antibodies, this is often referred to as a Human Anti-Mouse Antibody response, or "HAMA" response, or a Human Anti-Rat Antibody, or "HARA" response. Additionally, these "foreign" antibodies can be attacked by the immune system of the host such that they are, in effect, neutralized before they reach their target site. Furthermore, non-human monoclonal antibodies (e.g., murine monoclonal antibodies) typically lack human effector functionality, i.e., they are unable to, inter alia, mediate complement dependent lysis or lyse human target cells through antibody dependent cellular toxicity or Fc-receptor mediated phagocytosis.

Chimeric antibodies comprising portions of antibodies from two or more different species (e.g., mouse and human) have been developed as an alternative to "conjugated" antibodies. For example, U.S. Pat. No. 5,891,996 (Mateo de Acosta del Rio et al.) discusses a mouse/human chimeric antibody, R3, directed against EGFR, and U.S. Pat. No. 5,558,864 discusses generation of chimeric and humanized forms of the murine anti-EGFR MAb 425. Also, IMC-C225 (Erbitux®; ImClone) is a chimeric mouse/human anti-EGFR monoclonal antibody (based on mouse M225 monoclonal antibody, which resulted in HAMA responses in human clinical trials) that has been reported to demonstrate antitumor efficacy in various human xenograft models. (Herbst and Shin, *Cancer* 94:1593-1611 (2002)). The efficacy of IMC-C225 has been attributed to several mechanisms, including inhibition of cell events regulated by EGFR signaling pathways, and possibly by increased antibody-dependent cellular toxicity (ADCC) activity (Herbst and Shin, *Cancer* 94:1593-1611 (2002)). IMC-C225 was also used in clinical trials, including in combination with radiotherapy and chemotherapy (Herbst and Shin, *Cancer* 94:1593-1611 (2002)). Recently, Abgenix, Inc. (Fremont, Calif.) developed ABX-EGF for cancer therapy. ABX-EGF is a fully human anti-EGFR monoclonal antibody. (Yang et al., *Crit. Rev. Oncol./Hematol.* 38:17-23 (2001)).

Antibody Glycosylation

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein fuiction can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins et al., *Nature Biotechnol.* 14:975-81 (1996)).

Mammalian cells are the preferred hosts for production of therapeutic glycoproteins, due to their capability to glycosylate proteins in the most compatible form for human application. (Cumming et al., *Glycobiology* 1:115-30 (1991); Jenkins et al., *Nature Biotechnol.* 14:975-81(1996)). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NS0- and SP2/0-mouse myeloma cells. More recently, production from transgenic animals has also been tested. (Jenkins et al., *Nature Biotechnol.* 14:975-81 (1996)).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Morrison, S. L., *Trends Biotech.* 15:26-32 (1997)). The structure of the attached N-linked carbohydrate varies considerably, depending on the degree of processing, and can include high-mannose, multiply-branched as well as biantennary complex oligosaccharides. (Wright, A., and Morrison, S. L., *Trends Biotech.* 15:26-32 (1997)). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R. et al., *Glycobiology* 5(8):813-22 (1995)).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umaña, P. et al., *Nature Biotechnol.* 17:176-180 (1999) and U.S. Pat. No. 6,602,684, the contents of which are hereby incorporated by reference in their entirety. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., *Glycobiology* 5:813-822 (1995); Jefferis, R., et al., *Immunol Rev.* 163:59-76 (1998); Wright, A. and Morrison, S. L., *Trends Biotechnol.* 15:26-32 (1997)).

Umaña et al. showed previously that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of an anti-neuroblastoma chimeric monoclonal antibody (chCE7) produced by the engineered CHO cells. (See Umaña, P. et al., *Nature Biotechnol.* 17:176-180 (1999); and International Publication No. WO 99/54342, the entire contents of which are hereby incorporated by reference). The antibody chCE7 belongs to a large class of unconjugated mAbs which have high tumor affinity and specificity, but have too little potency to be clinically useful when produced in standard industrial cell lines lacking the GnTIII enzyme (Umana, P., et al., *Nature Biotechnol.* 17:176-180 (1999)). That study was the first to show that large increases of ADCC activity could be obtained by engineering the antibody-producing cells to express GnTIII, which also led to an increase in the proportion of constant region (Fc)-associated, bisected oligosaccharides, including bisected, nonfucosylated oligosaccharides, above the levels found in naturally-occurring antibodies.

There remains a need for enhanced therapeutic approaches targeting EGFR for the treatment of cell proliferation disorders in primates, including, but not limited to, humans, wherein such disorders are characterized by EGFR expression, particularly abnormal expression (e.g., overxpression) including, but not limited to, cancers of the bladder, brain, head and neck, pancreas, lung, breast, ovary, colon, prostate, and kidney.

BRIEF SUMMARY OF THE INVENTION

Recognizing the tremendous therapeutic potential of antigen binding molecules (ABMs) that have the binding specificity of the rat ICR62 antibody (e.g., bind the same epitope) and that have been glycoengineered to enhance Fc receptor binding affinity and effector function, the present inventors developed a method for producing such ABMs. Inter alia, this method involves producing recombinant, chimeric antibodies or chimeric fragments thereof. The efficacy of these ABMs is further enhanced by engineering the glycosylation profile of the antibody Fc region.

Accordingly, in one aspect, the invention is directed to an isolated polynucleotide comprising: (a) a sequence selected from a group consisting of: SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:122, and SEQ ID NO:124; (b) a sequence selected from a group consisting of: SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, and SEQ ID NO:126; and (c) SEQ ID NO:108. In another aspect, the invention is directed to an isolated polynucleotide comprising (a) a sequence selectd from the group consisting of SEQ ID NO:112 and SEQ ID NO:114; (b) a sequence selectd from the group consisting of SEQ ID NO:116 and SEQ ID NO:118; and (c) SEQ ID NO:119. In one embodiment, any of these polynucleotides encodes a fusion polypeptide.

In a further aspect, the invention is directed to an isolated polynucleotide comprising a sequence selected from the group consisting of SEQ ID No:2; SEQ ID No:4; SEQ ID No:6; SEQ ID No:8; SEQ ID No:10; SEQ ID No:12; SEQ ID No:14; SEQ ID No:16; SEQ ID No:18; SEQ ID No:20; SEQ ID No:22; SEQ ID No:24; SEQ ID No:26; SEQ ID No:28; SEQ ID No:30; SEQ ID No32; SEQ ID No:34; SEQ ID No:36; SEQ ID No:38; SEQ ID No:40 and SEQ ID No:120. In another aspect, the invention is directed to an isolated polynucleotide comprising a sequence selected from the group consisting of SEQ ID No:44; SEQ ID No:46; SEQ ID No:50; and SEQ ID No:52. In one embodiment, such polynucleotides encode fusion polypeptides.

The invention is further directed to an isolated polynucleotide comprising a sequence having at least 80%, 85%, 90%, 95%, or 99% identity to a sequence selected from the group consisting of SEQ ID No:2; SEQ ID No:4; SEQ ID No:6; SEQ ID No:8; SEQ ID No:10; SEQ ID No:12; SEQ ID No:14; SEQ ID No:16; SEQ ID No:18; SEQ ID No:20; SEQ ID No:22; SEQ ID No:24; SEQ ID No:26; SEQ ID No:28; SEQ ID No:30; SEQ ID No32; SEQ ID No:34; SEQ ID No:36; SEQ ID No:38; SEQ ID No:40 and SEQ ID No:120, wherein said isolated polynucleotide encodes a fusion polypeptide. In an additional aspect, the invention is directed to an isolated polynucleotide comprising a sequence having at least 80% identity to a sequence selected from the group consisting of SEQ ID No:44; SEQ ID No:46; SEQ ID No:50; and SEQ ID No:52, wherein said isolated polynucleotide encodes a fusion polypeptide.

The invention is also directed to an isolated polynucleotide encoding a chimeric polypeptide having the sequence of SEQ ID No:1. In one embodiment, the polynucleotide comprises a sequence encoding a polypeptide having the sequence of SEQ ID No:1; and a sequence encoding a polypeptide having the sequence of an antibody Fc region, or a fragment thereof, from a species other than rat. The invention is also directed to an isolated polynucleotide encoding a chimeric polypeptide having a sequence selected from the group consisting of SEQ ID No:3; SEQ ID No:5; SEQ ID No:7; SEQ ID No:9; SEQ ID No:11; SEQ ID No:13; SEQ ID No:15; SEQ ID No:17; SEQ ID No:19; SEQ ID No:21; SEQ ID No:23; SEQ ID No:25; SEQ ID No:27; SEQ ID No:29; SEQ ID No:31; SEQ ID No33; SEQ ID No:35; SEQ ID No:37; SEQ ID No:39; and SEQ ID No:121. In one embodiment, the polynucleotide comprises a sequence encoding a polypeptide having a sequence selected from the group consisting of SEQ ID No:3; SEQ ID No:5; SEQ ID No:7; SEQ ID No:9; SEQ ID No:11; SEQ ID No:13; SEQ ID No:15; SEQ ID No:17; SEQ ID No:19; SEQ ID No:21; SEQ ID No:23; SEQ ID No:25; SEQ ID No:27; SEQ ID No:29; SEQ ID No:31; SEQ ID No33; SEQ ID No:35; SEQ ID No:37; SEQ ID No:39; and SEQ ID No:121; and a sequence encoding a polypeptide having the sequence of an antibody Fc region, or a fragment thereof, from a species other than rat.

In yet another aspect, the invention is directed to an isolated polynucleotide encoding a chimeric polypeptide having the sequence of SEQ ID No:43. In one embodiment, the polynucleotide comprises a sequence encoding a polypeptide having the sequence of SEQ ID No:43; and a sequence encoding a polypeptide having the sequence of an antibody Fc region, or a fragment thereof, from a species other than rat. In yet another aspect, the invention is directed to an isolated polynucleotide encoding a chimeric polypeptide having a sequence selected from the group consisting of SEQ ID No:45; SEQ ID No:49; and SEQ ID No:51. In one embodiment, the polynucleotide comprises a sequence encoding a polypeptide having a sequence selected from the group consisting of SEQ ID No:45; SEQ ID No:49; and SEQ ID No:51, and a sequence encoding a polypeptide having the sequence of an antibody light chain constant region (CL), or a fragment thereof, from a species other than rat.

The invention is also directed to an isolated polynucleotide comprising a sequence encoding a polypeptide having the VH region of the ICR62 antibody, or functional variants thereof, and a sequence encoding a polypeptide having the sequence of an antibody Fc region, or a fragment thereof, from a species other than rat. In another aspect, the invention is directed to an isolated polynucleotide comprising a sequence encoding a polypeptide having the VL region of the ICR62 antibody, or functional variants thereof, and a sequence encoding a polypeptide having the sequence of an antibody CL region, or a fragment thereof, from a species other than rat.

The invention is further directed to an expression vector comprising any of the isolated polynucleotides described above, and to a host cell that comprises such an expression vector. In a further aspect, the invention is directed to a host cell comprising any of the isolated polynucleotides described above.

In one aspect, the invention is directed to an isolated polypeptide comprising: (a) a sequence selected from a group consisting of: SEQ ID NO:53 SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:123, and SEQ ID NO:125; (b) a sequence selected from a group consisting of: SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, and SEQ ID NO:127; and (c) SEQ ID NO:107. wherein said polypeptide is a fusion polypeptide.

In another aspect, the invention is directed to an isolated polypeptide comprising (a) a sequence selected from the group consisting of SEQ ID NO:111 and SEQ ID NO:113; (b) SEQ ID NO:115; and (c) SEQ ID NO:117, wherein said polypeptide is a fusion polypeptide.

The invention is also directed to a chimeric polypeptide comprising the sequence of SEQ ID NO:1 or a variant thereof. The invention is further directed to a chimeric polypeptide comprising the sequence of SEQ ID NO:43 or a variant thereof. In one embodiment, any one of these polypeptides further comprises a human Fc region and/or a human CL region. The invention is also directed to a chimeric polypeptide comprising a sequence selected from the group consisting of SEQ ID No:3; SEQ ID No:5; SEQ ID No:7; SEQ ID No:9; SEQ ID No:11; SEQ ID No:13; SEQ ID No:15; SEQ ID No:17; SEQ ID No:19; SEQ ID No:21; SEQ ID No:23; SEQ ID No:25; SEQ ID No:27; SEQ ID No:29; SEQ ID No:31; SEQ ID No33; SEQ ID No:35; SEQ ID No:37; SEQ ID No:39; and SEQ ID No: 121, or a variant thereof. The invention is further directed to a chimeric polypeptide comprising s sequence selected from the group consisting of SEQ ID No:45; SEQ ID No:49; and SEQ ID No:51, or a variant thereof. In one embodiment, any one of these polypeptides further comprises a human Fc region and/or a human CL region. In one embodiment, the human Fc region comprises IgG1.

In another aspect the invention is directed to a polypeptide comprising a sequence derived from the ICR62 antibody and a sequence derived from a heterologous polypeptide and to an antigen-binding molecule comprising such a polypeptide. In one embodiment the antigen-binding molecule is an antibody. In a preferred embodiment, the antibody is chimeric. In another preferred embodiment, the antibody is humanized or primatized.

In another aspect, the invention is directed to an ABM, which is capable of competing with the rat ICR62 antibody for binding to EGFR and which is chimeric. In one embodiment, the ABM is an antibody or a fragment thereof. In a further embodiment, the ABM is a recombinant antibody comprising a VH region having an amino acid sequence selected from the group consisting of SEQ ID NO: 1; SEQ ID No:3; SEQ ID No:5; SEQ ID No:7; SEQ ID No:9; SEQ ID No:11; SEQ ID No:13; SEQ ID No:15; SEQ ID No:17; SEQ ID No:19; SEQ ID No:21; SEQ ID No:23; SEQ ID No:25; SEQ ID No:27; SEQ ID No:29; SEQ ID No:31; SEQ ID No33; SEQ ID No:35; SEQ ID No:37; SEQ ID No:39; and SEQ ID No:121. In another embodiment, the ABM is a recombinant antibody comprising a VL region having an amino acid sequence selected from the group consisting of SEQ ID NO:43, SEQ ID No:45; SEQ ID No:49; and SEQ ID No:51. In a further embodiment the ABM is a recombinant antibody that is primatized. In yet a further embodiment the ABM is a recombinant antibody that is humanized. In another embodiment, the ABM is a recombinant antibody comprising a human Fc region. In a further embodiment, any of the ABMs discussed above may be conjugated to a moiety such as a toxin or a radiolabel.

The invention is further related to an ABM of the present invention, said ABM having modified oligosaccharides. In one embodiment the modified oligosaccharides have reduced fucosylation as compared to non-modified oligosaccharides. In other embodiments, the modified oligosaccharides are hybrid or complex. In a further embodiment, the ABM has an increased proportion of nonfucosylated oligosaccharides or bisected, nonfucosylated oligosaccharides in the Fc region of said molecule. In one embodiment, the bisected, nonfucosylated oligosaccharides are hybrid. In a further embodiment, the bisected, nonfucosylated oligosaccharides are complex. In a one embodiment, at least 20% of the oligosaccharides in the Fc region of said polypeptide are nonfucosylated or bisected, nonfucosylated. In more preferred embodiments, at least 30%, 35%, 40%, 45%, 50%, 55%, 60%, 65%, 70% or 75% or more of the oligosaccharides are nonfucosylated or bisected, nonfucosylated.

The invention is further related to a polynucleotide encoding any of the ABMs discussed above, and to expression vectors and cells comprising such a polynucleotide.

The invention is further related to a method of producing an ABM, which is capable of competing with the rat ICR62 antibody for binding to EGFR and wherein said ABM is chimeric; said method comprising: (a) culturing a host cell comprising a polynucleotide that encodes an ABM of the present invention in a medium under conditions allowing the expression of said polynucleotide encoding said ABM; and (b) recovering said ABM from the resultant culture.

In another aspect, the invention is related to a pharmaceutical composition comprising the ABM of the invention. It is contemplated that the pharmaceutical composition may further comprise a pharmaceutically acceptable carrier, an adjuvant or a combination thereof.

In a further aspect, the invention is related to a method of treating a disease characterized by expression of EGFR (e.g., abnormal or overexpression of EGFR). The method comprises administering a therapeutically effective amount of the ABM of the present invention to a subject, preferably a mammalian subject, and more preferably a human in need thereof. In a preferred embodiment, the disease is treated by administering an ABM that is a chimeric (e.g. humanized) antibody, or a chimeric fragment of an antibody. In one embodiment, the ABM is administered in an amount of about 1.0 mg/kg to about 15.0 mg/kg. In another embodiment, the ABM is administered in an amount of about 1.5 mg/kg to about 12.0 mg/kg. In a further embodiment, the ABM is administered in an amount of about 1.5 mg/kg to about 4.5 mg/kg. In a further embodiment, the ABM is adminstered in an amount of about 4.5 mg/kg to about 12.0 mg/kg. In a further embodiment, the ABM is administered in an amount selected from the group consisting of about 1.5, about 4.5, and about 12.0 mg/kg.

In yet another aspect, the invention is related to a host cell engineered to express at least one nucleic acid encoding a polypeptide having GnTIII activity in an amount sufficient to modify the oligosaccharides in the Fc region of the ABM produced by the host cell, wherein the ABM is capable of competing with the rat ICR62 antibody for binding to EGFR and wherein the ABM is chimeric. In one embodiment, the polypeptide having GnTIII activity is a fusion polypeptide. In another embodiment, the ABM produced by the host cell is an antibody or an antibody fragment. In one embodiment, the antibody or antibody fragment is humanized. In a further embodiment, the ABM comprises a region equivalent to the Fc region of a human IgG.

The invention is also directed to an isolated polynucleotide comprising at least one (e.g., one, two, three, four, five, or six) complementarity determining region of the rat ICR62 antibody, or a variant or truncated form thereof containing at least the specificity-determining residues for said complementarity determining region, wherein said isolated polynucleotide encodes a fusion polypeptide. Preferably, such isolated polynucleotides encode a fusion polypeptide that is an antigen binding molecule. In one embodiment, the polynucleotide comprises three complementarity determining regions of the rat ICR62 antibody, or variants or truncated forms thereof containing at least the specificity-determining residues for each of said three complementarity determining regions. In another embodiment, the polynucleotide encodes the entire variable region of the light or heavy chain of a chimeric (e.g., humanized) antibody. The invention is further directed to the polypeptides encoded by such polynucleotides.

In another embodiment, the invention is directed to an antigen binding molecule comprising at least one (e.g., one, two, three, four, five, or six) complementarity determining region of the rat ICR62 antibody, or a variant or truncated form thereof containing at least the specificity-determining residues for said complementarity determining region, and comprising a sequence derived from a heterologous polypeptide. In one embodiment, the antigen binding molecule comprises three complementarity determining regions of the rat ICR62 antibody, or variants or truncated forms thereof containing at least the specificity-determining residues for each of said three complementarity determining regions. In another aspect, the antigen binding molecule comprises the variable region of an antibody light or heavy chain. In one particularly useful embodiment, the antigen binding molecule is a chimeric, e.g., humanized, antibody. The invention is also directed to methods of making such antigen binding molecules, and the use of same in the treatment of disease, including malignancies such as cancers of the bladder, brain, head and neck, pancreas, lung, breast, ovary, colon, prostate, skin, and kidney.

The host cell of the present invention may be selected from the group that includes, but is not limited to, an HEK293-EBNA cell, a CHO cell, a BHK cell, a NS0 cell, a SP2/0 cell, a YO myeloma cell, a P3X63 mouse myeloma cell, a PER cell, a PER.C6 cell or a hybridoma cell. In one embodiment, the host cell of the invention further comprises a transfected polynucleotide comprising a polynucleotide encoding the VL region of the rat ICR62 antibody or variants thereof and a sequence encoding a region equivalent to the Fc region of a human immunoglobulin. In another embodiment, the host cell of the invention further comprises a transfected polynucleotide comprising a polynucleotide encoding the VH region of the rat ICR62 antibody or variants thereof and a sequence encoding a region equivalent to the Fc region of a human immunoglobulin.

In a further aspect, the invention is directed to a host cell that produces an ABM that exhibits increased Fc receptor binding affinity and/or increased effector function as a result of the modification of its oligosaccharides. In one embodiment, the increased binding affinity is to an Fc receptor, particularly, the FcγRIIIA receptor. The effector function contemplated herein may be selected from the group that includes, but is not limited to, increased Fc-mediated cellular cytotoxicity; increased binding to NK cells; increased binding to macrophages; increased binding to polymorphonuclear cells; increased binding to monocytes; increased direct signaling inducing apoptosis; increased dendritic cell maturation; and increased T cell priming.

In a further embodiment, the host cell of the present invention comprises at least one nucleic acid encoding a polypeptide having GnTIII activity that is operably linked to a constitutive promoter element.

In another aspect, the invention is directed to a method for producing an ABM in a host cell, comprising: (a) culturing a host cell engineered to express at least one polynucleotide encoding a fusion polypeptide having GnTIII activity under conditions which permit the production of said ABM and which permit the modification of the oligosaccharides present on the Fc region of said ABM; and (b) isolating said ABM; wherein said ABM is capable of competing with the rat ICR62 antibody for binding to EGFR and wherein said ABM is chimeric (e.g., humanized). In one embodiment, the polypeptide having GnTIII activity is a fusion polypeptide, preferably comprising the catalytic domain of GnTIII and the Golgi localization domain of a heterologous Golgi resident polypeptide selected from the group consisting of the localization domain of mannosidase II, the localization domain of β(1,2)-N-acetylglucosaminyltransferase I ("GnTI"), the localization domain of mannosidase I, the localization domain of β(1,2)-N-acetylglucosaminyltransferase II ("GnTII"), and the localization domain of α1-6 core fucosyltransferase. Preferably, the Golgi localization domain is from mannosidase II or GnTI.

In a further aspect, the invention is directed to a method for modifying the glycosylation profile of an anti-EGFR ABM produced by a host cell comprising introducing into the host cell at least one nucleic acid or expression vector of the invention. In one embodiment, the ABM is an antibody or a fragment thereof; preferably comprising the Fc region of an IgG. Alternatively, the polypeptide is a fusion protein that includes a region equivalent to the Fc region of a human IgG.

In one aspect, the invention is related to a recombinant, chimeric antibody, or a fragment thereof, capable of competing with the rat ICR62 antibody for binding to EGFR and having reduced fucosylation.

In another aspect, the present invention is directed to a method of modifying the glycosylation of the recombinant antibody or a fragment thereof of the invention by using a fusion polypeptide having GnTIII activity and comprising the Golgi localization domain of a heterologous Golgi resident polypeptide. In one embodiment, the fusion polypeptides of the invention comprise the catalytic domain of GnTIII. In another embodiment, the Golgi localization domain is selected from the group consisting of: the localization domain of mannosidase II, the localization domain of GnTI, the localization domain of mannosidase I, the localization domain of GnTII and the localization domain of α1-6 core fucosyltransferase. Preferably, the Golgi localization domain is from mannosidase II or GnTI.

In one embodiment, the method of the invention is directed towards producing a recombinant, chimeric antibody or a fragment thereof, with modified oligosaccharides wherein said modified oligosaccharides have reduced fucosylation as compared to non-modified oligosaccharides. According to the present invention, these modified oligosaccharides may be hybrid or complex. In another embodiment, the method of the invention is directed towards producing a recombinant, chimeric (e.g., humanized) antibody or a fragment thereof having an increased proportion of bisected, nonfucosylated oligosaccharides in the Fc region of said polypeptide. In one embodiment, the bisected, nonfucosylated oligosaccharides are hybrid. In another embodiment, the bisected, nonfucosylated oligosaccharides are complex. In a further embodiment, the method of the invention is directed towards producing a recombinant, chimeric antibody or a fragment thereof having at least 20% of the oligosaccharides in the Fc region of said polypeptide that are bisected, nonfucosylated. In a preferred embodiment, at least 30% of the oligosaccharides in the Fc region of said polypeptide are bisected, nonfucosylated. In another preferred embodiment, wherein at least 35% of the oligosaccharides in the Fc region of said polypeptide are bisected, nonfucosylated.

In a further aspect, the invention is directed to a recombinant, chimeric antibody or a fragment thereof, that exhibits increased Fc receptor binding affinity and/or increased effector function as a result of the modification of its oligosaccharides. In one embodiment, the increased binding affinity is to an Fc activating receptor. In a further embodiment, the Fc receptor is Fcγ activating receptor, particularly, the FcγRIIIA receptor. The effector function contemplated herein may be selected from the group that includes, but is not limited to, increased Fc-mediated cellular cytotoxicity; increased binding to NK cells; increased binding to macrophages; increased binding to polymorphonuclear cells; increased binding to monocytes; increased direct signaling inducing apoptosis; increased dendritic cell maturation; and increased T cell priming.

In another aspect, the invention is directed to a recombinant, chimeric (e.g., humanized) antibody fragment, having the binding specificity of the rat ICR62 antibody and containing the Fc region, that is engineered to have increased effector function produced by any of the methods of the present invention.

In another aspect, the present invention is directed to a fusion protein that includes a polypeptide having a sequence selected from the group consisting of SEQ ID NO: 1; SEQ ID No:3; SEQ ID No:5; SEQ ID No:7; SEQ ID No:9; SEQ ID No:11; SEQ ID No:13; SEQ ID No:15; SEQ ID No:17; SEQ ID No:19; SEQ ID No:21; SEQ ID No:23; SEQ ID No:25; SEQ ID No:27; SEQ ID No:29; SEQ ID No:31; SEQ ID No33; SEQ ID No:35; SEQ ID No:37; SEQ ID No:39; and SEQ ID No:121, and a region equivalent to the Fc region of an immunoglobulin and engineered to have increased effector function produced by any of the methods of the present invention.

In another aspect, the present invention is directed to a fusion protein that includes a polypeptide having a sequence selected from the group consisting of SEQ ID NO:43, SEQ ID No:45; SEQ ID No:49; and SEQ ID No:51 and a region equivalent to the Fc region of an immunoglobulin and engineered to have increased effector function produced by any of the methods of the present invention.

In one aspect, the present invention is directed to a pharmaceutical composition comprising a recombinant, chimeric (e.g., humanized) antibody, produced by any of the methods of the present invention, and a pharmaceutically acceptable carrier. In another aspect, the present invention is directed to a pharmaceutical composition comprising a recombinant, chimeric (e.g., humanized) antibody fragment produced by any of the methods of the present invention, and a pharmaceutically acceptable carrier. In another aspect, the present invention is directed to a pharmaceutical composition comprising a fusion protein produced by any of the methods of the present invention, and a pharmaceutically acceptable carrier.

In a further aspect, the invention is directed to a method for targetting in vivo or in vitro cells expressing EGFR. In one embodiment, the present invention is directed to a method for targetting cells expressing EGFR in a subject comprising administering to the subject a composition comprising an ABM of the invention.

In yet another aspect, the present invention is directed to a method for detecting in vivo or in vitro the presence of EGFR in a sample, e.g., for diagnosing a disorder related to EGFR expression. In one embodiment, the detection is performed by contacting a sample to be tested, optionally with a control sample, with an ABM of the present invention, under conditions that allow for formation of a complex between the ABM and EGFR. The complex formation is then detected (e.g., by ELISA or other methods known in the art). When using a control sample with the test sample, any statistically significant difference in the formation of ABM-EGFR complexes when comparing the test and control samples is indicative of the presence of EGFR in the test sample.

The invention is further directed to a method of treating a disorder related to EGFR expression, in particular, a cell proliferation disorder wherein EGFR is expressed, and more particularly, wherein EGFR is abnormally expressed (e.g. overexpressed), including cancers of the bladder, brain, head and neck, pancreas, lung, breast, ovary, colon, prostate, skin, and kidney comprising administering a therapeutically effective amount of the recombinant, chimeric (e.g., humanized) antibody or fragment thereof, produced by any of the methods of the present invention, to a human subject in need thereof.

BRIEF DESCRIPTION OF THE FIGURES

FIG. 10 shows a comparison of ADCC for the non-glycoengineered form (WT) and the G2 glycoform (i.e., glycoengineered by co-expression with GnTIII and ManII) of the humanized ICR62 antibody constructs I-HHB and I-HLA7. The same antibodies were applied to two different target cell lines: in Panel A, the target cell line LN229 was used; in Panel B, the cell line A431 was used. The humanzied heavy chain constructs were paired with the I-KC light chain construct.

Figure 13:
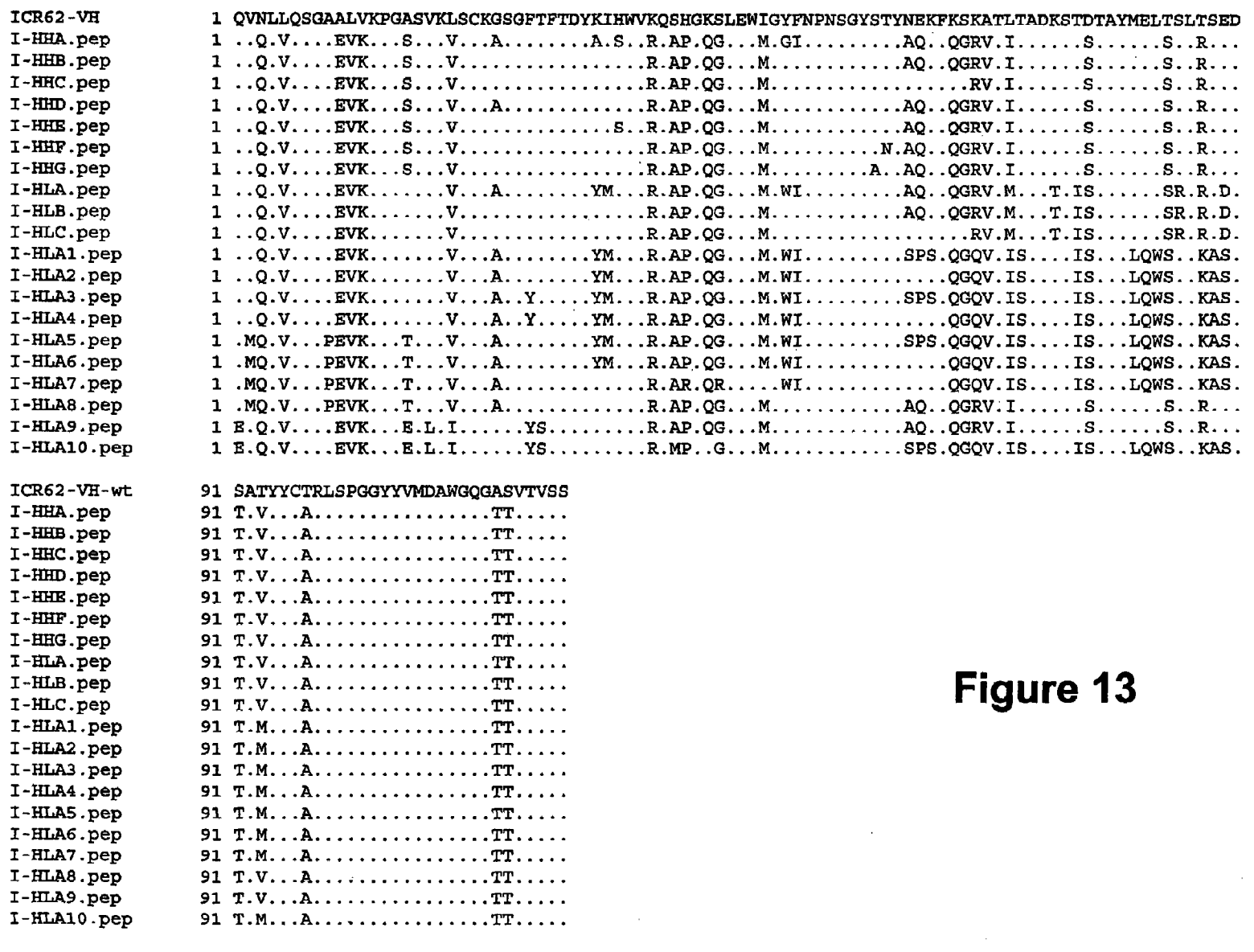

FIG. 13 shows an amino acid sequence alignment of humanized ICR62 heavy chain variable region constructs compared to the rat ICR62 sequences. Dots represent identity of amino acid residues at a given position within a given construct.

DETAILED DESCRIPTION OF THE INVENTION

Figure 1:
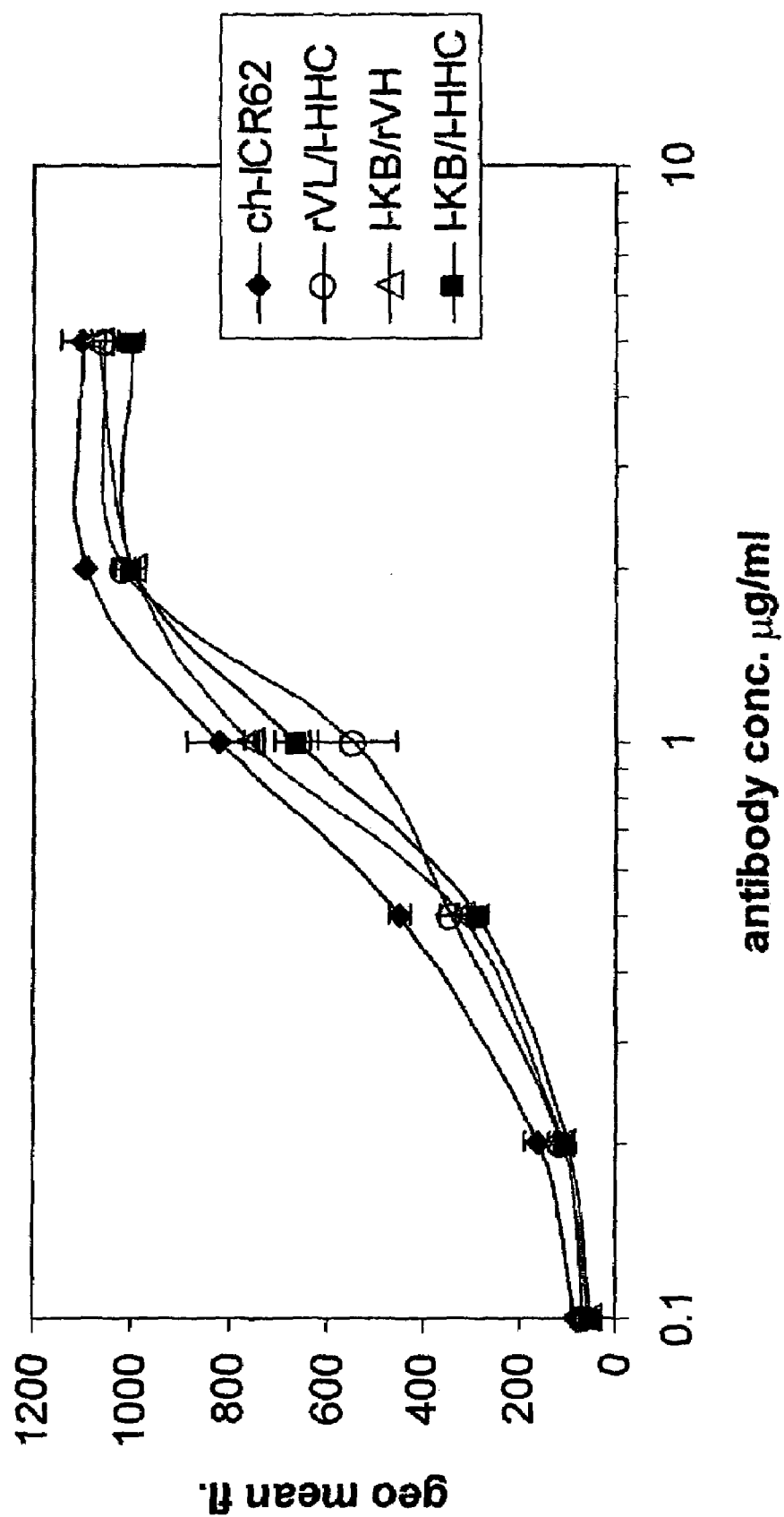
FIG. 1 shows the functional activity of individual heavy and light chimeric rat-human ICR62 polypeptide chains when combined with the humanized ICR62 constructs I-HHC (heavy chain) and I-KB (light chain). rVL represents the chimeric light chain, and rVH represents the chimeric heavy chain. The "r" designation indicates that the variable domains are from the original rat antibody.

Terms are used herein as generally used in the art, unless otherwise defined as follows.

As used herein, the term antibody is intended to include whole antibody molecules, including monoclonal, polyclonal and multispecific (e.g., bispecific) antibodies, as well as antibody fragments having the Fc region and retaining binding specificity, and fusion proteins that include a region equivalent to the Fc region of an immunoglobulin and that retain binding specificity. Also encompassed are antibody fragments that retain binding specificity including, but not limited to, VH fragments, VL fragments, Fab fragments, F(ab')$_2$ fragments, scFv fragments, Fv fragments, minibodies, diabodies, triabodies, and tetrabodies (see, e.g., Hudson and Souriau, Nature Med. 9: 129-134 (2003)). Also encompassed are humanized, primatized and chimeric antibodies.

As used herein, the term Fc region is intended to refer to a C-terninal region of an IgG heavy chain. Although the boundaries of the Fc region of an IgG heavy chain might vary slightly, the human IgG heavy chain Fc region is usually defined to stretch from the amino acid residue at position Cys226 to the carboxyl-terminus.

As used herein, the term region equivalent to the Fc region of an immunoglobulin is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody dependent cellular cytotoxicity). For example, one or more amino acids can be deleted from the N-terminus or C-terminus of the Fc region of an irnmunoglobulin without substantial loss of biological function. Such variants can be selected according to general rules known in the art so as to have minimal effect on activity. (See, e.g., Bowie, J. U. et al., *Science* 247:1306-1310 (1990).

As used herein, the term EGFR refers to the human epidermal growth factor receptor (also known as HER-1 or Erb-B1) (Ulrich, A. et al., *Nature* 309:418-425 (1984); SwissProt Accession #P00533; secondary accession numbers: O00688, O00732, P06268, Q14225, Q92795, Q9BZS2, Q9GZX1, Q9H2C9, Q9H3C9, Q9UMD7, Q9UMD8, Q9UMG5), as well as naturally-occurring isoforms and variants thereof. Such isoforms and variants include but are not limited to the EGFRvIII variant, alternative splicing products (e.g., as identified by SwissProt Accession numbers P00533-1, P00533-2, P00533-3, P00533-4), variants GLN-98, ARG-266, Lys-521, ILE-674, GLY-962, and PRO-988 (Livingston, R. J. et al., NIEHS-SNPs, environmental genome project, NIEHS ES15478, Department of Genome Sciences, Seattle, Wash. (2004)), and others identified by the following accession numbers: NM_005228.3, NM_201282.1, NM_201283.1, NM_201284.1 (REFSEQ mRNAs); AF125253.1, AF277897.1, AF288738.1, AI217671.1, AK127817.1, AL598260.1, AU137334.1, AW163038.1, AW295229.1, BC057802.1, CB160831.1, K03193.1, U48722.1, U95089.1, X00588.1, X00663.1; H54484S1, H54484S3, H54484S2 (MIPS assembly); DT.453606, DT.86855651, DT.95165593, DT.97822681, DT.95165600, DT.100752430, DT.91654361, DT.92034460, DT.92446349, DT.97784849, DT.101978019, DT.418647, DT.86842167, DT.91803457, DT.92446350, DT.95153003, DT.95254161, DT.97816654, DT.87014330, DT.87079224 (DOTS Assembly).

As used herein, the term EGFR ligand refers to a polypeptide which binds to and/or activates EGFR. The term includes membrane-bound precursor forms of the EGFR ligand, as well as proteolytically processed soluble forms of the EGFR ligand.

As used herein, the term ligand activation of EGFR refers to signal transduction (e.g., that caused by an intracellular kinase domain of EGFR receptor phosphorylating tyrosine residues in the EGFR or a substrate polypeptide) mediated by EGFR ligand binding.

As used herein, the term disease or disorder characterized by abnormal activation or production of EGFR or an EGFR ligand or disorder related to EGFR expression, refers to a condition, which may or may not involve malignancy or cancer, where abnormal activation and/or production of EGFR and/or an EGFR ligand is occurring in cells or tissues of a subject having, or predisposed to, the disease or disorder.

As used herein, the terms overexpress, overexpressed, and overexpressing, as used in connection with cells expressing EGFR, refer to cells which have measurably higher levels of EGFR on the surface thereof compared to a normal cell of the same tissue type. Such overexpression may be caused by gene amplification or by increased transcription or translation. EGFR expression (and, hence, overexpression) may be determined in a diagnostic or prognostic assay by evaluating levels of EGFR present on the suface of a cell or in a cell lysate by techniques that are known in the art: e.g., via an immunohistochemistry assay, immunofluorescence assay, immunoenzyme assay, ELISA, flow cytometry, radioimmunoassay, Western blot, ligand binding, kinase activity, etc. (See generally, CELL BIOLOGY: A LABORATORY HANDBOOK, Celis, J., ed., Academic Press (2d ed., 1998); CURRENT PROTOCOLS IN PROTEIN SCIENCE, Coligan, J. E. et al., eds., John Wiley & Sons (1995-2003); see also, Sumitomo et al., *Clin. Cancer Res.* 10: 794-801 (2004) (describing Western blot, flow cytometry, and immunohistochemstry) the entire contents of which are herein incorporated by reference)). Alternatively, or additionally, one may measure levels of EGFR-encoding nucleic acid molecules in the cell, e.g., via fluorescent in situ hybridization, Southern blotting, or PCR techniques. The levels of EGFR in normal cells are compared to the levels of cells affected by a cell proliferation disorder (e.g., cancer) to determine if EGFR is overexpressed.

As used herein, the term antigen binding molecule refers in its broadest sense to a molecule that specifically binds an antigenic determinant. More specifically, an antigen binding molecule that binds EGFR is a molecule which specifically binds to a transmembrane receptor of 170 kDa, typically designated as the epidermal growth factor receptor (EGFR), but also known as HER-1 or ErbB1. By "specifically binds" is meant that the binding is selective for the antigen and can be discriminated from unwanted or nonspecific interactions.

As used herein, the terms fusion and chimeric, when used in reference to polypeptides such as ABMs refer to polypeptides comprising amino acid sequences derived from two or more heterologous polypeptides, such as portions of antibodies from different species. For chimeric ABMs, for example, the non-antigen binding components may be derived from a wide variety of species, including primates such as chimpanzees and humans. The constant region of the chimeric ABM is most preferably substantially identical to the constant region of a natural human antibody; the variable region of the chimeric antibody is most preferably substantially identical to that of a recombinant anti-EGFR antibody having the amino acid sequence of the murine variable region. Humanized antibodies are a particularly preferred form of fusion or chimeric antibody.

As used herein, a polypeptide having GnTIII activity refers to polypeptides that are able to catalyze the addition of a N-acetylglucosamine (GlcNAc) residue in β-1-4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependence in a given activity as compared to the GnTIII (i.e., the candidate polypeptide will exhibit greater activity or not more than about 25-fold less and, preferably, not more than about tenfold less activity, and most preferably, not more than about three-fold less activity relative to the GnTIII.)

As used herein, the term variant (or analog) refers to a polypeptide differing from a specifically recited polypeptide of the invention by amino acid insertions, deletions, and substitutions, created using, e g., recombinant DNA techniques. Variants of the ABMs of the present invention include chimeric, primatized or humanized antigen binding molecules wherein one or several of the amino acid residues are modified by substitution, addition and/or deletion in such manner that does not substantially affect antigen (e.g., EGFR) binding affinity. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

As used herein, the term humanized is used to refer to an antigen-binding molecule derived from a non-human antigen-binding molecule, for example, a murine antibody, that retains or substantially retains the antigen-binding properties of the parent molecule but which is less immunogenic in humans. This may be achieved by various methods including (a) grafting the entire non-human variable domains onto human constant regions to generate chimeric antibodies, (b) grafting only the non-human CDRs onto human framework and constant regions with or without retention of critical framework residues (e.g., those that are important for retaining good antigen binding affinity or antibody functions), or (c) transplanting the entire non-human variable domains, but "cloaking" them with a human-like section by replacement of surface residues. Such methods are disclosed in Jones et al., Morrison et al., *Proc. Natl. Acad. Sci.*, 81:6851-6855 (1984); Morrison and Oi, *Adv. Immunol.*, 44:65-92 (1988); Verhoeyen et al., Science, 239:1534-1536 (1988); Padlan, *Molec. Immun.*, 28:489-498 (1991); Padlan, *Molec. Immun.*, 31(3): 169-217 (1994), all of which are incorporated by reference in their entirety herein. There are generally 3 complementarity determining regions, or CDRs, (CDR1, CDR2 and CDR3) in each of the heavy and light chain variable domains of an antibody, which are flanked by four framework subregions (i.e., FR1, FR2, FR3, and FR4) in each of the heavy and light chain variable domains of an antibody: FR1-CDR1-FR2-CDR2-FR3-CDR3-FR4. A discussion of humanized antibodies can be found, inter alia, in U.S. Pat. No. 6,632,927, and in published U.S. Application No. 2003/0175269, both of which are incorporated herein by reference in their entirety.

Similarly, as used herein, the term primatized is used to refer to an antigen-binding molecule derived from a non-primate antigen-binding molecule, for example, a murine antibody, that retains or substantially retains the antigen-binding properties of the parent molecule but which is less immunogenic in primates.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| | CDR Definitions[1] | | |
|---|---|---|---|
| | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1] Numbering of all CDR definitions in Table 1 is according to the numbering conventions set forth by Kabat et al. (see below).
[2] "AbM" refers to the CDRs as defined by Oxford Molecular's "AbM" antibody modeling software.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an ABM are according to the Kabat numbering system. The sequences of the sequence listing (i.e., SEQ ID NO:1 to SEQ ID NO:127) are not numbered according to the Kabat numbering system. However, as stated above, it is well within the ordinary skill of one in the art to determine the Kabat numbering scheme of any variable region sequence in the Sequence Listing based on the numbering of the sequences as presented therein.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polypeptide is at least 80%, 85%, 90%, 95%, 96%, 97%, 98% or 99% identical to a nucleotide sequence or polypeptide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237-245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to a reference polypeptide can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score.

That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

As used herein, a nucleic acid that "hybridizes under stringent conditions" to a nucleic acid sequence of the invention, refers to a polynucleotide that hybridizes in an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

As used herein, the term Golgi localization domain refers to the amino acid sequence of a Golgi resident polypeptide which is responsible for anchoring the polypeptide in location within the Golgi complex. Generally, localization domains comprise amino terminal "tails" of an enzyme.

As used herein, the term effector function refers to those biological activities attributable to the Fc region (a native sequence Fc region or amino acid sequence variant Fc region) of an antibody. Examples of antibody effector functions include, but are not limited to, Fc receptor binding affinity, antibody-dependent cellular cytotoxicity (ADCC), antibody-dependent cellular phagocytosis (ADCP), cytokine secretion, immune-complex-mediated antigen uptake by antigen-presenting cells, down-regulation of cell surface receptors, etc.

As used herein, the terms engineer, engineered, engineering and glycosylation engineering are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

As used herein, the term host cell covers any kind of cellular system which can be engineered to generate the polypeptides and antigen-binding molecules of the present invention. In one embodiment, the host cell is engineered to allow the production of an antigen binding molecule with modified glycoforns. In a preferred embodiment, the antigen binding molecule is an antibody, antibody fragment, or fusion protein. In certain embodiments, the host cells have been further manipulated to express increased levels of one or more polypeptides having GnTIII activity. Host cells include cultured cells, e.g., mammalian cultured cells, such as CHO cells, HEK293-EBNA cells, BHK cells, NS0 cells, SP2/0 cells, YO myeloma cells, P3X63 mouse myeloma cells, PER cells, PER.C6 cells or hybridoma cells, yeast cells; insect cells, and plant cells, to name only a few, but also cells comprised within a transgenic animal, transgenic plant or cultured plant or animal tissue.

As used herein, the term Fc-mediated cellular cytotoxicity includes antibody-dependent cellular cytotoxicity and cellular cytotoxicity mediated by a soluble Fc-fusion protein containing a human Fc-region. It is an immune mechanism leading to the lysis of "antibody-targeted cells" by "human immune effector cells", wherein:

The human immune effector cells are a population of leukocytes that display Fc receptors on their surface through which they bind to the Fc-region of antibodies or of Fc-fusion proteins and perform effector functions. Such a population may include, but is not limited to, peripheral blood mononuclear cells (PBMC) and/or natural killer (NK) cells.

The antibody-targeted cells are cells bound by the antibodies or Fc-fusion proteins. The antibodies or Fc fusion-proteins bind to target cells via the protein part N-terminal to the Fc region.

As used herein, the term increased Fc-mediated cellular cytotoxicity is defined as either an increase in the number of "antibody-targeted cells" that are lysed in a given time, at a given concentration of antibody, or of Fc-fusion protein, in the medium surrounding the target cells, by the mechanism of Fc-mediated cellular cytotoxicity defined above, and/or a reduction in the concentration of antibody, or of Fc-fusion protein, in the medium surrounding the target cells, required to achieve the lysis of a given number of "antibody-targeted cells", in a given time, by the mechanism of Fc-mediated cellular cytotoxicity. The increase in Fc-mediated cellular cytotoxicity is relative to the cellular cytotoxicity mediated by the same antibody, or Fc-fusion protein, produced by the same type of host cells, using the same standard production, purification, formulation and storage methods, which are known to those skilled in the art, but that has not been produced by host cells engineered to express the glycosyltransferase GnTIII by the methods described herein.

By antibody having increased antibody dependent cellular cytotoxicity (ADCC) is meant an antibody, as that term is defined herein, having increased ADCC as determined by any suitable method known to those of ordinary skill in the art. One accepted in vitro ADCC assay is as follows:
1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
  i) the PBMCs are isolated using standard density centrifugation procedures and are suspended at $5 \times 10^6$ cells/ml in RPMI cell culture medium;
  ii) the target cells are grown by standard tissue culture methods, harvested from the exponential growth phase with a viability higher than 90%, washed in RPMI cell culture medium, labeled with 100 micro-Curies of 51Cr, washed twice with cell culture medium, and resuspended in cell culture medium at a density of 105 cells/ml;

iii) 100 microliters of the final target cell suspension above are transferred to each well of a 96-well microtiter plate;

iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;

v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);

vi) for the spontaneous release (SR) controls, 3 additional wells in the plate containing the labeled target cells, receive 50 microliters of RPMI cell culture medium instead of the antibody solution (point iv above);

vii) the 96-well microtiter plate is then centrifuged at 50×g for 1 minute and incubated for 1 hour at 4° C.;

viii) 50 microliters of the PBMC suspension (point i above) are added to each well to yield an effector:target cell ratio of 25:1 and the plates are placed in an incubator under 5% $CO_2$ atmosphere at 37° C. for 4 hours;

ix) the cell-free supernatant from each well is harvested and the experimentally released radioactivity (ER) is quantified using a gamma counter;

x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

In one aspect, the present invention is related to antigen binding molecules having the binding specificity of the rat ICR62 (i.e., binds to substantially the same epitope), and to the discovery that their effector functions can be enhanced by altered glycosylation. In one embodiment, the antigen binding molecule is a chimeric antibody. In a preferred embodiment, the invention is directed to a chimeric antibody, or a fragment thereof, comprising one or more (e.g., one, two, three, four, five, or six) of the CDRs of any of SEQ ID NOs:53-108 and/or SEQ ID NO:s 122-127. Specifically, in a preferred embodiment, the invention is directed to an isolated polynucleotide comprising: (a) a sequence selected from a group consisting of: SEQ ID NO:54 SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:122, and SEQ ID NO:124; (b) a sequence selected from a group consisting of: SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, and SEQ ID NO:126; and (c) SEQ ID NO:108. In another preferred embodiment, the invention is directed to an isolated polynucleotide comprising (a) a sequence selectd from the group consisting of SEQ ID NO:112 and SEQ ID NO:114; (b) a sequence selectd from the group consisting of SEQ ID NO:116 and SEQ ID NO:118; and (c) SEQ ID NO:119. In one embodiment, any of these polynucleotides encodes a fusion polypeptide.

In another embodiment, the antigen binding molecule comprises the $V_H$ domain of the rat ICR62 antibody encoded by SEQ ID NO:1 or SEQ ID NO:2, or a variant thereof; and a non-murine polypeptide. In another preferred embodiment, the invention is directed to an antigen binding molecule comprising the $V_L$ domain of the rat antibody encoded by SEQ ID NO:43 or SEQ ID NO:44, or a variant thereof; and a non-murine polypeptide.

In another aspect, the invention is directed to antigen binding molecules comprising one or more (e.g., one, two, three, four, five, or six) truncated CDRs of ICR62. Such truncated CDRs will contain, at a minimum, the specificity-determining amino acid residues for the given CDR. By "specificity-determining residue" is meant those residues that are directly involved in the interaction with the antigen. In general, only about one-fifth to one-third of the residues in a given CDR participate in binding to antigen. The specificity-determining residues in a particular CDR can be identified by, for example, computation of interatomic contacts from three-dimensional modeling and determination of the sequence variability at a given residue position in accordance with the methods described in Padlan et al., *FASEB J.* 9(1):133-139 (1995), the contents of which is hereby incorporated by reference in their entirety.

Accordingly, the invention is also directed to an isolated polynucleotide comprising at least one (e.g., one, two, three, four, five, or six) complementarity determining region of the rat ICR62 antibody, or a variant or truncated form thereof containing at least the specificity-determining residues for said complementarity determining region, wherein said isolated polynucleotide encodes a fusion polypeptide. Preferably, such isolated polynucleotides encode a fusion polypeptide that is an antigen binding molecule. In one embodiment, the polynucleotide comprises three complementarity determining regions of the rat ICR62 antibody, or variants or truncated forms thereof containing at least the specificity-determining residues for each of said three complementarity determining regions. In one embodiment, the polynucleotide comprises at least one of the CDRs set forth in Tables 2-5, below. In another embodiment, the polynucleotide encodes the entire variable region of the light or heavy chain of a chimeric (e.g., humanized) antibody. The invention is further directed to the polypeptides encoded by such polynucleotides.

In another embodiment, the invention is directed to an antigen binding molecule comprising at least one (e.g., one, two, three, four, five, or six) complementarity determining region of the rat ICR62 antibody, or a variant or truncated form thereof containing at least the specificity-determining residues for said complementarity determining region, and comprising a sequence derived from a heterologous polypeptide. In one embodiment, the antigen binding molecule comprises three complementarity determining regions of the rat ICR62 antibody, or variants or truncated forms thereof containing at least the specificity-determining residues for each of said three complementarity determining regions. In one embodiment, the antigen binding molecule comprises at least one of the CDRs set forth in Tables 2-5, below. In another aspect, the antigen binding molecule comprises the variable region of an antibody light or heavy chain. In one particularly usefull embodiment, the antigen binding molecule is a chimeric, e.g., humanized, antibody. The invention is also directed to methods of making such antigen binding molecules, and the use of same in the treatment of disease, particularly cell proliferation disorders wherein EGFR is expressed, particularly wherein EGFR is abnormally expressed (e.g., overexpressed) compared to normal tissue of the same cell type. Such disorders include, but are not limited to cancers of the bladder, brain, head and neck, pancreas, lung, breast, ovary, colon, prostate, skin, and kidney. EGFR expression levels may be determined by methods known in the art and those described herein (e.g., via immunohistochemistry assay, immunofluorescence assay, immunoenzyme assay, ELISA, flow cytometry, radioimmunoassay, Western blot, ligand binding, kinase activity, etc.).

The invention is also directed to a method for targeting in vivo or in vitro cells expressing EGFR. Cells that express EGFR may be targeted for therapuetic purposes (e.g., to treat a disorder that is treatable by disruption of EGFR-mediated signaling, for example by blocking ligand binding, or by targeting EGFR-expressing cells for destruction by the immune system). In one embodiment, the present invention is directed to a method for targeting cells expressing EGFR in a subject comprising administering to the subject a composition comprising an ABM of the invention. Cells that express EGFR may also be targeted for diagnositic purposes (e.g., to determine if they are expressing EGFR, either normally or abnormally). Thus, the invention is also directed to methods for detecting the presence of EGFR or a cell expressing EGFR, either in vivo or in vitro. One method of detecting EGFR expression according to the present invention comprises contacting a sample to be tested, optionally with a control sample, with an ABM of the present invention, under conditions that allow for formation of a complex between the ABM and EGFR. The complex formation is then detected (e.g., by ELISA or other methods known in the art). When using a control sample with the test sample, any statistically significant difference in the formation of ABM-EGFR complexes when comparing the test and control samples is indicative of the presence of EGFR in the test sample.

TABLE 2

| CDR | Nucleotide Sequence | SEQ ID NO |
| --- | --- | --- |
| Heavy Chain CDR1 | | |
| Kabat | GACTACAAGATACAC | 54 |
| | GACTACGCCATCAGC | 56 |
| | GACTACTATATGCAC | 58 |
| | GACTACAAGATATCC | 122 |
| Chothia | GGTTTTACATTCACTGACTAC | 60 |
| | GGTTACACATTCACTGACTAC | 62 |
| | GGTTATTCATTCACTGACTAC | 64 |
| AbM | GGTTTTACATTCACTGACTACAAGATACAC | 66 |
| | GGTTTTACATTCACTGACTACGCCATCAGC | 68 |
| | GGTTTTACATTCACTGACTACTATATGCAC | 70 |
| | GGTTACACATTCACTGACTACTATATGCAC | 72 |
| | GGTTATTCATTCACTGACTACAAGATACAC | 74 |
| | GGTTTCACATTCACTGACTACAAGATATCC | 124 |

TABLE 2-continued

| CDR | Nucleotide Sequence | SEQ ID NO |
| --- | --- | --- |
| Heavy Chain CDR2 | | |
| Kabat | TATTTTAATCCTAACAGTGGTTATAGTACCTACAATGAAAAGTTCAAGAGC | 76 |
| | GGGATCAATCCTAACAGTGGTTATAGTACCTACGCACAGAAGTTCCAGGGC | 78 |
| | TATTTCAACCCTAACAGCGGTTATAGTACCTACGCACAGAAGTTCCAGGGC | 80 |
| | TGGATCAATCCTAACAGTGGTTATAGTACCTACGCACAGAAGTTTCAGGGC | 82 |
| | TGGATCAATCCTAACAGTGGTTATAGTACCTACAGCCCAAGCTTCCAAGGC | 84 |
| | TGGATCAATCCTAACAGTGGTTATAGTACCTACAACGAGAAGTTCCAAGGC | 86 |
| | TATTTCAACCCTAACAGCGGTTATTCGAACTACGCACAGAAGTTCCAGGGC | 88 |
| | TATTTCAACCCTAACAGCGGTTATGCCACGTACGCACAGAAGTTCCAGGGC | 90 |
| | TACTTCAATCCTAACAGTGGTTATAGTACCTACAGCCCAAGCTTCCAAGGC | 126 |
| Chothia | AATCCTAACAGTGGTTATAGTACC | 92 |
| | AACCCTAACAGCGGTTATTCGAAC | 94 |
| | AACCCTAACAGCGGTTATGCCACG | 96 |
| AbM | TATTTTAATCCTAACAGTGGTTATAGTACC | 98 |
| | GGGATCAATCCTAACAGTGGTTATAGTACC | 100 |
| | TGGATCAATCCTAACAGTGGTTATAGTACC | 102 |
| | TATTTCAACCCTAACAGCGGTTATTCGAAC | 104 |
| | TATTTCAACCCTAACAGCGGTTATGCCACG | 106 |
| Heavy Chain CDR3 | | |
| Kabat Chothia AbM | CTATCCCCAGGCGGTTACTATGTTATGGATGCC | 108 |

TABLE 3

| CDR | Amino Acid Sequence | SEQ ID NO |
| --- | --- | --- |
| Heavy Chain CDR1 | | |
| Kabat | DYKIH | 53 |
| | DYAIS | 55 |
| | DYYMH | 57 |
| | DYKIS | 123 |
| Chothia | GFTFTDY | 59 |
| | GYTFTDY | 61 |
| | GYSFTDY | 63 |
| AbM | GFTFTDYKIH | 65 |
| | GFTFTDYAIS | 67 |
| | GFTFTDYYMH | 69 |
| | GYTFTDYYMH | 71 |
| | GYSFTDYKIH | 73 |
| | GFTFTDYKIS | 125 |
| Heavy Chain CDR2 | | |
| Kabat | YFNPNSGYSTYNEKFKS | 75 |
| | GINPNSGYSTYAQKFQG | 77 |
| | YFNPNSGYSTYAQKFQG | 79 |

TABLE 3-continued

| CDR | Amino Acid Sequence | SEQ ID NO |
|---|---|---|
| | WINPNSGYSTYAQKFQG | 81 |
| | WINPNSGYSTYSPSFQG | 83 |
| | WINPNSGYSTYNEKFQG | 85 |
| | YFNPNSGYSNYAQKFQG | 87 |
| | YFNPNSGYATYAQKFQG | 89 |
| | YFNPNSGYSTYSPSFQG | 127 |
| Chothia | NPNSGYST | 91 |
| | NPNSGYSN | 93 |
| | NPNSGYAT | 95 |
| AbM | YFNPNSGYST | 97 |
| | GINPNSGYST | 99 |
| | WINPNSGYST | 101 |
| | YFNPNSGYSN | 103 |
| | YFNPNSGYAT | 105 |
| Heavy Chain CDR3 | | |
| Kabat Chothia AbM | LSPGGYYVMDA | 107 |

TABLE 4

| CDR | Amino Acid Sequence | SEQ ID NO |
|---|---|---|
| Kabat Light Chain CDR1 | KASQNINNYLN | 111 |
| | RASQGINNYLN | 113 |
| Kabat Light Chain CDR2 | NTNNLQT | 115 |
| Kabat Light Chain CDR3 | LQHNSFPT | 117 |

TABLE 5

| CDR | Nucleotide Sequence | SEQ ID NO |
|---|---|---|
| Kabat Light Chain CDR1 | AAAGCAAGTCAGAATATTAAC AATTACTTAAAC | 112 |
| | CGGGCAAGTCAGGGCATTAACA ATTACTTAAAT | 114 |
| Kabat Light Chain CDR2 | AATACAAACAATTTGCAAACA | 116 |
| | AATACCAACAACTTGCAGACA | 118 |
| Kabat Light Chain CDR3 | TTGCAGCATAATAGTTTTCCCA CG | 119 |

It is known that several mechanism are involved in the therapeutic efficacy of anti-EGFR antibodies, including blocking of ligand (e.g., EGF, TGF-α, etc.) binding to EGFR and subsequent activation of signaling pathways, antibody dependent cellular cytotoxicity (ADCC), and the induction of growth arrest or terminal differentiation.

The rat monoclonal antibody ICR62 (IgG2b) was discussed in PCT Publication No. WO 95/20045, which is incorporated herein by reference in its entirety. It was directed to the C epitope of EGFR, and was shown to inhibit ligand binding, inhibit growth in vitro of squamous cell carcinomas expressing EGFR, and induce regression of xenografts of tumors in athymic mice (WO 95/20045; Modjtahedi et al., *Br. J. Cancer* 73:228-235 (1996)). As a fully rodent antibody, administration of ICR62 rat monoclonal antibody to humans resulted a HARA response in some patients following even a single dose. (WO 95/20045; Modjtahedi et al., *Br. J. Cancer* 73:228-235 (1996)).

Chimeric mouse/human antibodies have been described. See, for example, Morrison, S. L. et al., *PNAS* 11:6851-6854 (November 1984); European Patent Publication No. 173494; Boulianna, G. L, et al., *Nature* 312:642 (December 1984); Neubeiger, M. S. et al., *Nature* 314:268 (March 1985); European Patent Publication No. 125023; Tan et al., *J. Immunol.* 135:8564 (November 1985); Sun, L. K et al., *Hybridoma* 5(1):517 (1986); Sahagan et al., *J. Immunol.* 137:1066-1074 (1986). See generally, Muron, *Nature* 312:597 (December 1984); Dickson, *Genetic Engineering News* 5(3) (March 1985); Marx, *Science* 229:455 (August 1985); and Morrison, *Science* 229:1202-1207 (September 1985). IMC-C225 (Erbitux®, Imclone) is a chimeric monoclonal antibody directed against EGFR and having a mouse variable region and a human constant region (See Herbst and Shin, *Cancer* 94: 1593-1611 (2002)). The murine portion of IMC-225 is derived from M225, which was found to bind EGFR and inhibit EGF-induced tyrosine kinase-dependent phosphorylation, as well as inducing apoptosis in tumor cell lines overexpressing EGFR (Herbst and Shin, *Cancer* 94: 1593-1611 (2002)). However, M225 elicited a HAMA reaction in patients treated with the antibody in Phase I clinical trials (Herbst and Shin, *Cancer* 94: 1593-1611 (2002)). IMC-225 has been tested in vivo and in vitro, and has been used in combination with radiation therapy and chemotherapy in a number of tumor types, including those associated with poor prognosis (Herbst and Shin, *Cancer* 94: 1593-1611 (2002)). However, IMC-225 has been associated with toxicities such as allergic and skin reactions in patients administered the IMC-225 antibody in clincial trials (Herbst and Shin, *Cancer* 94: 1593-1611 (2002)).

In a particularly preferred embodiment, the chimeric ABM of the present invention is a humanized antibody. Methods for humanizing non-human antibodies are known in the art. For example, humanized ABMs of the present invention can be prepared according to the methods of U.S. Pat. No. 5,225,539 to Winter, U.S. Pat. No. 6,180,370 to Queen et al., U.S. Pat. No. 6,632,927 to Adair et al., or U.S. Pat. Appl. Pub. No. 2003/0039649 to Foote, the entire contents of each of which is herein incorporated by reference. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321: 522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies. The subject humanized anti-EGFR antibodies will comprise constant regions of human immunoglobulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method of selecting the human framework sequence is to compare the sequence of each individual subregion of the full rodent framework (i.e., FR1, FR2, FR3, and FR4) or some combination of the individual subregions (e.g., FR1 and FR2) against a library of known human variable region sequences that correspond to that framework subregion (e.g., as determined by Kabat numbering), and choose the human sequence for each subregion or combination that is the closest to that of the rodent (Leung, U.S. Patent Application Publication No. 2003/0040606A1, published Feb. 27, 2003) (the entire contents of which are hereby incorporated by reference). Another method uses a particular framework region derived from the consensus sequence of all human antibodies of a particular subgroup of light or heavy chains. The same framework may be used for several different humanized antibodies (Carter et al., *Proc. Natl. Acad. Sci.* USA, 89:4285 (1992); Presta et al., *J Immunol.*, 151:2623 (1993)) (the entire contents of each of which are herein incorporated by reference).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models can be generated using computer programs familiar to those skilled in the art (e.g., InsightII, Accelrys, Inc. (formerly MSI), or SWISS-MODEL). These computer programs can illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In one embodiment, the antibodies of the present invention comprise a human Fc region. In a specific embodiment, the human constant region is IgG1, as set forth in SEQ ID NOs 109 and 110, and set forth below:

IgG1 Nucleotide Sequence (SEQ ID NO:110)

ACCAAGGGCCCATCGGTCTTCCCCCTG-GCACCCTCCTCCAAGAGCACCTCTGG GGGCA-CAGCGGCCCTGGGCTGCCTGGTCAAG-GACTACTTCCCCGAACCGGTG ACGGTGTCGTGGAACTCAGGCGCCCT-GACCAGCGGCGTGCACACCTTCCCGG CTGTCCTA-CAGTCCTCAGGACTCTACTCCCTCAG-CAGCGTGGTGACCGTGCCC TCCAGCAGCTTGGGCACCCAGACCTA-CATCTGCAACGTGAATCACAAGCCCA GCAACAC-CAAGGGTGGACAAGAAAGCAGAGC-CCAAATCTTGTGACAAAACTC ACACATGCCCACCGTGCCCAGCACCT-GAACTCCTGGGGGGACCGTCAGTCTTC CTCTTC-CCCCCAAAACCCAAGGACACCCTCAT-GATCTCCCGGACCCCTGAGGT CACATGCGTGGTGGTGGACGTGAGCCAC-GAAGACCCTGAGGTCAAGTTCAAC TGGTACGTG-GACGGCGTGGAGGTGCATAATGCCAAGA-CAAAGCCGCGGGAG GAGCAGTACAACAGCACGTACCGTGTG-GTCAGCGTCCTCACCGTCCTGCACC AGGACTGGCT-GAATGGCAAGGAGTACAAGTGCAAG-GTCTCCAACAAAGCCCT CCCAGCCCCCATCGAGAAAACCATCTC-CAAAGCCAAAGGGCAGCCCCGAGAA CCACAGGT-GTACACCCTGCCCCCATCCCGGGAT-GAGCTGACCAAGAACCAGG TCAGCCTGACCTGCCTGGTCAAAGGCT-TCTATCCCAGCGACATCGCCGTGGAG TGGGAGAG-CAATGGGCAGCCGGAGAACAACTACAA-GACCACGCCTCCCGTGC TGGACTCCGACGGCTCCTTCTTCCTCTA-CAGCAAGCTCACCGTGGACAAGAGC AGGTGGCAG-CAGGGGAACGTCTTCTCATGCTCCGT-GATGCATGAGGCTCTGC ACAACCACTACACGCAGAAGAGCCTCTC-CCTGTCTCCGGGTAAATGA

IgG1 Amino Acid Sequence (SEQ ID NO:109)

TKGPSVFPLAPSSKSTSGGTAALG-CLVKDYFPEPVTVSWNSGALTSGVHTFPAVL QSS-GLYSLSSVVTVPSSSLGTQTYICNVNH-KPSNTKVDKKAEPKSCDKTHTCPPCP APELLGGPSVFLFPPKPKDTLMISRTPE-VTCVVVDVSHEDPEVKFNWYVDGVEVH NAKTK-PREEQYNSTYRVVSVLTVLHQDWL-NGKEYKCKVSNKALPAPIEKTISKA KGQPREPQVYTLPPSRDELTKNQVSLT-CLVKGFYPSDIAVEWESNGQPENNYKTT PPVLDS-DGSFFLYSKLTVDKSRWQQGNVFSCSVM-HEALHNHYTQKSLSLSPGK

However, variants and isoforms of the human Fc region are also encompassed by the present invention. For example, variant Fc regions suitable for use in the present invention can be produced according to the methods taught in U.S. Pat. No. 6,737,056 to Presta (Fc region variants with altered effector function due to one or more amino acid modifications); or in U.S. Pat. Appl. Nos. 60/439,498; 60/456,041; 60/514,549; or WO 2004/063351 (variant Fc regions with increased binding affinity due to amino acid modification); or in U.S. patent Application Ser. No. 10/672,280 or WO 2004/099249 (Fc variants with altered binding to FcγR due to amino acid modification), the contents of each of which is herein incorporated by reference in its entirety.

In another embodiment, the antigen binding molecules of the present invention are engineered to have enhanced binding affinity according to, for example, the methods disclosed in U.S. Pat. Appl. Pub. No. 2004/0132066 to Balint et al., the entire contents of which are hereby incorporated by reference.

In one embodiment, the antigen binding molecule of the present invention is conjugated to an additional moiety, such as a radiolabel or a toxin. Such conjugated ABMs can be produced by numerous methods that are well known in the art.

A variety of radionuclides are applicable to the present invention and those skilled in the art are credited with the ability to readily determine which radionuclide is most appropriate under a variety of circumstances. For example, $^{131}$iodine is a well known radionuclide used for targeted immunotherapy. However, the clinical usefulness of $^{131}$iodine can be limited by several factors including: eight-day physical half-life;

dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}$indium and $^{90}$yttrium.

$^{90}$yttrium provides several benefits for utilization in radioimmunotherapeutic applications: the 64 hour half-life of $^{90}$yttrium is long enough to allow antibody accumulation by tumor and, unlike e.g., $^{131}$iodine, $^{90}$yttrium is a pure beta emitter of high energy with no accompanying gamma irradiation in its decay, with a range in tissue of 100 to 1000 cell diameters. Furthermore, the minimal amount of penetrating radiation allows for outpatient administration of 90yttrium-labeled antibodies. Additionally, internalization of labeled antibody is not required for cell killing, and the local emission of ionizing radiation should be lethal for adjacent tumor cells lacking the target antigen.

Effective single treatment dosages (i.e., therapeutically effective amounts) of $^{90}$yttrium labeled anti-EGFR antibodies range from between about 5 and about 75 mCi, more preferably between about 10 and about 40 mCi. Effective single treatment non-marrow ablative dosages of $^{131}$iodine labeled anti-EGFR antibodies range from between about 5 and about 70 mCi, more preferably between about 5 and about 40 mCi. Effective single treatment ablative dosages (i.e., may require autologous bone marrow transplantation) of $^{131}$iodine labeled anti-EGFR antibodies range from between about 30 and about 600 mCi, more preferably between about 50 and less than about 500 mCi. In conjunction with a chimeric anti-EGFR antibody, owing to the longer circulating half life vis-à-vis murine antibodies, an effective single treatment non-marrow ablative dosages of $^{131}$iodine labeled chimeric anti-EGFR antibodies range from between about 5 and about 40 mCi, more preferably less than about 30 mCi. Imaging criteria for, e.g., the $^{111}$indium label, are typically less than about 5 mCi.

With respect to radiolabeled anti-EGFR antibodies, therapy therewith can also occur using a single therapy treatment or using multiple treatments. Because of the radionuclide component, it is preferred that prior to treatment, peripheral stem cells ("PSC") or bone marrow ("BM") be "harvested" for patients experiencing potentially fatal bone marrow toxicity resulting from radiation. BM and/or PSC are harvested using standard techniques, and then purged and frozen for possible reinfusion. Additionally, it is most preferred that prior to treatment a diagnostic dosimetry study using a diagnostic labeled antibody (e.g., using $^{111}$indium) be conducted on the patient, a purpose of which is to ensure that the therapeutically labeled antibody (e.g., using $^{90}$yttrium) will not become unnecessarily "concentrated" in any normal organ or tissue.

In a preferred embodiment, the present invention is directed to an isolated polynucleotide comprising a sequence that encodes a polypeptide having an amino acid sequence in Table 7 below. In a preferred embodiment, the invention is directed to an isolated polynucleotide comprising a sequence shown in Table 6 below. The invention is further directed to an isolated nucleic acid comprising a sequence at least 80%, 85%, 90%, 95%, 96%, 97%, 98% or 99% identical to a nucleotide sequence shown in Table 6 below. In another embodiment, the invention is directed to an isolated nucleic acid comprising a sequence that encodes a polypeptide having an amino acid sequence at least 80%, 85%, 90%, 95%, 96%, 97%, 98% or 99% identical to an amino acid sequence in Table 7. The invention also encompasses an isolated nucleic acid comprising a sequence that encodes a polypeptide having the amino acid sequence of any of the constructs in Table 7 with conservative amino acid substitutions.

TABLE 6

| CONSTRUCT | NUCLEOTIDE SEQUENCE | SEQ ID NO |
|---|---|---|
| ICR62 VH | CAGGTCAACCTACTGCAGTCTGGGG CTGCACTGGTGAAGCCTGGGGCCTC TGTGAAGTTGTCTTGCAAAGGTTCT GGTTTTACATTCACTGACTACAAGA TACACTGGGTGAAGCAGAGTCATGG AAAGAGCCTTGAGTGGATTGGGTAT TTTAATCCTAACAGTGGTTATAGTA CCTACAATGAAAAGTTCAAGAGCAA GGCCACATTGACTGCAGACAAATCC ACCGATACAGCCTATATGGAGCTTA CCAGTCTGACATCTGAGGACTCTGC AACCTATTACTGTACAAGACTATCC CCAGGGGGTTACTATGTTATGGATG CCTGGGGTCAAGGAGCTTCAGTCAC TGTCTCCTC | 2 |
| I-HHA | CAGGTCAGCTGGTGCAGTCTGGGG CTGAGGTGAAGAAGCCTGGGTCCTC GGTGAAGGTCTCCTGCAAGGCTTCT GGATTTACATTCACTGACTACGCCA TCAGCTGGGTGCGACAGGCCCCTGG ACAAGGGCTCGAGTGGATGGGAGG GATCAATCCTAACAGTGGTTATAGT ACCTACGCACAGAAGTTCCAGGGCA GGGTCACCATTACCGCGGACAAATC CACGAGCACAGCCTACATGGAGCTG AGCAGCCTGAGATCTGAGGACACGG CCGTGTATTACTGTGCGAGACTATC CCCAGGCGGTTACTATGTTATGGAT GCCTGGGGCCAAGGGACCACCGTGA CCGTCTCCTCA | 4 |
| I-HHB | CAGGTCAGCTGGTGCAGTCTGGGG CTGAGGTGAAGAAGCCTGGGTCCTC GGTGAAGGTCTCCTGCAAGGGTTCT GGTTTTACATTCACTGACTACAAGA TACACTGGGTGCGACAGGCCCCTGG ACAAGGGCTCGAGTGGATGGGATAT TTCAACCCTAACAGCGGTTATAGTA CCTACGCACAGAAGTTCCAGGGCAG GGTCACCATTACCGCGGACAAATCC ACGAGCACAGCCTACATGGAGCTGA GCAGCCTGAGATCTGAGGACACGGC CGTGTATTACTGTGCGAGACTATCC CCAGGCGGTTACTATGTTATGGATG CCTGGGGCCAAGGGACCACCGTGAC CGTCTCCTCA | 6 |
| I-HHC | CAGGTCAGCTGGTGCAGTCTGGGG CTGAGGTGAAGAAGCCTGGGTCCTC GGTGAAGGTCTCCTGCAAGGGTTCT GGTTTTACATTCACTGACTACAAGA TACACTGGGTGCGACAGGCCCCTGG ACAAGGGCTCGAGTGGATGGGATAT TTCAACCCTAACAGCGGTTATAGTA CCTACAATGAAAAGTTCAAGAGCAG GGTCACCATTACCGCGGACAAATCC ACGAGCACAGCCTACATGGAGCTGA GCAGCCTGAGATCTGAGGACACGGC CGTGTATTACTGTGCGAGACTATCC CCAGGCGGTTACTATGTTATGGATG CCTGGGGCCAAGGGACCACCGTGAC CGTCTCCTCA | 8 |
| I-HLA | CAGGTCAGCTGGTGCAGTCTGGGG CTGAGGTGAAGAAGCCTGGGGCCTC GGTGAAGGTCTCCTGCAAGGCCTCT GGTTTTACATTCACTGACTACTATA TGCACTGGGTGCGACAGGCCCCTGG ACAAGGGCTCGAGTGGATGGGCTGG ATCAATCCTAACAGTGGTTATAGTA CCTACGCACAGAAGTTTCAGGGCAG GGTCACCATGACCGCCGACACGTCC ATCAGCACAGCCTACATGGAGCTGA GCAGGCTGAGATCTGACGACACGGC CGTGTATTACTGTGCGAGACTATCC CCAGGCGGTTACTATGTTATGGATG CCTGGGGCCAAGGGACCACCGTGAC CGTCTCCTCA | 10 |

TABLE 6-continued

| CONSTRUCT | NUCLEOTIDE SEQUENCE | SEQ ID NO |
|---|---|---|
| I-HLB | CAGGTGCAGCTGGTGCAGTCTGGGGCTGAGGTGAAGAAGCCTGGAGCCTCGGTGAAGGTCTCCTGCAAGGGTTCTGGTTTTACATTCACTGACTACAAGATCCACTGGGTGCGACAGGCCCCTGGACAAGGGCTCGAGTGGATGGGATACTTCAACCCTAACAGCGGTTATAGTACCTACGCACAGAAGTTCCAGGGCAGGGTCACCATGACCGCCGACACGTCCATCAGCACAGCCTACATGGAGCTGAGCAGGCTGAGATCTGACGACACGGCCGTGTATTACTGTGCGAGACTATCCCCAGGCGGTTACTATGTTATGGATGCCTGGGGCCAAGGGACCACCGTGACCGTCTCCTCA | 12 |
| I-HLC | CAGGTGCAGCTGGTGCAGTCTGGGGCTGAGGTGAAGAAGCCTGGAGCCTCAGTGAAGGTCTCCTGCAAGGGTTCTGGTTTTACATTCACTGACTACAAGATCCACTGGGTGCGACAGGCCCCTGGACAAGGGCTCGAGTGGATGGGATACTTCAACCCTAACAGCGGTTACAGTACTTACAACGAGAAGTTCAAGAGCCGGGTCACCATGACCGCCGACACGTCCATCAGCACAGCCTACATGGAGCTGAGCAGGCTGAGATCTGACGACACGGCCGTGTATTACTGTGCGAGACTATCCCCAGGGGGTTACTATGTTATGGATGCCTGGGGCCAAGGGACCACCGTGACCGTCTCCTCA | 14 |
| I-HHD | CAGGTGCAGCTGGTGCAGTCTGGGGCTGAGGTGAAGAAGCCTGGGTCCTCGGTGAAGGTCTCCTGCAAGGCCTCTGGTTTCACATTCACTGACTACAAGATACACTGGGTGCGACAGGCCCCTGGACAAGGGCTCGAGTGGATGGGATATTTCAACCCTAACAGCGGTTATAGTACCTACGCACAGAAGTTCCAGGGCAGGGTCACCATTACCGCGGACAAATCCACGAGCACAGCCTACATGGAGCTGAGCAGCCTGAGATCTGAGGACACGGCCGTGTATTACTGTGCGAGACTATCCCCAGGCGGTTACTATGTTATGGATGCCTGGGGCCAAGGGACCACCGTGACCGTCTCCTCA | 16 |
| I-HHE | CAGGTGCAGCTGGTGCAGTCTGGGGCTGAGGTGAAGAAGCCTGGGTCCTCGGTGAAGGTCTCCTGCAAGGGTTCTGGTTTCACATTCACTGACTACAAGATATCCTGGGTGCGACAGGCTCCTGGACAAGGGCTCGAGTGGATGGGATATTTCAACCCTAACAGCGGTTATAGTACCTACGCACAGAAGTTCCAGGGCAGGGTCACCATTACCGCGGACAAATCCACGAGCACAGCCTACATGGAGCTGAGCAGCCTGAGATCTGAGGACACGGCCGTGTATTACTGTGCGAGACTATCCCCAGGCGGTTACTATGTTATGGATGCCTGGGGCCAAGGGACCACCGTGACCGTCTCCTCA | 18 |
| I-HHF | CAGGTGCAGCTGGTGCAGTCTGGGGCTGAGGTGAAGAAGCCTGGGTCCTCGGTGAAGGTCTCCTGCAAGGGTTCTGGTTTTACATTCACTGACTACAAGATACACTGGGTGCGACAGGCCCCTGGACAAGGGCTCGAGTGGATGGGATATTTCAACCCTAACAGCGGTTATTCGAACTACGCACAGAAGTTCCAGGGCAGGGTCACCATTACCGCGGACAAATCCACGAGCACAGCCTACATGGAGCTGAGCAGCCTGAGATCTGAGGACACGGCCGTGTATTACTGTGCGAGACTATCCCCAGGCGGTTACTATGTTATGGATGCCTGGGGCCAAGGGACCACCGTGACCGTCTCCTCA | 20 |
| I-HHG | CAGGTGCAGCTGGTGCAGTCTGGGGCTGAGGTGAAGAAGCCTGGGTCCTCGGTGAAGGTCTCCTGCAAGGGTTCTGGTTTTACATTCACTGACTACAAGATACACTGGGTGCGACAGGCCCCTGGACAAGGGCTCGAGTGGATGGGATATTTCAACCCTAACAGCGGTTATGCCACGTACGCACAGAAGTTCCAGGGCAGGGTCACCATTACCGCGGACAAATCCACGAGCACAGCCTACATGGAGCTGAGCAGCCTGAGATCTGAGGACACGGCCGTGTATTACTGTGCGAGACTATCCCCAGGCGGTTACTATGTTATGGATGCCTGGGGCCAAGGGACCACCGTGACCGTCTCCTCA | 22 |
| I-HLA1 | CAGGTGCAGCTGGTGCAGTCTGGGGCTGAGGTGAAGAAGCCTGGAGCCTCGGTGAAGGTCTCCTGCAAGGCCTCTGGTTTTACATTCACTGACTACTATATGCACTGGGTGCGACAGGCCCCTGGACAAGGGCTCGAGTGGATGGGCTGGATCAATCCTAACAGTGGTTATAGTACCTACAGCCCAAGCTTCCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGACTATCCCCAGGCGGTTACTATGTTATGGATGCCTGGGGCCAAGGGACCACCGTGACCGTCTCCTCA | 24 |
| I-HLA2 | CAGGTGCAGCTGGTGCAGTCTGGGGCTGAGGTGAAGAAGCCTGGAGCCTCGGTGAAGGTCTCCTGCAAGGCCTCTGGTTTTACATTCACTGACTACTATATGCACTGGGTGCGACAGGCCCCTGGACAAGGGCTCGAGTGGATGGGCTGGATCAATCCTAACAGTGGTTATAGTACCTACAACGAGAAGTTCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGACTATCCCCAGGCGGTTACTATGTTATGGATGCCTGGGGCCAAGGGACCACCGTGACCGTCTCCTCA | 26 |
| I-HLA3 | CAGGTGCAGCTGGTGCAGTCTGGGGCTGAGGTGAAGAAGCCTGGAGCCTCGGTGAAGGTCTCCTGCAAGGCCTCTGGTTACACATTCACTGACTACTATATGCACTGGGTGCGACAGGCCCCTGGACAAGGGCTCGAGTGGATGGGCTGGATCAATCCTAACAGTGGTTATAGTACCTACAGCCCAAGCTTCCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGACTATCCCCAGGCGGTTACTATGTTATGGATGCCTGGGGCCAAGGGACCACCGTGACCGTCTCCTCA | 28 |
| I-HLA4 | CAGGTGCAGCTGGTGCAGTCTGGGGCTGAGGTGAAGAAGCCTGGAGCCTCGGTGAAGGTCTCCTGCAAGGCCTCTGGTTACACATTCACTGACTACTATATGCACTGGGTGCGACAGGCCCCTGGACAAGGGCTCGAGTGGATGGGCTGGATCAATCCTAACAGTGGTTATAGTACCTACAACGAGAAGTTCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGACTATCCCCAGGCGGTTACTATGTTATGGATGCCTGGGGCCAAGGGACCACCGTGACCGTCTCCTCA | 30 |

TABLE 6-continued

| CONSTRUCT | NUCLEOTIDE SEQUENCE | SEQ ID NO |
|---|---|---|
| I-HLA5 | CAGATGCAGCTGGTGCAGTCTGGGC CAGAGGTGAAGAAGCCTGGAACCTC GGTGAAGGTCTCCTGCAAGGCCTCT GGTTTTACATTCACTGACTACTATA TGCACTGGGTGCGACAGGCCCCTGG ACAAGGGCTCGAGTGGATGGGCTGG ATCAATCCTAACAGTGGTTATAGTA CCTACAGCCCAAGCTTCCAAGGCCA GGTCACCATCTCAGCCGACAAGTCC ATCAGCACCGCCTACCTGCAGTGGA GCAGCCTGAAGGCCTCGGACACCGC CATGTATTACTGTGCGAGACTATCC CCAGGCGGTTACTATGTTATGGATG CCTGGGGCCAAGGGACCACCGTGAC CGTCTCCTCA | 32 |
| I-HLA6 | CAGATGCAGCTGGTGCAGTCTGGGC CAGAGGTGAAGAAGCCTGGAACCTC GGTGAAGGTCTCCTGCAAGGCCTCT GGTTTTACATTCACTGACTACTATA TGCACTGGGTGCGACAGGCCCCTGG ACAAGGGCTCGAGTGGATGGGCTGG ATCAATCCTAACAGTGGTTATAGTA CCTACAACGAGAAGTTCCAAGGCCA GGTCACCATCTCAGCCGACAAGTCC ATCAGCACCGCCTACCTGCAGTGGA GCAGCCTGAAGGCCTCGGACACCGC CATGTATTACTGTGCGAGACTATCC CCAGGCGGTTACTATGTTATGGATG CCTGGGGCCAAGGGACCACCGTGAC CGTCTCCTCA | 34 |
| I-HLA7 | CAGATGCAGCTGGTGCAGTCTGGGC CAGAGGTGAAGAAGCCTGGAACCTC GGTGAAGGTCTCCTGCAAGGCCTCT GGTTTTACATTCACTGACTACAAGA TCCACTGGGTGCGACAGGCCCGCGG ACAACGGCTCGAGTGGATCGGCTGG ATCAATCCTAACAGTGGTTATAGTA CCTACAACGAGAAGTTCCAAGGCCA GGTCACCATCTCAGCCGACAAGTCC ATCAGCACCGCCTACCTGCAGTGGA GCAGCCTGAAGGCCTCGGACACCGC CATGTATTACTGTGCGAGACTATCC CCAGGCGGTTACTATGTTATGGATG CCTGGGGCCAAGGGACCACCGTGAC CGTCTCCTCA | 36 |
| I-HLA8 | CAGATGCAGCTGGTGCAGTCTGGGC CAGAGGTGAAGAAGCCTGGAACCTC GGTGAAGGTCTCCTGCAAGGCCTCT GGTTTTACATTCACTGACTACAAGA TCCACTGGGTGCGACAGGCCCCTGG ACAAGGGCTCGAGTGGATGGGATAT TTCAACCCTAACAGCGGTTATAGTA CCTACGCACAGAAGTTCCAGGGCAG GGTCACCATTACCGCGGACAAATCC ACGAGCACAGCCTACATGGAGCTGA GCAGCCTGAGATCTGAGGACACGGC CGTGTATTACTGTGCGAGACTATCC CCAGGCGGTTACTATGTTATGGATG CCTGGGGCCAAGGGACCACCGTGAC CGTCTCCTCA | 38 |
| I-HLA9 | GAGGTGCAGCTCGTGCAGTCTGGCG CTGAGGTGAAGAAGCCTGGCGAGTC GTTGAAGATCTCCTGCAAGGGTTCT GGTTATTCATTCACTGACTACAAGA TCCACTGGGTGCGACAGGCCCCTGG ACAAGGGCTCGAGTGGATGGGATAT TTCAACCCTAACAGCGGTTATAGTA CCTACGCACAGAAGTTCCAGGGCAG GGTCACCATTACCGCGGACAAATCC ACGAGCACAGCCTACATGGAGCTGA GCAGCCTGAGATCTGAGGACACGGC CGTGTATTACTGTGCGAGACTATCC CCAGGCGGTTACTATGTTATGGATG CCTGGGGCCAAGGGACCACCGTGAC CGTCTCCTCA | 40 |

TABLE 6-continued

| CONSTRUCT | NUCLEOTIDE SEQUENCE | SEQ ID NO |
|---|---|---|
| I-HLA10 | GAGGTGCAGCTCGTGCAGTCTGGCG CTGAGGTGAAGAAGCCTGGCGAGTC GTTGAAGATCTCCTGCAAGGGTTCT GGTTATTCATTCACTGACTACAAGA TCCACTGGGTGCGACAGATGCCTGG AAAGGGCCTCGAGTGGATGGGCTAC TTCAATCCTAACAGTGGTTATAGTA CCTACAGCCCAAGCTTCCAAGGCCA GGTCACCATCTCAGCCGACAAGTCC ATCAGCACCGCCTACCTGCAGTGGA GCAGCCTGAAGGCCTCGGACACCGC CATGTATTACTGTGCGAGACTATCC CCAGGCGGTTACTATGTTATGGATG CCTGGGGCCAAGGGACCACCGTGAC CGTCTCCTCAG | 120 |
| VH Signal Sequence | ATGGACTGGACCTGGAGGATCCTCT TCTTGGTGGCAGCAGCCACAGGAGC CCACTCC | 42 |
| ICR62 VL | GACATCCAGATGACCCAGTCTCCTT CATTCCTGTCTGCATCTGTGGGAGA CAGAGTCACTATCAACTGCAAAGCA AGTCAGAATATTAACAATTACTTAA ACTGGTATCAGCAAAAGCTTGGAGA AGCTCCCAAACGCCTGATATATAAT ACAAACAATTTGCAAACAGGCATCC CATCAAGGTTCAGTGGCAGTGGATC TGGTACAGATTACACACTCACCATC AGCAGCCTGCAGCCTGAAGATTTTG CCACATATTTCTGCTTGCAGCATAA TAAGTTTTCCCACGTTTGGAGCTGG GACCAAGCTGGAACTGAAACGTACG | 44 |
| I-KC | GATATCCAGATGACCCAGTCTCCAT CCTCCCTGTCTGCATCTGTCGGAGA CCGGGTCACCATCACCTGCCGGGCA AGTCAGGGCATTAACAATTACTTAA ATTGGTACCAGCAGAAGCCAGGGA AAGCCCCTAAGCGCCTGATCTATAA TACCAACAACTTGCAGACAGGCGTC CCATCAAGGTTCAGCGGCAGTGGAT CCGGGACAGAATTCACTCTCACCAT CAGCAGCCTGCAGCCTGAAGATTTT GCCACCTATTACTGCTTGCAGCATA ATAGTTTTCCCACGTTTGGCCAGG CACCAAGCTCGAGATCAAGCGTACG | 46 |
| VL Signal Sequence | ATGGACATGAGGGTCCCCGCTCAGC TCCTGGGCCTCCTGCTGCTCTGGTT CCCAGGTGCCAGGTGT | 48 |
| I-KA | GATATCCAGATGACCCAGTCTCCAT CCTCCCTGTCTGCATCTGTCGGAGA CCGGGTCACCATCACCTGCCGGGCA AGTCAGGGCATTAACAATTACTTAA ATTGGTACCAGCAGAAGCCAGGGA AAGCCCCTAAGCGCCTGATCTATAA TACCAACAACTTGCAGACAGGCGTC CCATCAAGGTTCAGCGGCAGTGGAT CCGGGACAGAATACACTCTCACCAT CAGCAGCCTGCAGCCTGAAGATTTT GCCACCTATTACTGCTTGCAGCATA ATAGTTTTCCCACGTTTGGCCAGGG CACCAAGCTCGAGATCAAGCGTACG GTG | 50 |
| I-KB | GATATCCAGATGACCCAGTCTCCAT CCTCCCTGTCTGCATCTGTCGGAGA CCGGGTCACCATCACCTGCAAAGCA AGTCAGAATATTAACAATTACTTAA ACTGGTACCAGCAGAAGCCAGGGA AAGCCCCTAAGCGCCTGATCTATAA TACCAACAACTTGCAGACAGGCGTC CCATCAAGGTTCAGCGGCAGTGGAT CCGGGACAGAATACACTCTCACCAT CAGCAGCCTGCAGCCTGAAGATTTT GCCACCTATTACTGCTTGCAGCATA ATAGTTTTCCCACGTTTGGCCAGGG CACCAAGCTCGAGATCAAGCGTACG GTG | 52 |

TABLE 7

| CONSTRUCT | AMINO ACID SEQUENCE | SEQ ID NO |
|---|---|---|
| ICR62 VH | QVNLLQSGAALVKPGASVKLSCKGSGFTFTDYKIHWVKQSHGKSLEWIGYFNPNSGYSTYNEKFKSKATLTADKSTDTAYMELTSLTSEDSATYYCTRLSPGGYYVMDAWGQGASVTVSS | 1 |
| I-HHA | QVQLVQSGAEVKKPGSSVKVSCKASGFTFTDYAISWVRQAPGQGLEWMGGINPNSGYSTYAQKFQGRVTITADKSTSTAYMELSSLRSEDTAVYYCARLSPGGYYVMDAWGQGTTVTVSS | 3 |
| I-HHB | QVQLVQSGAEVKKPGSSVKVSCKGSGFTFTDYKIHWVRQAPGQGLEWMGYFNPNSGYSTYAQKFQGRVTITADKSTSTAYMELSSLRSEDTAVYYCARLSPGGYYVMDAWGQGTTVTVSS | 5 |
| I-HHC | QVQLVQSGAEVKKPGSSVKVSCKGSGFTFTDYKIHWVRQAPGQGLEWMGYFNPNSGYSTYNEKFKSRVTITADKSTSTAYMELSSLRSEDTAVYYCARLSPGGYYVMDAWGQGTTVTVSS | 7 |
| I-HLA | QVQLVQSGAEVKKPGASVKVSCKASGFTFTDYYMHWVRQAPGQGLEWMGWINPNSGYSTYAQKFQGRVTMTADTSISTAYMELSRLRSDDTAVYYCARLSPGGYYVMDAWGQGTTVTVSS | 9 |
| I-HLB | QVQLVQSGAEVKKPGASVKVSCKGSGFTFTDYKIHWVRQAPGQGLEWMGYFNPNSGYSTYAQKFQGRVTMTADTSISTAYMELSRLRSDDTAVYYCARLSPGGYYVMDAWGQGTTVTVSS | 11 |
| I-HLC | QVQLVQSGAEVKKPGASVKVSCKGSGFTFTDYKIHWVRQAPGQGLEWMGYFNPNSGYSTYNEKFKSRVTMTADTSISTAYMELSRLRSDDTAVYYCARLSPGGYYVMDAWGQGTTVTVSS | 13 |
| I-HHD | QVQLVQSGAEVKKPGSSVKVSCKASGFTFTDYKIHWVRQAPGQGLEWMGYFNPNSGYSTYAQKFQGRVTITADKSTSTAYMELSSLRSEDTAVYYCARLSPGGYYVMDAWGQGTTVTVSS | 15 |
| I-HHE | QVQLVQSGAEVKKPGSSVKVSCKGSGFTFTDYKISWVRQAPGQGLEWMGYFNPNSGYSTYAQKFQGRVTITADKSTSTAYMELSSLRSEDTAVYYCARLSPGGYYVMDAWGQGTTVTVSS | 17 |
| I-HHF | QVQLVQSGAEVKKPGSSVKVSCKGSGFTFTDYKIHWVRQAPGQGLEWMGYFNPNSGYSNYAQKFQGRVTITADKSTSTAYMELSSLRSEDTAVYYCARLSPGGYYVMDAWGQGTTVTVSS | 19 |
| I-HHG | QVQLVQSGAEVKKPGSSVKVSCKGSGFTFTDYKIHWVRQAPGQGLEWMGYFNPNSGYATYAQKFQGRVTITADKSTSTAYMELSSLRSEDTAVYYCARLSPGGYYVMDAWGQGTTVTVSS | 21 |
| I-HLA1 | QVQLVQSGAEVKKPGASVKVSCKASGFTFTDYYMHWVRQAPGQGLEWMGWINPNSGYSTYSPSFQGQVTISADKSISTAYLQWSSLKASDTAMYYCARLSPGGYYVMDAWGQGTTVTVSS | 23 |
| I-HLA2 | QVQLVQSGAEVKKPGASVKVSCKASGFTFTDYYMHWVRQAPGQGLEWMGWINPNSGYSTYNEKFQGQVTISADKSISTAYLQWSSLKASDTAMYYCARLSPGGYYVMDAWGQGTTVTVSS | 25 |
| I-HLA3 | QVQLVQSGAEVKKPGASVKVSCKASGYTFTDYYMHWVRQAPGQGLEWMGWINPNSGYSTYSPSFQGQVTISADKSISTAYLQWSSLKASDTAMYYCARLSPGGYYVMDAWGQGTTVTVSS | 27 |
| I-HLA4 | QVQLVQSGAEVKKPGASVKVSCKASGYTFTDYYMHWVRQAPGQGLEWMGWINPNSGYSTYNEKFQGQVTISADKSISTAYLQWSSLKASDTAMYYCARLSPGGYYVMDAWGQGTTVTVSS | 29 |
| I-HLA5 | QMQLVQSGPEVKKPGTSVKVSCKASGFTFTDYYMHWVRQAPGQGLEWMGWLNIPNSGYSTYSPSFQGQVTISADKSISTAYLQWSSLKASDTAMYYCARLSPGGYYVMDAWGQGTTVTVSS | 31 |
| I-HLA6 | QMQLVQSGPEVKKPGTSVKVSCKASGFTFTDYYMHWVRQAPGQGLEWMGWINPNSGYSTYNEKFQGQVTISADKSISTAYLQWSSLKASDTAMYYCARLSPGGYYVMDAWGQGTTVTVSS | 33 |
| I-HLA7 | QMQLVQSGPEVKKPGTSVKVSCKASGFTFTDYKIHWVRQARGQRLEWIGWINPNSGYSTYNEKFQGQVTISADKSISTAYLQWSSLKASDTAMYYCARLSPGGYYVMDAWGQGTTVTVSS | 35 |
| I-HLA8 | QMQLVQSGPEVKKPGTSVKVSCKASGFTFTDYKIHWVRQAPGQGLEWMGYFNPNSGYSTYAQKFQGRVTITADKSTSTAYMELSSLRSEDTAVYYCARLSPGGYYVMDAWGQGTTVTVSS | 37 |
| I-HLA9 | EVQLVQSGAEVKKPGESLKISCKGSGYSFTDYKIHWVRQAPGQGLEWMGYFNPNSGYSTYAQKFQGRVTITADKSTSTAYMELSSLRSEDTAVYYCARLSPGGYYVMDAWGQGTTVTVSS | 39 |
| I-HLA10 | EVQLVQSGAEVKKPGESLKISCKGSGYSFTDYKIHWVRQMPGKGLEWMGYFNPNSGYSTYSPSFQGQVTISADKSISTAYLQWSSLKASDTAMYYCARLSPGGYYVMDAWGQGTTVTVSS | 121 |
| VH Signal Sequence | MDWTWRILFLVAAATGAHS | 41 |
| ICR62 VL | DIQMTQSPSFLSASVGDRVTINCKASQNINNYLNWYQQKLGEAPKRLIYNTNNLQTGIPSRFSGSGSGTDYTLTISSLQPEDFATYFCLQHNSFPTFGAGTKLELKRT | 43 |
| I-KC | DIQMTQSPSSLSASVGDRVTITCRASQGINNYLNWYQQKPGKAPKRLIYNTNNLQTGVPSRFSGSGSGTEFTLTISSLQPEDFATYYCLQHNSFPTFGQGTKLEIKRT | 45 |
| VL Signal Sequence | MDMRVPAQLLGLLLLWFPGARC | 47 |
| I-KA | DIQMTQSPSSLSASVGDRVTITCRASQGINNYLNWYQQKPGKAPKRLIYNTNNLQTGVPSRFSGSGSGTEYTLTISSLQPEDFATYYCLQHNSFPTFGQGTKLEIKRTV | 49 |
| I-KB | DIQMTQSPSSLSASVGDRVTITCKASQNINNYLNWYQQKPGKAPKRLIYNTNNLQTGVPSRFSGSGSGTEYTLTISSLQPEDFATYYCLQHNSFPTFGQGTKLEIKRTV | 51 |

In another embodiment, the present invention is directed to an expression vector and/or a host cell which comprise one or more isolated polynucleotides of the present invention.

Generally, any type of cultured cell line can be used to express the ABM of the present invention. In a preferred embodiment, HEK293-EBNA cells, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The therapeutic efficacy of the ABMs of the present invention can be enhanced by producing them in a host cell that further expresses a polynucleotide encoding a polypeptide having GnTIII activity. In a preferred embodiment, the polypeptide having GnTIII activity is a fusion polypeptide comprising the Golgi localization domain of a Golgi resident polypeptide. In another preferred embodiment, the expression of the ABMs of the present invention in a host cell that expresses a polynucleotide encoding a polypeptide having GnTIII activity results in ABMs with increased Fc receptor binding affinity and increased effector function. Accordingly, in one embodiment, the present invention is directed to a host cell comprising (a) an isolated nucleic acid comprising a sequence encoding a polypeptide having GnTIII activity; and (b) an isolated polynucleotide encoding an ABM of the present invention, such as a chimeric, primatized or humanized antibody that binds human EGFR. In a preferred embodiment, the polypeptide having GnTIII activity is a fusion polypeptide comprising the catalytic domain of GnTIII and the Golgi localization domain is the localization domain of mannosidase II. Methods for generating such fusion polypeptides and using them to produce antibodies with increased effector functions are disclosed in U.S. Provisional Pat. Appl. No. 60/495,142 and U.S. Pat. Appl. Publ. No. 2004/0241817 A1, the entire contents of each of which are expressly incorporated herein by reference. In another preferred embodiment, the chimeric ABM is a chimeric antibody or a fragment thereof, having the binding specificity of the rat ICR62 antibody. In a particularly preferred embodiment, the chimeric antibody comprises a human Fc. In another preferred embodiment, the antibody is primatized or humanized.

In one embodiment, one or several polynucleotides encoding an ABM of the present invention may be expressed under the control of a constitutive promoter or, alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding an ABM of the present invention are comprised within the host cell system, some of them may be expressed under the control of a constitutive promoter, while others are expressed under the control of a regulated promoter. The maximal expression level is considered to be the highest possible level of stable polypeptide expression that does not have a significant adverse effect on cell growth rate, and will be determined using routine experimentation. Expression levels are determined by methods generally known in the art, including Western blot analysis using an antibody specific for the ABM or an antibody specific for a peptide tag fused to the ABM; and Northern blot analysis. In a further alternative, the polynucleotide may be operatively linked to a reporter gene; the expression levels of a chimeric (e.g., humanized) ABM having substantially the same binding specificity of the rat ICR62 antibody are determined by measuring a signal correlated with the expression level of the reporter gene. The reporter gene may be transcribed together with the nucleic acid(s) encoding said fusion polypeptide as a single mRNA molecule; their respective coding sequences may be linked either by an internal ribosome entry site (IRES) or by a cap-independent translation enhancer (CITE). The reporter gene may be translated together with at least one nucleic acid encoding a chimeric (e.g., humanized) ABM having substantially the same binding specificity of the rat ICR62 antibody such that a single polypeptide chain is formed. The nucleic acids encoding the AMBs of the present invention may be operatively linked to the reporter gene under the control of a single promoter, such that the nucleic acid encoding the fusion polypeptide and the reporter gene are transcribed into an RNA molecule which is alternatively spliced into two separate messenger RNA (mRNA) molecules; one of the resulting mRNAs is translated into said reporter protein, and the other is translated into said fusion polypeptide.

Methods which are well known to those skilled in the art can be used to construct expression vectors containing the coding sequence of an ABM having substantially the same binding specificity of the rat ICR62 antibody along with appropriate transcriptional/translational control signals. These methods include in vitro recombinant DNA techniques, synthetic techniques and in vivo recombination/genetic recombination. See, for example, the techniques described in Maniatis et al., Molecular Cloning A Laboratory Manual, Cold Spring Harbor Laboratory, N.Y. (1989) and Ausubel et al., Current Protocols in Molecular Biology, Greene Publishing Associates and Wiley Interscience, N.Y (1989).

A variety of host-expression vector systems may be utilized to express the coding sequence of the ABMs of the present invention. Preferably, mammalian cells are used as host cell systems transfected with recombinant plasmid DNA or cosmid DNA expression vectors containing the coding sequence of the protein of interest and the coding sequence of the fusion polypeptide. Most preferably, HEK293-EBNA cells, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as host cell system. Some examples of expression systems and selection methods are described in the following references, and references therein: Borth et al., *Biotechnol. Bioen.* 71(4):266-73 (2000-2001), in Werner et al., *Arzneimittelforschung/Drug Res.* 48(8):870-80 (1998), in Andersen and Krummen, *Curr. Op. Biotechnol.* 13:117-123 (2002), in Chadd and Chamow, *Curr. Op. Biotechnol.* 12:188-194 (2001), and in Giddings, *Curr. Op. Biotechnol.* 12: 450-454 (2001). In alternate embodiments, other eukaryotic host cell systems may be used, including yeast cells transformed with recombinant yeast expression vectors containing the coding sequence of an ABM of the present invention, such as the expression systems taught in U.S. Pat. Appl. No. 60/344,169 and WO 03/056914 (methods for producing human-like glycoprotein in a non-human eukaryotic host cell) (the contents of each of which are incorporated by reference in their entirety); insect cell systems infected with recombinant virus expression vectors (e.g., baculovirus) containing the coding sequence of a chimeric ABM having substantially the same binding specificity of the rat ICR62 antibody; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of the ABM of the invention, including, but not limited to, the expression systems taught in U.S. Pat. No. 6,815,184 (methods for expression and secretion of biologically active polypeptides from genetically engineered duckweed); WO 2004/057002 (production of glycosylated proteins in bryophyte plant cells by introduction of a glycosyl transferase gene) and WO 2004/024927 (methods of generating extracellular heterologous non-plant protein in moss protoplast); and U.S. Pat. Appl. Nos. 60/365,769, 60/368,047, and WO 2003/078614 (glycoprotein processing in transgenic plants comprising a functional mammalian GnTIII enzyme) (the contents of each of which are herein incorporated by reference in its entirety); or animal cell systems infected with recombinant virus expression vectors (e.g., adenovirus, vaccinia virus) including cell lines engineered to contain multiple copies of the DNA encoding a chimeric ABM having substantially the same binding specificity of the rat ICR62 antibody either stably amplified (CHO/dhfr) or unstably amplified in double-minute chromosomes (e.g., murine cell lines). In one embodiment, the vector comprising the polynucleotide(s) encoding the ABM of the invention is polycistronic. Also, in one embodiment the ABM discussed above is an antibody or a fragment thereof. In a preferred embodiment, the ABM is a humanized antibody.

For the methods of this invention, stable expression is generally preferred to transient expression because it typically achieves more reproducible results and also is more amenable to large-scale production. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

A number of selection systems may be used, including, but not limited to, the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy et al., *Cell* 22:817 (1980)) genes, which can be employed in tk-, hgprt- or aprt-cells, respectively. Also, antimetabolite resistance can be used as the basis of selection for dhfr, which confers resistance to methotrexate (Wigler et al., *Natl. Acad. Sci. USA* 77:3567 (1989); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin et al., *J. Mol. Biol.* 150:1 (1981)); and hygro, which confers resistance to hygromycin (Santerre et al., *Gene* 30:147 (1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047 (1988)); the glutamine synthase system; and ODC (ornithine decarboxylase) which confers resistance to the ornithine decarboxylase inhibitor, 2-(difluoromethyl)-DL-ornithine, DFMO (McConlogue, in: *Current Communications in Molecular Biology*, Cold Spring Harbor Laboratory ed. (1987)).

The present invention is further directed to a method for modifying the glycosylation profile of the ABMs of the present invention that are produced by a host cell, comprising expressing in said host cell a nucleic acid encoding an ABM of the invention and a nucleic acid encoding a polypeptide with GnTIII activity, or a vector comprising such nucleic acids. Preferably, the modified polypeptide is IgG or a fragment thereof comprising the Fc region. In a particularly preferred embodiment the ABM is a humanized antibody or a fragment thereof.

The modified ABMs produced by the host cells of the invention exhibit increased Fc receptor binding affinity and/or increased effector function as a result of the modification. In a particularly preferred embodiment the ABM is a humanized antibody or a fragment thereof containing the Fc region. Preferably, the increased Fc receptor binding affinity is increased binding to a Fcγ activating receptor, such as the FcγRIIIa receptor. The increased effector function is preferably an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming.

The present invention is also directed to a method for producing an ABM of the present invention, having modified oligosaccharides in a host cell comprising (a) culturing a host cell engineered to express at least one nucleic acid encoding a polypeptide having GnTIII activity under conditions which permit the production of an ABM according to the present invention, wherein said polypeptide having GnTIII activity is expressed in an amount sufficient to modify the oligosaccharides in the Fc region of said ABM produced by said host cell; and (b) isolating said ABM. In a preferred embodiment, the polypeptide having GnTIII activity is a fusion polypeptide comprising the catalytic domain of GnTIII. In a particularly preferred embodiment, the fusion polypeptide further comprises the Golgi localization domain of a Golgi resident polypeptide.

Preferably, the Golgi localization domain is the localization domain of mannosidase II or GnTI. Alternatively, the Golgi localization domain is selected from the group consisting of: the localization domain of mannosidase I, the localization domain of GnTII, and the localization domain of α 1-6 core fucosyltransferase. The ABMs produced by the methods of the present invention have increased Fc receptor binding affinity and/or increased effector function. Preferably, the increased effector function is one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. The increased Fc receptor binding affinity is preferably increased binding to Fc activating receptors such as FcγRIIIa. In a particularly preferred embodiment the ABM is a humanized antibody or a fragment thereof.

In another embodiment, the present invention is directed to a chimeric ABM having substantially the same binding specificity of the rat ICR62 antibody produced by the methods of the invention which has an increased proportion of bisected oligosaccharides in the Fc region of said polypeptide. It is contemplated that such an ABM encompasses antibodies and fragments thereof comprising the Fc region. In a preferred embodiment, the ABM is a humanized antibody. In one embodiment, the percentage of bisected oligosaccharides in the Fc region of the ABM is at least 50%, more preferably, at least 60%, at least 70%, at least 80%, or at least 90%, and most preferably at least 90-95% of the total oligosaccharides. In yet another embodiment, the ABM produced by the methods of the invention has an increased proportion of nonfucosylated oligosaccharides in the Fc region as a result of the modification of its oligosaccharides by the methods of the present invention. In one embodiment, the percentage of nonfucosylated oligosaccharides is at least 50%, preferably, at least 60% to 70%, most preferably at least 75%. The nonfucosylated oligosaccharides may be of the hybrid or complex type. In a particularly preferred embodiment, the ABM produced by the host cells and methods of the invention has an increased proportion of bisected, nonfucosylated oligosaccharides in the Fc region. The bisected, nonfucosylated oligosaccharides may be either hybrid or complex. Specifically, the methods of the present invention may be used to produce ABMs in which at least 15%, more preferably at least 20%, more preferably at least 25%, more preferably at least 30%, more preferably at least 35% of the oligosaccharides in the Fc region of the ABM are bisected, nonfucosylated. The methods of the present invention may also be used to produce polypeptides in which at least 15%, more preferably at least 20%, more preferably at least 25%, more preferably at least 30%, more preferably at least 35% of the oligosaccharides in the Fc region of the polypeptide are bisected hybrid nonfucosylated.

In another embodiment, the present invention is directed to a chimeric ABM having substantially the same binding specificity of the rat ICR62 antibody engineered to have increased effector function and/or increased Fc receptor binding affinity, produced by the methods of the invention. Preferably, the increased effector function is one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a preferred embodiment, the increased Fc receptor binding affinity is increased binding to a Fc activating receptor, most preferably FcγRIIIa. In one embodiment, the ABM is an antibody, an antibody fragment containing the Fc region, or a fusion protein that includes a region equivalent to the Fc region of an immunoglobulin. In a particularly preferred embodiment, the ABM is a humanized antibody.

The present invention is further directed to pharmaceutical compositions comprising the ABMs of the present invention and a pharmaceutically acceptable carrier.

The present invention is further directed to the use of such pharmaceutical compositions in the method of treatment of cancer. Specifically, the present invention is directed to a method for the treatment of cancer comprising administering a therapeutically effective amount of the pharmaceutical composition of the invention.

The present invention further provides methods for the generation and use of host cell systems for the production of glycoforms of the ABMs of the present invention, having increased Fc receptor binding affinity, preferably increased binding to Fc activating receptors, and/or having increased effector functions, including antibody-dependent cellular cytotoxicity. The glycoengineering methodology that can be used with the ABMs of the present invention has been described in greater detail in U.S. Pat. No. 6,602,684, U.S. Pat. Appl. Publ. No. 2004/0241817 A1, U.S. Pat. Appl. Publ. No. 2003/0175884 A1, Provisional U.S. Patent Application No. 60/441,307 and WO 2004/065540, the entire contents of each of which is incorporated herein by reference in its entirety. The ABMs of the present invention can alternatively be glycoengineered to have reduced fucose residues in the Fc region according to the techniques. disclosed in U.S. Pat. Appl. Pub. No. 2003/0157108 (Genentech), or in EP 1 176 195 A1, WO 03/084570, WO 03/085119 and U.S. Pat. Appl. Pub. Nos. 2003/0115614, 2004/093621, 2004/110282, 2004/110704, 2004/132140 (Kyowa). The contents of each of these documents are herein incorporated by reference in their entireties. Glycoengineered ABMs of the invention may also be produced in expression systems that produce modified glycoproteins, such as those taught in U.S. Pat. Appl. Pub. No. 60/344,169 and WO 03/056914 (GlycoFi, Inc.) or in WO 2004/057002 and WO 2004/024927 (Greenovation), the contents of each of which are hereby incorporated by reference in their entirety.

Generation of Cell Lines for the Production of Proteins with Altered Glycosylation Pattern The present invention provides host cell expression systems for the generation of the ABMs of the present invention having modified glycosylation patterns. In particular, the present invention provides host cell systems for the generation of glycoforms of the ABMs of the present invention having an improved therapeutic value. Therefore, the invention provides host cell expression systems selected or engineered to express a polypeptide having GnTIII activity. In one embodiment, the polypeptide having GnTIII activity is a fusion polypeptide comprising the Golgi localization domain of a heterologous Golgi resident polypeptide. Specifically, such host cell expression systems may be engineered to comprise a recombinant nucleic acid molecule encoding a polypeptide having GnTIII, operatively linked to a constitutive or regulated promoter system.

In one specific embodiment, the present invention provides a host cell that has been engineered to express at least one nucleic acid encoding a fusion polypeptide having GnTIII activity and comprising the Golgi localization domain of a heterologous Golgi resident polypeptide. In one aspect, the host cell is engineered with a nucleic acid molecule comprising at least one gene encoding a fusion polypeptide having GnTIII activity and comprising the Golgi localization domain of a heterologous Golgi resident polypeptide.

Generally, any type of cultured cell line, including the cell lines discussed above, can be used as a background to engineer the host cell lines of the present invention. In a preferred embodiment, HEK293-EBNA cells, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The invention is contemplated to encompass any engineered host cells expressing a polypeptide having GnTIII activity, including a fusion polypeptide that comprises the Golgi localization domain of a heterologous Golgi resident polypeptide as defined herein.

One or several nucleic acids encoding a polypeptide having GnTIII activity may be expressed under the control of a coristitutive promoter or, alternately, a regulated expression system. Such systems are well known in the art, and include the systems discussed above. If several different nucleic acids encoding fusion polypeptides having GnTIII activity and comprising the Golgi localization domain of a heterologous Golgi resident polypeptide are comprised within the host cell system, some of them may be expressed under the control of a constitutive promoter, while others are expressed under the control of a regulated promoter. Expression levels of the fusion polypeptides having GnTIII activity are determined by methods generally known in the art, including Western blot analysis, Northern blot analysis, reporter gene expression analysis or measurement of GnTIII activity. Alternatively, a lectin may be employed which binds to biosynthetic products of the GnTIII, for example, $E_4$-PHA lectin. Alternatively, a functional assay which measures the increased Fc receptor binding or increased effector function mediated by antibodies produced by the cells engineered with the nucleic acid encoding a polypeptide with GnTIII activity may be used.

Identification of Transfectants or Transformants that Express the Protein Having A Modified Glycosylation Pattern The host cells which contain the coding sequence of a chimeric (e.g., humanized) ABM having substantially the same binding specificity of the rat ICR62 antibody and which express the biologically active gene products may be identified by at least four general approaches; (a) DNA-DNA or DNA-RNA hybridization; (b) the presence or absence of "marker" gene functions; (c) assessing the level of transcription as measured by the expression of the respective MRNA transcripts in the host cell; and (d) detection of the gene product as measured by immunoassay or by its biological activity.

In the first approach, the presence of the coding sequence of a chimeric (e.g., humanized) ABM having substantially the same binding specificity of the rat ICR62 antibody and the coding sequence of the polypeptide having GnTIII activity can be detected by DNA-DNA or DNA-RNA hybridization using probes comprising nucleotide sequences that are homologous to the respective coding sequences, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.).

For example, if the coding sequence of the ABM of the invention, or a fragment thereof, and the coding sequence of the polypeptide having GnTIII activity are inserted within a marker gene sequence of the vector, recombinants containing the respective coding sequences can be identified by the absence of the marker gene function. Alternatively, a marker gene can be placed in tandem with the coding sequences under the control of the same or different promoter used to control the expression of the coding sequences. Expression of the marker in response to induction or selection indicates expression of the coding sequence of the ABM of the invention and the coding sequence of the polypeptide having GnTIII activity.

In the third approach, transcriptional activity for the coding region of the ABM of the invention, or a fragment thereof, and the coding sequence of the polypeptide having GnTIII activity can be assessed by hybridization assays. For example, RNA can be isolated and analyzed by Northern blot using a probe homologous to the coding sequences of the ABM of the invention, or a fragment thereof, and the coding sequence of the polypeptide having GnTIII activity or particular portions thereof. Alternatively, total nucleic acids of the host cell may be extracted and assayed for hybridization to such probes.

In the fourth approach, the expression of the protein products can be assessed immunologically, for example by Western blots, immunoassays such as radioimmuno-precipitation, enzyme-linked immunoassays and the like. The ultimate test of the success of the expression system, however, involves the detection of the biologically active gene products.

Generation and Use of ABMs Having Increased Effector Function Including Antibody-Dependent Cellular Cytotoxicity In preferred embodiments, the present invention provides glycoforms of chimeric (e.g., humanized) ABMs having substantially the same binding specificity of the rat ICR62 antibody and having increased effector function including antibody-dependent cellular cytotoxicity. Glycosylation engineering of antibodies has been previously described. See e.g., U.S. Pat. No. 6,602,684, incorporated herein by reference in its entirety.

Clinical trials of unconjugated monoclonal antibodies (mAbs) for the treatment of some types of cancer have recently yielded encouraging results. Dillman, *Cancer Biother. & Radiopharm.* 12:223-25 (1997); Deo et al., *Immunology Today* 18:127 (1997). A chimeric, unconjugated IgG1 has been approved for low-grade or follicular B-cell non-Hodgkin's lymphoma. Dillman, *Cancer Biother. & Radiopharm.* 12:223-25 (1997), while another unconjugated mAb, a humanized IgG1 targeting solid breast tumors, has also been showing promising results in phase III clinical trials. Deo et al., *Immunology Today* 18:127 (1997). The antigens of these two mAbs are highly expressed in their respective tumor cells and the antibodies mediate potent tumor destruction by effector cells in vitro and in vivo. In contrast, many other unconjugated mAbs with fine tumor specificities cannot trigger effector functions of sufficient potency to be clinically useful. Frost et al., *Cancer* 80:317-33 (1997); Surfus et al., *J. Immunother.* 19:184-91 (1996). For some of these weaker mAbs, adjunct cytokine therapy is currently being tested. Addition of cytokines can stimulate antibody-dependent cellular cytotoxicity (ADCC) by increasing the activity and number of circulating lymphocytes. Frost et al., *Cancer* 80:317-33 (1997); Surfus et al., *J. Immunother.* 19:184-91 (1996). ADCC, a lytic attack on antibody-targeted cells, is triggered upon binding of leukocyte receptors to the constant region (Fc) of antibodies. Deo et al., *Immunology Today* 18:127 (1997).

A different, but complementary, approach to increase ADCC activity of unconjugated IgG1s is to engineer the Fc region of the antibody. Protein engineering studies have shown that FcγRs interact with the lower hinge region of the IgG CH2 domain. Lund et al., *J. Immunol.* 157:4963-69 (1996). However, FcγR binding also requires the presence of oligosaccharides covalently attached at the conserved Asn 297 in the CH2 region. Lund et al., *J. Immunol.* 157:4963-69 (1996); Wright and Morrison, *Trends Biotech.* 15:26-31 (1997), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction.

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., *Biochemistry* 36:130-38 (1997), with a low level of terminal sialic acid and bisecting N-acetylglucosamine (GlcNAc), and a variable degree of terminal galactosylation and core fucosylation. Some studies suggest that the minimal carbohydrate structure required for FcγR binding lies within the oligosaccharide core. Lund et al., *J. Immunol.* 157:4963-69 (1996).

The mouse- or hamster-derived cell lines used in industry and academia for production of unconjugated therapeutic mAbs normally attach the required oligosaccharide determinants to Fc sites. IgGs expressed in these cell lines lack, however, the bisecting GlcNAc found in low amounts in serum IgGs. Lifely et al., *Glycobiology* 318:813-22 (1995). In contrast, it was recently observed that a rat myeloma-produced, humanized IgG1 (CAMPATH-1H) carried a bisecting GlcNAc in some of its glycoforms. Lifely et al., *Glycobiology* 318:813-22 (1995). The rat cell-derived antibody reached a similar maximal in vitro ADCC activity as CAMPATH-1H antibodies produced in standard cell lines, but at significantly lower antibody concentrations.

The CAMPATH antigen is normally present at high levels on lymphoma cells, and this chimeric mAb has high ADCC activity in the absence of a bisecting GlcNAc.

Lifely et al., *Glycobiology* 318:813-22 (1995). In the N-linked glycosylation pathway, a bisecting GlcNAc is added by GnTIII. Schachter, *Biochem. Cell Biol.* 64:163-81 (1986).

Previous studies used a single antibody-producing CHO cell line, that was previously engineered to express, in an externally-regulated fashion, different levels of a cloned GnT III gene enzyme (Umana, P., et al., *Nature Biotechnol.* 17:176-180 (1999)). This approach established for the first time a rigorous correlation between expression of GnTIII and the ADCC activity of the modified antibody. Thus, the invention contemplates a recombinant, chimeric antibody or a fragment thereof with the binding specificity of the rat ICR62 antibody, having altered glycosylation resulting from increased GnTIII activity. The increased GnTIII activity results in an increase in the percentage of bisected oligosaccharides, as well as a decrease in the percentage of fucose residues, in the Fc region of the ABM. This antibody, or fragment thereof, has increased Fc receptor binding affinity and increased effector function. In addition, the invention is directed to antibody fragment and fusion proteins comprising a region that is equivalent to the Fc region of immunoglobulins. In a preferred embodiment, the antibody is humanized.

Therapeutic Applications of ABMs Produced According to the Methods of the Invention In the broadest sense, the ABMs of the present invention can be used target cells in vivo or in vitro that express EGFR. The cells expressing EGFR can be targetted for diagnostic or therapeutic purposes. In one aspect, the ABMs of the present invention can be used to detect the presence of EGFR in a sample. In another aspect, the ABMs of the present invention can be used to inhibit or reduce EGFR-mediated signal transduction in cells expressing EGFR on the surface. EGFR is abnormally expressed (e.g., overexpressed) in many human tumors compared to non-tumor tissue of the same cell type. Thus, the ABMs of the invention are particularly useful in the prevention of tumor formation, eradication of tumors and inhibition of tumor growth. By blocking the binding of EGFR ligands to EGFR, the ABMs of the invention inhibit EGF-dependent tumor cell activation, including EGFR tyrosine phosphorylation, increased extracellular acidification rate, and cell proliferation. The ABMs of the invention also act to arrest the cell cycle, cause apoptosis of the target cells (e.g., tumor cells), and inhibit angiogenesis and/or differentiation of target cells. The ABMs of the invention can be used to treat any tumor expressing EGFR. Particular malignancies that can be treated with the ABMs of the invention include, but are not limited to, epidermal and squamous cell carcinomas, non-small cell lung carcinomas, gliomas, pancreatic cancer, ovarian cancer, prostate cancer, breast cancer, bladder cancer, head and neck cancer, and renal cell carcinomas.

The ABMs of the present can be used alone to target and kill tumor cells in vivo. The ABMs can also be used in conjunction with an appropriate therapeutic agent to treat human carcinoma. For example, the ABMs can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma. The conjugates of the ABMs of this invention that are of prime importance are (1) immunotoxins (conjugates of the ABM and a cytotoxic moiety) and (2) labeled (e.g. radiolabeled, enzyme-labeled, or fluorochrome-labeled) ABMs in which the label provides a means for identifying immune complexes that include the labeled ABM. The ABMs can also be used to induce lysis through the natural complement process, and to interact with antibody dependent cytotoxic cells normally present.

The cytotoxic moiety of the immunotoxin may be a cytotoxic drug or an enzymatically active toxin of bacterial or plant origin, or an enzymatically active fragment ("A chain") of such a toxin. Enzymatically active toxins and fragments thereof used are diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolacca americana proteins (PAPI, PAPII, and PAP-S), momordica charantia inhibitor, curcin, crotin, sapaonaria officinalis inhibitor, gelonin, mitogellin, restrictocin, phenomycin, and enomycin. In another embodiment, the ABMs are conjugated to small molecule anticancer drugs.

Conjugates of the ABM and such cytotoxic moieties are made using a variety of bifunctional protein coupling agents. Examples of such reagents are SPDP, IT, bi functional derivatives of imidoesters such a dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of the ABMs. Additional appropriate toxins are known in the art, as evidenced in e.g., published U.S. Patent Application No. 2002/0128448, incorporated herein by reference in its entirety.

In one embodiment, a chimeric (e.g., humanized), glycoengineered ABM having substantially the same binding specificity of the rat ICR62 antibody, is conjugated to ricin A chain. Most advantageously, the ricin A chain is deglycosylated and produced through recombinant means. An advantageous method of making the ricin immunotoxin is described in Vitetta et al., *Science* 238, 1098 (1987), hereby incorporated by reference.

When used to kill human cancer cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques to determine the presence or degree of cancer.

As discussed above, a cytotoxic radiopharmaceutical for treating cancer may be made by conjugating a radioactive isotope (e.g., I, Y, Pr) to a chimeric, glycoengineered ABM having substantially the same binding specificity of the rat ICR62 antibody. The term "cytotoxic moiety" as used herein is intended to include such isotopes.

In another embodiment, liposomes are filled with a cytotoxic drug and the liposomes are coated with the ABMs of the present invention. Because there are many EGFR molecules on the surface of the EGFR-expressing malignant cell, this method permits delivery of large amounts of drug to the correct cell type.

Techniques for conjugating such therapeutic agents to antibodies are well known (see, e.g., Arnon et al., "Monoclonal Antibodies for Immunotargeting of Drugs in Cancer Therapy", in *Monoclonal Antibodies and Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); and Thorpe et al., "The Preparation And Cytotoxic Properties Of Antibody-Toxin Conjugates", *Immunol. Rev.*, 62:119-58 (1982)).

Still other therapeutic applications for the ABMs of the invention include conjugation or linkage, e.g., by recombinant DNA techniques, to an enzyme capable of converting a prodrug into a cytotoxic drug and the use of that antibody-enzyme conjugate in combination with the prodrug to convert the prodrug to a cytotoxic agent at the tumor site (see, e.g., Senter et al., "Anti-Tumor Effects of Antibody-alkaline Phosphatase", *Proc. Natl. Acad. Sci. USA* 85:4842-46 (1988); "Enhancement of the in vitro and in vivo Antitumor Activites of Phosphorylated Mitocycin C and Etoposide Derivatives by Monoclonal Antibody-Alkaline Phosphatase Conjugates", *Cancer Research* 49:5789-5792 (1989); and Senter, "Activation of Prodrugs by Antibody-Enzyme Conjugates: A New Approach to Cancer Therapy," *FASEB J.* 4:188-193 (1990)).

Still another therapeutic use for the ABMs of the invention involves use, either unconjugated, in the presence of complement, or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient [see, e.g., Ramsay et al., "Bone Marrow Purging Using Monoclonal Antibodies", *J. Clin. Immunol.*, 8(2):81-88 (1988)].

Furthermore, it is contemplated that the invention comprises a single-chain immunotoxin comprising antigen binding domains that allow substantially the same specificity of binding as the rat ICR62 antibody (e.g., polypeptides comprising the CDRs of the rat ICR62 antibody) and further comprising a toxin polypeptide. The single-chain immunotoxins of the invention may be used to treat human carcinoma in vivo.

Similarly, a fusion protein comprising at least the antigen-binding region of an ABM of the invention joined to at least a functionally active portion of a second protein having anti-tumor acitivty, e.g., a lymphokine or oncostatin, can be used to treat human carcinoma in vivo.

The present invention provides a method for selectively killing tumor cells expressing EGFR. This method comprises reacting the immunoconjugate (e.g., the immunotoxin) of the invention with said tumor cells. These tumor cells may be from a human carcinoma.

Additionally, this invention provides a method of treating carcinomas (for example, human carcinomas) in vivo. This method comprises administering to a subject a pharmaceutically effective amount of a composition containing at least one of the immunoconjugates (e.g., the immunotoxin) of the invention.

In a further aspect, the invention is directed to an improved method for treating cell proliferation disorders wherein EGFR is expressed, particularly wherein EGFR is abnormally expressed (e.g. overexpressed), including cancers of the bladder, brain, head and neck, pancreas, lung, breast, ovary, colon, prostate, skin, and kidney, comprising administering a therapeutically effective amount of an ABM of the present invention to a human subject in need thereof. In a preferred embodiment, the ABM is a glycoengineered anti-EGFR antibody with a binding specificity substantially the same as that of the rat ICR62 antibody. In another preferred embodiment the antibody is humanized. Examples of cell proliferation disorders that can be treated by an ABM of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system.

Similarly, other cell proliferation disorders can also be treated by the ABMs of the present invention. Examples of such cell proliferation disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other cell proliferation disease, besides neoplasia, located in an organ system listed above.

In accordance with the practice of this invention, the subject may be a human, equine, porcine, bovine, murine, canine, feline, and avian subjects. Other warm blooded animals are also included in this invention.

The subject invention further provides methods for inhibiting the growth of human tumor cells, treating a tumor in a subject, and treating a proliferative type disease in a subject. These methods comprise administering to the subject an effective amount of the composition of the invention.

The invention is further directed to methods for treating non-malignant diseases or disorders in a mammal characterized by abnormal activation or production of EGFR or one or more EGFR ligands, comprising administering to the mammal a therapeutically effective amount of the ABMs of the invention. The subject will generally have EGFR-expressing cells, for instance in diseased tissue thereof, such that the ABMs of the invention are able to bind to cells within the subject.

Abnormal activation or expression of EGFR or an EGFR ligand may be occurring in cells of the subject, e.g. in diseased tissue of the subject. Abnormal activation of EGFR may be attributable to amplification, overexpression or aberrant production of the EGFR and/or EGFR ligand. In one embodiment of the invention, a diagnostic or prognostic assay will be performed to determine whether abnormal production or activation of EGFR (or EGFR ligand) is occurring the subject. For example, gene amplification and/or overexpression of EGFR and/or ligand may be determined. Various assays for determining such amplification/overexpression are available in the art and include the IHC, FISH and shed antigen assays described above. Alternatively, or additionally, levels of an EGFR ligand, such as TGF-α in or associated with the sample may be determined according to known procedures. Such assays may detect protein and/or nucleic acid encoding it in the sample to be tested. In one embodiment, EGFR ligand levels in a sample may be determined using immunohistochemistry (IHC); see, for example, Scher et al. *Clin. Cancer Research* 1:545-550 (1995). Alternatively, or additionally, one may evaluate levels of EGFR -encoding nucleic acid in the sample to be tested; e.g. via FISH, southern blotting, or PCR techniques.

Moreover, EGFR or EGFR ligand overexpression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

Alternatively, one may detect EGFR heterodimers, especially EGFR-ErbB2, EGFR-ErbB3 or EGFR-ErbB4 heterodimers, in the patient, e.g. in diseased tissue thereof, prior to therapy. Various methods to detect noncovalent protein-protein interactions or otherwise indicate proximity between proteins of interest are available.

Exemplary methods for detecting EGFR heterodimers include, without limitation, immunoaffinity-based methods, such as immunoprecipitation; fluorescence resonance energy transfer (FRET) (Selvin, *Nat. Struct. Biol.* 7:730-34 (2000); Gadella & Jovin, *J. Cell Biol.* 129:1543-58 (1995); and Nagy et al., *Cytometry* 32:120-131 (1998)); co-localization of EGFR with either ErbB2 or ErbB3 using standard direct or indirect immunofluorescence techniques and confocal laser scanning microscopy; laser scanning imaging (LSI) to detect antibody binding and co-localization of EGFR with either ErbB2 or ErbB3 in a high-throughput format, such as a microwell plate (Zuck et al, *Proc. Natl. Acad. Sci. USA* 96:11122-11127 (1999)); or eTag/m assay system (Aclara Bio Sciences, Mountain View, Calif.; and U.S. Patent Application 2001/0049105, published Dec. 6, 2001).

It is apparent, therefore, that the present invention encompasses pharmaceutical compositions, combinations and methods for treating human malignancies such as cancers of the bladder, brain, head and neck, pancreas, lung, breast, ovary, colon, prostate, skin, and kidney. For example, the invention includes pharmaceutical compositions for use in the treatment of human malignancies comprising a pharmaceutically effective amount of an antibody of the present invention and a pharmaceutically acceptable carrier.

The ABM compositions of the invention can be administered using conventional modes of administration including, but not limited to, intravenous, intraperitoneal, oral, intralymphatic or administration directly into the tumor. Intravenous administration is preferred.

In one aspect of the invention, therapeutic formulations containing the ABMs of the invention are prepared for storage by mixing an antibody having the desired degree of purity with optional pharmaceutically acceptable carriers, excipients or stabilizers (REMINGTON'S PHARMACEUTICAL SCIENCES, 16$^{th}$ edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The ABMs of the present invention may be administered to a subject to treat a disease or disorder characterized by abnormal EGFR or EGFR ligand activity, such as a tumor, either alone or in combination therapy with, for example, a chemotherapeutic agent and/or radiation therapy. Exemplary anti-EGFR antibody formulations are described in Herbst and Shen, *Cancer* 94(5):1593-161 1. Suitable chemotherapeutic agents include cisplatin, doxorubicin, topotecan, paclitaxel, vinblastine, carboplatin, and etoposide.

Lyophilized formulations adapted for subcutaneous administration are described in WO97/04801. Such lyophized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g., one which binds LFA-1). The effective amount of such other agents depends on the amount of antagonist present in the formulation, the type of disease or disorder or treatment, and other factors discussed above. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16*th edition,* Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(yinylalcohol)), polylactides (U.S. Pat. No. 3,773,919), copolymers of L-glutamic acid and γethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

The compositions of the invention may be in a variety of dosage forms which include, but are not limited to, liquid solutions or suspension, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the pharmaceutical compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention will generally be in the range of from about 0.01 to about 2000 mg/kg. In one embodiment, the effective dose is in the range of from about 1.0 mg/kg to about 15.0 mg/kg. In a more specific embodiment, the dose is in the range of from about 1.5 mg/kg to about 12 mg/kg. In other embodiments, the dose is in the range of from about 1.5 mg/kg to about 4.5 mg/kg, or from about 4.5 mg/kg to about 12 mg/kg. The dose of the present invention may also be any dose within these ranges, including, but not limited to, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, 11.0 mg/kg, 11.5 mg/kg, 12.0 mg/kg, 12.5 mg/kg, 13.0 mg/kg, 13.5 mg/kg, 14.0 mg/kg, 14.5 mg/kg, or 15.0 mg/kg.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The dosages of the present invention may, in some cases, be determined by the use of predictive biomarkers. Predictive biomarkers are molecular markers that are used to determine (i.e., observe and/or quanitate) a pattern of expression and/or activation of tumor related genes or proteins, or cellular components of a tumor related signalling pathway. Elucidating the biological effects of targeted-therapies in tumor tissue and correlating these effects with clinical response helps identify the predominant growth and survival pathways operative in tumors, thereby establishing a profile of likely responders and conversely providing a rational for designing strategies to overcoming resistance. For example, biomarkers for anti-EGFR therapy may comprise molecules that are in the EGFR downstream signalling pathway that leads to a cell proliferation disorder including, but not limited to, Akt, RAS, RAF, MAPK, ERKl, ERK2, PKC, STAT3, STAT5 (Mitchell, *Nature Biotech.* 22: 363-364 (2004); Becker, *Nature Biotech* 22:15-18 (2004); Tsao and Herbst, *Signal* 4:4-9 (2003)). Biomarkers for anti-EGFR therapy may also comprise growth factor receptors such as EGFR, ErbB-2 (HER2/neu), and ErbB-3 (HER3), and may be positive or negative predictors of patient response to anti-EGFR therapy. For example, the growth factor receptor ErbB-3 (HER3) was determined to be a negative predictive biomarker for the anti-EGFR antibody ABX-EGF (U.S. Pat. Appl. Pub. No. 2004/0132097 A1).

Predictive biomarkers may be measured by cellular assays that are well known in the art including, but not limited to immunohistochemistry, flow cytometry, immunofluorescence, capture-and-detection assays, and reversed phase assays, and/or assays set forth in U.S. Pat. Appl. Pub. No. 2004/0132097 A1, the entire contents of which are herein incorporated by reference . Predictive biomarkers of anti-EGFR therapy, themselves, can be identified according to the techniques set forth in U.S. Pat. Appl. Pub. No. 2003/0190689A1, the entire contents of which are hereby incorporated by reference.

In one aspect, the present invention provides for a method for treating an EGFR-related disorder comprising predicting a response to anti-EGFR therapy in a human subject in need of treatment by assaying a sample from the human subject prior to therapy with one or a plurality of reagents that detect expression and/or activiation of predictive biomarkers for an EGFR-related disorder such as cancer; determining a pattern of expression and/opr activation of one or more of the predictive biomarkers, wherein the pattern predicts the human subject's response to the anti-EGFR therapy; and administering to a human subject who is predicted to respond positively to anti-EGFR treatment a therapeutically effective amount of a composition comprising an ABM of the present invention. As used herein, a human subject who is predicted to respond-positively to anti-EGFR treatment is one for whom anti-EGFR will have a measurable effect on the EGFR-related disorder (e.g., tumor regression/shrinkage) and for whom the benefits of anti-EGFR therapy are not outweighed by adverse effects (e.g., toxicity). As used herein, a sample means any biological sample from an organism, particularly a human, comprising one or more cells, including single cells of any origin, tissue or biopsy samples which has been removed from organs such as breast, lung, gastrointestinal tract, skin, cervix, ovary, prostate, kidney, brain, head and neck ,or any other organ or tissue of the body, and other body samples including, but not limited to, smears, sputum, secretions, cerebrospinal fluid, bile, blood, lymph fluid, urine and feces.

The composition comprising an ABM of the present invention will be formulated, dosed, and administered in a fashion consistent with good medical practice. Factors for consideration in this context include the particular disease or disorder being treated, the particular mammal being treated, the clinic condition of the individual patient, the cause of the disease or disorder, the site of delivery of the agent, the method of administration, the scheduling of administration, and other factors known to medical practitioners. The therapeutically effective amount of the antagonist to be administered will be governed by such considerations.

As a general proposition, the therapeutically effective amount of the antibody administered parenterally per dose will be in the range of about 0.1 to 20 mg/kg of patient body weight per day, with the typical initial range of antagonist used being in the range of about 2 to 10 mg/kg. In one embodiment, the therapeutically effective amount is in the range of from about 1.0 mg/kg to about 15.0 mg/kg. In a more specific embodiment, the dose is in the range of from about 1.5 mg/kg to about 12 mg/kg. In other embodiments, the dose is in the range of from about 1.5 mg/kg to about 4.5 mg/kg, or from about 4.5 mg/kg to about 12 mg/kg. The dose of the present invention may also be any dose within these ranges, including, but not limited to, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, 11.0 mg/kg, 11.5 mg/kg, 12.0 mg/kg, 12.5 mg/kg, 13.0 mg/kg, 13.5 mg/kg, 14.0 mg/kg, 14.5 mg/kg, or 15.0 mg/kg.

In a preferred embodiment, the ABM is an antibody, preferably a humanized antibody. Suitable dosages for such an unconjugated antibody are, for example, in the range from about 20 mg/m$^2$ to about 1000 mg/m$^2$. For example, one may administer to the patient one or more doses of substantially less than 375 mg/m$^2$ of the antibody, e.g., where the dose is in the range from about 20 mg/m² to about 250 mg/m², for example from about 50 mg/m² to about 200 mg/m².

Moreover, one may administer one or more initial dose(s) of the antibody followed by one or more subsequent dose(s), wherein the mg/m² dose of the antibody in the subsequent dose(s) exceeds the mg/m² dose of the antibody in the initial dose(s). For example, the initial dose may be in the range from about 20 mg/m² to about 250 mg/m² (e.g., from about 50 mg/m² to about 200 mg/m²) and the subsequent dose may be in the range from about 250 mg/M² to about 1000 mg/M².

As noted above, however, these suggested amounts of ABM are subject to a great deal of therapeutic discretion. The key factor in selecting an appropriate dose and scheduling is the result obtained, as indicated above. For example, relatively higher doses may be needed initially for the treatment of ongoing and acute diseases. To obtain the most efficacious results, depending on the disease or disorder, the antagonist is administered as close to the first sign, diagnosis, appearance, or occurrence of the disease or disorder as possible or during remissions of the disease or disorder.

In the case of anti-EGFR antibodies used to treat tumors, optimum therapeutic results have generally been achieved with a dose that is sufficient to completely saturate the EGF receptors on the target cells. The dose necessary to achieve saturation will depend on the number of EGF receptors expressed per tumor cell (which can vary significantly between different tumor types). Serum concentrations as low as 30 nM have been effective in treating some tumors, while concentrations above 100 nM may be necessary to achieve optimum therapeutic effect with other tumors. The dose necessary to achieve saturation for a given tumor can be readily determined in vitro by radioimmunoassay or immunoprecipitation.

In general, for combination therapy with radiation, one suitable therapeutic regimen involves eight weekly infusions of an anti-EGFR ABM of the invention at a loading dose of 100-500 mg/M² followed by maintenance doses at 100-250 mg/M² and radiation in the amount of 70.0 Gy at a dose of 2.0 Gy daily. For combination therapy with chemotherapy, one suitable therapeutic regimen involves administering an anti-EGFR ABM of the invention as loading/maintenance doses weekly of 100/100 mg/M², 400/250 mg/M², or 500/250 mg/M² in combination with cisplatin at a dose of 100 mg/M² every three weeks. Alternatively, gemcitabine or irinotecan can be used in place of cisplatin.

The ABM of the present invention is administered by any suitable means, including parenteral, subcutaneous, intraperitoneal, intrapulinonary, and intranasal, and, if desired for local immunosuppressive treatment, intralesional administration. Parenteral infusions include intramuscular, intravenous, intraarterial, intraperitoneal, or subcutaneous administration. In addition, the antagonist may suitably be administered by pulse infusion, e.g., with declining doses of the antagonist. Preferably the dosing is given by injections, most preferably intravenous or subcutaneous injections, depending in part on whether the administration is brief or chronic.

One may administer other compounds, such as cytotoxic agents, chemotherapeutic agents, immunosuppressive agents and/or cytokines with the antagonists herein. The combined administration includes coadministration, using separate formulations or a single pharmaceutical formulation, and consecutive administration in either order, wherein preferably there is a time period while both (or all) active agents simultaneously exert their biological activities.

It would be clear that the dose of the composition of the invention required to achieve cures may be further reduced with schedule optimization.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

In yet another embodiment, the invention relates to an ABM according to the present invention for use as a medicament, in particular for use in the treatment or prophylaxis of cancer or for use in a precancerous condition or lesion. The cancer may be, for example, lung cancer, non small cell lung (NSCL) cancer, bronchioalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme; astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions.

Preferably, said cancer is selected from the group consisting of breast cancer, bladder cancer, head & neck cancer, skin cancer, pancreatic cancer, lung cancer, ovarian cancer, colon cancer, prostate cancer, kidney cancer, and brain cancer.

Yet another embodiment is the use of the ABM according to the present invention for the manufacture of a medicament for the treatment or prophylaxis of cancer. Cancer is as defined above.

Preferably, said cancer is selected from the group consisting of breast cancer, bladder cancer, head & neck cancer, skin cancer, pancreatic cancer, lung cancer, ovarian cancer, colon cancer, prostate cancer, kidney cancer, and brain cancer.

Also preferably, said antigen binding molecule is used in a therapeutically effective amount from about 1.0 mg/kg to about 15 mg/kg.

Also more preferably, said antigen binding molecule is used in a therapeutically effective amount from about 1.5 mg/kg to about 12 mg/kg.

Also more preferably, said antigen binding molecule is used in a therapeutically effective amount from about 1.5 mg/kg to about 4.5 mg/kg.

Also more preferably, said antigen binding molecule is used in a therapeutically effective amount from about 4.5 mg/kg to about 12 mg/kg.

Most preferably, said antigen binding molecule is used in a therapeutically effective amount of about 1.5 mg/kg.

Also most preferably, said antigen binding molecule is used in a therapeutically effective amount of about 4.5 mg/kg.

Also most preferably, said antigen binding molecule is used in a therapeutically effective amount of about 12 mg/kg.

In another embodiment, the present invention is directed to method of treating an EGFR-related disorder in a mammal in need of treatment thereof comprising administering to the mammal an ABM of the present invention, wherein the treatment results in serum concentrations of said ABM between about 1 and about 500 μg/ml, for a period of at least 4 weeks, and wherein the treatment does not cause a clinically significant level of toxicity in said mammal. In other embodiments, the serum concentration is an amount selected from the group consisting of above 1 μg/ml, above 25 μg/ml, above 50 μg/ml, above 100 μg/ml, above 200 μg/ml, above 300 μg/ml, above 400 μg/ml, above 500 μg/ml, between about 1 and about 100 μg/ml, between about 1 and about 200 μg/ml, between about 1 and about 300 μg/ml, between about 1 and about 400 μg/ml, and between about 1 and about 500 μg/ml. In a preferred embodiment, the mammal is a human. In one embodiment the ABM is an antibody. In a preferred embodiment, the antibody is glycoengineered and has increased FcgammaRIII binding compared to a non-glycoengineered form of the antibody.

Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-EGFR antibody. The label or package insert indicates that the composition is used for treating the condition of choice, such as a non-malignant disease or disorder, where the disease or disorder involves abnormal activation or production of an EGFR receptor and/or a EGFR-ligand, for example a benign hyperproliferative disease or disorder. Moreover, the article of manufacture may comprise (a) a first container with a composition contained therein, wherein the composition comprises a first antibody which binds EGFR and inhibits growth of cells which overexpress EGFR; and (b) a second container with a composition contained therein, wherein the composition comprises a second antibody which binds EGFR and blocks ligand activation of an EGFR receptor. The article of manufacture in this embodiment of the invention may further comprises a package insert indicating that the first and second antibody compositions can be used to treat a non-malignant disease or disorder from the list of such diseases or disorders in the definition section above. Moreover, the package insert may instruct the user of the composition (comprising an antibody which binds EGFR and blocks ligand activation of an EGFR receptor) to combine therapy with the antibody and any of the adjunct therapies described in the preceding section (e.g. a chemotherapeutic agent, an EGFR-targeted drug, an anti-angiogenic agent, an immunosuppressive agent, tyrosine kinase inhibitor, an anti-hormonal compound, a cardioprotectant and/or a cytokine). Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All patents, applications, and publications cited in this application are hereby incorporated by reference in their entirety.

EXAMPLES

Unless otherwise specified, references to the numbering of specific amino acid residue positions in the following Examples are according to the Kabat numbering system. Unless otherwise noted, the materials and methods used to make the antibodies described in these working examples are in accordance with those set forth in the examples of U.S. patent application Ser. No. 10/981,738, which is herein incorporated by reference in its entirety.

Example 1

Materials and Methods

High Homology Acceptor Approach

The high homology antibody acceptor framework search was performed by aligning the rat ICR62 protein sequence to a collection of human germ-line sequences and choosing that human sequence that showed the highest sequence identity, while conserving all canonical residues on a functional level. Here, the sequence 1-e from the VH1 family within the VBase database was chosen as the heavy chain framework acceptor sequence, and the A30 sequence from the VK1 family of the VBase database was chosen to be the framework acceptor for the light chain. On these two acceptor frameworks the three complementarity determining regions (CDRs) and/or specificity-determining residues of those CDRs of the rat ICR62 heavy and light variable domains were grafted. Since the framework 4 region is not part of the variable region of the germ line gene, the alignment for that position was performed individually. The JH6 region was chosen for the heavy chain, and the JK2 region was chosen for the light chain. Molecular modelling of the designed immunoglobulin domain revealed one position outside of the Kabat CDR1 potentially requiring the murine amino acid residues instead of the human ones outside of the CDR. Reintroduction of murine amino acid residues into the human framework would generate so-called "back mutations." For example, the human acceptor amino acid residue at Kabat position 27 (Glycine in 1-e) was back mutated to a tyrosine residue. To show the importance of the residues for antigen binding, humanized antibody variants were designed that either included or omitted the back mutations. The humanized antibody light chain did not require any back mutations. After designing the protein sequences, DNA sequences encoding these proteins were synthesized as detailed below.

Mixed Framework Approach

To avoid the need for introducing back mutations at critical positions (critical to retain good antigen binding affinity or antibody functions) of the human acceptor framework, it was investigated whether framework region 1 (FR1), framework regions 1 (FR1) and 2 (FR2) together, or framework region 3 (FR3) of a functionally humanized antibody could be replaced by human antibody sequences already having donor residues, or amino acid residues that are fuictionally equivalent to donor residues, at important residue positions in the natural human germline sequence. For this purpose, the VH frameworks 1, 2 and 3 of the rat ICR62 VH sequence were aligned individually to human germ-line sequences. Here, highest sequence identity was not used for choosing acceptor frameworks; instead matching of several critical residues was performed. Those critical residues comprise the so-called canonical residues, and also those residues at position 27, 28, and 30 (Kabat numbering), which lie outside of the CDR1 definition by Kabat, but often are involved in antigen binding. In addition, critical residues are those that show important interaction with the CDRs, as can be determined using molecular modelling. The IMGT sequence IGHV1-58 (Accession No. M29809), IGHV5-51 (Accession No. M99686), as well as the VBase sequence 1-02 from the VH1 family were chosen as suitable ones for replacing either FR1, 2, or 3. In brief: IGHV1-58 showed a promising pattern in the Kabat positions 27 to 30, but does not fulfill the criteria for the canonical position 71. The IGHV5-51 has a matching residue 71, so its FR3 could be used. Also its FR1 is close to the desired FR1 sequence.

The 1-e of VH1 fulfilled all criteria apart from position 27. Sequence 1-02 was considered acceptable for the FR1 and FR2 regions, but would require a back mutation in FR3.

After designing the protein sequences, DNA sequences encoding these proteins were synthesized as detailed below. Using this approach back mutations were not necessary in most of the constructs of the heavy chain, in order to retain good levels of antigen binding. The chronology and the reasoning of the mixed framework constructs is explained in the results section.

Synthesis of the Antibody Genes

After having designed the amino acid sequence of the humanized antibody V region, the DNA sequence was generated. The DNA sequence data of the individual frame work regions was found in the databases (e.g. IMGT or VBase) for human germ line sequences. The DNA sequence information of the CDR regions was taken from the published sequence of the rat ICR62 antibody (see, e.g., PCT Publication WO 95/20045). With these sequences, the whole DNA sequence was virtually assembled. Having this DNA sequence data, diagnostic restriction sites were introduced in the virtual sequence by introducing silent mutations, creating recognition sites for restriction endonucleases. To obtain the physical DNA chain, gene synthesis was performed (see, e.g., Wheeler et al. 1995). In this method, oligonucleotides are designed from the genes of interest, such, that a series of oligonucleotides is derived from the coding strand, and one other series is from the non-coding strand. The 3' and 5' ends of each oligonucleotide (except the very first and last in the row) always show complementary sequences to two primers derived from the opposite strand. When putting these oligonucleotides into a reaction buffer suitable for any heat stable polymerase, and adding $Mg^{2+}$, dNTPs and a DNA polymerase, each oligonucleotide is extended from its 3' end. The newly formed 3' end of one primer then anneals with the next primer of the opposite strand, and extending its sequence further under conditions suitable for template dependant DNA chain elongation. The final product was cloned into a conventional vector for propagation in E. coli.

Antibody Production

For construction of the chimeric (i.e., fully rat V region and human C region) and humanized anti-EGFR light and heavy chain expression vectors, human heavy and light chain leader sequences (for secretion) were added upstream of the variable region DNA sequences. Downstream of the variable regions, the constant regions of IgG1 for the heavy chain were added, and the kappa constant region for the light chain using standard molecular biology techniques. The resulting full antibody heavy and light chain DNA sequences were subcloned into mammalian expression vectors (one for the light chain and one for the heavy chain) under the control of the MPSV promoter and upstream of a synthetic polyA site, each vector carrying an EBV OriP sequence.

Antibodies were produced by co-transfecting HEK293-EBNA cells with the mammalian antibody heavy and light chain expression vectors using a calcium phosphate-transfection approach. Exponentially growing HEK293-EBNA cells were transfected by the calcium phosphate method. For the production of unmodified antibody, the cells were transfected only with antibody heavy and light chain expression vectors in a 1:1 ratio. For the production of the glycoengineered antibody, the cells were co-transfected with four plasmids, two for antibody expression, one for a fusion GnTIII polypeptide expression, and one for mannosidase II expression at a ratio of 4:4:1:1, respectively. Cells were grown as adherent monolayer cultures in T flasks using DMEM culture medium supplemented with 10% FCS, and were transfected when they were between 50 and 80% confluent. For the transfection of a T75 flask, 8 million cells were seeded 24 hours before transfection in 14 ml DMEM culture medium supplemented with FCS (at 10% V/V final), 250 µg/ml neomycin, and cells were placed at 37° C. in an incubator with a 5% CO2 atmosphere overnight. For each T75 flask to be transfected, a solution of DNA, CaCl2 and water was prepared by mixing 47 µg total plasmid vector DNA divided equally between the light and heavy chain expression vectors, 235 µl of a 1M CaCl2 solution, and adding water to a final volume of 469 µl. To this solution, 469 µl of a 50 mM HEPES, 280 mM NaCl, 1.5 mM Na2HPO4 solution at pH 7.05 were added, mixed immediately for 10 sec and left to stand at room temperature for 20 sec. The suspension was diluted with 12 ml of DMEM supplemented with 2% FCS, and added to the T75 in place of the existing medium. The cells were incubated at 37° C., 5% CO2 for about 17 to 20 hours, then medium was replaced with 12 ml DMEM, 10% FCS. The conditioned culture medium was harvested 5 to 7 days post-transfection centrifuged for 5 min at 1200 rpm, followed by a second centrifugation for 10 min at 4000 rpm and kept at 4° C.

The secreted antibodies were purified by Protein A affinity chromatography, followed by cation exchange chromatography and a final size exclusion chromatographic step on a Superdex 200 column (Amersham Pharmacia) exchanging the buffer to phosphate buffer saline and collecting the pure monomeric IgG1 antibodies. Antibody concentration was estimated using a spectrophotometer from the absorbance at 280 nm. The antibodies were formulated in a 25 mM potassium phosphate, 125 mM sodium chloride, 100 mM glycine solution of pH 6.7.

Glycoengineered variants of the humanized antibody were produced by co-transfection of the antibody expression vectors together with a GnT-III glycosyltransferase expression vector, or together with a GnT-III expression vector plus a Golgi mannosidase II expression vector. Glycoengineered antibodies were purified and formulated as described above for the non-glycoengineered antibodies. The oligosaccharides attached to the Fc region of the antibodies were analysed by MALDI/TOF-MS as described below.

Oligosaccharide Analysis

Oligosaccharides were enzymatically released from the antibodies by PNGaseF digestion, with the antibodies being either immobilized on a PVDF membrane or in solution.

The resulting digest solution containing the released oligosaccharides either prepared directly for MALDI/TOF-MS analysis or was further digested with EndoH glycosidase prior to sample preparation for MALDI/TOF-MS analysis.

Oligosaccharide Release Method for PVDF Membrane-Immobilized Antibodies

The wells of a 96-well plate made with a PVDF (Immobilon P, Millipore, Bedford, Mass.) membrane were wetted with 100 µl methanol and the liquid was drawn through the PVDF membrane using vacuum applied to the Multiscreen vacuum manifold (Millipore, Bedford, Mass.). The PVDF membranes were washed three times with 300 µl of water. The wells were then washed with 50 µl RCM buffer (8M Urea, 360 mM Tris, 3.2 mM EDTA, pH 8.6). Between 30-40 µg antibody was loaded in a well containing 10 µl RCM buffer. The liquid in the well was drawn through the membrane by applying vacuum, and the membrane was subsequently washed twice with 50 µl RCM buffer. The reduction of disulfide bridges was performed by addition of 50 µl of 0.1M dithiothreitol in RCM and incubation at 37° C. for 1 h.

Following reduction, a vacuum was applied to remove the dithiothreitol solution from the well. The wells were washed three times with 300 µl water before performing the carboxymethylation of the cysteine residues by addition of 50 µl 0.1M iodoacetic acid in RCM buffer and incubation at room temperature in the dark for 30 min.

After carboxymethylation, the wells were drawn with vacuum and subsequently washed three times with 300 µl water. The PVDF membrane was then blocked, to prevent adsorption of the endoglycosidase, by incubating 100 µl of a 1% aqueous solution of polyvinylpyrrolidone 360 at room temperature for 1 hour. The blocking reagent was then removed by gentle vacuum followed by three washes with 300 µl water.

N-linked oligosaccharides were released by addition of 2.5 mU peptide-N-glycosydase F (recombinat N-Glycanase, GLYKO, Novato, Calif.) and 0.1 mU Sialidase (GLYKO, Novato, Calif.), to remove any potential charged monosaccharide residues, in a final volume of 25 µl in 2OmM NaHCO$_3$, pH7.0). Digestion was performed for 3 hours at 37° C.

Oligosaccharide Release Method for Antibodies in Solution

Between 40 and 50 µg of antibody were mixed with 2.5 mU of PNGaseF (Glyko, U.S.A.) in 2 mM Tris, pH7.0 in a final volume of 25 microliters, and the mix was incubated for 3 hours at 37° C.

Use of Endoglycosidase H Digestion of PNGaseF-Released Oligosaccharides for the Assignment of Hybrid Bisected Oligosaccharide Structures to MALDI/TOF-MS Neutral Oligosaccharide Peaks The PNGaseF released oligosaccharides were subsequently digested with Endoglycosidase H (EC 3.2.1.96). For the EndoH digestion, 15 mU of EndoH (Roche, Switzerland) were added to the PNGaseF digest (antibody in solution method above) to give a final volume of 30 microliters, and the mix was incubated for 3 hours at 37° C. EndoH cleaves between the N-acetylglucosamine residues of the chitobiose core of N-linked oligosaccharides. The enzyme can only digest oligomannose and most hybrid type glycans, whereas complex type oligosaccharides are not hydrolyzed.

Sample Preparation for MALDI/TOF-MS

The enzymatic digests containing the released oligosaccharides were incubated for a further 3 h at room after the addition of acetic acid to a final concentration of 150 mM, and were subsequently passed through 0.6 ml of cation exchange resin (AG50W-X8 resin, hydrogen form, 100-200 mesh, Bio-Rad, Switzerland) packed into a micro-bio-spin chromatography column (BioRad, Switzerland) to remove cations and proteins. One microliter of the resulting sample was applied to a stainless steel target plate, and mixed on the plate with 1 µl of sDHB matrix. sDHB matrix was prepared by dissolving 2 mg of 2,5-dihydroxybenzoic acid plus 0.1 mg of 5-methoxysalicylic acid in 1 ml of ethanol/10 mM aqueous sodium chloride 1:1 (v/v). The samples were air dried, 0.2 µl ethanol was applied, and the samples were finally allowed to re-crystallize under air.

MALDI/TOF-MS

The MALDI-TOF mass spectrometer used to acquire the mass spectra was a Voyager Elite (Perspective Biosystems). The instrument was operated in the linear configuration, with an acceleration of 20kV and 80 ns delay. External calibration using oligosaccharide standards was used for mass assignment of the ions. The spectra from 200 laser shots were summed to obtain the final spectrum.

Antigen Binding Assay

The purified, monomeric humanized antibody variants were tested for binding to human epidermal growth factor receptor (EGFR, also referred to in the literature as HER-1 or ErbB1) on the A431 human epidermal cell line, using a flow cytometry-based assay. 200,000 cells (e.g., from human A431 cell line) in 180 µl FACS buffer (PBS containing 2% FCS and 5 mM EDTA) were transferred to 5 ml polystyrene tubes and 20 µl 10 fold concentrated anti-EGFR antibody (primary antibody) samples (1-5000 ng/ml final concentration) or PBS only were added. After gently mixing the samples, the tubes were incubated at 4° C. for 30 min in the dark. Subsequently, samples were washed twice with FACS buffer and pelleted at 300×g for 3min. Supernatant was aspirated off and cells were taken up in 50 µl FACS buffer and 2 µl secondary antibody (anti-Fc-specific F(ab')2-FITC fragments (Jackson Immuno Research Laboratories, USA)) was added and the tubes were incubated at 4° C. for 30 min. Samples were washed twice with FACS buffer and taken up in 500 µl of FACS buffer for analysis by Flow Cytometry. Binding was determined by plotting the geometric mean fluorescence against the antibody concentrations.

Binding of Monomeric IgG1 Glycovariants to FcγRIIIA-Expressing CHO Cell Line

CHO cells were transfected by electroporation (280 V, 950 μF, 0.4 cm) with an expression vector coding for theFcgammaRIIIA-Val158 α-chain and the γ-chain. Transfectants were selected by addition of 6 μg/ml puromycin and stable clones were analyzed by FACS using 10 μl FITC-conjugated-anti-FcgammaRIII 3G8 monoclonal antibody (BD Biosciences, Allschwil/Switzerland) for 106 cells. Binding of IgG1 to FcgammaRIIIA-Val158-expressing CHO cells was performed. Briefly, the anti-FcgammaRIIIA 3G8 F(ab')2 fragments (Ancell, Bayport, Minn. USA) were added at a concentration of 10 μg/ml to compete binding of antibody glycovariants (3 μg/ml). The fluorescence intensity referring to the bound antibody variants was determined on a FACS-Calibur (BD Biosciences, Allschwil /Switzerland).

ADCC assay

Human peripheral blood mononuclear cells (PBMC) were used as effector cells and were prepared using Histopaque-1077 (Sigma Diagnostics Inc., St. Louis, Mo. 63178 USA) following essentially the manufacturer's instructions. In brief, venous blood was taken with heparinized syringes from healthy volunteers. The blood was diluted 1:0.75-1.3 with PBS (not containing $Ca^{++}$ or $Mg^{++}$) and layered on Histopaque-1077. The gradient was centrifuged at 400×g for 30 min at room temperature (RT) without breaks. The interphase containing the PBMC was collected and washed with PBS (50 ml per cells from two gradients) and harvested by centrifugation at 300×g for 10 minutes at RT. After resuspension of the pellet with PBS, the PBMC were counted and washed a second time by centrifugation at 200×g for 10 minutes at RT. The cells were then resuspended in the appropriate medium for the subsequent procedures.

The effector to target ratio used for the ADCC assays was 25:1 and 10:1 for PBMC and NK cells, respectively. The effector cells were prepared in AIM-V medium at the appropriate concentration in order to add 50 μl per well of round bottom 96 well plates. Target cells were human EGFR expressing cells (e.g., A431, EBC-1, or LN229) grown in DMEM containing 10% FCS. Target cells were washed in PBS, counted and resuspended in AIM-V at 0.3 million per ml in order to add 30,000 cells in 100 μl per microwell. Antibodies were diluted in AIM-V, added in 50 μl to the pre-plated target cells and allowed to bind to the targets for 10 minutes at RT. Then the effector cells were added and the plate was incubated for 4 hours at 37° C. in a humidified atmosphere containing 5% $CO2$. Killing of target cells was assessed by measurement of lactate dehydrogenase (LDH) release from damaged cells using the Cytotoxicity Detection kit (Roche Diagnostics, Rotkreuz, Switzerland). After the 4-hour incubation the plates were centrifuged at 800×g. 100 μl supernatant from each well was transferred to a new transparent flat bottom 96 well plate. 100 μl color substrate buffer from the kit were added per well. The Vmax values of the color reaction were determined in an ELISA reader at 490 nm for at least 10 min using SOFTmax PRO software (Molecular Devices, Sunnyvale, Calif. 94089, USA). Spontaneous LDH release was measured from wells containing only target and effector cells but no antibodies. Maximal release was determined from wells containing only target cells and 1% Triton X-100. Percentage of specific antibody-mediated killing was calculated as follows: ((x−SR)/(MR−SR)*100, where x is the mean of Vmax at a specific antibody concentration, SR is the mean of Vmax of the spontaneous release and MR is the mean of Vmax of the maximal release.

Example 2

Results and Discussion

Comparison of the binding to human EGF-receptor of antibody variants I-HHA, I-HHB, I-HHC, I-HLA, I-HLB, I-HLC, I-HLA1, I-HLA2, I-HLA3, I-HLA4, I-HLA5, I-HLA6, I-HLA7, I-HLA8, I-HLA-9, I-HHD, I-HHE, I-HHF, and I-HHG, either complexed with the chimeric ICR62 light chain or with the humanized ICR62 light chains (I-KA, I-KB, or I-KC) and the parental, chimeric antibody ch-ICR62 shows that all antibodies have within one log unit similar EC50 values. Only the I-HHA has strongly diminished binding activity (see FIG. 2). FIG. 1 shows the functional activity of the individual chimeric ICR62 (ch-ICR62) polypeptide chains when combined with the humanized constructs I-HHC and I-KB, respectively. In this experiment, eiher the light chain, the heavy chain or both chains simultaneously of the ch-ICR62 were replaced by the above mentioned humanized constructs. This shows that the VH/VL interface formation seems to work as well in the rodent antibody as well as in the humanized constructs.

Figure 2:
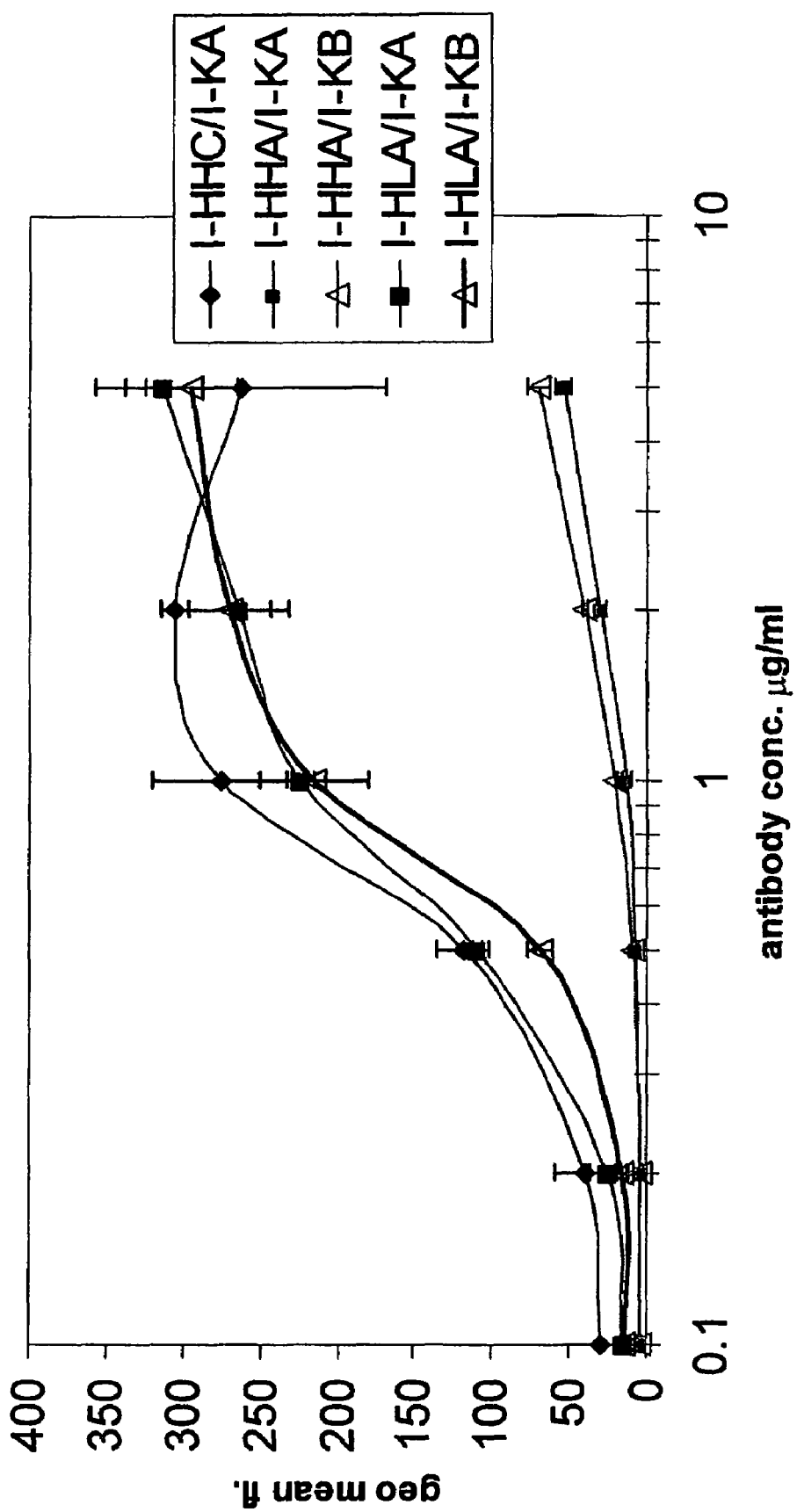
FIG. 2 shows binding activity of humanized ICR62 antibodies comprising heavy chain variable region constructs I-HHC, I-HHA and I-HLA and humanized light chain variable region constructs I-KA and I-KB paired in various configurations.
Figure 3:
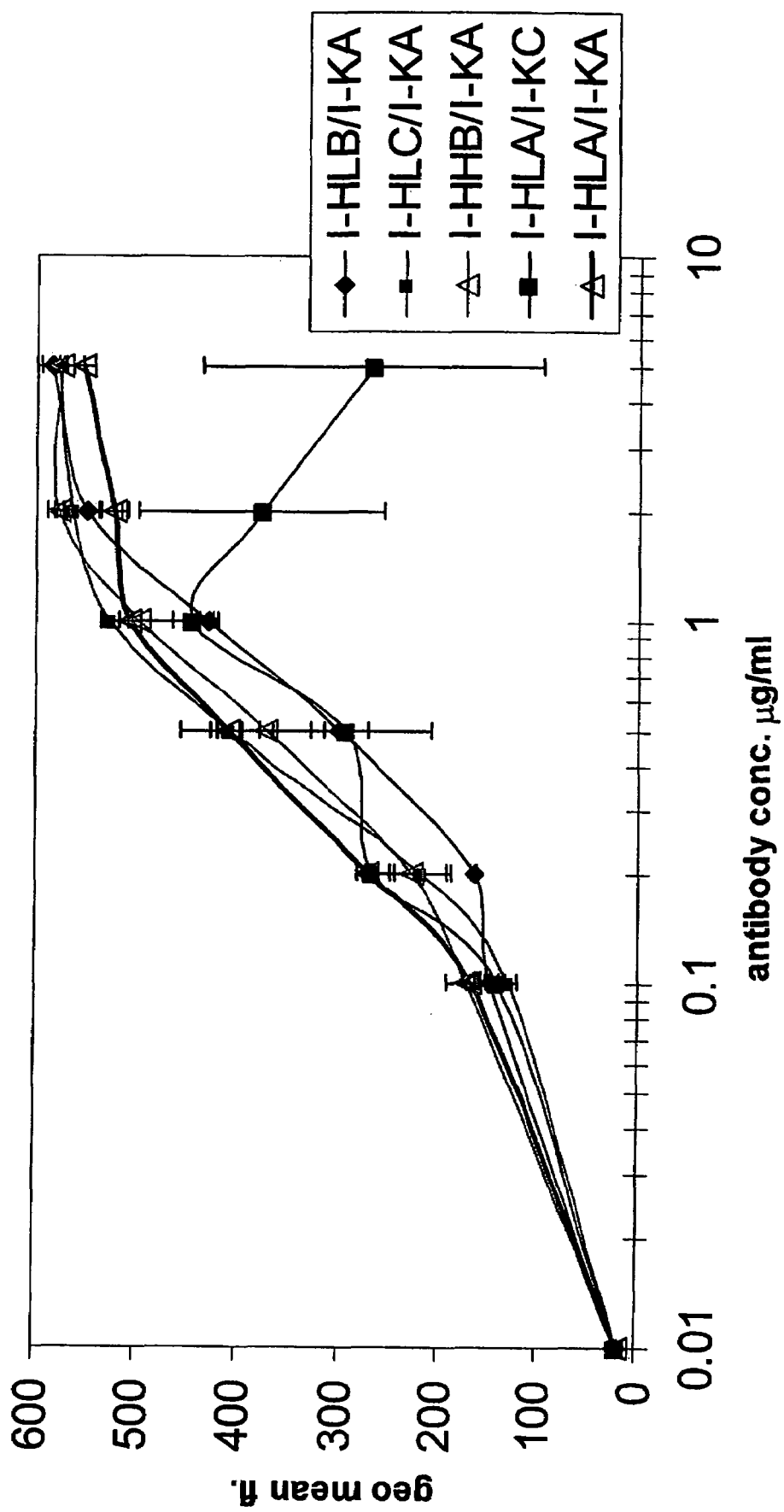
FIG. 3 shows binding activity of humanized ICR62 antibodies comprising heavy chain variable region constructs I-HLB, I-HLC and I-HLA and humanized light chain variable region constructs I-KA and I-KC paired in various configurations.

As shown in FIG. 2, the humanized heavy chain I-HHA could not restore binding activity with either the I-KA, or the I-KB light chain. Since the I-HLA did show binding with both the I-KA, and the I-KB, the present inventors concluded that the heavy chain of I-HHA is not functional in antigen binding. FIGS. 1 and 2, combined with FIG. 3, show that the light chain constructs I-KA, I-KB, and I-KC show binding behavior indistinguishable from the rodent counterpart. Variant I-KC does not possess any back mutations, and additionally has its CDR1 partially humanized, such that residues 24-29 can be derived from the human acceptor sequence (A30 of VK1, as mentioned before).

In the series I-HHA, I-HHB, and I-HHC, only the latter two variants showed satisfactory binding behavior (FIGS. 2 and 3). Sequence analysis of the I-HHA revealed three potential amino acid residues responsible for this behavior: Lys33, His35, and Tyr50. Constructs that have Lys33 replaced by tyrosine showed good binding, as well as constructs having the Tyr50 replaced by tryptophane. Only when these two residues were replaced by alanine and glycine, respectively, was the binding lost. Since I-HHC did not show better binding than I-HHB, the present inventors concluded that residues Asn60, Glu61, Lys64, and Ser65 need not be of rodent origin; or they can be replaced by Ala, Gln, Gln, and Gly, respectively. This procedure leads to a construct in which the CDR2 is more humanized, since amino acid positions 60 to 65 are part of the Kabat CDR definition, but there is no need to graft the rodent donor residues for this antibody.

Figure 4:
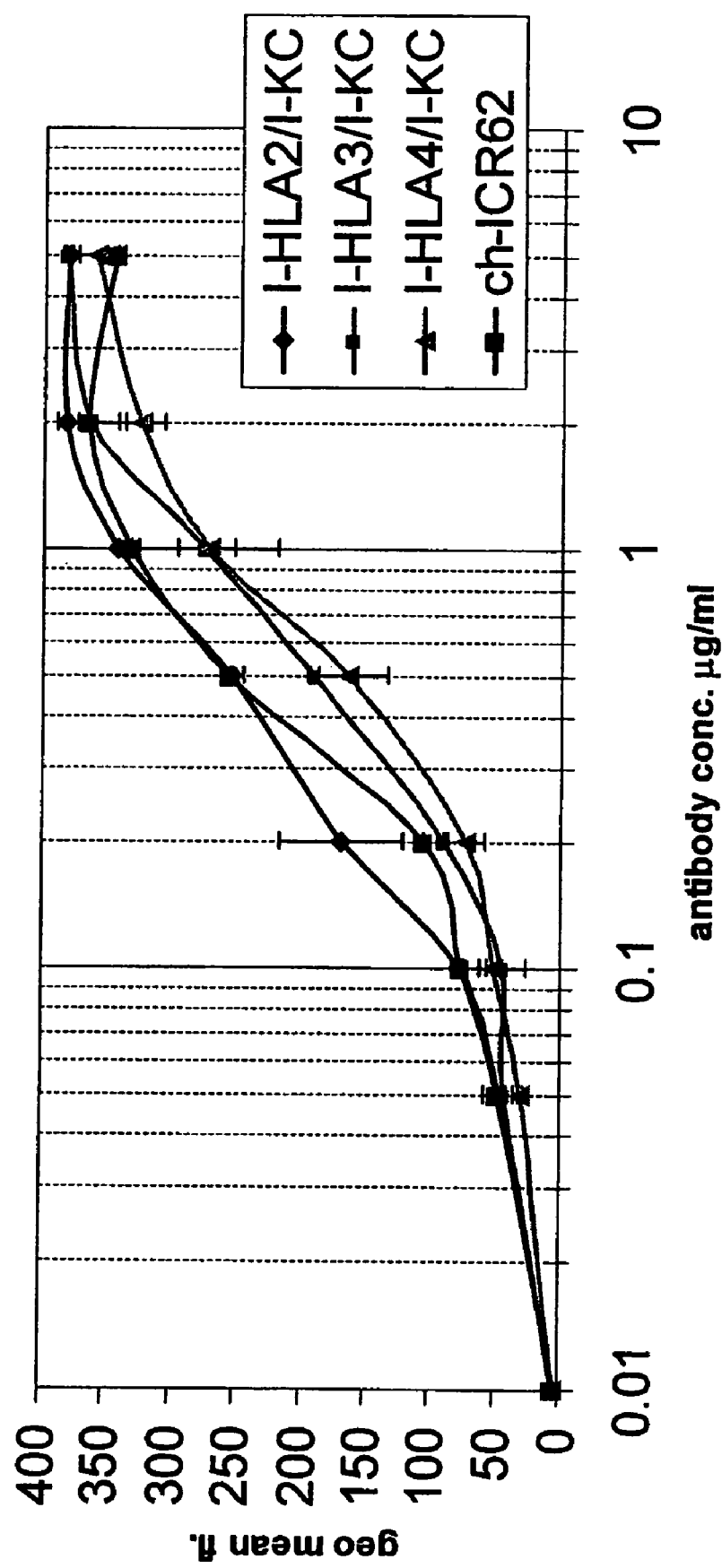
FIG. 4 shows binding activity of humanized ICR62 antibodies comprising heavy chain variable region constructs I-HLA2, I-HLA3 and I-HLA4 and humanized light chain variable region construct I-KC as compared to chimeric rat-human ICR62 antibody.
Figure 5:
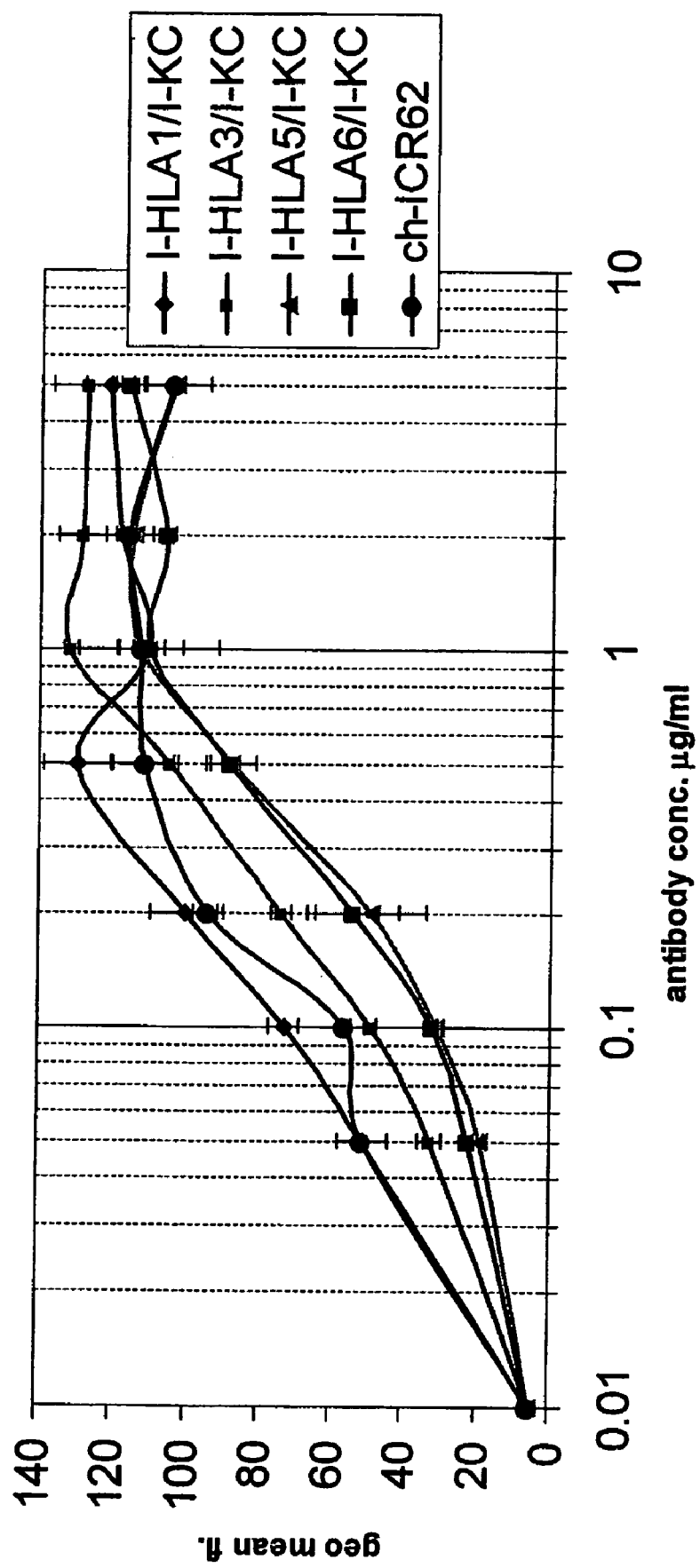
FIG. 5 shows binding activity of humanized ICR62 antibodies comprising heavy chain variable region constructs I-HLA1, I-HLA3, I-HLA5 and I-HLA6 and humanized light chain variable region construct I-KC as compared to chimeric rat-human ICR62 antibody.

FIGS. 4 and 5 compare the constructs of the series I-HLA1, I-HLA2, I-HLA3, I-HLA4, I-HLA5, and I-HLA6. The best binding behavior was observed in the constructs ch-ICR62, I-HLA1, and IHLA2, with an EC50 value of approx. 300 ng/ml. The other constructs had this value increased by a factor of two, and therefore have slightly reduced binding activity. The first conclusion from this data is that, within the Kabat CDR1, the Lys33Tyr, and the Ile34Met substitutions were tolerated. These two positions are located within the Kabat definition of CDR1, but outside of the Chothia CDR boundaries (that were based on structural rather than sequence analysis). In the latter part of CDR1, then, at least some promiscuity is permitted.

The second conclusion is that, within CDR2, in addition to the above-mentioned replacement of residues Asn60 and Glu61 by non-donor residues, Asn60Ser, Glu61Pro, and Lys62Ser non-donor substitutions within the Kabat CDR were also allowed. These residues were derived from the human germ-line IGHV5-51 acceptor sequence, which was used as an FR3 acceptor sequence. Constructs I-HLA3 and I-HLA4 differ from I-HLA1 and I-HLA2 only by the removal of the Phe27Tyr back mutation, and both the I-HLA3 and I-HLA4 constructs lose affinity compared to their parental construct. Therefore, the third conclusion of the comparison of I-HLA1, I-HLA2, I-HLA3, I-HLA4, I-HLA5, and I-HLA6 is the involvement of Phe27 in antigen binding, either directly or indirectly, via modifying the loop conformation of CDR1.

Variants I-HLA5 and I-HLA6 have the FR1 of I-HLA1 and I-HLA2, respectively, replaced by another germ-line acceptor sequence with the Phe27 naturally present (i.e., IGHV1-58). This could only be achieved by simultaneously introducing several other mutations which are: Val2Met, Ala9Pro, and Ala16Thr. By doing so, the beneficial effect of (re-)introducing the Phe27 was again abrogated.

Figure 6:
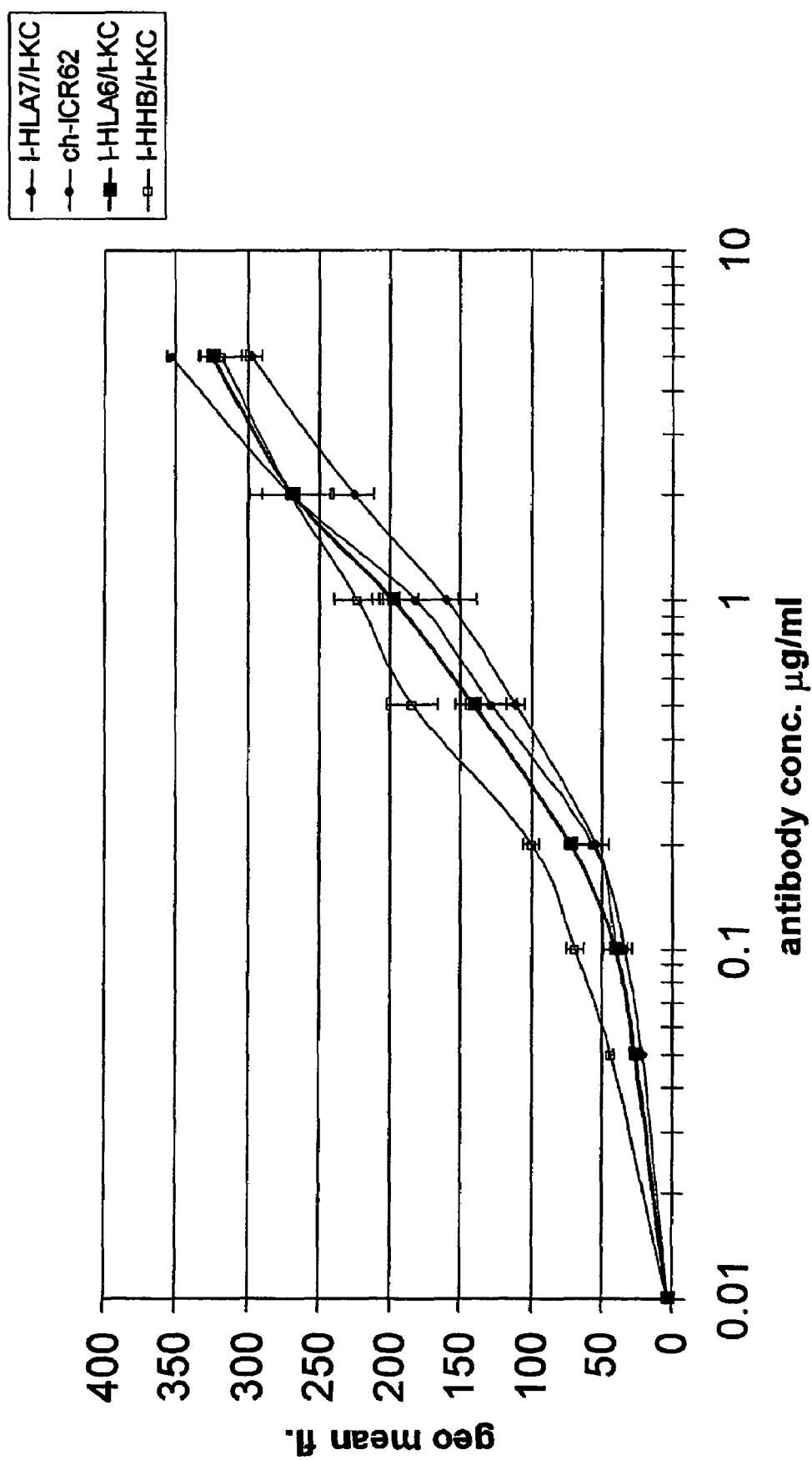
FIG. 6 shows binding activity of humanized ICR62 antibodies comprising heavy chain variable region constructs I-HLA7, I-HLA6, and I-HHB and humanized light chain variable region construct I-KC as compared to chimeric rat-human ICR62 antibody.

The I-HLA7 construct was assessed to determine whether the restoration of additional donor residues in the heavy chain CDR1 and CDR2 of the I-HLA6 construct would restore full binding activity as compared to ICR62. As shown in FIG. 6, this was not the case.

Figure 7:
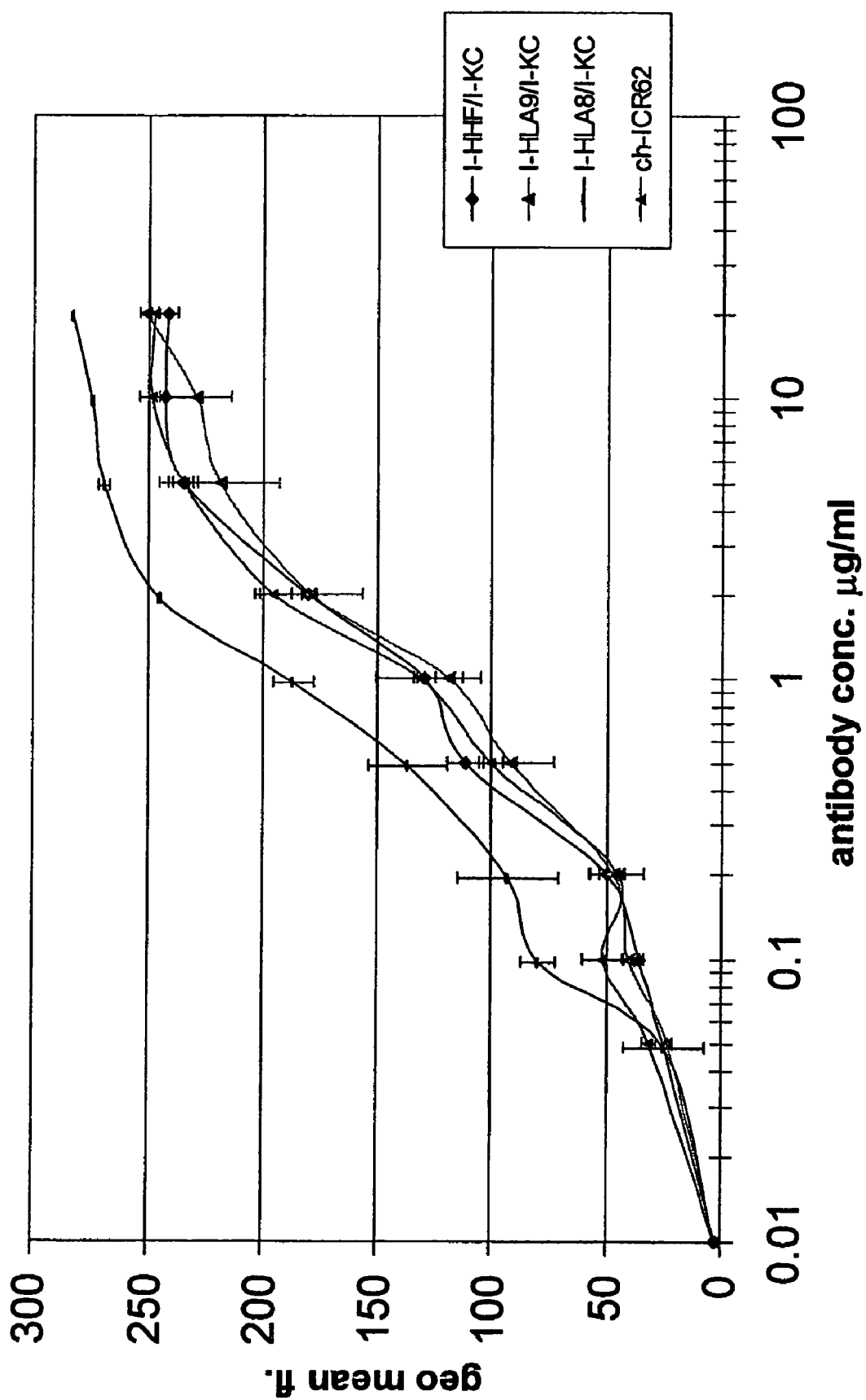
FIG. 7 shows binding activity of humanized ICR62 antibodies comprising heavy chain variable region constructs I-HHF, I-HLA9, and I-HLA8 and humanized light chain variable region construct I-KC as compared to chimeric rat-human ICR62 antibody.
Figure 8:
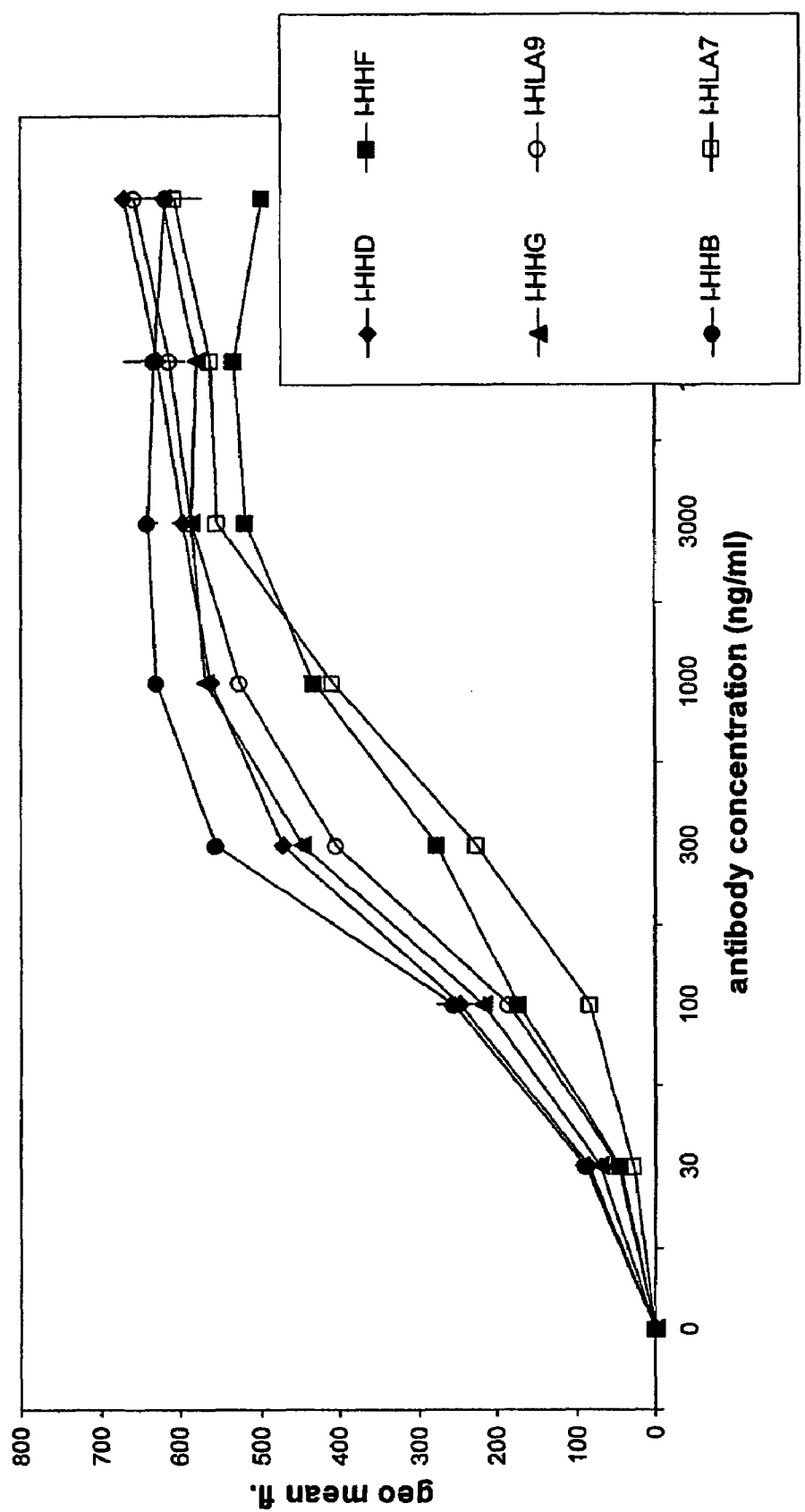
FIG. 8 shows binding activity of humanized antibodies comprising heavy chain varible region constructs I-HHB, I-HHD, I-HHG, I-HHF, I-HLA7, and I-HLA9 and humanized light chain variable region construct I-KC.

As shown in FIGS. 7 and 8, two additional constructs, I-HLA8 and I-HLA9, were tested to determine if the full binding activity compared to ch-ICR62 could be achieved. Starting from the I-HHB construct, the FR1 regions were replaced by FR1 regions having maximal homology within the Chothia CDR1 region. The I-HLA8 construct has the FR1 of the IGHV1-58 sequence, and the I-HLA9 has the IGHV5-51 FR1 region. Both constructs bound the antigen at least as well as the ch-ICR62 antibody. The I-HLA8 construct may, in fact, be even better, with the EC50 lowered by a factor of 2. The I-HLA8 construct has the same FR1 sequence as the I-HLA5 and I-HLA6 constructs and therefore has the same non-donor residues (i.e., Val2Met, Ala9Pro, and Ala16Thr), suggesting that the presence of these non-donor residues does not have a negative effect on binding. Non-beneficial mutations occurring in the I-HLA5 and 6 arise from the combination of a VH1 FR1 paired with a VH5 FR3, which could potentially be compensated for by having a FR1 and a FR3 of the same VH family.

Shown in FIG. 8 are constructs that contain non-donor residues within the CDRs. Thus, these constructs are even further humanized within the CDRs because the non-donor residues occur in the human framework regions that were chosen for these constructs. The I-HHE (His35Ser), I-HHF (Thr58Asn) and I-HHG (Ser57Ala) constructs all have one residue within the CDR1 or CDR2 that is humanized (compared to the I-HHB construct). Construct I-HHD (Gly24Ala) was also assayed. I-HHF showed reduced binding indicating the importance of Thr58. In contrast to the Kabat CDR residue 58, amino acid 57 is more tolerant to substitutions, since the Ser57Ala mutation apparently has no influence on binding (FIG. 8).

Since the FR3 region of IGHV5-51 seemed to show promising properties in the I-HLA1 and 2 constructs, and the FR1 of the same germ-line sequence proved to be useful in the I-HLA9 construct, the FR1, FR2, and FR3 of IGHV5-51 was designed to be used together as an acceptor for loop grafting.

Summary of the analysis of the canonical residues in humanized ICR62 constructs:
VL: Kabat position 2: Ile probably required.
Kabat position 71: Ile or Phe allowed.
VH: Pos. 24, Gly, Thr, Ala, Val, Ser allowed.
Pos. 26, Gly allowed.
Pos. 29, Phe, Ile, Leu, Val, Ser allowed.
Pos. 34, Ile, Met, Leu, Val, Trp, Tyr, Thr allowed.
Pos. 71, Ala, Leu, Val, Thr allowed.
Pos 94, Arg, Gly, Asn, Lys, Ser, His, Thr, Ala allowed.

Results of the ADCC Experiments

Figure 9:
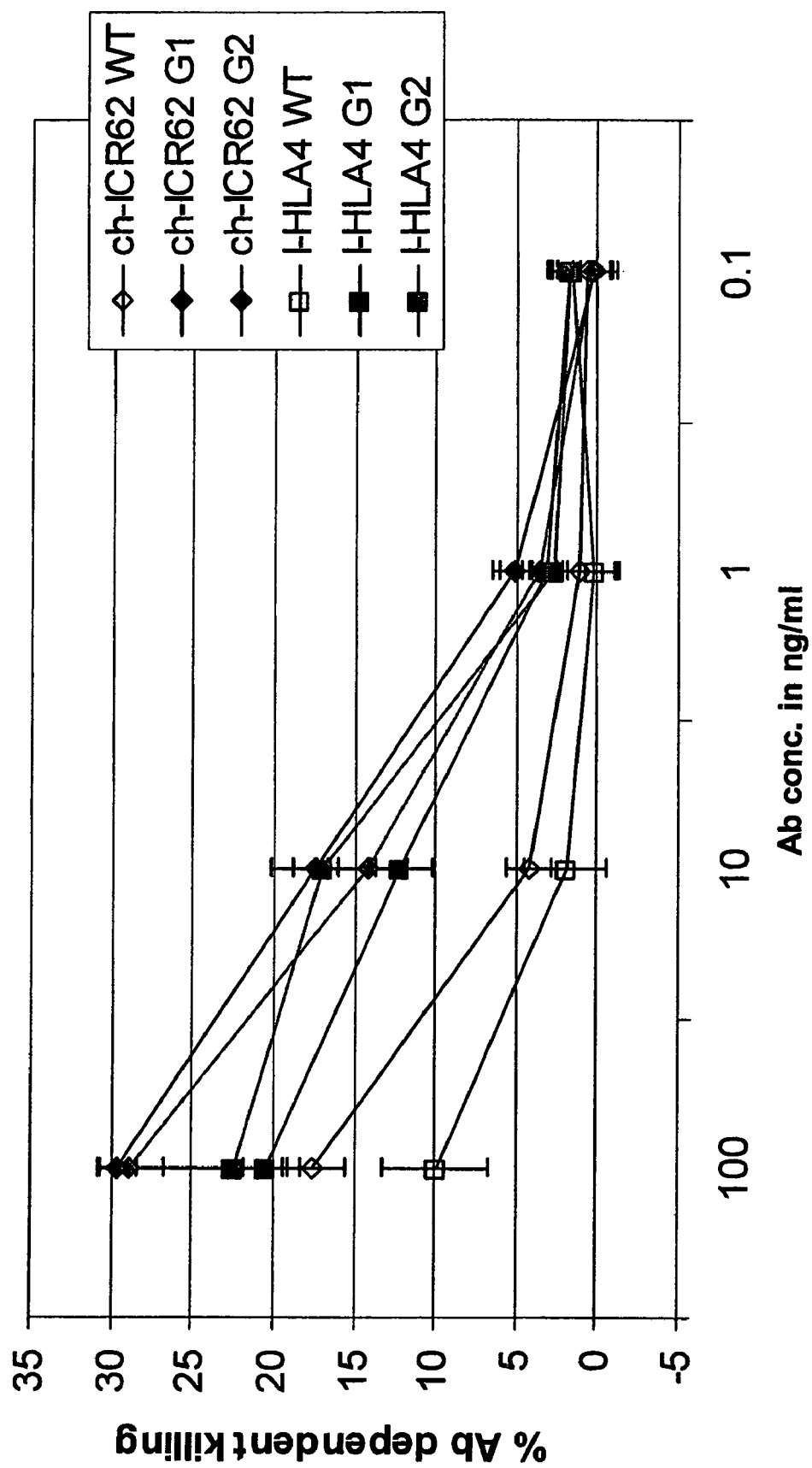
FIG. 9 shows a comparison of antibody mediated cellular cytotoxicity (ADCC) for various glycoforms of the chimeric ICR62 antibody, as well as for the humanized variant I-HLA4. "G1" refers to glcyoengineering of the antibody by co-expression with GnTIII. "G2" refers to glycoengineering of the antibody by co-expression with GnTIII and ManII. "WT" refers to antibodies that were not glycoengineered. The humanzied heavy chain constructs were paired with the I-KC light chain construct.

FIG. 9 shows a comparison of the antibody mediated cellular cyotoxicity (ADCC) is shown for the various glycoforms of the chimeric ICR62 antibody, as well as for the humanized variant I-HLA4. The different glycoforms are marked by a label that either indicates not-glycoengineered (WT), Glycoform 1 (G1), or Glycoform 2 (G2). "G1" refers to glcyoengineering of the antibody by co-expression with GnTIII. "G2" refers to glycoengineering of the antibody by co-expression with GnTIII and ManII. "WT" refers to antibodies that were not glycoengineered. The light chain for all the humanized constructs is the I-KC variant, and was not labeled explicitly.

The chimeric, as well as the humanized antibody were improved in their potency and efficacy by the two different glycoengineering approaches. The ch-ICR62 construct performed slightly better than I-HLA4 for the wild-type or the glycoforms, respectively. As seen in FIG. 4, when comparing the affinities of the two antibodies towards their antigen, the ch-ICR62 had a twofold lower EC50 value. This difference in affinity is here reflected in differences in efficacy.

Figure 11:
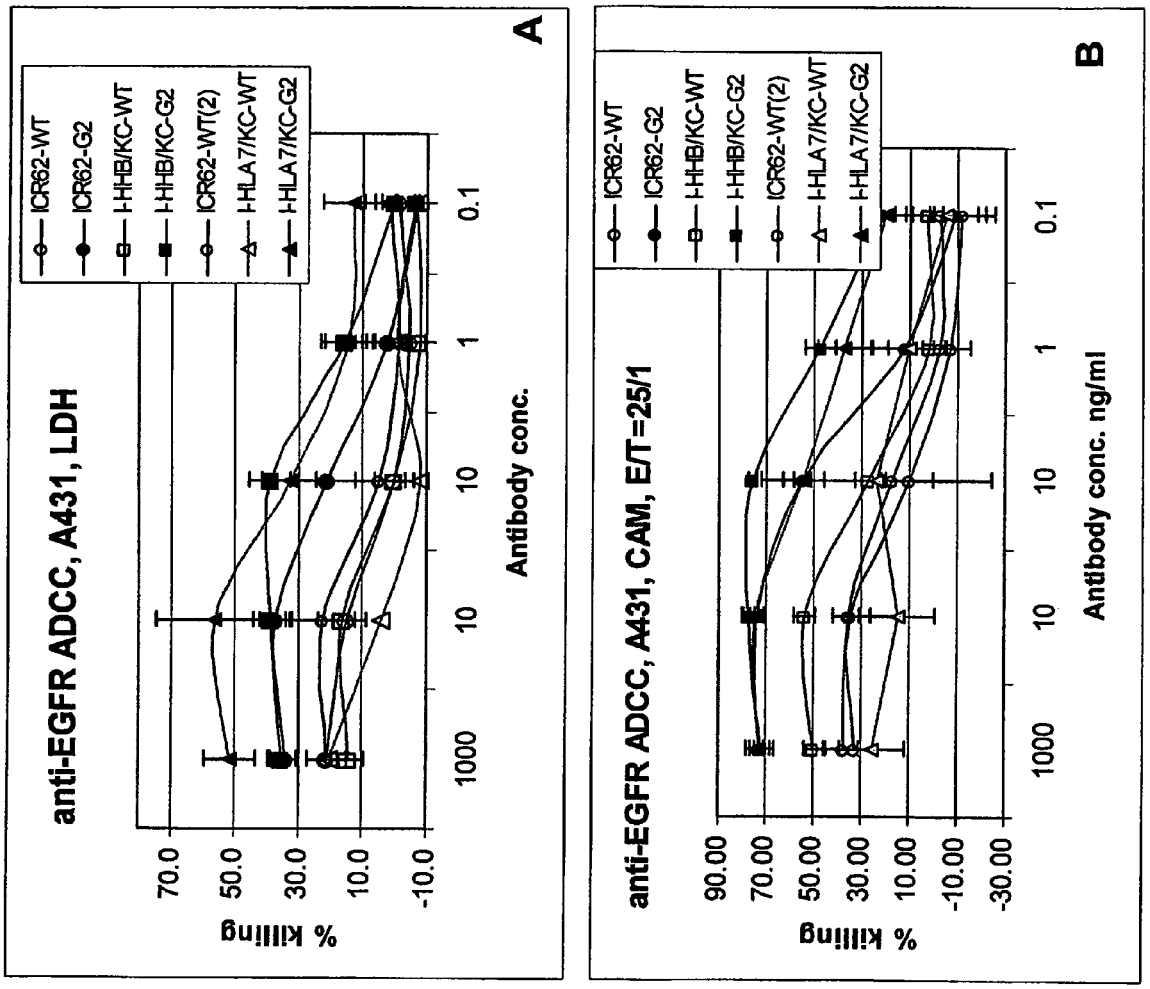
FIG. 11A and 11B show a comparison of ADCC for non-glycoengineered forms (WT) and G2 glcyoforms of chimeric ICR62 and the humanized ICR62 antibody constructs I-HHB and I-HLA7. The target cell line A431 was used. The humanzied heavy chain constructs were paired with the I-KC light chain construct.
Figure 12:
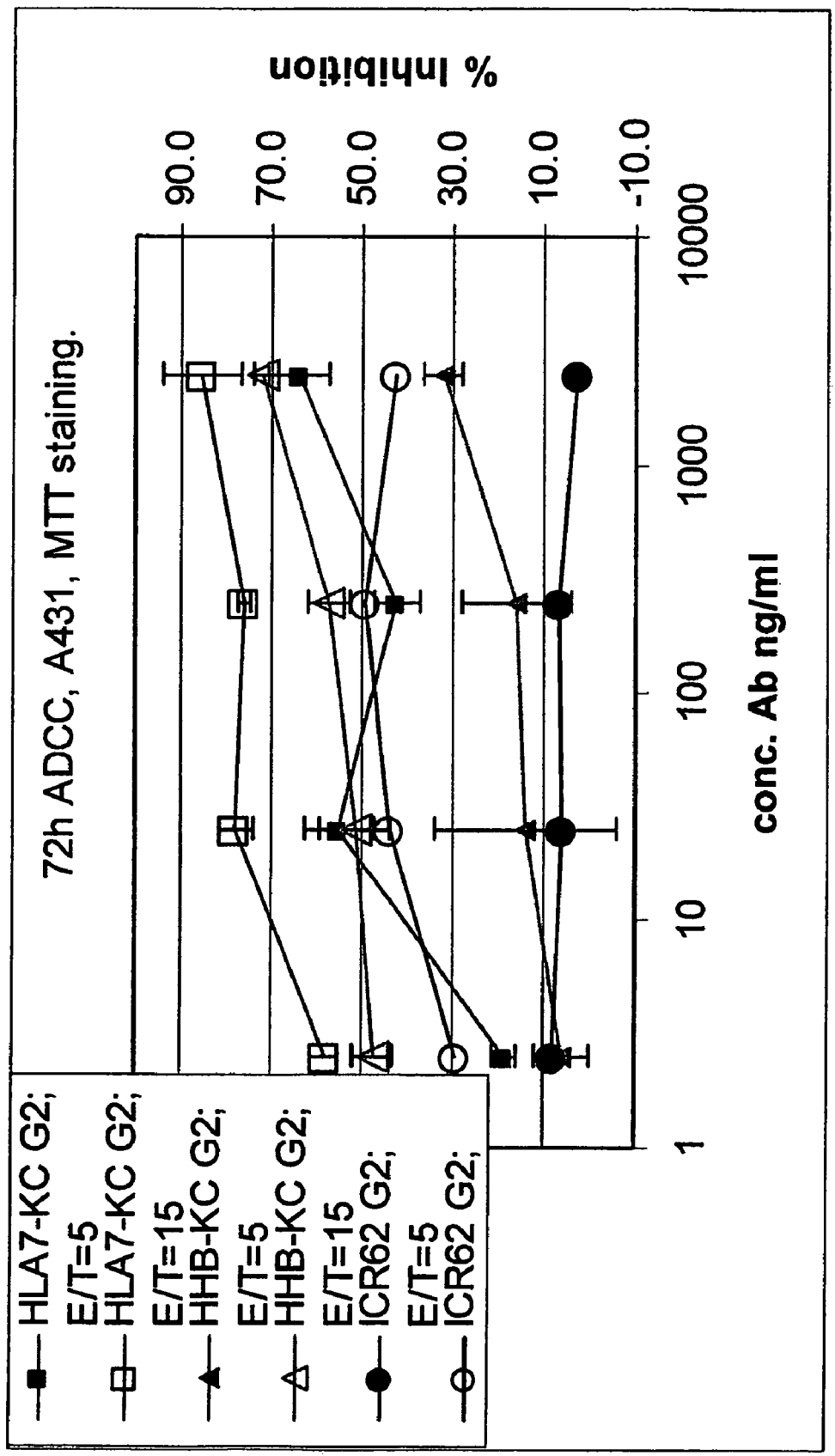
FIG. 12 shows a comparison of 72h ADCC for G2 glcyoforms of chimeric ICR62 and the humanized ICR62 antibody constructs I-HHB and I-HLA7. The humanzied heavy chain constructs were paired with the I-KC light chain construct.
Figure 14:
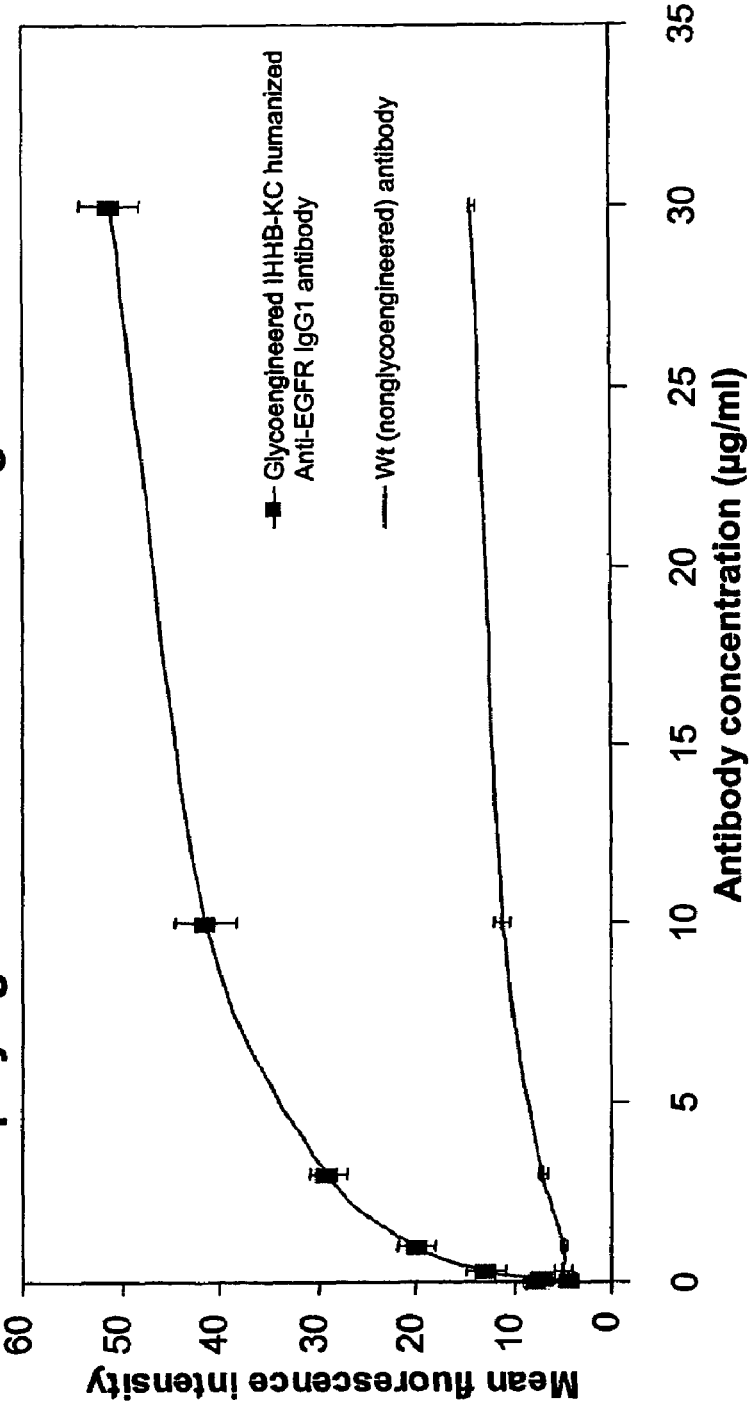
FIG. 14 shows an FcgammaRIIIa-Fc binding assay using CHO cells displaying recombinant human FcgammaRIIIa. A glycoengineered I-HHB/KC humanized anti-EGFR IgG1 antibody was compared to a non-glycoengineered (Wt) antibody.
Figure 15:
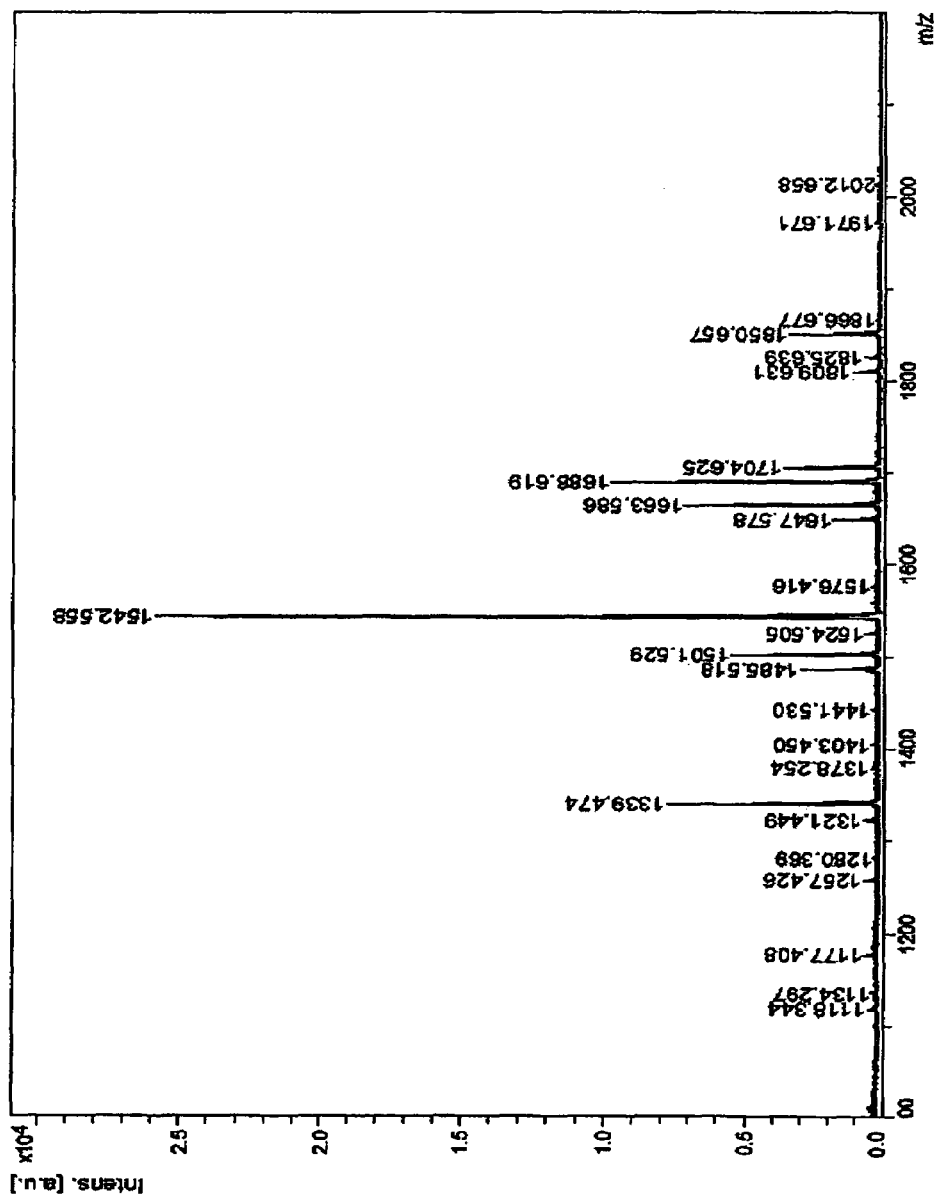
FIG. 15 shows a MALD/TOF-MS oligosaccharide profile for glycoengineered humanized anti-EGFR IgG1 antibody, I-HHB/KC. Glycoengineering achieved by overexpression in the antibody-producing cells of genes encoding enzymes with GnTIII and Golgi Mannosidase II activities, yielding over 70% of non-fucosylated Fc-Asn297-linked oligosaccharides.
Figure 16:
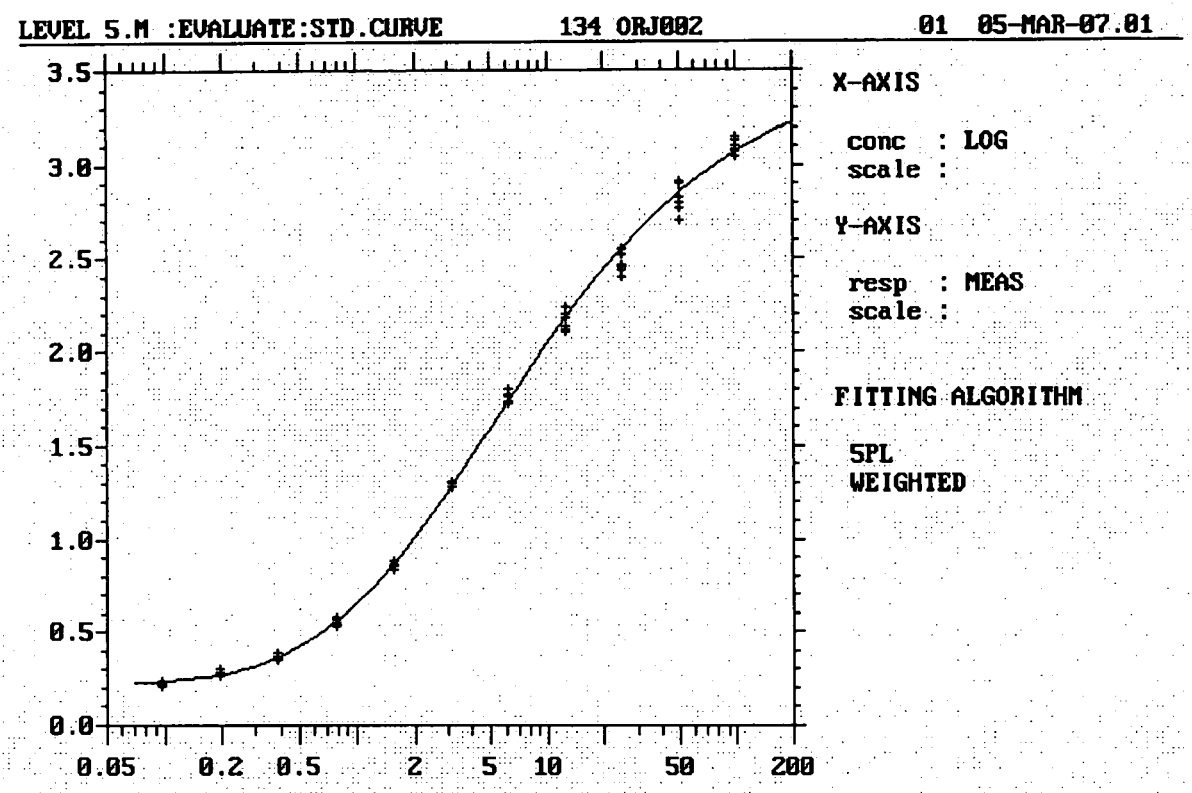
FIG. 16 shows an anti-EGFR precision profile (n=6 replicates across the calibration range) for the determination of anti-EGFR in 1% monkey serum matrix (monkey serum pool CMS25/31/33, supplied by HLS).
Figure 17:
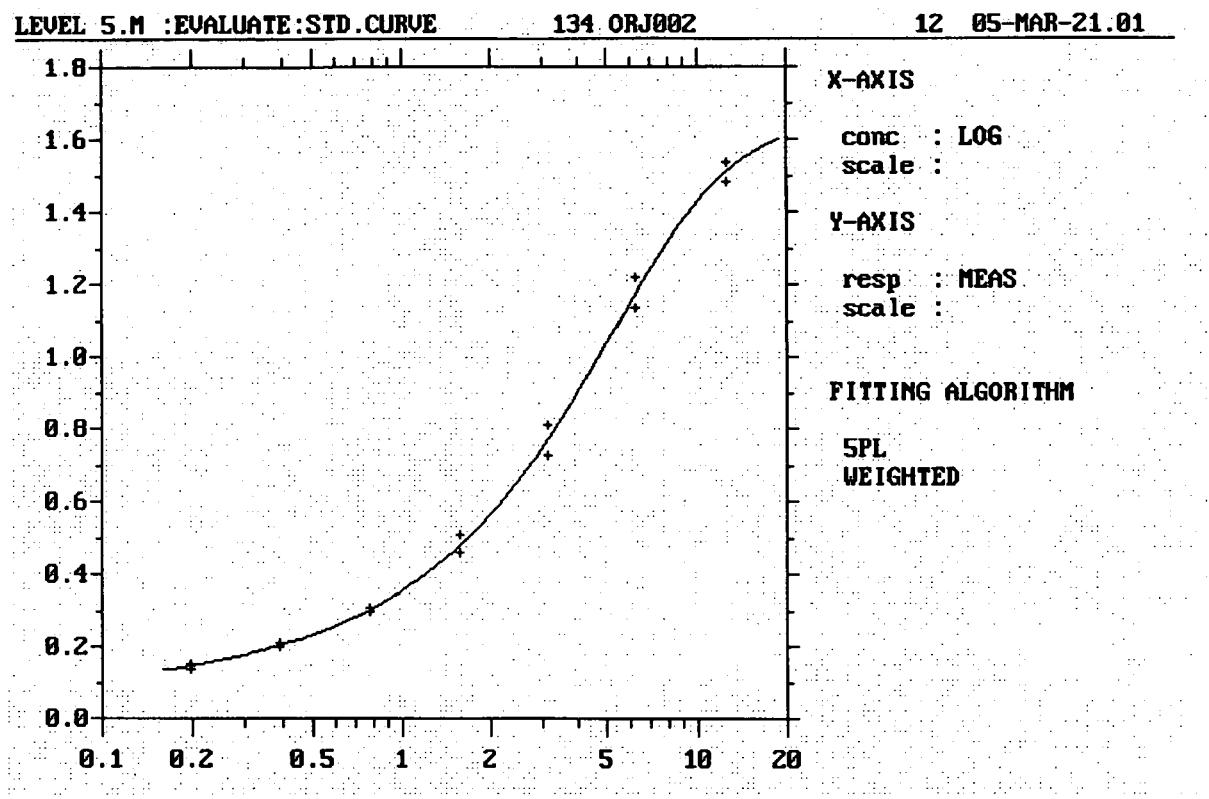
FIG. 17 shows a representative anti-EGFR calibration curve for the determination of anti-EGFR in 1% monkey serum matrix.

FIG. 10 shows a comparison of the antibody mediated cellular cyotoxicity (ADCC) for the non-glycoengineered ("wild-type") and the G2 glycoform of the humanized ICR62 antibody constructs I-HHB and I-HLA7. The same antibodies were applied to two different target cell lines. In panel A of FIG. 10, the target cell line LN229 is used; and in panel B of FIG. 10, the cell line A431 was used. The A431 cells are apparently more susceptible towards antibody mediated cell killing than the LN229 cells. More importantly, the glycoengineering enhanced the potency of both antibodies. This effect seemed to be more pronounced for the I-HLA7 than for the I-HHB. The percentage of cell killing at maximal antibody concentration for the I-HHB could be shifted from ~30% to ~40% by introducing the G2 glycoengineered variant, when using the LN229 target cell line. When using the A431 cell line, this value was apparently unchanged. This behavior was completely different for the I-HLA7 antibody. Target cell killing at maximal antibody concentration was shifted from about 10% to about 50%, for the LN229 cells, and from about 40% to about 70% for the A431 cells by introducing the G2 glycoengineering variants. In this case, despite having lower activity in the non glycoengineered antibody for the I-HLA7 relative to I-HHB, the ranking of activity is reversed for the glycoengineered antibodies. FIGS. 11 and 12 also show comparisons of non-glycoengineered forms (WT) and G2 glcyoforms of chimeric ICR62 and the humanized ICR62 antibody constructs I-HHB and I-HLA7.

Example 3

Preliminary Toxicity Study by Intravenous (Bolus) Administration to Cynomolgus Monkeys—Bioanalytical Analysis Introduction
Glyco-Engineered Anti-EGFR Assay
This Bioanalytical Analysis describes the measurement of anti-EGFR in samples originating from cynomolgus monkeys following intravenous (bolus) administration of anti-EGFR (recombinant, glycoengineered anti-EGFR antibody produced from transfected mammalian cells in culture with antibody expression vectors harboring the heavy chain I-HHB and the light chain I-KC genes as described above, and purified as described above) as described in the protocol set forth herein below. A total of 78 monkey serum samples were stored frozen at about −20° C. until use.

The Bioanalytical methods used for the determination of anti-EGFR used an ELISA method to measure serum concentrations of anti-EGFR. Acceptance criteria were set at ±20% (±25% low QC) for precision and inaccuracy.

Materials and Methods

Objective: The objective of this study was the assessment of systemic toxic potential of Glyco-mAb (anti-EGFR) intravenous (bolus) administration to Cynomolgus Monkeys followed by an 8-week recovery period.

TABLE 8

| | |
|---|---|
| Animal model | Cynomolgus Monkeys, accepted by regulatory agencies, background data available. |
| Justification for use of the primate | The primate was the non-rodent species of choice because it alone conserves two critical parameters: EGFR antigen recognition by the test antibody, and test antibody Fc region recognition by immune system Fc receptors. |
| Route | Intravenous (Bolus), to simulate the conditions of clinical administration. |

TABLE 9

Treatment groups and dosages

| Group | 1 | 2 | 3 |
|---|---|---|---|
| Compound | | Glyco-mAb(Anti-EGFR) | |
| Dosage (mg/kg/day) | 1.5 | 4.5 | 12 |

Rationale for Dosage Level Selection 1.5-7.5 mg/kg is the expected range for human studies (7.5 mg/kg being the corresponding dose for a similar compound in humans).

TABLE 10

Identity of treatment groups

| Group | Treatment | Dosage (mg/kg/day) # | Number of animals Male | Number of animals Female | Animal ID Numbers Male | Animal ID Numbers Female |
|---|---|---|---|---|---|---|
| 1 | Glyco-mAb (Anti-EGFR) | 1.5 | 1 | 1 | 623 | 590 |
| 2 | Glyco-mAb (Anti-EGFR) | 4.5 | 1 | 1 | 461 | 462 |
| 3 | Glyco-mAb (Anti-EGFR) | 12 | 1 | 1 | 463 | 612 |

Expressed in terms of the test substance as supplied.

TABLE 11

Animals

| | |
|---|---|
| Species | Cynomolgus monkey (purpose bred). |
| Age received | Approximately 15 months. |
| Weight range ordered | 1.5 to 2.5 kg. |

TABLE 12

Administration of Anti-EGFR

| | |
|---|---|
| Route | Intravenous injection. |
| Treated at | Constant dosages in mg/kg/occasion. |
| Volume dosage | Calculated in advance, based on the most recently recorded bodyweight. |
| Individual dose volume | 1 ml/kg/day |
| Frequency | Days 1, 8, 15 and 22, immediately before feeding. |
| Sequence | By group. |
| Dose sites | Using left saphenous veins. |
| Injection | Bolus, new sterile disposable needle per animal. |
| Formulation | A record of the usage of formulation was maintained based on weights. This balance is compared with the expected usage as a check of correct administration. |

TABLE 13

Clinical observations

| | |
|---|---|
| Animals and their cage trays | Visually inspected at least twice daily for evidence of reaction to treatment or ill-health. |
| Deviations from normal recorded at the time in respect of | Nature and severity. Date and time of onset. Duration and progress of the observed condition. |
| Physical examination | Once each week for all animals. |
| Daily records of cage trays | For vomitus, blood, diarrhoea, etc. |

TABLE 14

Dosing Frequency:

| | |
|---|---|
| Frequency | 1. Immediately pre-dose. 2. ½ to 2 hours after completion of dosing. 3. As late as possible in the working day. |
| Injection sites | Daily. |

TABLE 15

Toxicokinetics

| Day | Animals | Sample times hours after dosing. |
|---|---|---|
| 1 | All animals | 1, 4, 12, 24, 72, 120. |
| 8 | All animals | Predose, 1 hour post-dose (169 hours post Day 1 dose). |
| 15 | All animals | Pre-dose, 1 hour post-dose (337 hours post Day 1 dose). |
| 22 | All animals | Pre-dose, 1 hour post-dose (505 hours post Day 1 dose). |
| 29 | All animals | 672 hours post Day 1 dose. |

TABLE 16

Samples

| | |
|---|---|
| Sample site | Suitable vein. |
| Anticoagulant/Sample volume | No anticoagulant/0.7 ml. |
| Total number of samples taken | 104. |
| Separation of serum | By centrifugation at ambient temperature unless otherwise indicated to provide a minimum of 0.3 ml, where possible. |
| Storage of serum | Appropriately labeled plastic tubes. Deep frozen (approximately −20° C.), while awaiting bioanalysis. |

Histology

TABLE 17

| | Tissue Fixation |
|---|---|
| Standard | 10% Neutral Buffered Formalin. |
| Others | Testes and epididymides: Initially in Bouin's fluid. |
| | Eyes: Initially in Davidson's fluid. |

TABLE 18

| | Histology |
|---|---|
| Processing | All animals. |
| Routine staining | 4-5 μm sections stained with haematoxylin and eosin. |

Immunoassay Procedure

A plate was coated with 100 μl per well of coating solution (5 μl sheep anti-human IgG (monkey adsorbed IgG, the Binding Site, UK) added to 11495 μl bicarbonate buffer (0.05M, pH9.6) and incubated for approximately 2 hours at room temperature. The plate was washed 3 times with 400 μl per well of wash solution (PBS (Sigma Chemical Co., UK) 0.01% (v/v) Triton-X100 (Sigma Chemical Co., UK)) and tapped dry.

Assay buffer (1% w/v BSA, Sigma Chemical Co., UK) was added at 200 μl per well and incubated for approximately 1 hour at room temperature. The plate was washed 3 times with 400 μl per well of wash solution and tapped dry.

The calibration standards, Quality Controls (QC) and/or samples were added at 100 μl per well and incubated for approximately 2 hours at room temperature, after which the plate was washed 3 times with 400 μl per well of wash solution and tapped dry.

The conjugate solution (6 μl goat anti-human IgG kappa-HRP conjugate (Bethyl Laboratories Inc., USA) added to 12 ml assay buffer) was added at 100 μl per well and incubated for approximately 1 hour at room temperature. The plate was washed 3 times with 400 μl per well of wash solution and tapped dry.

Trimethylbenzidine (TMB; Europa Bioproducts, Ely, UK) was added at 100 μl per well. The plate was covered and incubated for approximately 15 minutes at room temperature. 100 μl of stop solution (0.5M HCl, Fisher, UK) was then added to each well. Absorbances were read at 450 nm (reference filter 630 nm) on a DYNATECH MRX microplate reader (Mettler Instruments, UK).

Results and Discussion

Test Sample Analysis

Concentrations of anti-EGFR were measured by an immunoassay method (ELISA) in 78 monkey serum samples generated according to the protocol described herein above. These results are presented in Tables 19-21, below.

TABLE 29

Serum concentration of anti-EGFR in monkey serum (μg/ml) following Intravenous administration of 1.5 mg/kg anti-EGFR on days 1, 8, 15 and 22 (GROUP 1)

| | Animal number | | | |
|---|---|---|---|---|
| Timepoint | 1M 623 | 1F 590 | Mean | sd |
| Day 1 1 hour | 33.42 | 30.86 | 32.14 | 1.8 |
| Day 1 4 hours | 27.33 | 27.49 | 27.41 | 0.1 |
| Day 1 12 hours | 13.09 | 17.01 | 15.05 | 2.8 |
| Day 1 24 hours | 9.656 | 9.468 | 9.562 | 0.1 |
| Day 1 72 hours | 2.528 | 0.786 | 1.657 | 1.2 |
| Day 1 120 hours | 0.845 | 0.431 | 0.638 | 0.3 |
| Day 8 predose | 0.538 | 0.287 | 0.413 | 0.2 |
| Day 8 1 hour | 30.02 | 19.07 | 24.55 | 7.7 |
| Day 15 predose | 0.902 | 0.382 | 0.642 | 0.4 |
| Day 15 1 hour | 17.91 | 33.08 | 25.50 | 10.7 |
| Day 22 predose | 1.065 | 0.595 | 0.830 | 0.3 |
| Day 22 1 hour | 19.41 | 33.00 | 26.21 | 9.6 |
| Day 1 672 hours | 1.202 | 0.362 | 0.782 | 0.6 | sd  standard deviation

TABLE 20

Serum concentration of anti-EGFR in monkey serum (μg/ml) following Intravenous administration of 5.0 mg/kg anti-EGFR on days 1, 8, 15 and 22 (GROUP 2)

| | Animal number | | | |
|---|---|---|---|---|
| Timepoint | 2M 461 | 2F 462 | Mean | sd |
| Day 1 1 hour | 32.45 | 29.51 | 30.98 | 2.1 |
| Day 1 4 hours | 32.39 | 29.57 | 30.98 | 2.0 |
| Day 1 12 hours | 28.05 | 25.88 | 26.97 | 1.5 |
| Day 1 24 hours | 23.70 | 23.78 | 23.74 | 0.1 |
| Day 1 72 hours | 14.03 | 14.38 | 14.21 | 0.2 |
| Day 1 120 hours | 10.42 | 8.137 | 9.279 | 1.6 |
| Day 8 predose | 4.672 | 3.683 | 4.178 | 0.7 |
| Day 8 1 hour | 25.91 | 31.06 | 28.49 | 3.6 |
| Day 15 predose | 5.752 | 5.450 | 5.601 | 0.2 |
| Day 15 1 hour | 32.20 | 35.38 | 33.79 | 2.2 |
| Day 22 predose | BLQ | 6.497 | 3.249 | — |
| Day 22 1 hour | 26.98 | 30.23 | 28.61 | 2.3 |
| Day 1 672 hours | BLQ | 4.845 | 2.423 | — |

BLQ  below limit of quantification (<0.195 μg/ml)
sd  standard deviation
Note: BLQ entered as zero in calculations

TABLE 21

Serum concentration of anti-EGFR in monkey serum (μg/ml) following Intravenous administration of 15 mg/kg anti-EGFR on days 1, 8, 15 and 22 (GROUP 3)

| | Animal number | | | |
|---|---|---|---|---|
| Timepoint | 3M 463 | 3F 612 | Mean | sd |
| Day 1 1 hour | 262.2 | 168.0 | 215.1 | 66.6 |
| Day 1 4 hours | 223.3 | 174.5 | 198.9 | 34.5 |
| Day 1 12 hours | 164.9 | 165.7 | 165.3 | 0.6 |
| Day 1 24 hours | 141.7 | 146.0 | 143.9 | 3.0 |
| Day 1 72 hours | 99.54 | 86.64 | 93.09 | 9.1 |
| Day 1 120 hours | 86.64 | 69.08 | 77.86 | 12.4 |
| Day 8 predose | 65.86 | 45.21 | 55.54 | 14.6 |
| Day 8 1 hour | 282.1 | 209.9 | 246.0 | 51.1 |
| Day 15 predose | 98.43 | 71.21 | 84.82 | 19.2 |
| Day 15 1 hour | 385.9 | 231.4 | 308.7 | 109.2 |
| Day 22 predose | 117.3 | 105.6 | 111.5 | 8.3 |
| Day 22 1 hour | 234.1 | 402.5 | 318.3 | 119.1 |
| Day 1 672 hours | 127.5 | 122.9 | 125.2 | 3.3 | sd  standard deviation

Example 4

Preliminary Toxicity Study by Intravenous (Bolus) Administration to Cynomolgus Monkeys—Toxicokinetics Summary Three groups of cynomolgus monkeys (1 male and 1 female per group) were administered intravenous bolus doses of anti-EGFR on Days 1, 8, 15 and 22 of a 28-day toxicity study in order to assess the systemic exposure of the animals to anti-EGFR. Serum concentrations of anti-EGFR in samples collected up to 672 hours after the first dose were determined by means of an immunoassay method. Pharmacokinetic analysis of serum concentration-time data resulted in the following pharmacokinetic parameters:

TABLE 22

| Dose (mg/kg) | Animal | $C_{max}$ (μg/mL) | $T_{max}$ (h) | $AUC_t$ (μg·h/mL) | AUC (μg·h/mL) | CL (mL/h/kg) | $V_{ss}$ (mL/kg) | k (1/h) | $t_{1/2}$ (h) |
|---|---|---|---|---|---|---|---|---|---|
| 1.5 | 1M623 | 33.42 | 1 | 830.4 | 849.4 | 1.778 | 60.79 | 0.0214 | 32.5 |
| 1.5 | 1F590 | 30.86 | 1 | 748.4 | 774.9$^a$ | 1.962$^a$ | 57.85$^a$ | 0.0105$^a$ | 66.0$^a$ |
| 4.5 | 2M461 | 32.45 | 1 | 2537 | 3005 | 1.488 | 133.6 | 0.0110 | 63.1 |
| 4.5 | 2F462 | 29.57 | 4 | 2378 | 2719 | 1.663 | 133.2 | 0.0121 | 57.4 |
| 12 | 3M463 | 262.2 | 1 | 18310 | 29870$^a$ | 0.4058$^a$ | 71.33$^a$ | 0.0056$^a$ | 124.3$^a$ |
| 12 | 3F612 | 174.5 | 4 | 15980 | 21400$^a$ | 0.5552$^a$ | 66.94$^a$ | 0.0082$^a$ | 84.4$^a$ |

$^a$Value is an estimate as the data did not meet all the acceptance criteria defined in Data Processing and should be treated with caution The relationships between areas under the serum anti-EGFR concentration-time curves ($AUC_{168}$) and dose level on Day 1 are presented below:

TABLE 23

| Dose level (mg/kg/occasion) | Dose level ratio | $AUC_{168}$ ratio Males | $AUC_{168}$ ratio Females |
|---|---|---|---|
| 1.5 | 1 | 1 | 1 |
| 4.5 | 3.0 | 3.1 | 3.2 |
| 12 | 8.0 | 22.0 | 21.4 |

The rate and extent of systemic exposure of monkeys to anti-EGFR, characterised by $AUC_{168}$, increased approximately proportionately with increasing dose over the dose range 1.5 to 4.5 mg/kg/occasion but by more than the proportionate dose increase over the dose range 4.5 to 12 mg/kg/occasion on Day 1. At the highest dose (12 mg/kg/occasion) the $AUC_{168}$ was ca 2.8-fold higher than that predicted by a linear relationship.

The extent ($AUC_{168}$) of systemic exposure of female monkeys to anti-EGFR was generally similar to the exposure in male monkeys.

After repeated intravenous doses, the pre-dose serum concentrations of anti-EGFR were generally higher than those values after a single dose and indicated accumulation of anti-EGFR in serum throughout the period of the study.

The terminal half-life could not be estimated adequately for all animals, but where it could be estimated was in the range 32.5 to 63.1 hours, and appeared to increase with dose in male animals. Total serum clearance of anti-EGFR appeared to be independent of dose over the range 1.5-4.5 mg/kg/occasion but was reduced at the top dose level in male and female monkeys.

In conclusion, the extent of systemic exposure of cynomolgus monkeys to anti-EGFR appeared to be characterised by non-linear (dose-dependent) kinetics over the dose range 1.5 to 12 mg/kg/occasion on Day 1 of the intravenous toxicity study. Increasing the dose of anti-EGFR above 4.5 mg/kg/occasion is likely to result in a higher systemic exposure than would be predicted from a linear relationship, which is consistent with the possibility of a capacity limited process for the elimination of anti-EGFR.

In addition, the study also provided evidence that in general there were no differences in the systemic exposure of male and female monkeys to anti-EGFR and that there was accumulation after repeated intravenous administration.

Introduction

Three groups of one male and one female cynomolgus monkey were administered anti-EGFR by intravenous bolus injection, at dose levels of 1.5, 4.5 and 12 mg/kg/occasion on Days 1, 8, 15 and 22 of a preliminary toxicity study. Blood samples were taken from each animal at the following time-points following administration on Day 1: 1, 4, 12, 24, 72 and 120 hours post-dose. In addition, samples were taken pre-dose and at 1 hour post-dose on Days 8, 15 and 22 and at 672 hours after the first dose on Day 1. The separated serum was frozen at ca −20° C. prior to analysis of serum concentrations of anti-EGFR by an immunoassay method.

| Abbreviations | |
|---|---|
| AUC | Area under the serum concentration-time curve to infinite time |
| $AUC_{168}$ | Area under the serum concentration-time curve during a 168-hour dosing interval |
| BLQ | Below the limit of quantification |
| ca | Approximately |
| CL | Total serum clearance |
| Cmax | Maximum serum concentration |
| F | Female |
| k | Terminal rate constant |
| M | Male |
| $t_{1/2}$ | Terminal half-life |
| Tmax | Time at which Cmax occurred |
| Vss | Volume of distribution at steady-state |

Antibody Used for Study

Glyco-mAb (Anti-EGFR), an anti-EGFR antibody Fc-engineered for increased Fc-FcgammaRIII receptor binding affinity and increased ADCC, was produced, purified and characterized as described above. Briefly, antibody was produced by co-transfection of HEK-293-EBNA cells with plasmid DNA vectors for expression of I-HHB antibody heavy chain, I-KC antibody light chain, GnT-III and ManII. A linearly scaled-up version of the transfection method described above was employed, transfecting cell monolayers cultured in roller bottles instead of T-flasks. An additional flow-through anion-exchange chromatographic step using Q-sepharose matrix was included in the purification process immediately before the size exclusion chromatographic step described above.

Figure 23:
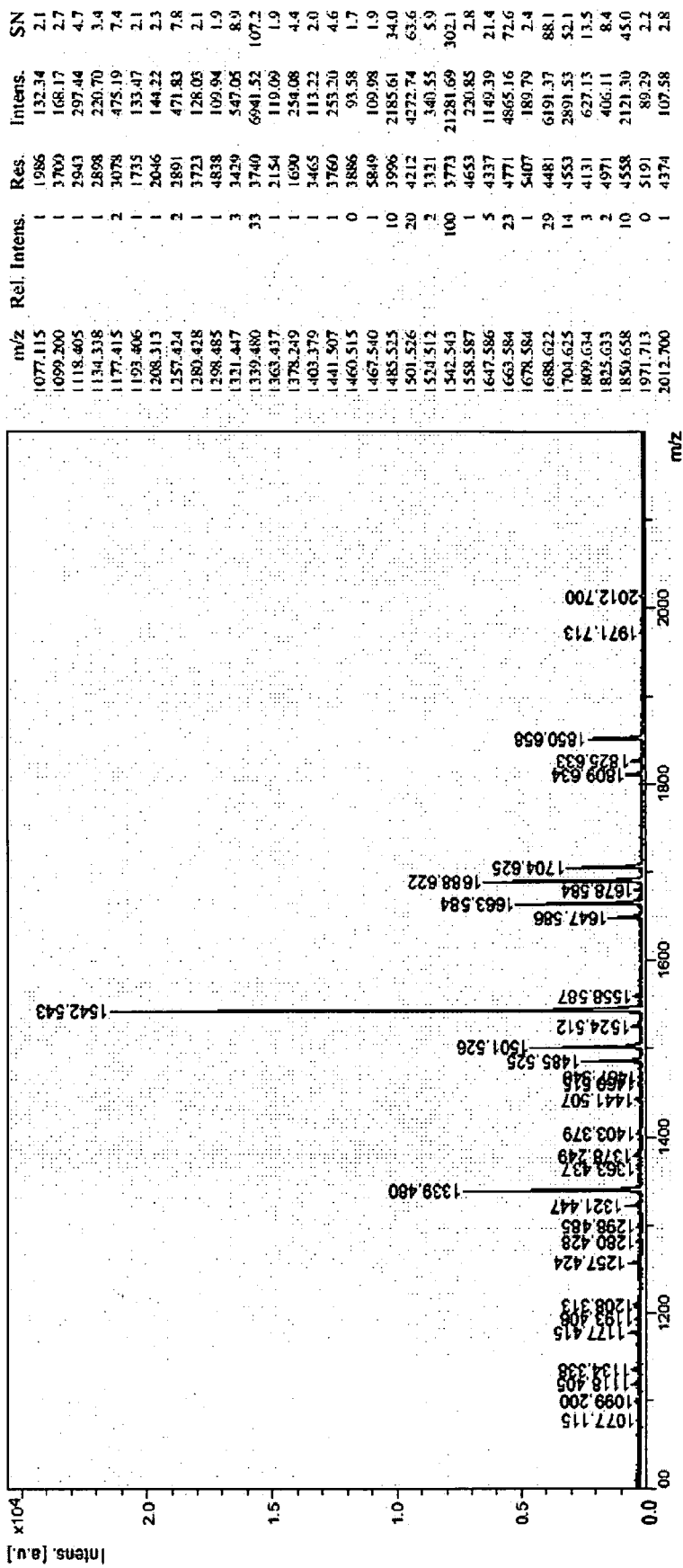
FIG. 23 shows the MALDI/TOF-MS profile of oligosaccharides from Fc-engineered (glycoengineered) anti-EGFR antibody used for the in vivo monkey studies described in the Examples herein below.

The glycosylation pattern of the Fc-engineered antibody was analyzed as described above using MALDI/TOF-MS spectrometry of enzymatically released Fc-derived oligosaccharides. The oligosaccharide profile is shown in FIG. 23.

Figure 24:
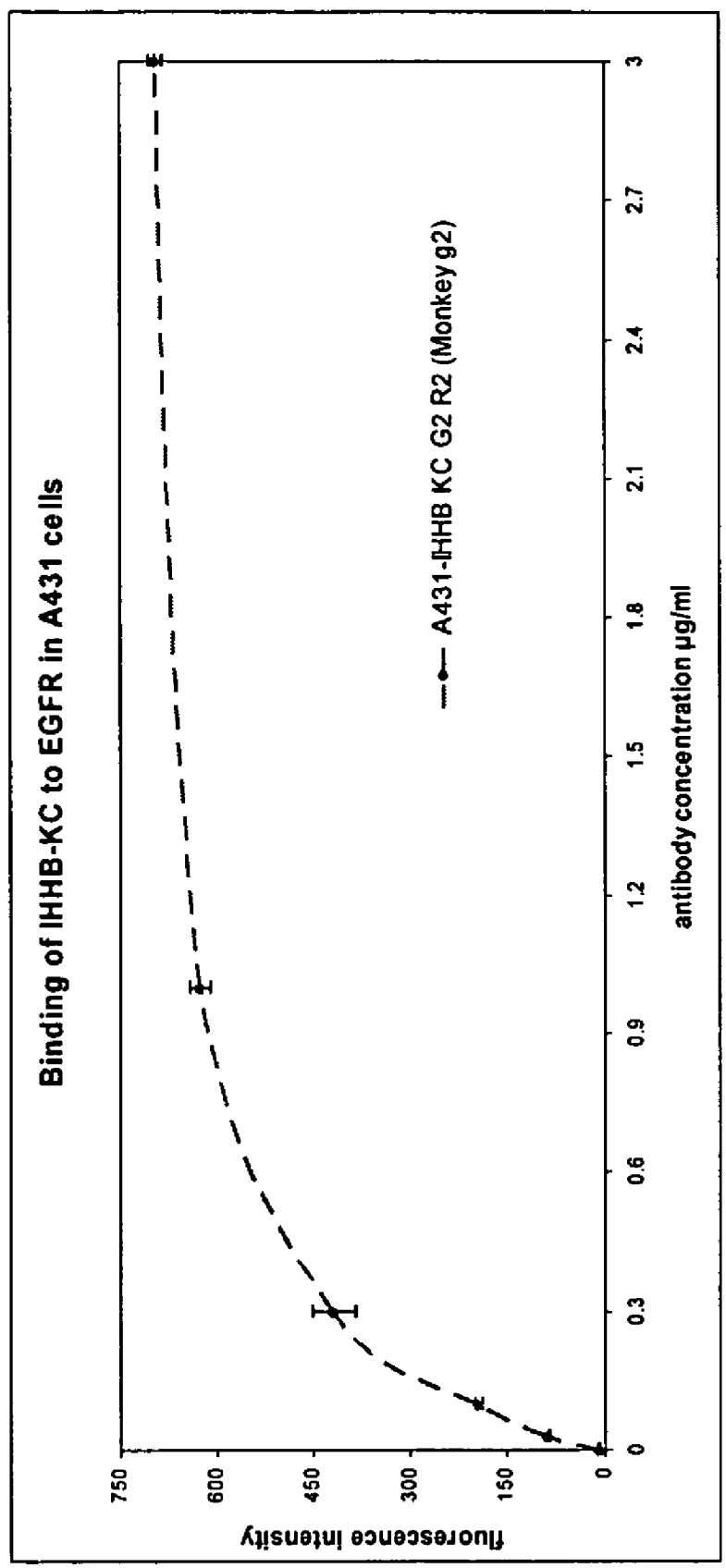
FIG. 24 shows binding to EGFR expressed on the surface of human A431 epidermoid carcinoma cells. The antibody used for the binding study was the Fc-engineered anti-EGFR antibody (I-HHB construct) used for the in vivo monkey studies described in the Examples herein below.
Figure 25:
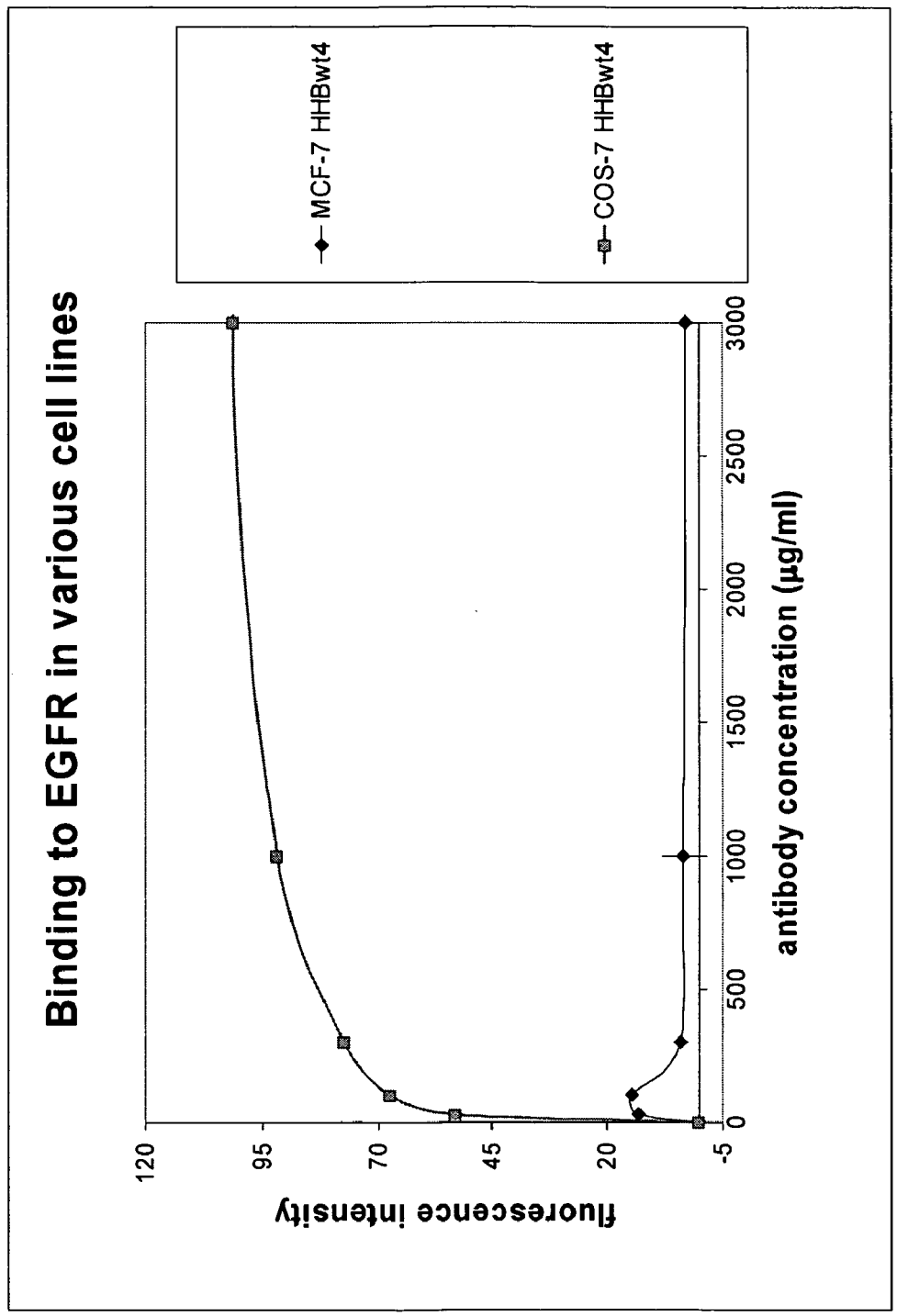
FIG. 25 shows binding to EGFR expressed on surface of monkey COS-7 kidney cells. The antibody used was anti-EGFR antibody (I-HHB heavy chain; I-KC light chain). For reference, binding to low human EGFR-expressing cells, MCF-7 breast cancer cells, is shown.

Binding to human EGFR and monkey EGFR was demonstrated by whole-cell binding as described above using A431 and COS-7 cells, respectively, and FACS-based analysis. Binding curves are shown in FIGS. 24 and 25 respectively.

Figure 26:
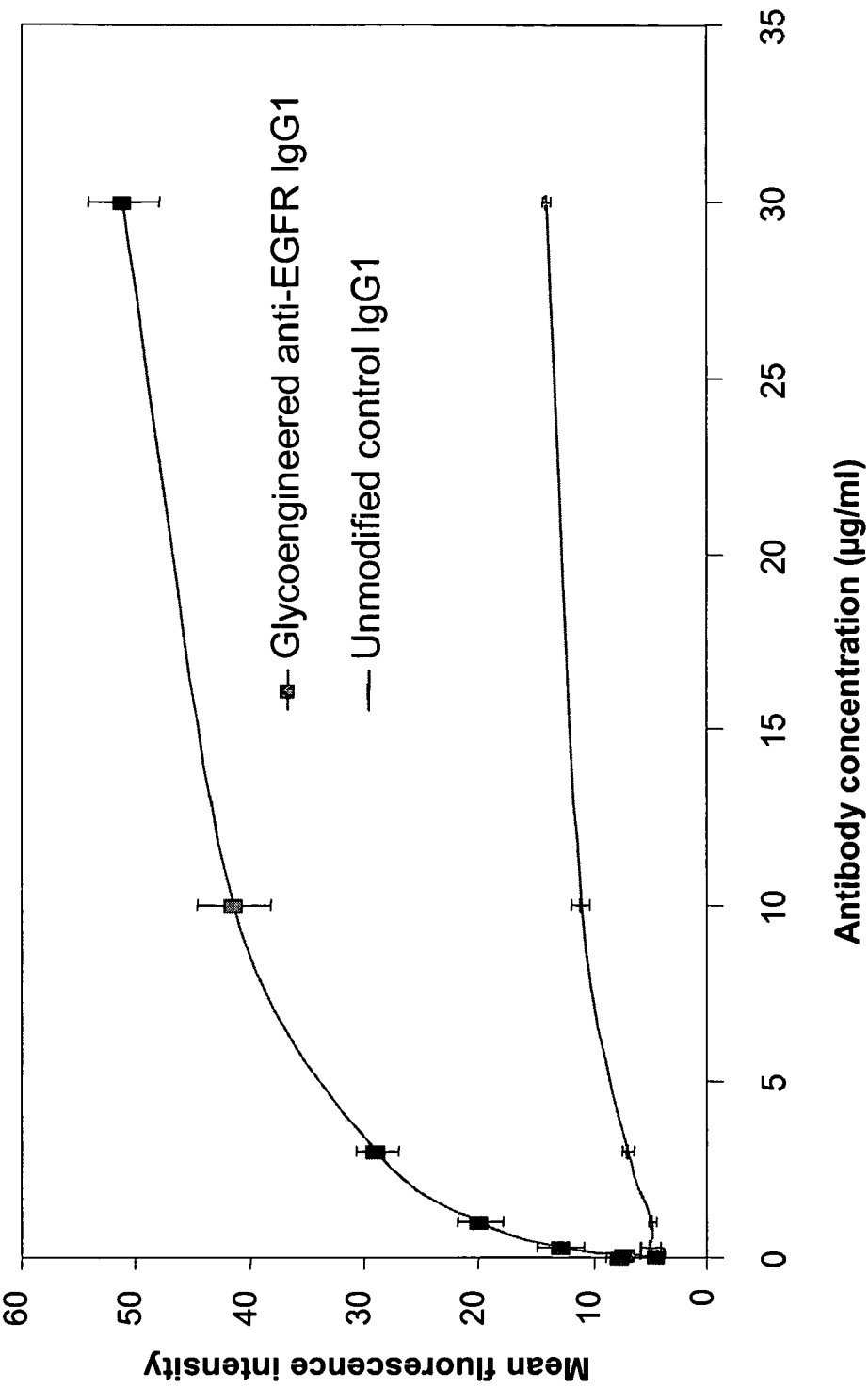
FIG. 26 shows Fc-FcgammaRIIIa binding using a whole cell (CHO cells engineered to express human FcgRIIIa on their surface). The antibody used was the Fc-engineered (glycoengineered) anti-EGFR antibody used for the in vivo monkey studies described in the Examples herein below. Binding for a non-Fc-engineered (unmodified) control IgG1 antibody is shown for comparison.

Increased FcgammaRIII receptor binding resulting from the applied Fc engineering was demonstrated as described above using whole cell binding to CHO cells engineered for surface expression of human FcgammaRIII and FACS-based analysis. Results are shown in FIG. 26. Additionally, the engineered antibody has equivalent degree of Fc-engineering to the "Glyco-2" antibody (75% on Fc-oligosaccharides being of non-fucosylated type) described elsewhere (Ferrara, C. et al., *J Biol Chem.* 2005 Dec. 5; [E-publication ahead of print]). Such Fc-engineered antibodies have up to 50-fold increased binding affinity for human FcgammaRIII relative to a standard non-Fc engineered antibody (Equilibrium dissociation constanst of 15 and 150 nM for the 158V and 158F polymorphic variants of the human receptor vs. 750 and 5000 nM for the same receptor variants, respectively, when binding to non-Fc engineered human IgG1 antibodies).

Figure 27:
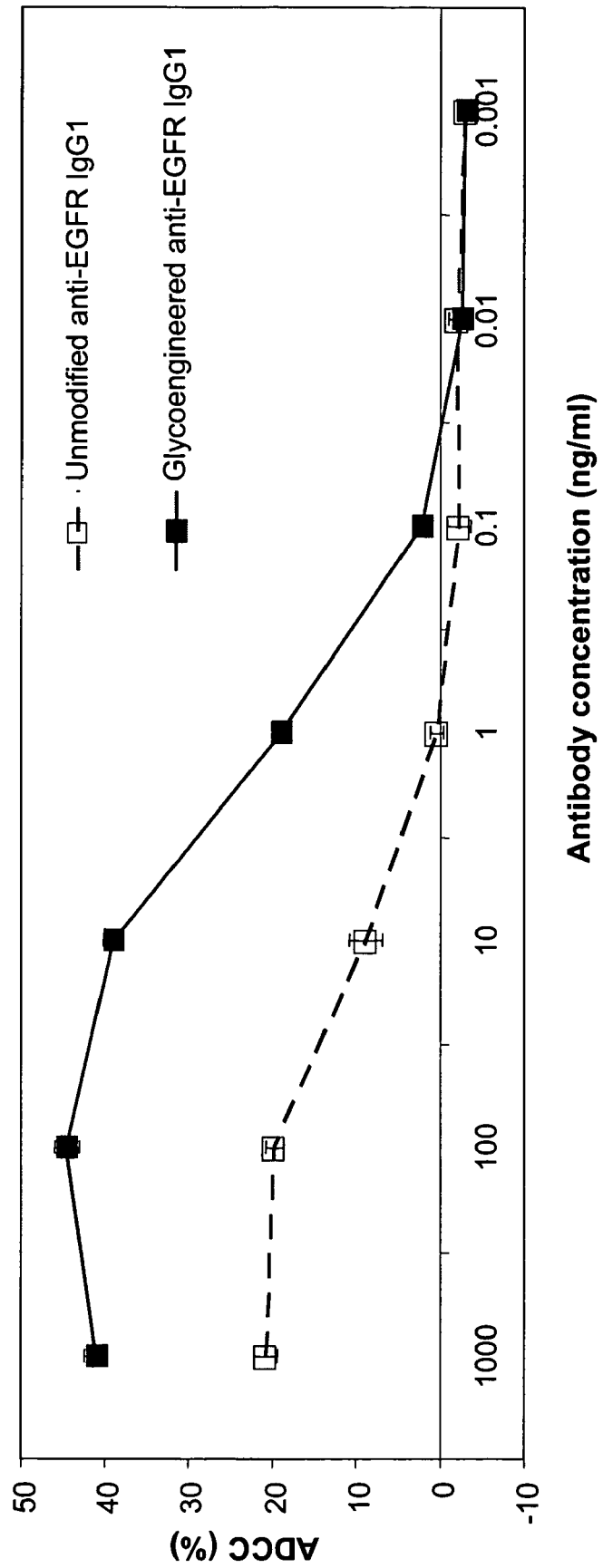
FIG. 27 shows ADCC mediated by Fc-engineered (glycoengineered) anti-EGFR antibody. Target cells are A549 human lung carcinoma cells. ADCC activity for the non-Fc engineered (unmodified) form of the antibody is shown for comparison.
Figure 28:
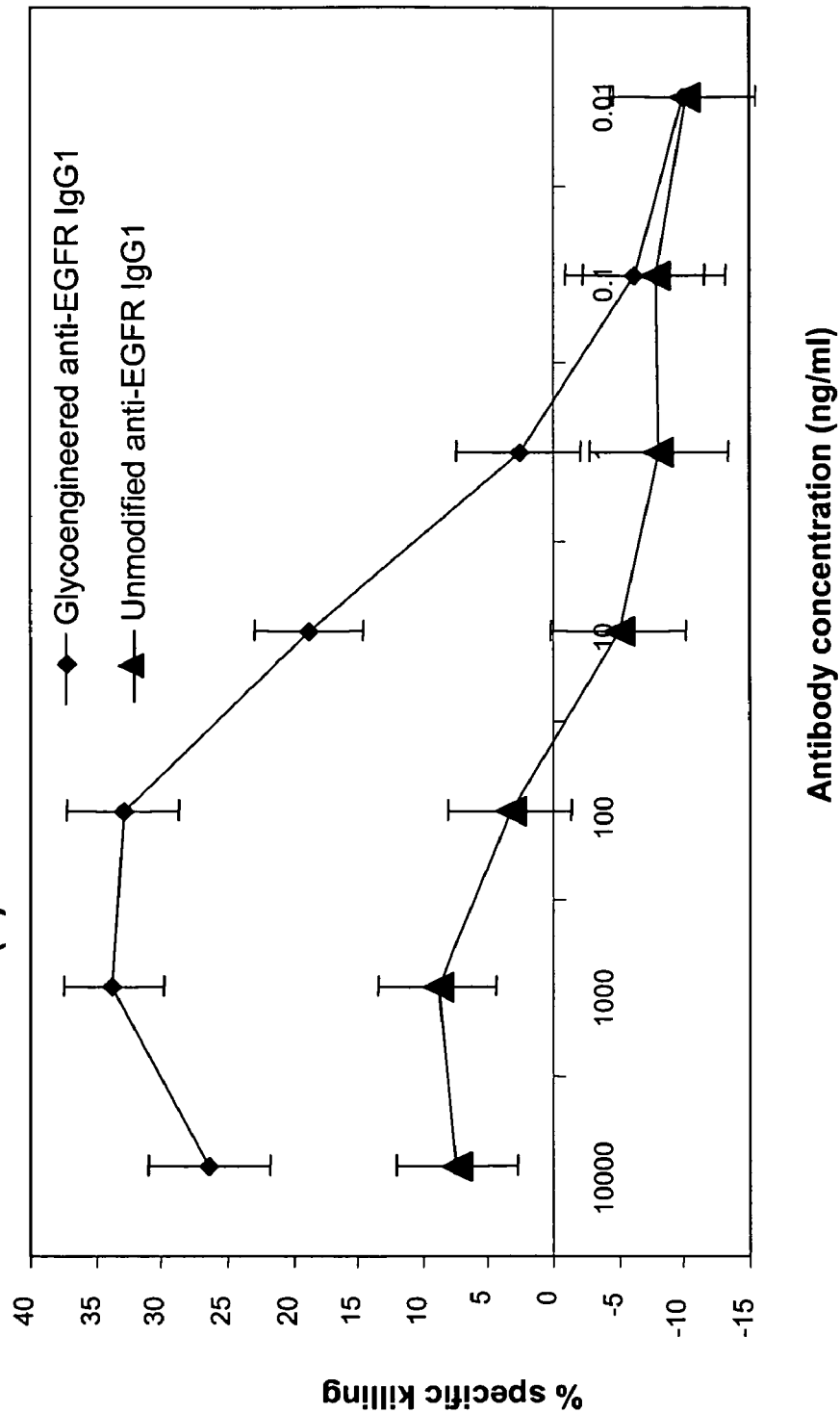
FIG. 28 shows ADCC mediated by Fc-engineered (glycoengineered) anti-EGFR antibody. Target cells are CYNOM-K1 cynomolgus monkey keratinocyte cell line. ADCC activity for the non-Fc engineered (unmodified) form of the antibody is shown for comparison.

ADCC was measured as described above using two target cell lines: A549 human lung carcinoma cells and CYNOM-K1 cynomolgus monkey keratinocyte cells. Results are shown in FIGS. 27 and 28, respectively.

Data Processing

Pharmacokinetic parameters were calculated using the computer program WinNonlin Pro version 3.3 (Pharsight Corporation, USA).

All serum concentrations supplied as part of this study were reported to 4 significant figures or 3 decimal places. Pharmacokinetic parameters were reported as follows: Cmax, $AUC_{168}$, CL and Vss to 4 significant figures; k to 4 decimal places; $t_{1/2}$ to 1 decimal place.

Values that were BLQ (<0.195 µg/mL) were entered as zero in the pharmacokinetic processing.

Toxicokinetics

Maximum serum concentrations of anti-EGFR (Cmax) and their times of occurrence (Tmax) were the observed values. Areas under the serum anti-EGFR concentration-time curves within a 168-hour dosing interval ($AUC_{168}$), were estimated by the linear trapezoidal rule. In the calculation of $AUC_{168}$ values the serum anti-EGFR concentrations at zero hours were estimated by back extrapolation using log-linear regression analysis, based on the first two sampling times, however, if the serum concentration did not decline during this period then the serum concentration at zero hours was considered to be equivalent to the concentration at the first sampling time. Areas under the serum anti-EGFR concentration-time curves to infinite time (AUC), were estimated by the following expression:

$$AUC = AUC_{168} + Clast/k$$

Where Clast is the predicted serum concentration at the last quantifiable sample point and k is the terminal rate constant.

Terminal rate constants (k) were estimated by fitting a linear regression of log concentration against time. For the estimate of k to be accepted as reliable, the following criteria were imposed:

1. The terminal data points were apparently randomly distributed about a single straight line (on visual inspection)
2. A minimum of 3 data points was available for the regression
3. The regression coefficient was $\geq 0.95$, and the fraction of the variance accounted for was $\geq 0.90$
4. The interval including the data points chosen for the regression was at least two-fold greater than the half-life itself Terminal half-lives ($t_{1/2}$) were calculated as ln2/k. Total serum clearance (CL) was calculated as Dose/AUC. Volume of distribution at steady-state (Vss) was calculated as Dose·AUMC/AUC2. Accumulation (R) was assessed as the ratio of the trough concentration following the last dose (Day 22) to the trough concentration following the first dose (Day 1) i.e. serum concentration at 672 hours/serum concentration at 168 hours (pre-dose on Day 8).

Results and Discussion

Figure 18:
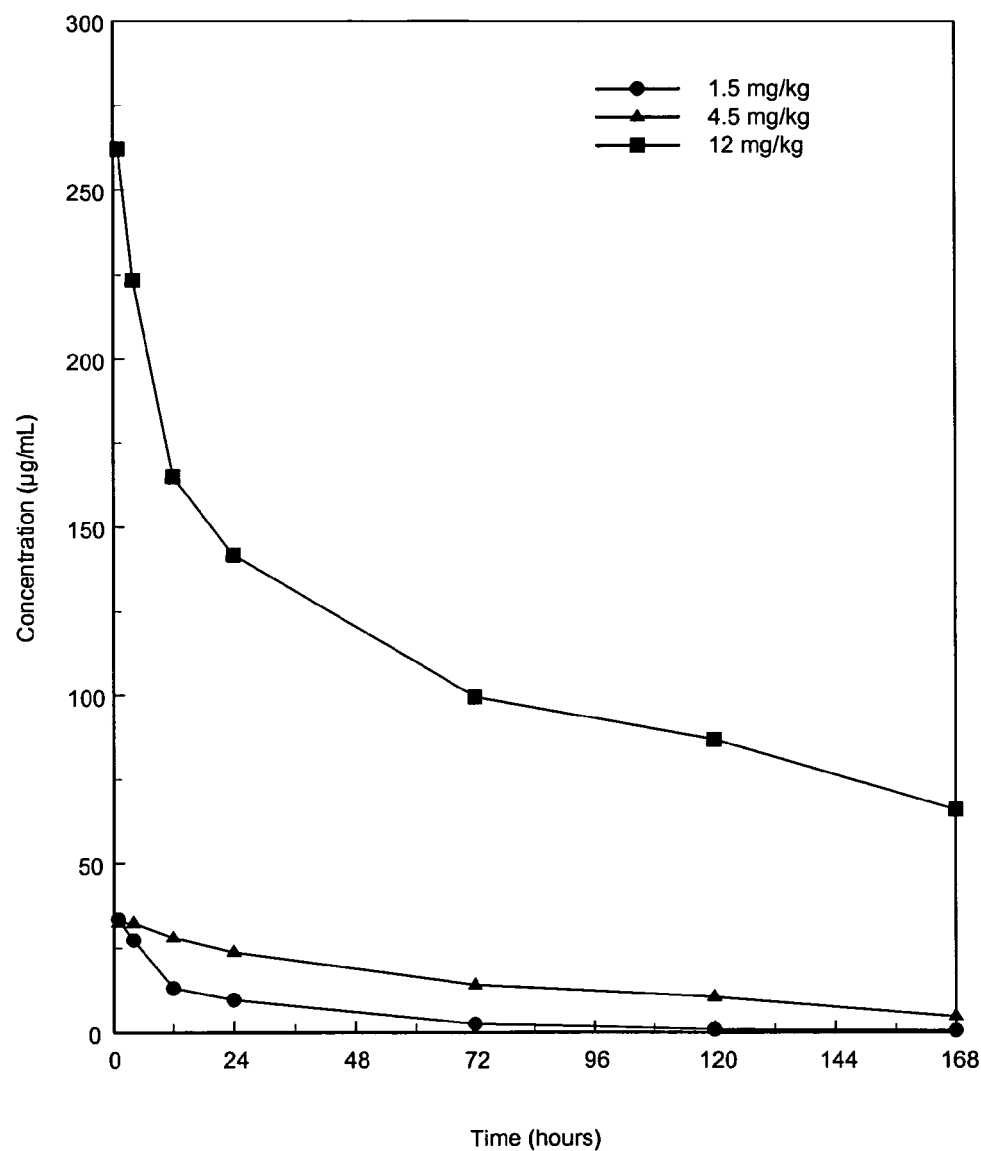
FIG. 18 shows serum concentrations of anti-EGFR on Day 1 of weekly intravenous administration of anti-EGFR to male cynomolgous monkeys.
Figure 19:
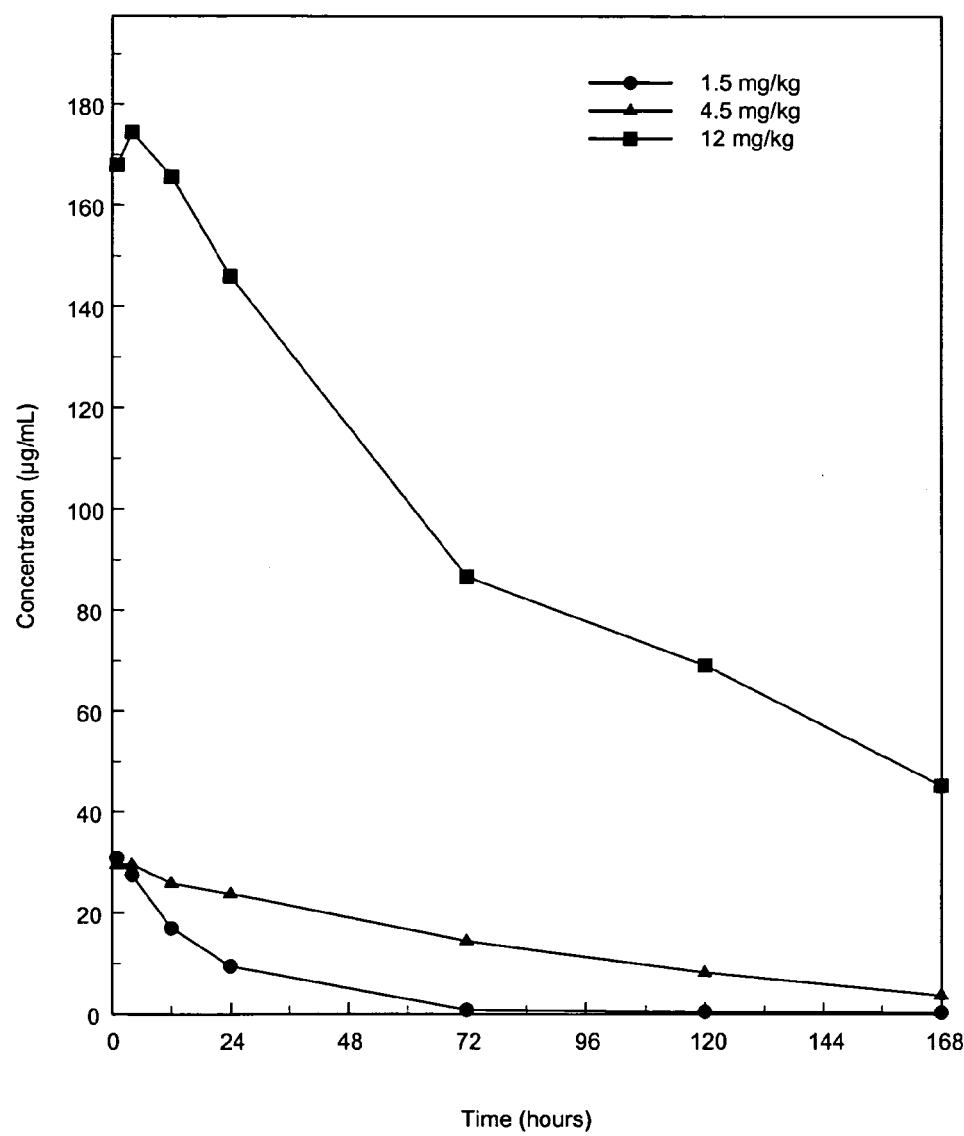
FIG. 19 shows serum concentrations of anti-EGFR on Day 1 of weekly intravenous administration of anti-EGFR to female cynomolgous monkeys.

Blood samples were taken up to 120 hours after dosing on Day 1; at pre-dose and 1 hour post-dose on Days 8, 15 and 22, and at 672 hours post dosing on Day 1 during a toxicity study to assess the systemic exposure of male and female monkeys to anti-EGFR following intravenous bolus administration of anti-EGFR at dose levels of 1.5, 4.5 and 12 mg/kg/occasion on Days 1, 8, 15 and 22 of the study. Serum concentrations of anti-EGFR in samples taken up to 168 hours post-dose are presented in Tables 27-29, and the mean serum concentration-time profiles are illustrated in FIGS. 18 and 19.

Pharmacokinetic parameters of anti-EGFR are presented in Table 50, and the $AUC_{168}$ values are summarised below:

TABLE 24

| Dose level | $AUC168$ (µg · h/mL) | |
|---|---|---|
| (mg/kg/occasion) | Males | Females |
| 1.5 | 830.4 | 748.4 |
| 4.5 | 2537 | 2378 |
| 12 | 18310 | 15980 |

The times at which the maximum serum concentrations occurred ($T_{max}$) were generally 1 hour post-dose (the first sample point) but occurred at 4 hours post-dose (the second sample point) in females 2F462 (4.5 mg/kg) and 3F612 (12 mg/kg). However, for both these females, the concentrations at 4 hours post-dose were very similar to those concentrations at 1 hour post-dose and were probably within the variability of the assay. Therefore the apparent delay in Tmax is unlikely to be of any significance.

Serum concentrations of anti-EGFR prior to the succeeding dose were quantifiable in all animals except male 2M461 on Day 22 (4.5 mg/kg/occasion dose level) therefore, in general, animals were continuously exposed to quantifiable concentrations of anti-EGFR during a dosing interval.

The relationships between areas under the serum anti-EGFR concentration-time curves ($AUC_{68}$) and dose level on Day 1 are presented below:

TABLE 25

| Dose level | | $AUC_{168}$ ratio | |
|---|---|---|---|
| (mg/kg/occasion) | Dose level ratio | Males | Females |
| 1.5 | 1 | 1 | 1 |
| 4.5 | 3.0 | 3.1 | 3.2 |
| 12 | 8.0 | 22.0 | 21.4 |

Figure 20:
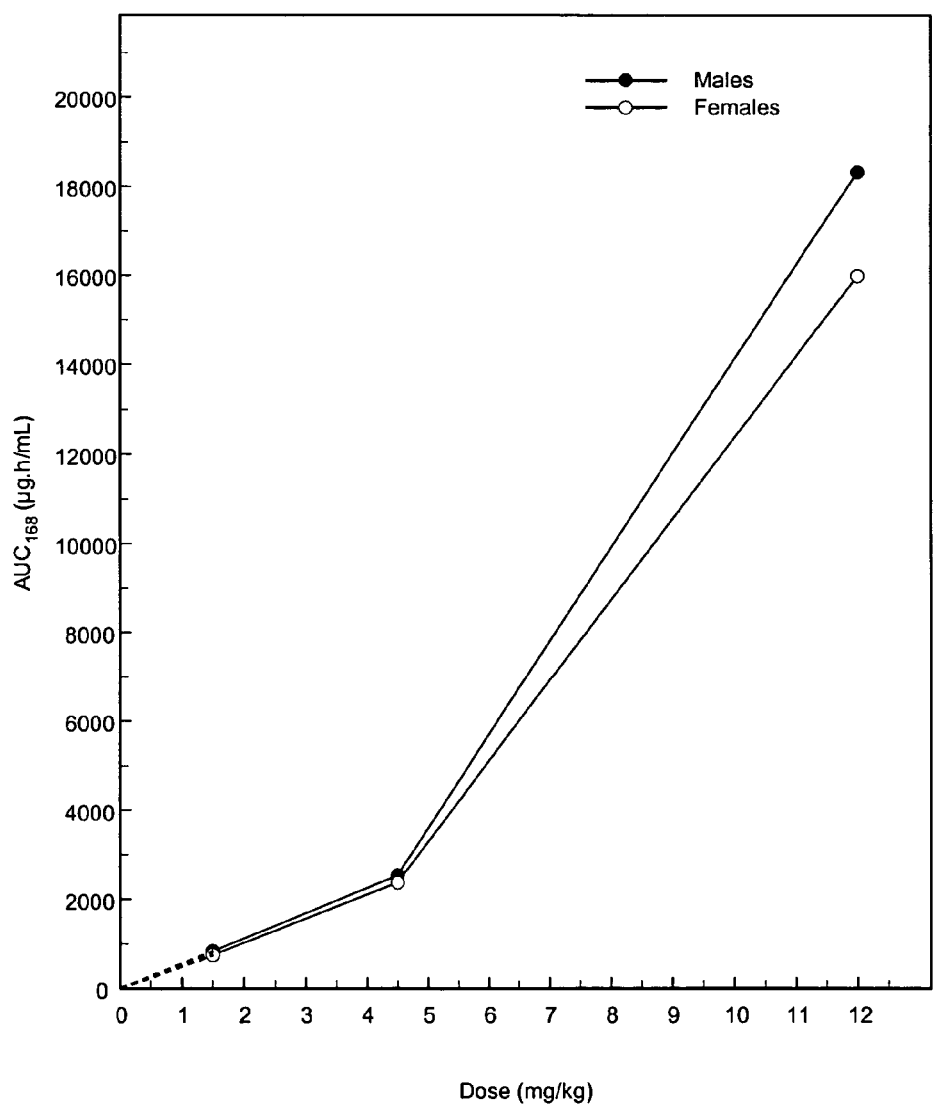
FIG. 20 shows the relationship between areas under the serum anti-EGFR concentration-time curves ($AUC_{168}$) and dose level on Day 1 of weekly intravenous administration of anti-EGFR to cynomolgous monkeys.

The rate and extent of systemic exposure of monkeys to anti-EGFR, characterised by $AUC_{168}$, increased approximately proportionately with increasing dose over the dose range 1.5 to 4.5 mg/kg/occasion but by more than the proportionate dose increase over the dose range 4.5 to 12 mg/kg/occasion on Day 1. At the highest dose (12 mg/kg/occasion) the $AUC_{168}$ was ca 2.8-fold higher than that predicted by a linear relationship (FIG. 20).

The extent ($AUC_{168}$) of systemic exposure of female monkeys to anti-EGFR was generally similar to the exposure in male monkeys.

Figure 21:
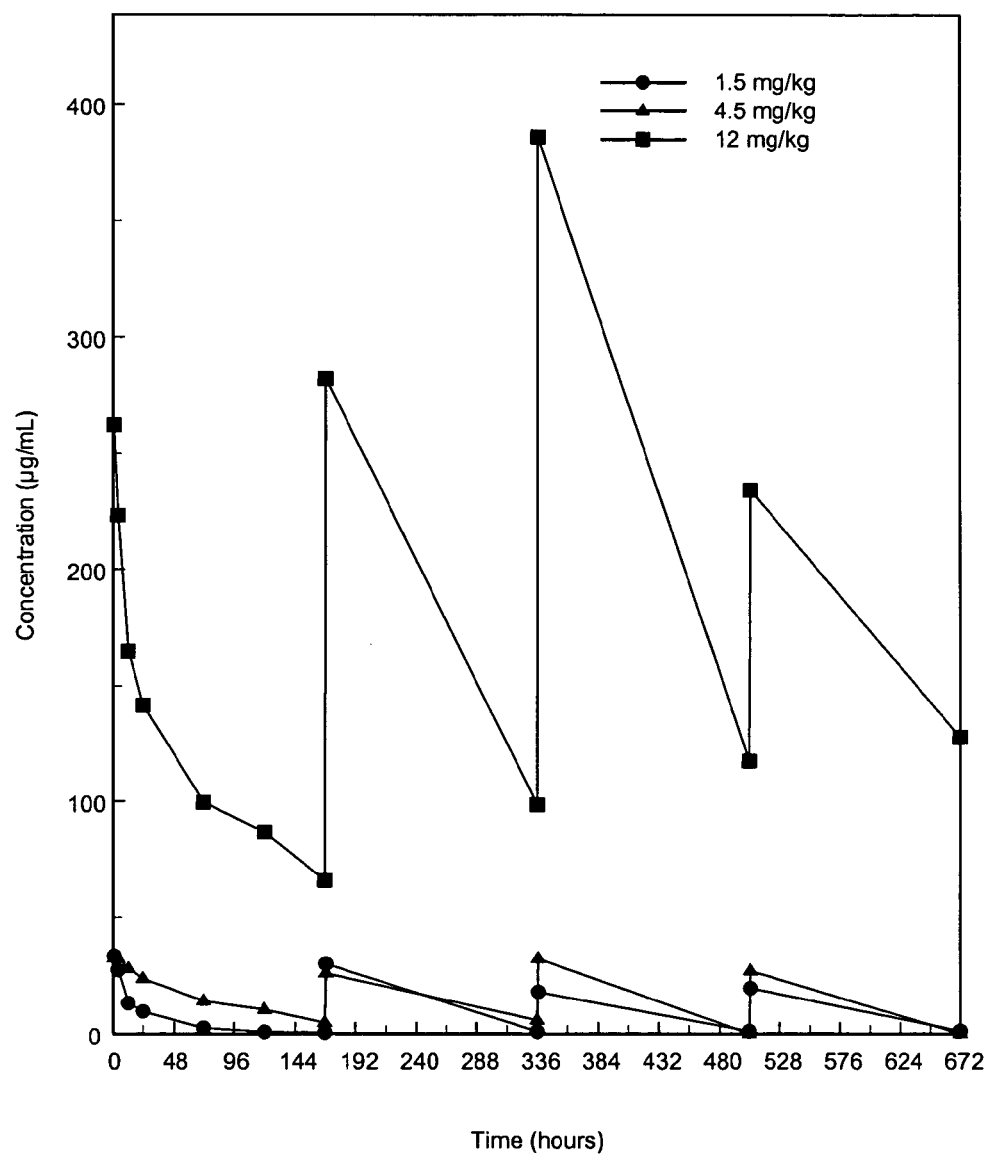
FIG. 21 shows serum concentrations of anti-EGFR during weekly intravenous administration of anti-EGFR to male cynomolgous monkeys.
Figure 22:
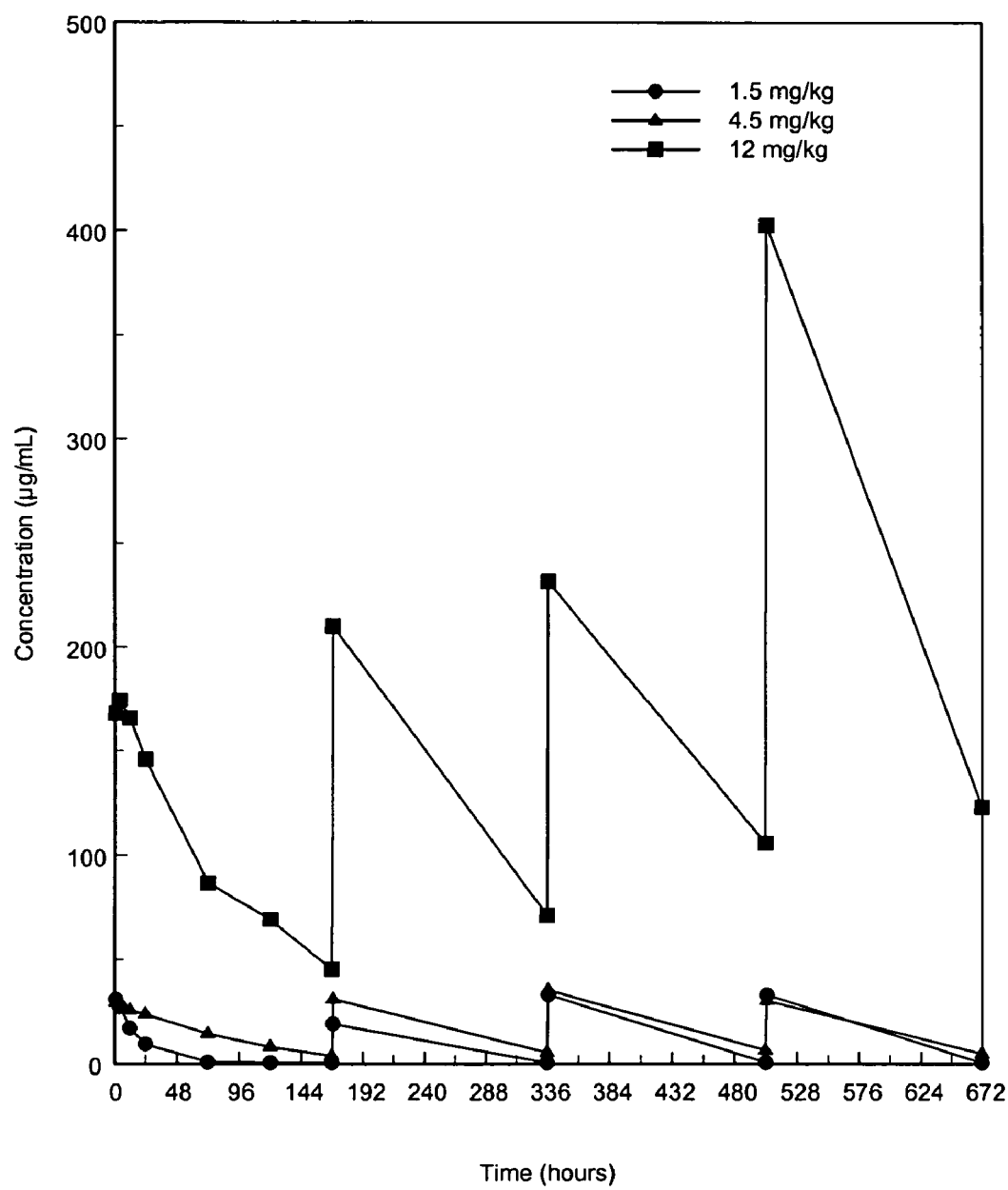
FIG. 22 shows serum concentrations of anti-EGFR during weekly intravenous administration of anti-EGFR to female cynomolgous monkeys.

After repeated intravenous doses, the pre-dose serum concentrations of anti-EGFR were generally higher than those values after a single dose (FIGS. 21-22) and indicated accumulation of anti-EGFR in serum throughout the period of the study. This accumulation was generally lower in females than in males, except at the highest dose level. The ratios of the trough (pre-dose) concentrations following the last dose on Day 22 (672 hours post Day 1 dose) to the trough concentration following the first dose on Day 1 are presented in the Table 26, below:

TABLE 26

| Dose level (mg/kg/occasion) | R | |
| --- | --- | --- |
|  | Males | Females |
| 1.5 | 2.23 | 1.26 |
| 4.5 | * | 1.32 |
| 12 | 1.94 | 2.72 |

*Could not be calculated as trough concentration was BLQ

The terminal rate constants (k), and corresponding terminal half-lives ($t_{1/2}$), of anti-EGFR on Day 1 are presented in Table 30. The terminal half-life could not be estimated adequately for all animals, but where it could be estimated was in the range 32.5 to 63.1 hours, and appeared to increase with dose in male animals. Total serum clearance of anti-EGFR appeared to be independent of dose over the range 1.5-4.5 mg/kg/occasion but was reduced at the highest dose level in male and female monkeys.

In conclusion, the extent of systemic exposure of cynomolgus monkeys to anti-EGFR appeared to be characterised by non-linear (dose-dependent) kinetics over the dose range 1.5 to 12 mg/kg/occasion on Day 1 of the intravenous toxicity study. Increasing the dose of anti-EGFR above 4.5 mg/kg/occasion is likely to result in a higher systemic exposure than would be predicted from a linear relationship, which is consistent with the possibility of a capacity limited process for the elimination of anti-EGFR.

In addition, the study also provided evidence that in general there were no differences in the systemic exposure of male and female monkeys to anti-EGFR and that there was accumulation after repeated intravenous administration.

TABLE 27

Serum concentrations (μg/ml) of anti-EGFR in monkey serum following intravenous administration of 1.5 mg/kg anti-EGFR on Days 1, 8, 15 and 22

| Timepoint | | Animal number | |
| --- | --- | --- | --- |
|  |  | 1M 623 | 1F 590 |
| Day 1 | 1 hour | 33.42 | 30.86 |
| Day 1 | 4 hours | 27.33 | 27.49 |
| Day 1 | 12 hours | 13.09 | 17.01 |
| Day 1 | 24 hours | 9.656 | 9.468 |
| Day 1 | 72 hours | 2.528 | 0.786 |
| Day 1 | 120 hours | 0.845 | 0.431 |
| Day 8 pre-dose | | 0.538 | 0.287 |
| Day 8 | 1 hour | 30.02 | 19.07 |
| Day 15 pre-dose | | 0.902 | 0.382 |
| Day 15 | 1 hour | 17.91 | 33.08 |
| Day 22 pre-dose | | 1.065 | 0.595 |

TABLE 27-continued

Serum concentrations (μg/ml) of anti-EGFR in monkey serum following intravenous administration of 1.5 mg/kg anti-EGFR on Days 1, 8, 15 and 22

| Timepoint | | Animal number | |
| --- | --- | --- | --- |
|  |  | 1M 623 | 1F 590 |
| Day 22 | 1 hour | 19.41 | 33.00 |
| Day 1 | 672 hours | 1.202 | 0.362 |

TABLE 28

Serum concentrations (μg/ml) of anti-EGFR in cynomolgus monkey serum following intravenous administration of 4.5 mg/kg anti-EGFR on Days 1, 8, 15 and 22

| Timepoint | | Animal number | |
| --- | --- | --- | --- |
|  |  | 2M 461 | 2F 462 |
| Day 1 | 1 hour | 32.45 | 29.51 |
| Day 1 | 4 hours | 32.39 | 29.57 |
| Day 1 | 12 hours | 28.05 | 25.88 |
| Day 1 | 24 hours | 23.70 | 23.78 |
| Day 1 | 72 hours | 14.03 | 14.38 |
| Day 1 | 120 hours | 10.42 | 8.137 |
| Day 8 pre-dose | | 4.672 | 3.683 |
| Day 8 | 1 hour | 25.91 | 31.06 |
| Day 15 pre-dose | | 5.752 | 5.450 |
| Day 15 | 1 hour | 32.20 | 35.38 |
| Day 22 pre-dose | | BLQ | 6.497 |
| Day 22 | 1 hour | 26.98 | 30.23 |
| Day 1 | 672 hours | BLQ | 4.845 |

TABLE 29

Serum concentrations (μg/ml) of anti-EGFR in cynomolgus monkey serum following intravenous administration of 12 mg/kg anti-EGFR on Days 1, 8, 15 and 22

| Timepoint | | Animal number | |
| --- | --- | --- | --- |
|  |  | 1M 623 | 1F 590 |
| Day 1 | 1 hour | 262.2 | 168.0 |
| Day 1 | 4 hours | 223.3 | 174.5 |
| Day 1 | 12 hours | 164.9 | 165.7 |
| Day 1 | 24 hours | 141.7 | 146.0 |
| Day 1 | 72 hours | 99.54 | 86.64 |
| Day 1 | 120 hours | 86.64 | 69.08 |
| Day 8 pre-dose | | 65.86 | 45.21 |
| Day 8 | 1 hour | 282.1 | 209.9 |
| Day 15 pre-dose | | 98.43 | 71.21 |
| Day 15 | 1 hour | 385.9 | 231.4 |
| Day 22 pre-dose | | 117.3 | 105.6 |
| Day 22 | 1 hour | 234.1 | 402.5 |
| Day 1 | 672 hours | 127.5 | 122.9 |

TABLE 30

Pharmacokinetic parameters of anti-EGFR on Day 1 of weekly intravenous administration of anti-EGFR to cynomolgus monkeys

| Dose (mg/kg) | Animal | $C_{max}$ (µg/mL) | $T_{max}$ (h) | $AUC_t$ (µg.h/mL) | AUC (µg.h/mL) | CL (mL/h/kg) | $V_{ss}$ (mL/kg) | k (1/h) | $t_{1/2}$ (h) |
|---|---|---|---|---|---|---|---|---|---|
| 1.5 | 1M623 | 33.42 | 1 | 830.4 | 849.4 | 1.778 | 60.79 | 0.0214 | 32.5 |
| 1.5 | 1F590 | 30.86 | 1 | 748.4 | 7749[a] | 1.962[a] | 57.85[a] | 0.0105[a] | 66.0[a] |
| 4.5 | 2M461 | 32.45 | 1 | 2537 | 3005 | 1.488 | 133.6 | 0.0110 | 63.1 |
| 4.5 | 2F462 | 29.57 | 4 | 2378 | 2719 | 1.663 | 133.2 | 0.0121 | 57.4 |
| 12 | 3M463 | 262.2 | 1 | 18310 | 29870[a] | 0.4058[a] | 71.33[a] | 0.0056[a] | 124.3[a] |
| 12 | 3F612 | 174.5 | 4 | 15980 | 21400[a] | 0.5552[a] | 66.94[a] | 0.0082[a] | 84.4[a] |

[a]Value is an estimate as the data did not meet all the acceptance criteria defined in Data Processing and should be treated with caution Blood Chemistry and Haematology Blood samples were taken from the femoral vein of cynomolgous monkeys that had been administered an intravenous bolus injection of GlycoMAB anti-EGFR on days 1, 8, 15, and 22. Samples were taken from the limb not used for dose administration, following overnight deprivation of food (not decedents). Samples were examined at pretreatment, three days after the second dose, and on termination for the following parameters, using lithium heparin as anticoagulant:

Alkaline phosphatase
Alanine amino-transferase
Aspartate amino-transferase
Bilirubin—total
Urea
Creatinine
Glucose
Cholesterol—total
Triglycerides
Sodium
Potassium
Chloride
Calcium
Phosphorus
Total protein
Protein electrophoretogram
Albumin/globulin ratio Average normal cynomolgus monkey blood chemistry analysis data are presented in Table 31.

TABLE 31

Cynomolgus monkeys (origin Mauritius)--Blood Chemistry

| Parameter | sex | n | 1% | 5% | 50% | 95% | 99% | mean | s.d. |
|---|---|---|---|---|---|---|---|---|---|
| ALP | M | 949 | 837 | 1339 | 2147 | 3201 | 3899 | 2175.5 | 565.44 |
|  | F | 881 | 946 | 1342 | 2144 | 3163 | 3740 | 2164.1 | 552.82 |
| ALP-N | M | 511 | 481 | 579 | 881 | 1453 | 1771 | 928.0 | 260.88 |
|  | F | 499 | 427 | 546 | 846 | 1362 | 1694 | 879.5 | 240.24 |
| ALT | M | 1489 | 24 | 30 | 50 | 87 | 127 | 53.7 | 19.07 |
|  | F | 1407 | 23 | 28 | 46 | 84 | 111 | 49.3 | 18.65 |
| AST | M | 1487 | 26 | 30 | 41 | 63 | 101 | 43.6 | 17.57 |
|  | F | 1404 | 25 | 29 | 39 | 61 | 89 | 41.7 | 13.59 |
| gGT | M | 663 | 95 | 118 | 178 | 292 | 342 | 188.5 | 52.47 |
|  | F | 641 | 81 | 102 | 153 | 232 | 266 | 158.6 | 38.38 |
| LAP | M | 207 | 18 | 26 | 40 | 79 | 217 | 45.1 | 28.25 |
|  | F | 205 | 15 | 20 | 35 | 62 | 89 | 37.1 | 12.73 |
| GLDH | M | 159 | 8 | 10 | 17 | 35 | 126 | 20.1 | 16.46 |
|  | F | 159 | 6 | 8 | 15 | 27 | 35 | 16.3 | 5.97 |
| Bilirubin | M | 1494 | 1 | 1 | 3 | 8 | 11 | 3.8 | 2.04 |
|  | F | 1413 | 1 | 2 | 4 | 8 | 11 | 4.1 | 2.07 |
| LDH | M | 99 | 160 | 596 | 808 | 1166 | 2029 | 838.3 | 218.75 |
|  | F | 82 | 477 | 529 | 711 | 945 | 1021 | 715.0 | 117.07 |
| CPK | M | 331 | 68 | 83 | 179 | 713 | 1867 | 287.4 | 464.03 |
|  | F | 335 | 57 | 77 | 184 | 925 | 2628 | 309.7 | 534.02 |
| Indir Bili | M | 59 | 1 | 2 | 4 | 10 | 11 | 4.2 | 2.15 |
|  | F | 57 | 1 | 2 | 4 | 5 | 7 | 3.6 | 1.13 |
| Direct Bilirubin | M | 59 | 0 | 0 | 0 | 2 | 3 | 0.2 | 0.65 |
|  | F | 57 | 0 | 0 | 0 | 1 | 3 | 0.2 | 0.52 |
| Bile Acids | M | 386 | 0.9 | 2.5 | 6.4 | 15.3 | 23.4 | 7.38 | 4.574 |
|  | F | 380 | 1.4 | 3.0 | 7.0 | 12.9 | 17.8 | 7.41 | 3.474 |
| Urea | M | 1457 | 3.01 | 3.66 | 5.50 | 8.81 | 10.53 | 5.775 | 1.5710 |
|  | F | 1379 | 2.77 | 3.42 | 5.33 | 8.56 | 9.90 | 5.559 | 1.5432 |
| Creatinine | M | 1458 | 55 | 59 | 71 | 87 | 94 | 71.6 | 8.67 |
|  | F | 1383 | 56 | 60 | 72 | 87 | 85 | 72.7 | 8.36 |
| Glucose | M | 1455 | 2.22 | 2.64 | 3.71 | 5.21 | 6.37 | 3.809 | 0.8135 |
|  | F | 1380 | 2.23 | 2.65 | 3.63 | 5.18 | 6.34 | 3.735 | 0.7990 |
| Cholesterol | M | 1455 | 1.69 | 1.93 | 2.68 | 3.55 | 3.96 | 2.706 | 1.4909 |
|  | F | 1382 | 1.83 | 2.15 | 2.86 | 3.69 | 4.05 | 2.885 | 0.4813 |
| Chol HDL | M | 45 | 1.26 | 1.34 | 1.79 | 2.23 | 2.59 | 1.784 | 0.3128 |
|  | F | 45 | 1.09 | 1.31 | 1.82 | 2.43 | 2.55 | 1.844 | 0.3179 |

TABLE 31-continued

Cynomolgus monkeys (origin Mauritius)--Blood Chemistry

| Parameter | sex | n | 1% | 5% | 50% | 95% | 99% | mean | s.d. |
|---|---|---|---|---|---|---|---|---|---|
| Chol VLDL | M | 45 | 0.00 | 0.00 | 0.00 | 0.03 | 0.11 | 0.004 | 0.0175 |
|  | F | 45 | 0.00 | 0.00 | 0.00 | 0.12 | 0.19 | 0.012 | 0.0370 |
| NEFA | M | 132 | 0.10 | 0.28 | 0.98 | 1.84 | 2.44 | 0.994 | 0.4700 |
|  | F | 132 | 0.14 | 0.22 | 1.06 | 1.90 | 2.18 | 1.070 | 0.4704 |
| Triglycerides | M | 1453 | 0.26 | 0.32 | 0.53 | 0.86 | 1.30 | 0.561 | 0.2051 |
|  | F | 1374 | 0.26 | 0.34 | 0.57 | 0.90 | 1.14 | 0.587 | 0.1778 |
| Ph Lipid | M | 64 | 1.65 | 1.68 | 2.18 | 2.91 | 3.15 | 2.254 | 0.3769 |
|  | F | 49 | 1.77 | 1.83 | 2.44 | 2.91 | 2.98 | 2.405 | 0.3267 |
| Uric Acid | M | 17 | 0 | 0 | 0 | 8 | 8 | 1.1 | 2.34 |
|  | F | 17 | 0 | 0 | 0 | 1 | 1 | 0.4 | 0.51 |
| Na | M | 1461 | 141 | 142 | 147 | 152 | 155 | 146.8 | 3.00 |
|  | F | 1382 | 140 | 142 | 147 | 153 | 157 | 147.3 | 3.34 |
| K | M | 1460 | 3.2 | 3.4 | 4.0 | 5.0 | 5.6 | 4.08 | 0.511 |
|  | F | 1382 | 3.2 | 3.3 | 4.0 | 4.9 | 5.4 | 4.01 | 0.484 |
| Cl | M | 1461 | 102 | 104 | 108 | 112 | 115 | 107.7 | 2.71 |
|  | F | 1382 | 102 | 104 | 108 | 113 | 116 | 108.4 | 2.83 |
| Ca | M | 1462 | 2.31 | 2.39 | 2.56 | 2.76 | 2.87 | 2.568 | 0.1176 |
|  | F | 1382 | 2.32 | 2.39 | 2.57 | 2.77 | 2.89 | 2.572 | 0.1168 |
| Phos | M | 1172 | 1.16 | 1.40 | 1.93 | 2.43 | 2.69 | 1.921 | 0.3126 |
|  | F | 1098 | 1.17 | 1.37 | 1.84 | 2.35 | 2.60 | 1.844 | 0.2978 |
| Chol LDL | M | 45 | 0.54 | 0.62 | 1.20 | 1.87 | 1.92 | 1.253 | 0.3694 |
|  | F | 45 | 0.69 | 0.78 | 1.19 | 1.83 | 1.88 | 1.233 | 0.2906 |
| Bicarbonate | M | 288 | 7 | 10 | 17 | 22 | 25 | 16.5 | 3.51 |
|  | F | 283 | 6 | 10 | 16 | 22 | 25 | 15.9 | 3.81 |
| Total Protein | M | 1455 | 71 | 74 | 80 | 87 | 90 | 80.2 | 4.06 |
|  | F | 1381 | 71 | 74 | 81 | 89 | 92 | 81.2 | 4.32 |
| Albumin | M | 346 | 34 | 38 | 43 | 46 | 49 | 42.6 | 2.67 |
| (Chemical) | F | 342 | 36 | 38 | 43 | 47 | 49 | 42.7 | 2.60 |
| Albumin | M | 1089 | 33 | 36 | 45 | 51 | 54 | 44.3 | 4.46 |
|  | F | 1019 | 34 | 37 | 45 | 52 | 55 | 44.7 | 4.58 |
| Globulin | M | 289 | 31 | 32 | 36 | 41 | 45 | 36.3 | 2.83 |
|  | F | 285 | 30 | 32 | 37 | 43 | 48 | 37.5 | 3.59 |
| A/G Ratio | M | 340 | 0.79 | 0.98 | 1.17 | 1.39 | 1.45 | 1.172 | 0.1215 |
| (Chemical) | F | 336 | 0.84 | 0.95 | 1.14 | 1.34 | 1.42 | 1.143 | 0.1274 |
| A/G Ratio | M | 1068 | 0.68 | 0.80 | 1.26 | 1.65 | 1.82 | 1.252 | 0.2522 |
|  | F | 998 | 0.67 | 0.79 | 1.26 | 1.66 | 1.81 | 1.247 | 0.2647 |
| A1 Globulin | M | 1105 | 2 | 2 | 3 | 4 | 4 | 2.8 | 0.62 |
|  | F | 1035 | 2 | 2 | 3 | 4 | 5 | 2.8 | 0.64 |
| A2 Globulin | M | 1105 | 3 | 3 | 4 | 6 | 7 | 4.2 | 0.92 |
|  | F | 1035 | 3 | 3 | 4 | 6 | 7 | 4.2 | 1.01 |
| beta Globulin | M | 1105 | 12 | 13 | 16 | 22 | 24 | 16.6 | 2.63 |
|  | F | 1035 | 12 | 13 | 16 | 22 | 25 | 16.8 | 2.85 |
| gamma Globulin | M | 1105 | 8 | 9 | 12 | 17 | 18 | 12.6 | 2.26 |
|  | F | 1035 | 8 | 9 | 13 | 17 | 20 | 13.1 | 2.52 |
| Aldolase | M | 96 | 9 | 14 | 21 | 38 | 57 | 22.0 | 7.48 |
|  | F | 97 | 10 | 13 | 19 | 48 | 84 | 21.9 | 11.91 |
| Plasm CHE | M | 17 | 4159 | 4159 | 5745 | 9160 | 9160 | 5919.8 | 1181.68 |
|  | F | 17 | 3371 | 3371 | 5869 | 8367 | 8367 | 5689.2 | 1512.98 |
| CRP | M | 57 | 0.000 | 0.000 | 0.002 | 0.013 | 0.026 | 0.0032 | 0.00414 |
|  | F | 56 | 0.000 | 0.000 | 0.002 | 0.004 | 0.007 | 0.0017 | 0.00167 |
| T3 | M | 40 | 1.90 | 1.90 | 2.50 | 3.38 | 3.58 | 2.537 | 0.4011 |
|  | F | 40 | 1.71 | 1.96 | 2.59 | 3.06 | 4.02 | 2.631 | 0.3799 |
| T4 | M | 40 | 35 | 42 | 59 | 86 | 92 | 59.7 | 11.84 |
|  | F | 40 | 38 | 40 | 56 | 81 | 107 | 58.6 | 14.37 |

Samples for haematological, peripheral blood analysis were taken from the femoral vein of cynomolgous monkey that had been administered an intravenous bolus injection of GlycoMAB anti-EGFR on days 1, 8, 15, and 22. Samples were taken from the limb not used for dose administration, following overnight deprivation of food (not decedents). Samples were examined at pretreatment, three days after the second dose, and on termination for the following parameters:

1) Using EDTA as anticoagulant—
   Haematocrit Haemoglobin concentration
   Erythrocyte count
   Reticulocytes
   Mean cell haemoglobin
   Mean cell haemoglobin concentration
   Mean cell volume
   Total leucocyte count
   Differential leucocyte count
   Platelet count
   Abnormalities of the blood morphology
      Anisocytosis
      Microcytosis
      Macrocytosis
      Hypochromasia
      Hyperchromasia
2) Using citrate as anticoagulant—
   Prothrombin time
   Activated partial thromboplastin time Average normal cynomolgus monkey hematology analysis data are presented in Table 32.

TABLE 32

Cynomolgus monkeys (origin Mauritius)--Hematology

| Parameter | sex | n | 1% | 5% | 50% | 95% | 99% | mean | s.d. |
|---|---|---|---|---|---|---|---|---|---|
| HCT | M | 1495 | 0.385 | 0.401 | 0.443 | 0.488 | 0.512 | 0.4435 | 0.02776 |
| | F | 1426 | 0.376 | 0.399 | 0.442 | 0.489 | 0.508 | 0.4424 | 0.02947 |
| Haemoglobin | M | 1495 | 11.4 | 12.1 | 13.3 | 14.5 | 15.1 | 13.31 | 0.769 |
| | F | 1426 | 11.2 | 11.9 | 13.2 | 14.5 | 15.1 | 13.21 | 0.855 |
| RBC | M | 1495 | 5.67 | 6.04 | 6.74 | 7.51 | 7.92 | 6.744 | 0.4792 |
| | F | 1426 | 5.58 | 5.96 | 6.71 | 7.45 | 7.73 | 6.707 | 0.4894 |
| Retic (1) % | M | 20 | 0.1 | 0.1 | 0.4 | 1.8 | 1.8 | 0.48 | 0.438 |
| | F | 20 | 0.1 | 0.1 | 0.3 | 0.9 | 0.9 | 0.42 | 0.268 |
| Retic (2) % | M | 1476 | 0.21 | 0.27 | 0.49 | 0.95 | 1.58 | 0.551 | 0.3804 |
| | F | 1408 | 0.22 | 0.28 | 0.54 | 1.06 | 1.60 | 0.595 | 0.2934 |
| MCH | M | 1495 | 17.0 | 17.8 | 19.8 | 21.6 | 22.5 | 19.80 | 1.432 |
| | F | 1425 | 16.7 | 17.7 | 19.7 | 21.8 | 22.6 | 19.74 | 1.216 |
| MCHC | M | 1495 | 27.2 | 28.2 | 30.1 | 31.9 | 32.7 | 30.06 | 1.801 |
| | F | 1425 | 27.0 | 27.9 | 29.9 | 31.8 | 32.6 | 29.88 | 1.174 |
| MCV | M | 1495 | 57.9 | 60.5 | 65.8 | 71.4 | 73.5 | 65.88 | 3.278 |
| | F | 1425 | 58.3 | 60.4 | 66.0 | 71.7 | 74.5 | 66.07 | 3.353 |
| RDW | M | 280 | 12.6 | 12.9 | 14.4 | 16.1 | 16.7 | 14.40 | 0.934 |
| | F | 285 | 12.4 | 12.8 | 14.2 | 15.7 | 16.3 | 14.21 | 0.879 |
| WBC | M | 1507 | 5.61 | 6.62 | 10.52 | 18.59 | 30.24 | 11.372 | 4.7766 |
| | F | 1432 | 5.39 | 6.58 | 10.62 | 19.55 | 28.79 | 11.637 | 4.7307 |
| Neutrophils | M | 1507 | 0.88 | 1.28 | 3.49 | 10.24 | 16.27 | 4.319 | 3.1741 |
| | F | 1432 | 1.06 | 1.62 | 4.45 | 12.27 | 17.41 | 5.392 | 3.4777 |
| Lymphocytes | M | 1507 | 2.19 | 2.96 | 5.53 | 9.81 | 15.91 | 6.021 | 3.4066 |
| | F | 1432 | 2.16 | 2.67 | 4.86 | 8.55 | 13.95 | 5.265 | 2.9997 |
| Eosinophils | M | 1507 | 0.00 | 0.01 | 0.17 | 0.81 | 1.49 | 0.254 | 0.3127 |
| | F | 1432 | 0.00 | 0.01 | 0.14 | 0.73 | 1.55 | 0.232 | 0.3188 |
| Basophils | M | 1507 | 0.01 | 0.02 | 0.04 | 0.10 | 0.25 | 0.053 | 0.0627 |
| | F | 1432 | 0.01 | 0.02 | 0.04 | 0.10 | 0.21 | 0.051 | 0.0540 |
| Monocytes | M | 1507 | 0.17 | 0.25 | 0.51 | 1.03 | 1.45 | 0.562 | 0.2575 |
| | F | 1432 | 0.16 | 0.23 | 0.49 | 1.04 | 1.56 | 0.547 | 0.2705 |
| Large Unstained Cells | M | 1507 | 0.04 | 0.06 | 0.14 | 0.32 | 0.60 | 0.163 | 0.1330 |
| | F | 1432 | 0.04 | 0.06 | 0.13 | 0.29 | 0.50 | 0.148 | 0.1147 |
| Platelets | M | 1495 | 158 | 238 | 359 | 497 | 575 | 362.1 | 81.69 |
| | F | 1426 | 181 | 234 | 359 | 496 | 560 | 360.5 | 80.04 |
| PT | M | 1481 | 9.6 | 9.9 | 10.8 | 12.0 | 14.8 | 10.88 | 0.877 |
| | F | 1406 | 9.7 | 10.0 | 10.8 | 12.1 | 14.1 | 10.93 | 0.847 |
| Act PTT | M | 1483 | 23.1 | 24.4 | 29.1 | 37.9 | 50.1 | 30.06 | 5.267 |
| | F | 1408 | 22.8 | 24.4 | 29.4 | 37.4 | 47.2 | 30.19 | 5.185 |
| Fibrinogen | M | 265 | 1.61 | 1.86 | 2.61 | 3.51 | 4.88 | 2.664 | 0.6178 |
| | F | 252 | 1.58 | 1.84 | 2.43 | 3.27 | 3.89 | 2.487 | 0.4545 |

The Biochemistry Cumulative Individual Values for the monkeys are presented in Tables 33a-h, below:

TABLE 33a

| Animal Number | Group/ Sex | Occn. Code | ALP U/L | ALT U/L | AST U/L | Bili μmol/L | Urea mmol/L | Creat μmol/L | Gluc mmol/L | Chol mmol/L |
|---|---|---|---|---|---|---|---|---|---|---|
| 615 | 1M | PT | 740 | 36 | 39 | 3 | 5.35 | 69 | 3.65 | 2.34 |
| | | D11 | 743 | 35 | 33 | 3 | 5.43 | 73 | 3.66 | 2.00 |
| | | TERM | 597 | 29 | 31 | 2 | 5.16 | 76 | 3.74 | 2.30 |
| 465 | 2M | PT | 647 | 44 | 33 | 3 | 5.73 | 70 | 4.69 | 2.50 |
| | | PD | 775 | 47 | 36 | 2 | 3.60 | 73 | 4.50 | 2.72 |
| | | D11 | 655 | 74 | 46 | 5 | 4.34 | 74 | 3.35 | 2.64 |
| | | TERM | 768 | 48 | 38 | 3 | 4.42 | 73 | 3.67 | 2.54 |
| 639 | 2M | PD | 741 | 29 | 26 | 2 | 4.41 | 87 | 3.31 | 3.22 |
| | | D11 | 629 | 29 | 28 | 3 | 3.87 | 99 | 2.64 | 2.99 |
| | | TERM | 599 | 34 | 22 | 2 | 3.62 | 83 | 3.46 | 2.45 |
| 613 | 3M | PT | 1003 | 37 | 31 | 5 | 3.80 | 90 | 5.72 | 2.61 |
| | | D11 | 793 | 36 | 29 | 4 | 4.45 | 80 | 3.28 | 2.70 |
| | | TERM | 931 | 34 | 32 | 5 | 5.16 | 83 | 2.78 | 2.46 |
| 631 | 4M | PD | 590 | 34 | 37 | 2 | 3.43 | 83 | 3.92 | 2.49 |
| | | D11 | 508 | 38 | 36 | 3 | 3.33 | 82 | 3.38 | 2.30 |
| | | TERM | 578 | 25 | 25 | 2 | 4.00 | 89 | 3.70 | 2.26 |

TABLE 33b

| Animal Number | Group/Sex | Occn. Code | Trig mmol/L | Na mmol/L | K mmol/L | Cl mmol/L | Ca mmol/L | Phos mmol/L | Total Prot g/L | Alb g/L |
|---|---|---|---|---|---|---|---|---|---|---|
| 615 | 1M | PT | 0.24 | 146 | 4.7 | 108 | 2.54 | 1.77 | 91 | 35 |
|  |  | D11 | 0.39 | 145 | 3.9 | 106 | 2.55 | 1.85 | 94 | 41 |
|  |  | TERM | 0.34 | 147 | 4.2 | 107 | 2.47 | 1.63 | 87 | 38 |
| 465 | 2M | PT | 0.74 | 147 | 3.7 | 108 | 2.71 | 1.32 | 81 | 37 |
|  |  | PD | 0.93 | 147 | 4.1 | 109 | 2.70 | 1.54 | 84 | 46 |
|  |  | D11 | 0.66 | 151 | 3.9 | 111 | 2.70 | 1.98 | 83 | 39 |
|  |  | TERM | 0.51 | 146 | 3.6 | 105 | 2.67 | 1.85 | 80 | 40 |
| 639 | 2M | PD | 0.27 | 146 | 4.2 | 107 | 2.68 | 1.85 | 84 | 44 |
|  |  | D11 | 0.32 | 150 | 4.8 | 108 | 2.81 | 2.07 | 85 | 42 |
|  |  | TERM | 0.38 | 146 | 4.5 | 107 | 2.70 | 2.03 | 74 | 39 |
| 613 | 3M | PT | 0.47 | 151 | 4.5 | 106 | 2.75 | 1.85 | 83 | 41 |
|  |  | D11 | 0.44 | 147 | 4.2 | 106 | 2.69 | 1.76 | 80 | 45 |
|  |  | TERM | 0.69 | 147 | 4.3 | 106 | 2.63 | 1.62 | 76 | 40 |
| 631 | 4M | PD | 0.45 | 149 | 4.2 | 107 | 2.67 | 2.00 | 87 | 46 |
|  |  | D11 | 0.77 | 151 | 5.0 | 112 | 2.68 | 2.00 | 84 | 39 |
|  |  | TERM | 0.64 | 150 | 4.7 | 107 | 2.77 | 1.89 | 86 | 46 |

TABLE 33c

| Animal Number | Group/Sex | Occn. Code | a1 g/L | a2 g/L | Beta g/L | Gamma g/L | A/G Ratio | Alb % | a1 % | a2 % |
|---|---|---|---|---|---|---|---|---|---|---|
| 615 | 1M | PT | 3 | 5 | 25 | 23 | 0.63 | 39.0 | 3.4 | 5.1 |
|  |  | D11 | 3 | 4 | 22 | 25 | 0.77 | 43.1 | 3.0 | 4.5 |
|  |  | TERM | 3 | 4 | 21 | 21 | 0.78 | 43.5 | 3.3 | 4.9 |
| 465 | 2M | PT | 4 | 5 | 22 | 13 | 0.84 | 45.7 | 4.5 | 5.9 |
|  |  | PD | 3 | 4 | 18 | 12 | 1.21 | 54.9 | 3.6 | 5.0 |
|  |  | D11 | 4 | 5 | 20 | 15 | 0.89 | 46.7 | 4.9 | 6.4 |
|  |  | TERM | 3 | 5 | 20 | 11 | 1.00 | 50.5 | 4.0 | 5.8 |
| 639 | 2M | PD | 3 | 5 | 17 | 14 | 1.10 | 52.9 | 3.5 | 5.8 |
|  |  | D11 | 3 | 6 | 18 | 16 | 0.98 | 49.1 | 4.1 | 6.6 |
|  |  | TERM | 3 | 4 | 17 | 11 | 1.11 | 52.2 | 3.7 | 6.0 |
| 613 | 3M | PT | 4 | 4 | 20 | 14 | 0.98 | 49.5 | 5.0 | 4.7 |
|  |  | D11 | 3 | 3 | 17 | 13 | 1.29 | 55.8 | 3.7 | 3.7 |
|  |  | TERM | 3 | 3 | 15 | 14 | 1.11 | 53.0 | 4.6 | 3.9 |
| 631 | 4M | PD | 3 | 4 | 18 | 16 | 1.12 | 53.3 | 3.6 | 4.3 |
|  |  | D11 | 4 | 4 | 19 | 18 | 0.87 | 46.4 | 4.4 | 4.4 |
|  |  | TERM | 3 | 4 | 19 | 15 | 1.15 | 53.1 | 3.4 | 4.3 |

TABLE 33d

| Animal Number | Group/Sex | Occn. Code | Beta % | Gamma % |
|---|---|---|---|---|
| 615 | 1M | PT | 27.3 | 25.3 |
|  |  | D11 | 23.2 | 26.2 |
|  |  | TERM | 24.4 | 23.9 |
| 465 | 2M | PT | 27.4 | 16.6 |
|  |  | PD | 21.8 | 14.7 |
|  |  | D11 | 24.0 | 17.9 |
|  |  | TERM | 25.5 | 14.2 |
| 639 | 2M | PD | 20.7 | 17.0 |
|  |  | D11 | 21.5 | 18.7 |
|  |  | TERM | 23.2 | 14.9 |
| 613 | 3M | PT | 24.5 | 16.3 |
|  |  | D11 | 21.0 | 15.8 |
|  |  | TERM | 20.0 | 18.5 |
| 631 | 4M | PD | 20.7 | 18.0 |
|  |  | D11 | 22.8 | 22.0 |
|  |  | TERM | 22.1 | 17.1 |

TABLE 33e

| Animal Number | Group/Sex | Occn. Code | ALP U/L | ALT U/L | AST U/L | Bili μmol/L | Urea mmol/L | Creat μmol/L | Gluc mmol/L | Chol mmol/L |
|---|---|---|---|---|---|---|---|---|---|---|
| 614 | 1F | PT | 687 | 71 | 50 | 3 | 4.92 | 60 | 4.45 | 2.77 |
|  |  | D11 | 576 | 63 | 44 | 2 | 5.22 | 63 | 4.32 | 2.73 |
|  |  | TERM | 517 | 59 | 41 | 3 | 4.78 | 70 | 3.98 | 2.83 |
| 652 | 1F | PT | 598 | 43 | 25 | 3 | 7.26 | 69 | 3.26 | 2.42 |
|  |  | D11 | 540 | 40 | 28 | 3 | 6.94 | 78 | 3.28 | 2.46 |
|  |  | TERM | 511 | 40 | 27 | 4 | 6.78 | 80 | 3.46 | 2.38 |
| 624 | 2F | PD | 533 | 56 | 35 | 3 | 3.85 | 73 | 3.91 | 2.31 |
|  |  | D11 | 410 | 40 | 34 | 13 | 4.18 | 78 | 2.72 | 2.56 |
|  |  | TERM | 432 | 41 | 25 | 3 | 3.70 | 78 | 3.30 | 2.16 |
| 632 | 3F | PT | 559 | 35 | 34 | 5 | 5.44 | 80 | 3.08 | 2.47 |
|  |  | D11 | 510 | 37 | 31 | 5 | 4.36 | 85 | 3.89 | 2.61 |
|  |  | TERM | 428 | 37 | 34 | 5 | 5.32 | 88 | 3.10 | 2.63 |
| 640 | 4F | PD | 343 | 23 | 32 | 4 | 4.09 | 65 | 3.46 | 1.24 |
|  |  | D11 | 292 | 25 | 28 | 4 | 4.12 | 63 | 2.69 | 1.13 |
|  |  | TERM | 266 | 22 | 27 | 2 | 4.55 | 69 | 3.69 | 1.00 |

TABLE 33f

| Animal Number | Group/Sex | Occn. Code | Trig mmol/L | Na mmol/L | K mmol/L | Cl mmol/L | Ca mmol/L | Phos mmol/L | Total Prot g/L | Alb g/L |
|---|---|---|---|---|---|---|---|---|---|---|
| 614 | 1F | PT | 0.37 | 148 | 4.6 | 109 | 2.69 | 2.03 | 80 | 39 |
|  |  | D11 | 0.33 | 147 | 4.1 | 109 | 2.72 | 2.08 | 82 | 43 |
|  |  | TERM | 0.54 | 148 | 3.6 | 108 | 2.59 | 1.84 | 80 | 41 |
| 652 | 1F | PT | 0.57 | 147 | 4.3 | 105 | 2.58 | 1.52 | 78 | 35 |
|  |  | D11 | 0.43 | 149 | 4.7 | 108 | 2.74 | 1.80 | 88 | 43 |
|  |  | TERM | 0.59 | 149 | 4.4 | 108 | 2.59 | 1.51 | 80 | 40 |
| 624 | 2F | PD | 0.60 | 145 | 4.1 | 108 | 2.54 | 1.50 | 77 | 40 |
|  |  | D11 | 0.51 | 148 | 4.0 | 111 | 2.58 | 1.42 | 77 | 39 |
|  |  | TERM | 0.43 | 146 | 3.9 | 108 | 2.56 | 1.46 | 76 | 44 |
| 632 | 3F | PT | 0.31 | 151 | 4.5 | 109 | 2.48 | 1.72 | 76 | 34 |
|  |  | D11 | 0.34 | 149 | 4.6 | 109 | 2.58 | 1.85 | 80 | 39 |
|  |  | TERM | 0.49 | 150 | 4.5 | 111 | 2.55 | 1.47 | 78 | 38 |
| 640 | 4F | PD | 0.36 | 144 | 4.8 | 111 | 2.31 | 1.45 | 68 | 29 |
|  |  | D11 | 0.31 | 145 | 4.3 | 112 | 2.24 | 1.53 | 63 | 25 |
|  |  | TERM | 0.27 | 144 | 4.7 | 108 | 2.20 | 1.33 | 60 | 25 |

TABLE 33g

| Animal Number | Group/Sex | Occn. Code | a1 g/L | a2 g/L | Beta g/L | Gamma g/L | A/G Ratio | Alb % | a1 % | a2 % |
|---|---|---|---|---|---|---|---|---|---|---|
| 614 | 1F | PT | 4 | 5 | 20 | 13 | 0.95 | 49.2 | 4.4 | 5.9 |
|  |  | D11 | 3 | 4 | 19 | 13 | 1.10 | 52.7 | 3.3 | 4.9 |
|  |  | TERM | 3 | 4 | 18 | 13 | 1.05 | 51.7 | 3.8 | 5.2 |
| 652 | 1F | PT | 4 | 5 | 19 | 15 | 0.81 | 45.1 | 4.6 | 5.9 |
|  |  | D11 | 3 | 5 | 20 | 17 | 0.96 | 49.3 | 3.4 | 5.5 |
|  |  | TERM | 4 | 5 | 18 | 14 | 1.00 | 49.4 | 4.7 | 6.2 |
| 624 | 2F | PD | 3 | 4 | 16 | 14 | 1.08 | 52.2 | 4.1 | 5.4 |
|  |  | D11 | 4 | 4 | 17 | 14 | 1.03 | 50.1 | 4.9 | 5.5 |
|  |  | TERM | 3 | 4 | 15 | 10 | 1.38 | 58.5 | 3.4 | 5.3 |
| 632 | 3F | PT | 4 | 4 | 19 | 15 | 0.81 | 44.7 | 5.1 | 5.0 |
|  |  | D11 | 3 | 4 | 17 | 16 | 0.95 | 49.2 | 4.2 | 4.7 |
|  |  | TERM | 4 | 4 | 17 | 15 | 0.95 | 49.2 | 4.6 | 4.9 |
| 640 | 4F | PD | 4 | 4 | 17 | 15 | 0.74 | 42.2 | 5.7 | 5.6 |
|  |  | D11 | 4 | 3 | 17 | 13 | 0.66 | 40.1 | 6.6 | 5.5 |
|  |  | TERM | 4 | 3 | 16 | 13 | 0.71 | 41.4 | 6.4 | 4.6 |

TABLE 33h

| Animal Number | Group/Sex | Occn. Code | Beta % | Gamma % |
|---|---|---|---|---|
| 614 | 1F | PT | 24.8 | 15.7 |
|  |  | D11 | 23.1 | 16.0 |
|  |  | TERM | 22.8 | 16.5 |
| 652 | 1F | PT | 24.7 | 19.7 |
|  |  | D11 | 22.3 | 19.4 |
|  |  | TERM | 22.1 | 17.6 |
| 624 | 2F | PD | 20.7 | 17.6 |
|  |  | D11 | 21.6 | 18.0 |
|  |  | TERM | 19.9 | 12.9 |
| 632 | 3F | PT | 24.9 | 20.2 |
|  |  | D11 | 21.5 | 20.4 |
|  |  | TERM | 21.8 | 19.5 |
| 640 | 4F | PD | 24.9 | 21.6 |
|  |  | D11 | 26.9 | 20.9 |
|  |  | TERM | 26.5 | 21.1 |

The Haematology Cumulative Individual Values for the monkeys are presented in Table 34a-l, below:

TABLE 34a

| Animal Number | Group/Sex | Occn. Code | Hct L/L | Hb g/dL | RRC ×10$^{12}$/L | Retic % | MCH pg | MCHC g/dL | MCV fL |
|---|---|---|---|---|---|---|---|---|---|
| 615 | 1M | PT | 0.389 | 12.4 | 5.94 | 0.38 | 20.9 | 31.9 | 65.5 |
|  |  | D11 | 0.366 | 11.5 | 5.59 | 0.76 | 20.6 | 31.4 | 65.5 |
|  |  | TERM | 0.381 | 11.8 | 5.91 | 0.25 | 20.0 | 31.0 | 64.5 |
| 465 | 2M | PT | 0.439 | 13.2 | 6.76 | 0.56 | 19.5 | 30.1 | 65.0 |
|  |  | PTR |  |  |  |  |  |  |  |
|  |  | PD | 0.460 | 13.7 | 7.22 | 0.50 | 19.0 | 29.9 | 63.8 |
|  |  | D11 | 0.391 | 11.7 | 6.11 | 1.62 | 19.1 | 29.9 | 64.0 |
|  |  | TERM | 0.441 | 13.6 | 6.93 | 0.65 | 19.7 | 30.9 | 63.7 |
| 639 | 2M | PD | 0.419 | 12.7 | 6.23 | 0.51 | 20.4 | 30.3 | 67.2 |
|  |  | D11 | 0.400 | 11.7 | 5.99 | 0.52 | 19.6 | 29.3 | 66.7 |
|  |  | TERM | 0.388 | 12.2 | 5.70 | 1.14 | 21.4 | 31.4 | 68.1 |
| 613 | 3M | PT | 0.461 | 14.1 | 6.79 | 0.48 | 20.7 | 30.5 | 67.8 |
|  |  | PTR |  |  |  |  |  |  |  |
|  |  | D11 | 0.396 | 12.7 | 6.05 | 0.92 | 21.0 | 32.1 | 65.4 |
|  |  | TERM | 0.410 | 12.9 | 6.23 | 0.49 | 20.8 | 31.5 | 65.9 |

TABLE 34b

| Animal Number | Group/Sex | Occn. Code | WBC ×10⁹/L | N ×10⁹/L | L ×10⁹/L | E ×10⁹/L | Basophil ×10-9/L | Monocyte ×10-9/L | LUC ×10-9/L | Plt ×10⁹/L |
|---|---|---|---|---|---|---|---|---|---|---|
| 615 | 1M | PT | 7.57 | 3.06 | 3.68 | 0.06 | 0.03 | 0.53 | 0.20 | 236 |
|  |  | D11 | 7.56 | 2.78 | 4.35 | 0.06 | 0.02 | 0.21 | 0.13 | 284 |
|  |  | TERM | 7.93 | 3.77 | 3.52 | 0.06 | 0.02 | 0.49 | 0.07 | 254 |
| 465 | 2M | PT | 14.19 | 1.78 | 10.37 | 1.24 | 0.05 | 0.55 | 0.20 | 302 |
|  |  | PTR | 13.69 | 3.69 | 8.25 | 0.93 | 0.04 | 0.47 | 0.29 |  |
|  |  | PD | 13.36 | 1.55 | 9.95 | 1.01 | 0.04 | 0.58 | 0.25 | 325 |
|  |  | D11 | 12.26 | 4.70 | 5.63 | 1.27 | 0.04 | 0.51 | 0.11 | 403 |
|  |  | TERM | 15.45 | 1.54 | 11.57 | 1.65 | 0.07 | 0.42 | 0.20 | 356 |
| 639 | 2M | PD | 10.02 | 5.21 | 3.42 | 0.90 | 0.01 | 0.39 | 0.10 | 306 |
|  |  | D11 | 8.26 | 4.06 | 2.47 | 1.17 | 0.01 | 0.45 | 0.10 | 371 |
|  |  | TERM | 8.70 | 2.55 | 4.20 | 1.04 | 0.02 | 0.80 | 0.09 | 253 |
| 613 | 3M | PT | 20.21 | 12.99 | 6.45 | 0.02 | 0.04 | 0.50 | 0.21 | 438 |
|  |  | PTR | 16.85 | 8.87 | 6.90 | 0.08 | 0.06 | 0.67 | 0.26 |  |
|  |  | D11 | 10.85 | 6.11 | 4.15 | 0.03 | 0.02 | 0.41 | 0.12 | 441 |
|  |  | TERM | 23.26 | 17.70 | 4.27 | 0.05 | 0.04 | 1.11 | 0.08 | 434 |

TABLE 34c

| Animal Number | Group/Sex | Occn. Code | PT sec | APTT sec |
|---|---|---|---|---|
| 615 | 1M | PT | 11.3 | 37.3 |
|  |  | D11 | 10.3 | 32.7 |
|  |  | TERM | 11.3 | 33.3 |
| 465 | 2M | PT | 10.0 | 33.9 |
|  |  | PTR |  |  |
|  |  | PD | 9.9 | 26.1 |
|  |  | D11 | 10.0 | 31.6 |
|  |  | TERM | 10.2 | 29.4 |
| 639 | 2M | PD | 10.6 | 22.6 |
|  |  | D11 | 10.5 | 26.3 |
|  |  | TERM | 10.3 | 28.9 |
| 613 | 3M | PT | 10.3 | 35.5 |
|  |  | PTR |  |  |
|  |  | D11 | 11.4 | 26.7 |
|  |  | TERM | 10.3 | 30.8 |

TABLE 34d

| Animal Number | Group/Sex | Occn. Code | Aniso-cytosis | Micro-cytosis | Macro-cytosis | Hypo-chromasia | Hyper-chromasia |
|---|---|---|---|---|---|---|---|
| 615 | 1M | PT | − | − | − | − | + |
|  |  | D11 | − | − | − | − | − |
|  |  | TERM | − | − | − | − | + |
| 465 | 2M | PT | − | − | − | − | − |
|  |  | PTR |  |  |  |  |  |
|  |  | PD | − | − | − | − | − |
|  |  | D11 | − | − | − | − | − |
|  |  | TERM | − | − | − | − | − |
| 639 | 2M | PD | − | − | − | − | − |
|  |  | D11 | − | − | − | − | − |
|  |  | TERM | − | − | − | − | − |
| 613 | 3M | PT | − | − | − | − | − |
|  |  | PTR |  |  |  |  |  |
|  |  | D11 | − | − | − | − | + |
|  |  | TERM | − | − | − | − | − |

TABLE 34e

| Animal Number | Group/Sex | Occn. Code | Hct L/L | Hb g/dL | RBC ×10¹²/L | Retic % | MCH pg | MCHC g/dL | MCV fL |
|---|---|---|---|---|---|---|---|---|---|
| 631 | 4M | PD | 0.460 | 13.6 | 7.11 | 0.43 | 19.1 | 29.5 | 64.6 |
|  |  | D11 | 0.395 | 11.9 | 6.36 | 0.45 | 18.7 | 30.2 | 62.1 |
|  |  | TERM | 0.449 | 13.7 | 6.97 | 0.30 | 19.6 | 30.5 | 64.4 |
| 614 | 1F | PT | CTD | CTD | CTD | CTD | CTD | CTD | CTD |
|  |  | PTR |  |  |  |  |  |  |  |
|  |  | D11 | 0.404 | 13.1 | 6.33 | 0.57 | 20.6 | 32.3 | 63.8 |
|  |  | TERM | 0.424 | 13.0 | 6.59 | 0.68 | 19.7 | 30.7 | 64.3 |
| 652 | 1F | PT | 0.390 | 11.3 | 5.72 | 1.15 | 19.8 | 29.1 | 68.2 |
|  |  | D11 | 0.374 | 11.9 | 5.55 | 1.06 | 21.4 | 31.7 | 67.4 |
|  |  | TERM | 0.384 | 11.5 | 5.71 | 0.58 | 20.2 | 30.0 | 67.2 |
| 624 | 2F | PD | 0.407 | 11.8 | 7.14 | 0.73 | 16.6 | 29.0 | 57.1 |
|  |  | D11 | 0.377 | 10.8 | 6.69 | 0.48 | 16.1 | 28.6 | 56.3 |
|  |  | TERM | 0.401 | 11.7 | 6.99 | 1.07 | 16.7 | 29.1 | 57.4 |

TABLE 34f

| Animal Number | Group/Sex | Occn. Code | WBC ×10⁹/L | N ×10⁹/L | L ×10⁹/L | E ×10⁹/L | Basophil | Monocyte | LUC ×10⁹/L | Plt ×10⁹/L |
|---|---|---|---|---|---|---|---|---|---|---|
| 631 | 4M | PD | 10.53 | 2.82 | 6.36 | 0.62 | 0.02 | 0.58 | 0.13 | 378 |
|  |  | D11 | 7.97 | 2.86 | 3.81 | 0.61 | 0.01 | 0.53 | 0.16 | 424 |
|  |  | TERM | 8.08 | 1.73 | 5.04 | 0.63 | 0.02 | 0.60 | 0.05 | 384 |
| 614 | 1F | PT | CTD | CTD | CTD | CTD | CTD | CTD | CTD | CTD |
|  |  | PTR | 11.32 | 3.47 | 6.36 | 0.17 | 0.05 | 0.96 | 0.31 |  |
|  |  | D11 | 9.70 | 4.74 | 3.73 | 0.09 | 0.02 | 0.84 | 0.28 | 429 |
|  |  | TERM | 9.64 | 3.65 | 5.09 | 0.13 | 0.01 | 0.62 | 0.13 | 414 |
| 652 | 1F | PT | 10.66 | 3.21 | 6.05 | 0.42 | 0.03 | 0.80 | 0.15 | 373 |
|  |  | D11 | 12.01 | 5.53 | 5.20 | 0.34 | 0.02 | 0.78 | 0.13 | 380 |
|  |  | TERM | 11.88 | 7.59 | 3.24 | 0.35 | 0.02 | 0.61 | 0.08 | 338 |
| 624 | 2F | PD | 9.06 | 3.10 | 5.02 | 0.41 | 0.02 | 0.33 | 0.18 | 362 |
|  |  | D11 | 7.82 | 5.14 | 2.06 | 0.14 | 0.02 | 0.34 | 0.13 | 353 |
|  |  | TERM | 11.69 | 4.33 | 5.46 | 0.96 | 0.02 | 0.76 | 0.16 | 426 |

TABLE 34g

| Animal Number | Group/Sex | Occn. Code | PT sec | APTT sec |
|---|---|---|---|---|
| 631 | 4M | PD | 10.9 | 29.3 |
|  |  | D11 | 11.3 | 27.9 |
|  |  | TERM | 10.8 | 32.1 |
| 614 | 1F | PT | CTD | CTD |
|  |  | PTR |  |  |
|  |  | D11 | 10.2 | 32.1 |
|  |  | TERM | 10.5 | 29.3 |
| 652 | 1F | PT | 10.2 | 33.0 |
|  |  | D11 | 9.6 | 27.9 |
|  |  | TERM | 10.3 | 30.3 |
| 624 | 2F | PD | 10.6 | 27.1 |
|  |  | D11 | 10.6 | 29.7 |
|  |  | TERM | 10.8 | 33.3 |

TABLE 34h

| Animal Number | Group/Sex | Occn. Code | Aniso-cytosis | Micro-cytosis | Macro-cytosis | Hypo-chromasia | Hyper-Chromasia |
|---|---|---|---|---|---|---|---|
| 631 | 4M | PD | − | − | − | − | − |
|  |  | D11 | − | − | − | − | − |
|  |  | TERM | − | − | − | − | − |
| 614 | 1F | PT | CTD | CTD | CTD | CTD | CTD |
|  |  | PTR |  |  |  |  |  |
|  |  | D11 | − | − | − | − | − |
|  |  | TERM | − | − | − | − | − |
| 652 | 1F | PT | − | − | − | − | − |
|  |  | D11 | − | − | − | − | − |
|  |  | TERM | − | − | − | − | − |
| 624 | 2F | PD | − | + | − | − | − |
|  |  | D11 | − | + | − | − | − |
|  |  | TERM | + | + | − | − | − |

TABLE 34i

| Animal Number | Group/Sex | Occn. Code | Hct L/L | Hb g/dL | RBC ×10¹²/L | Retic % | MCH pg | MCHC g/dL | MCV fL |
|---|---|---|---|---|---|---|---|---|---|
| 632 | 3F | PT | 0.416 | 12.4 | 6.36 | 0.83 | 19.6 | 29.9 | 65.4 |
|  |  | PTR | 0.410 | 12.2 | 6.29 | 0.64 | 19.5 | 29.8 | 65.3 |
|  |  | D11 | 0.392 | 12.2 | 6.19 | 0.73 | 19.7 | 31.0 | 63.4 |
|  |  | TERM | 0.412 | 12.3 | 6.46 | 0.55 | 19.1 | 29.9 | 63.8 |
| 640 | 4F | PD | 0.398 | 11.8 | 5.81 | 0.95 | 20.3 | 29.7 | 68.5 |
|  |  | D11 | 0.369 | 11.0 | 5.30 | 1.17 | 20.7 | 29.8 | 69.6 |
|  |  | TERM | 0.401 | 11.9 | 5.58 | 0.83 | 21.3 | 29.6 | 71.9 |

TABLE 34j

| Animal Number | Group/Sex | Occn. Code | WBC ×10⁹/L | N ×10⁹/L | L ×10⁹/L | E ×10⁹/L | Basophil | Monocyte | LUC ×10⁹/L | Plt ×10⁹/L |
|---|---|---|---|---|---|---|---|---|---|---|
| 632 | 3F | PT | 18.12 | 10.58 | 5.61 | 1.07 | 0.04 | 0.61 | 0.21 | 335 |
|  |  | PTR | 15.16 | 5.99 | 7.24 | 0.95 | 0.03 | 0.63 | 0.31 | 308 |
|  |  | D11 | 10.23 | 4.69 | 4.15 | 0.66 | 0.01 | 0.48 | 0.23 | 348 |
|  |  | TERM | 13.04 | 6.89 | 4.62 | 0.44 | 0.03 | 0.93 | 0.13 | 321 |
| 640 | 4F | PD | 12.49 | 8.29 | 2.91 | 0.46 | 0.02 | 0.64 | 0.17 | 567 |
|  |  | D11 | 13.71 | 10.31 | 2.18 | 0.34 | 0.01 | 0.74 | 0.12 | 578 |
|  |  | TERM | 11.49 | 5.41 | 4.18 | 0.63 | 0.03 | 1.12 | 0.12 | 555 |

TABLE 34k

| Animal Number | Group/Sex | Occn. Code | PT sec | APTT sec |
|---|---|---|---|---|
| 632 | 3F | PT | 10.6 | 47.8 |
|  |  | PTR | 10.6 | 44.7 |
|  |  | D11 | 10.2 | 33.1 |
|  |  | TERM | 10.6 | 37.2 |
| 640 | 4F | PD | 12.0 | 25.8 |
|  |  | D11 | 12.4 | 28.0 |
|  |  | TERM | 12.8 | 30.1 |

TABLE 34l

| Animal Number | Group/Sex | Occn. Code | Aniso-cytosis | Micro-cytosis | Macro-cytosis | Hypo-chromasia | Hyper-chromasia |
|---|---|---|---|---|---|---|---|
| 632 | 3F | PT | – | – | – | – | – |
|  |  | PTR | – | – | – | – | – |
|  |  | D11 | – | – | – | – | – |
|  |  | TERM | – | – | – | – | – |
| 640 | 4F | PD | – | – | – | – | – |
|  |  | D11 | – | – | – | – | – |
|  |  | TERM | – | – | – | – | – |

Microscopic Pathology—Treatment-Related Findings

Pericholangitis (inflammation of connective tissue around the bile duct) was reported in the female monkey dosed at 12 mg/kg/day, but not in any other female or male monkeys. This finding may be related to treatment with Glyco-mAb (Anti-EGFR), but with such small numbers of animals the significance is uncertain. All other findings were considered to be incidental and of no toxicological significance.

Macropathology and Histopathology

The summary of histopathological for all animals tested is set forth in Table 35, below:

TABLE 35

Histopathology - group distribution and severity of findings for all animals

| Group | 1 | 2 | 3 |
|---|---|---|---|
| Compound | -GLYCO-MAB (ANTI-EGFR)- | | |
| Dosage | 1.5 | 4.5 | 12 |

| | | Number of Animals Affected | | | | | |
|---|---|---|---|---|---|---|---|
| | Sex | Male | | | Female | | |
| Organ/Tissue Examined | Group Number | 1 | 2 | 3 | 1 | 2 | 3 |
| | | 1 | 1 | 1 | 1 | 1 | 1 |
| Colon | No. Examined | 1 | 1 | 1 | 1 | 1 | 1 |
| Heart | No. Examined | 1 | 1 | 1 | 1 | 1 | 1 |
| Kidneys | No. Examined | 1 | 1 | 1 | 1 | 1 | 1 |
| Cortical Lymphocytic Infiltration | Minimal | 1 | 1 | 0 | 0 | 1 | 1 |
|  | Slight | 0 | 0 | 0 | 1 | 0 | [?] |
|  | Total | 1 | 1 | 0 | 1 | 1 | 1 |
| Left Cephalic | No. Examined | 0 | 0 | 0 | 0 | 0 | 0 |
| Left Saphenous | No. Examined | 1 | 1 | 1 | 1 | 1 | 1 |
| Epidermal Hyperplasia | Minimal | 0 | 0 | 0 | 1 | 0 | 0 |
|  | Total | 0 | 0 | 0 | 1 | 0 | 0 |
| Liver | No. Examined | 1 | 1 | 1 | 1 | 1 | 1 |
| Inflammatory Cell Foci | Minimal | 1 | 1 | 1 | 1 | 1 | 1 |
|  | Total | 1 | 1 | 1 | 1 | 1 | 1 |
| Bile Duct Proliferation | Minimal | 0 | 0 | 0 | 0 | 0 | 1 |
|  | Total | 0 | 0 | 0 | 0 | 0 | 1 |
| Hepatocyte Vacuolation - Median Cleft | Minimal | 0 | 1 | 0 | 0 | 0 | 0 |
|  | Total | 0 | 1 | 0 | 0 | 0 | 0 |
| Pericholangitis | Minimal | 0 | 0 | 0 | 0 | 0 | 1 |
|  | Total | 0 | 0 | 0 | 0 | 0 | 1 |
| Lungs & Bronchi | No. Examined | 1 | 1 | 1 | 1 | 1 | 1 |
| Bronchi/Bronchioles - Mucosal/Submucosal Inflammatory Cells | Slight | 1 | 0 | 0 | 0 | 0 | 0 |
|  | Total | 1 | 0 | 0 | 0 | 0 | 0 |
| Alveolar Macrophages | Minimal | 0 | 1 | 0 | 0 | 0 | 1 |
|  | Total | 0 | 1 | 0 | 0 | 0 | 1 |
| Perivascular Inflammatory/Lymphoid Cells | Minimal | 0 | 0 | 1 | 0 | 0 | 1 |
|  | Total | 0 | 0 | 1 | 0 | 0 | 1 |
| Lymphoid Aggregates | Minimal | 0 | 0 | 1 | 0 | 0 | 0 |
|  | Total | 0 | 0 | 1 | 0 | 0 | 0 |
| Oesophagus | No. Examined | 1 | 1 | 1 | 1 | 1 | 1 |
| Lymphoid Aggregates | Minimal | 0 | 0 | 0 | 0 | 0 | 1 |
|  | Total | 0 | 0 | 0 | 0 | 0 | 1 |
| Ovaries | No. Examined | 0 | 0 | 0 | 1 | 1 | 1 |
| Follicular Cyst(S) | Present | 0 | 0 | 0 | 1 | 0 | 0 |
|  | Total | 0 | 0 | 0 | 1 | 0 | 0 |
| Prominent Corpora Lutea | Present | 0 | 0 | 0 | 0 | 1 | 0 |
|  | Total | 0 | 0 | 0 | 0 | 1 | 0 |
| Pancreas | No. Examined | 1 | 1 | 1 | 1 | 1 | 1 |
| Acinar Atrophy | Minimal | 0 | 0 | 1 | 0 | 0 | 1 |
|  | Total | 0 | 0 | 1 | 0 | 0 | 1 |
| Lymphoid Aggregates | Minimal | 0 | 0 | 0 | 1 | 0 | 0 |
|  | Total | 0 | 0 | 0 | 1 | 0 | 0 |
| Right Cephalic | No. Examined | 0 | 0 | 0 | 0 | 0 | 0 |
| Right Saphenous | No. Examined | 0 | 0 | 0 | 0 | 0 | 0 |
| Skin (Protocol) | No. Examined | 1 | 1 | 1 | 1 | 1 | 1 |
| Epidermal Hyperplasia | Minimal | 0 | 0 | 0 | 0 | 0 | 1 |
|  | Moderate | 0 | 0 | 0 | 1 | 0 | 0 |
|  | Total | 0 | 0 | 0 | 1 | 0 | 1 |
| Spinal Cord | No. Examined | 1 | 1 | 1 | 1 | 1 | 1 |
| Haemorrhage | Minimal | 0 | 0 | 1 | 1 | 1 | 1 |
|  | Slight | 0 | 1 | 0 | 0 | 0 | 0 |
|  | Total | 0 | 1 | 1 | 1 | 1 | 1 |
| Spleen | No. Examined | 1 | 1 | 1 | 1 | 1 | 1 |
| Sternum & Marrow | No. Examined | 0 | 0 | 0 | 0 | 0 | 0 |
| Stomach | No. Examined | 1 | 1 | 1 | 1 | 1 | 1 |
| Testes | No. Examined | 1 | 1 | 1 | 0 | 0 | 0 |
| Immaturity | Present | 1 | 1 | 1 | 0 | 0 | 0 |
|  | Total | 1 | 1 | 1 | 0 | 0 | 0 |
| Thymus | No. Examined | 1 | 1 | 1 | 1 | 1 | 1 |
| Cyst(S) | Present | 0 | 0 | 0 | 0 | 1 | 0 |
|  | Total | 0 | 0 | 0 | 0 | 1 | 0 |
| Involution/Atrophy | Minimal | 0 | 0 | 0 | 0 | 1 | 0 |
|  | Total | 0 | 0 | 0 | 0 | 1 | 0 |
| Urinary Bladder | No. Examined | 1 | 1 | 1 | 1 | 1 | 1 |
| Uterine Cervix | No. Examined | 0 | 0 | 0 | 1 | 1 | 1 |
| Epithelial Mucification | Present | 0 | 0 | 0 | 1 | 1 | 1 |
|  | Total | 0 | 0 | 0 | 1 | 1 | 1 |

TABLE 35-continued

Histopathology - group distribution and severity of findings for all animals

| | | | | | | | |
|---|---|---|---|---|---|---|---|
| Uterus | No. Examined | 0 | 0 | 0 | 1 | 1 | 1 |
| Congestion | Minimal | 0 | 0 | 0 | 0 | 1 | 0 |
| | Total | 0 | 0 | 0 | 0 | 1 | 0 |
| Caecum | No. Examined | 1 | 0 | 0 | 1 | 0 | 0 |
| Prominent Submucosal Adipose Tissue | Minimal | 1 | 0 | 0 | 1 | 0 | 0 |
| | Total | 1 | 0 | 0 | 1 | 0 | 0 |
| Fallopian Tube | No. Examined | 0 | 0 | 0 | 1 | 1 | 1 |
| Ln Mesenteric | No. Examined | 0 | 0 | 0 | 1 | 0 | 0 |
| Increased Pigmented Macrophages | Slight | 0 | 0 | 0 | 1 | 0 | 0 |
| | Total | 0 | 0 | 0 | 1 | 0 | 0 |

Individual Findings for All Animals

The pathology observations for individual animals are set forth in Table 36, below:

TABLE 36

Macropathology and histopathology - individual findings for all animals

| Group | 1 | 2 | 3 |
|---|---|---|---|
| Compound | -GLYCO-MAB (ANTI-EGFR)- | | |
| Dosage | 1.5 | 4.5 | 12 |

Pathology Observations

| Sex | Male | Dose Group | 1 |
|---|---|---|---|
| Animal No. | 0623 | Study week of Sacrifice | 11 |
| Terminal body weight | 2715.0 grams | Study day of sacrifice | 77 |

| NECROPSY | HISTOPATHOLOGY |
|---|---|
| Caecum: | Caecum: |
| -Raised Area(S); Mucosal Aspect, Multiple, Up To 3 mm. | -Prominent Submucosal Adipose Tissue,-Minimal, Focal |
| Colon: | Colon: |
| -Raised Area(S); Mucosal Aspect, Multiple, Up To 2 mm. | No Significant Lesion |
| | Kidneys: |
| | -Cortical Lymphocytic Infiltration, Minimal |
| Liver: | Liver: |
| -Median Cleft Pale Area(S); One, Subcapsular, 3 mm. | -Inflammatory Cell Foci,-Minimal |
| | Lungs & Bronchi: |
| | -Bronchi/Bronchioles Mucosal/Submucosal Inflammatory Cells,-Slight |
| Stomach: | Stomach: |
| -Corpus Raised Area(S); Mucosa, One, Near To Antrum, 3 mm. | >No Significant Lesion |
| | Testes: |
| | -Immaturity,-Present |

| Sex | Male | Dose Group | 2 |
|---|---|---|---|
| Animal No. | 0461 | Study week of Sacrifice | 18 |
| Terminal body weight | 2573.0 grams | Study day of sacrifice | 125 |

| NECROPSY | HISTOPATHOLOGY |
|---|---|
| | Kidneys |
| | -Cortical Lymphocytic Infiltration, Minimal |
| Liver: | Liver |
| Median Cleft Pale Area(S); One, Subcapsular, 4 mm. | -Inflammatory Cell Foci, Minimal |
| | -Hepatocyte Vacuolation - Median Cleft,-Minimal |
| Lungs & Bronchi: | Lungs & Bronchi: |
| -Incomplete Collapse; Right Lobes. | -Alveolar Macrophages, Minimal |
| | Spinal Cord: |
| | -Haemorrhage,-Slight, Multi-Focal |
| | Testes: |
| | -Immaturity, Present |

| Sex | Male | Dose Group | 3 |
|---|---|---|---|
| Animal No. | 0463 | Study week of Sacrifice | 18 |
| Terminal body weight | 2919.0 grams | Study day of sacrifice | 125 |

| NECROPSY | HISTOPATHOLOGY |
|---|---|
| | Liver: |
| | -Inflammatory Cell Foci,-Minimal |
| | Lungs & Bronchi: |
| | -Perivascular Inflammatory/Lymphoid Cells, Minimal |
| | -Lymphoid Aggregates,Minimal, Focal |
| | Pancreas: |
| | -Acinar Atrophy, Minimal, Focal |
| | Spinal Cord: |
| | -Haemorrhage,-Minimal |
| | Testes: |
| | -Immaturity,-Present |

*Ammal has no gross observations recorded*

| Sex | Female | Dose Group | 1 |
|---|---|---|---|
| Animal No. | 0590 | Study week of Sacrifice | 11 |
| Terminal body weight | 3176.0 grams | Study day of sacrifice | 77 |

| NECROPSY | HISTOPATHOLOGY |
|---|---|
| Caecum: | Caecum: |
| -Raised Area(S); Mucosal Aspect, Multiple, Up To 2 mm. | -Prominent Submucosal Adipose Tissue, Minimal, Multi-Focal |
| Colon: | Colon: |
| -Raised Area(S); Mucosal Aspect, Multiple, Up To 2 mm. | >No Significant Lesion |
| | Kidneys: |
| | -Cortical Lymphocytic Infiltration, |
| | -Slight, Focal |
| | Left Saphenous: |
| | Epidermal Hyperplasia,-Minimal |
| Liver: | Liver: |
| -Median Cleft Pale Area(S); One, Subcapsular, 3 mm. | -Inflammatory Cell Foci,-Minimal |
| Ln Mesenteric: | Ln Mesenteric: |
| -Congested, Minimal | Increased Pigmented Macrophages, Slight |
| Ovaries: | Ovaries: |
| -Cyst(S); Left, One, Clear Fluid-Filled, 4 mm. | Follicular Cyst(S),-Present |
| | Pancreas: |
| | -Acinar Atrophy,-Minimal |
| | -Lymphoid Aggregates,-Minimal |
| | Skin (Protocol): |
| | Epidermal Hyperplasia,-Moderate |
| | Spinal Cord: |
| | Haemorrhage,-Minimal |
| Spleen: | Spleen: |
| -Capsule Thickened; Area, Diffuse. | >No Significant Lesion |
| | Uterine Cervix: |
| | -Epithelial Mucification,-Present |

| Sex | Female | Dose Group | 2 |
|---|---|---|---|
| Animal No. | 0462 | Study week of Sacrifice | 18 |
| Terminal body weight | 2910.0 grams | Study day of sacrifice | 125 |

| NECROPSY | HISTOPATHOLOGY |
|---|---|
| | Kidneys: |
| | -Cortical Lymphocytic Infiltration, |
| | -Minimal, Focal |
| | Liver: |
| | -Inflammatory Cell Foci, Minimal |
| Lungs & Bronchi: | Lungs & Bronchi: |
| -Incomplete Collapse; Left Lobes. | No Significant Lesion |
| Ovaries: | Ovaries: |
| -Raised Area(S); One On Each, Left, 3 mm; Right, 2 mm. | -Prominent Corpora Lutea,-Present |

TABLE 36-continued

| (Follicles) | Spinal Cord:<br>-Haemorrhage,-Minimal |
|---|---|
| Thymus:<br>-Small; 1.066 g. | Thymus:<br>-Cyst(S),-Present<br>-Involution/Atrophy,-Minimal<br>Uterine Cervix:<br>-Epithelial Mucification,-Present |
| Uterus:<br>-Congested, Minimal | Uterus:<br>-Congestion,-Minimal |

| Sex | Female | Dose Group | 3 |
|---|---|---|---|
| Animal No. | 0612 | Study week of Sacrifice | 18 |
| Terminal body weight | 2934.0 grams | Study day of sacrifice | 125 |

| NECROPSY | HISTOPATHOLOGY |
|---|---|
| | Kidneys:<br>-Cortical Lymphocytic Infiltration, Minimal, Focal |

TABLE 36-continued

| Liver:<br>-Median Cleft Pale Area(S); One, Subcapsular, 3 mm.<br>-Cyst(S); Within Cleft, One, Dark Fluid-Filled, Green, 2 mm.<br>Lungs & Bronchi:<br>-Incomplete Collapse; Left Lobes. | Liver:<br>-Inflammatory Cell Foci,-Minimal<br>-Bile Duct Proliferation,-Minimal<br>-Pericholangitis,-Minimal |
|---|---|
| | Lungs & Bronchi:<br>-Alveolar Macrophages,-Minimal<br>-Perivascular Inflammatory/ Lymphoid Cells,-Minimal<br>Oesophagus:<br>-Lymphoid Aggregates,-Minimal<br>Pancreas:<br>-Acinar Atrophy,-Minimal, Focal<br>Skin (Protocol):<br>-Epidermal Hyperplasia,-Minimal<br>Spinal Cord:<br>-Haemorrhage,-Minimal<br>Uterine Cervix:<br>-Epithelial Mucification,-Present |

Individual body weights of the cynomolgus monkeys are presented in Table 37, below:

TABLE 37

Bodyweights: Individual Values

| Animal No. | Bodyweight (kg) on Day | | | | | | | |
|---|---|---|---|---|---|---|---|---|
| | −17 | −9 | 1* | 8* | 15* | 22* | 29 | 36 |
| Group 1: GA201-ge, 1.5 mg/kg/occasion | | | | | | | | |
| 623m | 2.67 | 2.65<br>(−0.02) | 2.69<br>(+0.04) | 2.72<br>(+0.03) | 2.76<br>(+0.04) | 2.62<br>(−0.14) | 2.72<br>(+0.10) | 2.65<br>(−0.07) | 2.71<br>(+0.06) |
| 590f | 2.98 | 2.92<br>(−0.06) | 2.97<br>(+0.05) | 3.14<br>(+0.17) | 3.13<br>(−0.01) | 3.01<br>(−0.12) | 3.06<br>(+0.05) | 3.00<br>(−0.06) | 3.19<br>(+0.19) |
| Group 2: GA201-ge, 4.5 mg/kg/occasion | | | | | | | | |
| 461m | 2.50 | 2.56<br>(+0.06) | 2.53<br>(−0.03) | 2.47<br>(−0.06) | 2.53<br>(+0.06) | 2.53<br>NC | 2.53<br>NC | 2.61<br>(+0.08) | 2.53<br>(−0.08) |
| 426f | 2.87 | 2.96<br>(+0.09) | 2.91<br>(−0.05) | 2.82<br>(−0.09) | 2.95<br>(+0.13) | 2.89<br>(−0.06) | 2.88<br>(−0.01) | 2.79<br>(−0.09) | 2.91<br>(+0.12) |
| Group 3: GA201-ge, 12 mg/kg/occasion | | | | | | | | |
| 463m | 2.69 | 2.81<br>(+0.12) | 2.86<br>(+0.05) | 2.74<br>(−0.12) | 2.81<br>(+0.07) | 2.81<br>NC | 2.81<br>NC | 2.81<br>NC | 2.75<br>(−0.06) |
| 612f | 2.84 | 2.96<br>(+0.12) | 2.92<br>(−0.04) | 2.98<br>(+0.06) | 3.06<br>(+0.08) | 3.01<br>(−0.05) | 3.01<br>NC | 2.94<br>(−0.07) | 2.91<br>(−0.03) |

| Animal No. | Bodyweight (kg) on Day | | | | | Weight change (kg) | |
|---|---|---|---|---|---|---|---|
| | 50 | 57 | 64 | 71 | 77 | D 1 to 71 | D 29 to 71 |
| Group 1: GA201-ge, 1.5 mg/kg/occasion | | | | | | | |
| 623m | 2.73<br>(+0.02) | 2.61<br>(−0.12) | 2.74<br>(+0.13) | 2.71<br>(−0.03) | 2.75<br>(+0.04) | +0.06 | +0.03 |
| 590f | 3.16<br>(−0.03) | 3.11<br>(−0.05) | 3.18<br>(+0.07) | 3.27<br>(+0.09) | 3.23<br>(−0.04) | +0.27 | +0.17 |
| Group 2: GA201-ge, 4.5 mg/kg/occasion | | | | | | | |
| 461m | 2.45<br>(−0.08) | 2.54<br>(+0.09) | 2.60<br>(+0.06) | 2.59<br>(−0.01) | | +0.03 | +0.06 |
| 462f | 2.95<br>(+0.04) | 3.05<br>(+0.10) | 3.02<br>(−0.03) | 2.96<br>(−0.06) | | +0.05 | +0.08 |
| Group 3: GA201-ge, 12 mg/kg/occasion | | | | | | | |
| 463m | 2.71<br>(−0.04) | 2.92<br>(+0.21) | 2.98<br>(+0.06) | 3.09<br>(+0.11) | | +0.23 | +0.28 |
| 612f | 2.81<br>(−0.10) | 3.04<br>(+0.23) | 3.05<br>(+0.01) | 3.10<br>(0.05) | | +0.18 | +0.09 |

Conclusions

There was no effect of treatment at the injection sites and no clinical findings considered to be related to treatment with Glyco-mAb (anti-EGFR). Bodyweight changes were within normal expected ranges. There were no findings considered to be related to treatment at macroscopic examination and organ weights of animals were within normal expected ranges. In conclusion, treatment at 1.5, 4.5 or 12 mg/kg/occasion was well tolerated with no clear findings of systemic toxicity.

EGFR is not a tumor specific target, since it is present on the surface of various normal tissues including liver, kidney and skin. Anti-EGFR antibodies with human IgG1 Fc region have previously been administered to humans and have shown a tolerable side-effect profile (Vanhoefer, U. et al., *Clin. Oncol.* 2004 Jan. 1; 22(1):175-84; Needle M N, *Semin Oncol.* 2002 October; 29 (5 Suppl 14):55-60). Clearly, there would be significant concerns for administering to a human or other mammal an anti-EGFR antibody with significantly increased ADCC, due to enhanced killing activity that could be displayed against critical normal tissues such as liver, kidney and skin. Surprisingly, the present inventors have found that administering such an anti-EGFR antibody, Fc engineered as described above and with up to 1000-fold increased ADCC activity, in vivo to mammals did not lead to significant toxicities. The concentrations of antibody were kept above 1 microgram per milliliter for at least 4 weeks (and above 100 micrograms per milliliter for some animals). Such exposure levels are typical for antibody therapy. Maximal ADCC for the antibody of this study is already achieved at concentrations of 1 microgram per milliliter. Single dose administrations of doses of 40 and 100 mg of anti-EGFR antibody (the parental rat ICR62 antibody) to human cancer patients have shown specific targeting of tumors in vivo (Modjtahedi, H. et al., *Br J Cancer.* 1996 January; 73(2):228-35.).

Cynomolgus monkey effector cells have highly-homologous FcgammaRIII receptor and have been shown to mediate enhanced ADCC with Fc engineered antibodies (and with antibodies glycoengineered for increased levels of non-fucosylated oligosaccharides in the Fc region). The level of ADCC increase is very similar to that observed with human effector cells (PBMCs).

In summary, we have found that anti-EGFR antibodies Fc engineered for increased Fc-FcgammaRIII binding affinity and for increased ADCC can be administered to mammals to give concentrations above 1 microgram of antibody per milliliter of serum for a period of at least 4 weeks in order to give drug exposures nornally associated with significant accumulation of antibody on target cells in vivo, without leading to significant toxicity.

Toxicity of an antigen binding molecule of the present invention can be measured and/or determined using any of the methods and/or parameters (e.g. blood chemistry values, histopathological indicators, etc.) described herein above, or by any means known to those of skill in the art. A clinically significant level of toxicity is understood by one of skill in the art to be a level that exceeds levels generally accepted by the U.S. Food and Drug Administration for antibodies administered clinically.

Example 5

Modifications to the Light Chain CDRs

Using methods described above, anti-EGFR light chain variable region variants were generated from the I-KC light chain variable region construct (SEQ ID NO:43 and SEQ ID NO:45), wherein the sequence encoding the amino acid residue at varous positions in the rat ICR62 CDRs were replaced with the corresponding amino acid residue from a human germline variable gene sequence. Table 38 shows the substitutions that were made within the CDRs of the I-KC light chain variable region construct (SEQ ID NO:45):

TABLE 38

Minimized Light Chain CDRs

| NAME OF CONSTRUCT | AMINO ACID SUBSTITUTION MADE IN SEQ ID NO:45 | LIGHT CHAIN CDR IN WHICH SUBSTITUTION WAS MADE |
|---|---|---|
| I-KC1 | N30R* | CDR1 |
| I-KC2 | Y32W | CDR1 |
| I-KC3 | N34G | CDR1 |
| I-KC4 | N50T | CDR2 |
| I-KC5 | T51A | CDR2 |
| I-KC6 | N52S | CDR2 |
| I-KC7 | N53S | CDR2 |
| I-KC8 | T56S | CDR2 |
| I-KC9 | F94Y | CDR3 |

*Identified according to standard nomenclature (e.g., "N30R" means the Asparagine (N) residue at position 30 of SEQ ID NO:45 is replaced with an argininen (R) residue).

All substitution residues identified above were derived from the human VK1_6 acceptor sequence except for the Y32W exchange, wherein the W of a related human germline sequence was substituted for the Y at position 32 in SEQ ID NO:45.

Each of the I-KC variant constructs (I-KC1 to I-KC9) was paired with a heavy chain variable region comprising construct I-HHD (SEQ ID NO:16 and SEQ ID NO:15) and a binding assay performed according to the methods described in the previous examples. Constructs I-KC1 to I-KC9 were compared to the I-KC construct (SEQ ID NO:46 and SEQ ID NO:45) for binding affinity to EGFR in A431 target cells (FIG. 29).

Figure 29:
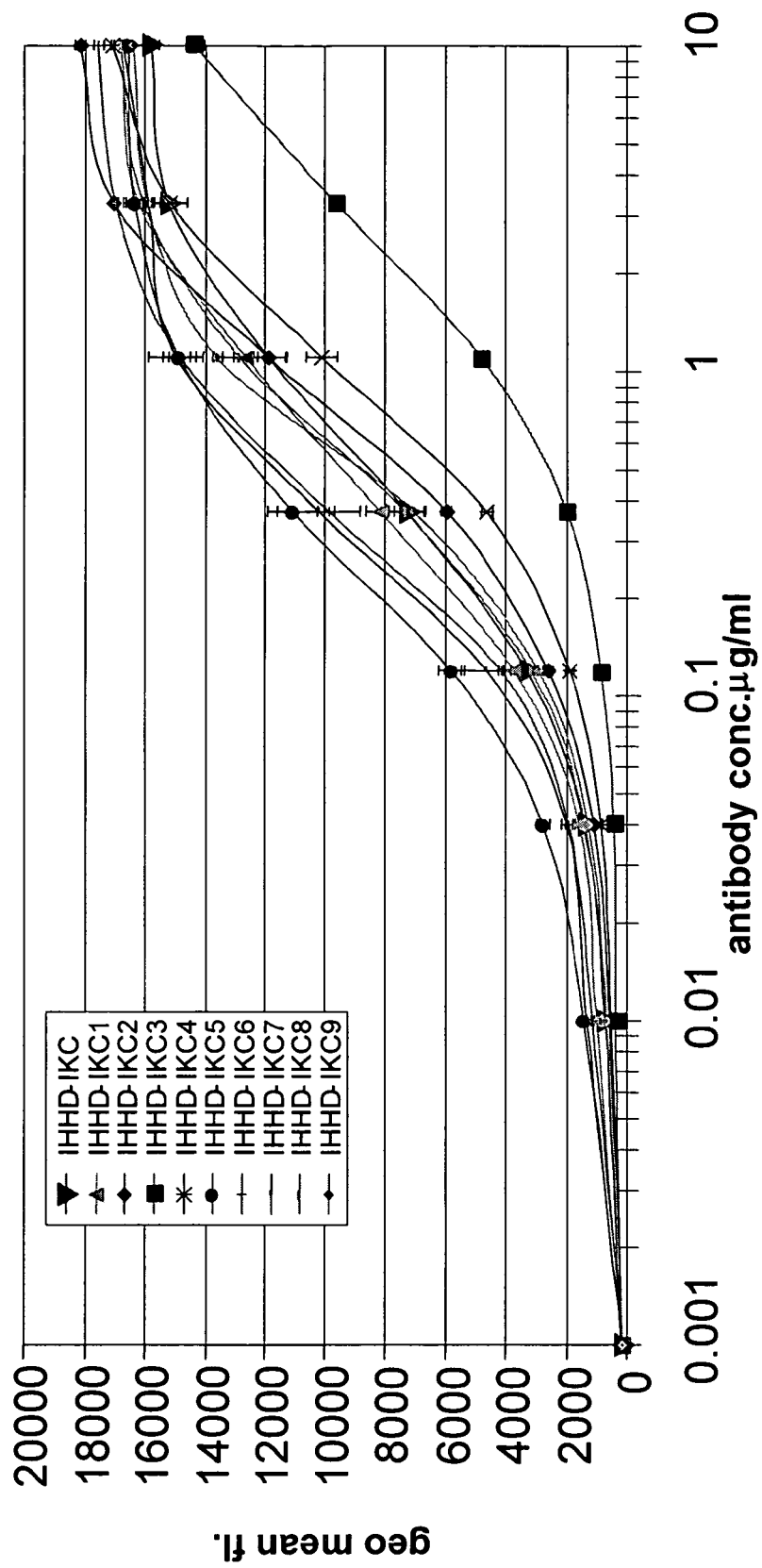
FIG. 29 shows EGFR target binding of various light chain construct variants based on the I-KC construct paired with the heavy chain I-HHD construct.

As seen in FIG. 29, only the modfication of residue 34 to its corresponding human sequence (N34G) resulted in a slight decrease in binding affinity (EC50 value increased by a factor of 10). All other constructs retained binding activity comparable to the I-KC construct (SEQ ID NO:45). Therefore, when paired with a chimeric (e.g., humanized) heavy chain construct specific for EGFR, the light chain can be entirely human (e.g., from a human light chain V gene sequence) and still retain specific binding for EGFR. In particular, CDR2 and CDR3 can be entirely in human germline form.

Antigen Binding Molecules Comprising EGFR-Specific CDRs

The present invention therefore contemplates an antigen binding molecule comprising a chimeric (e.g., humanized) heavy chain variable region comprising EGFR-specific CDRs paired with a light chain variable region, wherein the light chain variable region has fewer than ten non-human amino acid residues. In other embodiments, the light chain variable region has fewer than nine, eight seven, six, five, four, three, two, or one non-human amino acid residue(s). In preferred embodiments, the light chain variable region has fewer than two or fewer than one (i.e., no) non-human amino acid residues. In one embodiment, the light chain variable region comprises one or more human germline variable region gene sequences. Human germline variable region gene sequences encoding light chain variable regions are known in the art, and can be found, for example, in the IMGT database. In a preferred embodiment, the human germline sequence is derived from the VK1_6 germline sequence. In other embodiments, amino acid residues within the human germline light chain variable region amino acid sequence can be substituted with one or more residues from another human germline light chain variable region sequence.

In one embodiment, the present invention is directed to an antigen binding molecule comprising a sequence selected from the group consisting of SEQ ID NO.:1; SEQ ID No:3; SEQ ID No:5; SEQ ID No:7; SEQ ID No:9; SEQ ID No:11; SEQ ID No:13; SEQ ID No:15; SEQ ID No:17; SEQ ID No:19; SEQ ID No:21; SEQ ID No:23; SEQ ID No:25; SEQ ID No:27; SEQ ID No:29; SEQ ID No:31; SEQ ID No33; SEQ ID No:35; SEQ ID No:37; SEQ ID No:39; and SEQ ID No:121, and a light chain comprising a polypeptide encoded by one or more human germline variable gene sequence. In a preferred embodiment, the human germline sequence is derived from the VK1_6 germline sequence.

In another embodiment, the present invention is directed to an antigen binding molecule comprising a sequence selected from the group consisting of: SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:122, and SEQ ID NO:124; (b) a sequence selected from a group consisting of: SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, and SEQ ID NO:126; (c) SEQ ID NO:108; and (d) a polypeptide comprising a human light chain variable region encoded by one or more human germline gene sequences. In a particular embodiment, the human germline sequence is derived from the VK1_6 germline sequence. In another embodiment, the human germline variable region gene sequence comprises the VK1_6 germline gene sequence with a substitution of one or more amino acid codons with a sequence from a different human germline light chain variable region gene sequence.

In other embodiments, the antigen binding molecule of the present invention comprises an EGFR-specific heavy chain variable region of the present invention, and a variant of SEQ ID NO:45. In one embodiment, the variant of SEQ ID NO:45 comprises an amino acid substitution at one or more positions in the complementarity determining regions (CDRs). In specific embodiments, the substitution is of an amino acid residue at a position selected from the group consisting of: amino acid position 30 of SEQ ID NO:45; amino acid position 32 of SEQ ID NO:45; amino acid position 34 of SEQ ID NO:45; amino acid position 50 of SEQ ID NO:45; amino acid position 51 of SEQ ID NO:45; amino acid position 52 of SEQ ID NO:45; amino acid position 53 of SEQ ID NO:45; amino acid position 56 of SEQ ID NO:45; amino acid position 94 of SEQ ID NO:45; and any combination of substitutions thereof. In more specific embodiments, the substitution in SEQ ID NO:45 is selected from the group consisting of: substitution of an arginine (R) for the asparagine (N) at position 30 of SEQ ID NO:45; substitution of a tryptophan (W) for the tyrosine (Y) at position 32 of SEQ ID NO:45; substitution of a glycine (G) for the asparagine (N) at position 34 of SEQ ID NO:45; substitution of a threonine (T) for the asparagine (N) at position 50 of SEQ ID NO:45; substitution of an alanine (A) for the threonine (T) at position 51 of SEQ ID NO:45; substitution of a serine (S) for the asparagine (N) at position 52 of SEQ ID NO:45; substitution of a serine (S) for the asparagine (N) at position 53 of SEQ ID NO:45; substitution of a serine (S) for the threonine (T) at position 56 of SEQ ID NO:45; substitution of a tyrosine (Y) for the phenylalanine (F) at position 94 of SEQ ID NO:45; and any combination thereof. In a particular embodiment, all of these substitutions of amino acid residues in SEQ ID NO:45 are incorporated in a single light chain variant. In preferred embodiments, antigen binding molecules comprising the light chain variants with amino acid substitutions for the ICR62 CDRs retain specific binding to EGFR (as compared to an antigen binding molecule comprising a light chain variable region comprising the sequence of SEQ ID NO:45) when the light chain variant is paired with a polypeptide comprising a heavy chain variable region of the present invention.

The present invention is also directed to polynucleotides that encode any of the above polypeptides and/or antigen binding molecules. The present invention is further directed to the antigen binding molecules described above, with a pharmaceutically acceptable carrier.

All publications such as textbooks, journal articles, GenBank or other sequence database entries, published applications, and patent applications mentioned in this specification are herein incorporated by reference to the same extent as if each individual publication or patent application was specifically and individually indicated to be incorporated by reference.

What is claimed is:

1. An antigen binding molecule that specifically binds EGFR, said antigen binding molecule comprising a heavy chain variable region and a light chain variable region, wherein said heavy chain variable region comprises:
   (a) the heavy chain CDR1 of SEQ ID NO: 53;
   (b) the heavy chain CDR2 of SEQ ID NO: 79; and
   (c) the heavy chain CDR3 of SEQ ID NO: 107; and
wherein said light chain variable region comprises:
   (a) the light chain CDR1 of SEQ ID NO: 113;
   (b) the light chain CDR2 of SEQ ID NO: 115; and
   (c) the light chain CDR3 of SEQ ID NO: 117.

2. An isolated polypeptide comprising the sequence of SEQ ID NO: 15.

3. An isolated polypeptide comprising the sequence of SEQ ID NO: 45.

4. An antigen binding molecule that specifically binds EGFR, said antigen binding molecule comprising a heavy chain variable region and a light chain variable region,
   wherein said heavy chain variable region comprises the sequence of SEQ ID NO: 15, and
   wherein said light chain variable region comprises the sequence of SEQ ID NO: 45.

5. The antigen binding molecule of claim 1 or 4, wherein said antigen binding molecule is an antibody.

6. The antigen binding molecule of claim 1 or 4, wherein said antigen binding molecule is an antibody fragment.

7. The antigen binding molecule of claim 6, wherein said antibody fragment is selected from the group consisting of an scFv fragment, an Fv fragment, an F(ab')2 fragment, a minibody, a diabody, a triabody, and a tetrabody.

8. The antigen binding molecule of claim 1 or 4, wherein said antigen binding molecule comprises a human Fc region.

9. The antigen binding molecule of claim 8, wherein said human Fc region is a human IgG Fc region.

10. The antigen binding molecule of claim 8, wherein said antigen binding molecule has been glycoengineered to modify the oligosaccharides in the Fc region.

11. The antigen binding molecule of claim 10, wherein said Fc region has a reduced number of fucose residues as compared to the nonglycoengineered antigen binding molecule.

12. The antigen binding molecule of claim 10, wherein said glycoengineered antigen binding molecule has an increased ratio of GlcNAc residues to fucose residues in the Fc region compared to the nonglycoengineered antigen binding molecule.

13. The antigen binding molecule of claim 10, wherein said Fc region has an increased proportion of bisected oligosaccharides as compared to the nonglycoengineered antigen binding molecule.

14. The antigen binding molecule of claim 10, wherein said modified oligosaccharides are bisected complex.

15. The antigen binding molecule of claim 10, wherein said modified oligosaccharides have an increased proportion of bisected, nonfucosylated oligosaccharides in the Fc region of said antigen binding molecule compared to the nonglycoengineered antigen binding molecule.

16. The antigen binding molecule of claim 15, wherein said bisected, nonfucosylated oligosaccharides are hybrid.

17. The antigen binding molecule of claim 15, wherein said bisected, nonfucosylated oligosaccharides are complex.

18. The antigen binding molecule of claim 10, wherein said antigen binding molecule has increased effector function compared to the nonglycoengineered antigen binding molecule.

19. The antigen binding molecule of claim 18, wherein said increased effector function is selected from the group consisting of: increased Fc-mediated cellular cytotoxicity, increased binding to NK cells, increased binding to macrophages, increased binding to monocytes, increased binding to polymorphonuclear cells, direct signaling inducing apoptosis, increased dendritic cell maturation, and increased T cell priming.

20. The antigen binding molecule of claim 10, wherein said antigen binding molecule has increased Fc receptor binding compared to the nonglycoengineered antigen binding molecule.

21. The antigen binding molecule of claim 20, wherein said Fc receptor is Fc activating receptor.

22. The antigen binding molecule of claim 20, wherein said Fc receptor is FcγRIIIa receptor.

23. The antigen binding molecule of claim 8, wherein at least 50% of the oligosaccharides in said Fc region are bisected.

24. The antigen binding molecule of claim 8, wherein at least 70% of the oligosaccharides in said Fc region are bisected.

25. The antigen binding molecule of claim 8, wherein at least 90% of the oligosaceharides in said Fc region are bisected.

26. The antigen binding molecule of claim 8, wherein at least 50% of the oligosaccharides in said Fc region are nonfucosylated.

27. The antigen binding molecule of claim 8, wherein at least 75% of the oligosaccharides in said Fe region are nonfucosylated.

28. The antigen binding molecule of claim 8, wherein at least 90% of the oligosaceharides in said Fc region are nonfucosylated.

29. The antigen binding molecule of claim 8, wherein at least 20% of the oligosaccharides in said Fc region are bisected, nonfucosylated.

30. The antigen binding molecule of claim 8, wherein at least 35% of the oligosaccharides in said Fc region are bisected, nonfucosylated.

31. The antigen binding molecule of claim 8, wherein at least 70% of the oligosaccharides in said Fc region are bisected, nonfucosylated.

32. A composition comprising the antigen binding molecule according to claim 1 or 4 and a pharmaceutically acceptable carrier.

33. The composition of claim 32, wherein said composition further comprises an adjuvant.

34. An antigen binding molecule comprising an Fc region engineered to have increased effector function produced by a method comprising:
   (a) culturing a host cell engineered to express at least one nucleic acid encoding a polypeptide having β(1,4)-N-acetylglucosaminyltransferase III activity under conditions which permit the production of said antigen binding molecule and the modification of the oligosaccharides present on said Fc region of said antigen binding molecule; and
   (b) isolating said antigen binding molecule,
   wherein said antigen binding molecule comprises a heavy chain variable region and a light chain variable region,
   wherein said heavy chain variable region comprises the sequence of SEQ ID NO:15, and
   wherein said light chain variable region comprises the sequence of SEQ ID NO:45.

35. An antigen binding molecule comprising an Fc region engineered to have increased Fc receptor binding affinity produced by a method comprising:
(a) culturing a host cell engineered to express at least one nucleic acid encoding a polypeptide having β(1,4)-N-acetylglucosaminyltransferase III activity under conditions which permit the production of said antigen binding molecule and the modification of the oligosaccharides present on said Fc region of said antigen binding molecule; and
(b) isolating said antigen binding molecule,
wherein said antigen binding molecule comprises a heavy chain variable region and a light chain variable region,
wherein said heavy chain variable region comprises the sequence of SEQ ID NO:15, and
wherein said light chain variable region comprises the sequence of SEQ ID NO:45.

36. The antigen binding molecule of claim 34, wherein said antigen binding molecule is an antibody.

37. The antigen binding molecule of claim 34, wherein said increased effector function is selected from the group consisting of: increased Fc-mediated cellular cytotoxicity, increased binding to NK cells, increased binding to macrophages, increased binding to monocytes, increased binding to polymorphonuclear cells, direct signaling inducing apoptosis, increased dendritic cell maturation, and increased T cell priming.

38. The antigen binding molecule of claim 37, wherein said increased effector function is increased binding to NK cells.

39. The antigen binding molecule of claim 35, wherein said antigen binding molecule is an antibody.

40. The antigen binding molecule of claim 35, wherein said Fc receptor is Fc activating receptor.

41. The antigen binding molecule of claim 35, wherein said Fc receptor is FcγRIIIa receptor.

42. An antibody that specifically binds EGFR, said antibody comprising: a heavy chain variable region comprising the sequence of SEQ ID NO:15, a light chain variable region comprising the sequence of SEQ ID NO:45, and a human Fc region.

43. The antibody of claim 42, wherein said antibody has been glycoengineered to modify the oligosaccharides in said Fc region.

44. The antibody of claim 43, wherein said antibody has a reduced number of fucose residues in said Fc region compared to a nonglycoengineered form of the antibody.

45. The antibody of claim 43, wherein said antibody has an increased ratio of GlcNAc residues to fucose residues in said Fc region compared to a nonglycoengineered form of the antibody.

46. The antibody of claim 43, wherein said antibody has an increased proportion of bisected oligosaccharides in the Fc region as compared to a nonglycoengineered form of the antibody.

47. The antibody of claim 43, wherein said modified oligosaccharides are bisected complex.

48. The antibody of claim 43, wherein said modified oligosaccharides have an increased proportion of bisected, nonfucosylated oligosaccharides in said Fc region compared to a nonglycoengineered form of the antibody.

49. The antibody of claim 43, wherein said bisected, nonfucosylated oligosaccharides are hybrid.

50. The antibody of claim 43, wherein said bisected, nonfucosylated oligosaccharides are complex.

51. The antibody of claim 43 wherein said antibody has increased effector function or increased Fc receptor binding compared to a nonglycoengineered form of the antibody.

52. The antibody of claim 42, wherein at least about 50% of the oligosaccharides in said Fc region are bisected.

53. The antibody of claim 42, wherein at least about 50% of the oligosaccharides in said Fc region are nonfucosylated.

54. The antibody of claim 42, wherein at least about 20% of the oligosaccharides in said Fc region are bisected, nonfucosylated.

55. The antibody of claim 42, wherein said antibody, when administered to a mammalian subject at concentrations above one microgram per milliliter of serum, does not cause a clinically significant level of toxicity in said subject.

56. The antigen binding molecule of claim 34, wherein the host cell is further engineered to express a nucleic acid encoding a polypeptide having mannosidase II activity.

57. The antigen binding molecule of claim 35, wherein the host cell is further engineered to express a nucleic acid encoding a polypeptide having mannosidase II activity.

* * * * *